United States Patent
Kitazato et al.

(10) Patent No.: US 7,226,786 B2
(45) Date of Patent: *Jun. 5, 2007

(54) ENVELOPE GENE-DEFICIENT PARAMYXOVIRUS VECTOR

(75) Inventors: Kaio Kitazato, Ibaraki (JP); Tsugumine Shu, Ibaraki (JP); Hidekazu Kuma, Ibaraki (JP); Yasuji Ueda, Ibaraki (JP); Makoto Asakawa, Osaka (JP); Mamoru Hasegawa, Ibaraki (JP); Akihiro Iida, Ibaraki (JP); Fumino Tokito, Ibaraki (JP); Takahiro Hirata, Ibaraki (JP); Tsuyoshi Tokusumi, Ibaraki (JP); Makoto Inoue, Ibaraki (JP); Yumiko Tokusumi, Ibaraki (JP)

(73) Assignee: DNAVEC Research Inc., Tsukuba-Shi, Ibaraki (JP)

( * ) Notice: Subject to any disclaimer, the term of this patent is extended or adjusted under 35 U.S.C. 154(b) by 196 days.

This patent is subject to a terminal disclaimer.

(21) Appl. No.: 10/316,535

(22) Filed: Dec. 10, 2002

(65) Prior Publication Data

US 2003/0170266 A1 Sep. 11, 2003

Related U.S. Application Data

(63) Continuation-in-part of application No. 09/966,277, filed on Sep. 27, 2001, now abandoned, which is a continuation-in-part of application No. PCT/JP00/03195, filed on May 18, 2000.

(30) Foreign Application Priority Data

May 18, 1999 (JP) .................................. 11-200739
Sep. 18, 2001 (JP) ............................. 2001-283451
Sep. 18, 2002 (WO) ...................... PCT/JP02/09558

(51) Int. Cl.
*C12N 15/00* (2006.01)
*C12N 15/86* (2006.01)

(52) U.S. Cl. ...................................... 435/456; 435/455

(58) Field of Classification Search .............. 435/320.1, 435/235.1, 236, 455, 456, 457, 466, 471, 435/472, 475; 424/199.1, 93.2, 475; 536/252.3, 536/23.72
See application file for complete search history.

(56) References Cited

U.S. PATENT DOCUMENTS

| 5,962,274 | A | * | 10/1999 | Parks ........................ 435/91.1 |
| 6,040,174 | A | | 3/2000 | Imler et al. |
| 6,645,760 | B2 | | 11/2003 | Nagai et al. |
| 6,723,532 | B2 | | 4/2004 | Nagai et al. |
| 6,746,860 | B1 | | 6/2004 | Tokusumi et al. |
| 6,828,138 | B1 | | 12/2004 | Nagai et al. |
| 2002/0002143 | A1 | | 1/2002 | Kano et al. |
| 2002/0081706 | A1 | | 6/2002 | Nagai et al. |
| 2002/0098576 | A1 | | 7/2002 | Nagai et al. |
| 2002/0100066 | A1 | | 7/2002 | Nagai et al. |
| 2003/0166252 | A1 | | 9/2003 | Kitazato et al. |
| 2003/0170210 | A1 | | 9/2003 | Masaki et al. |
| 2003/0170897 | A1 | | 9/2003 | Imai et al. |
| 2003/0203489 | A1 | | 10/2003 | Yonemitsu et al. |
| 2004/0005296 | A1 | | 1/2004 | Yonemitsu et al. |
| 2004/0053877 | A1 | | 3/2004 | Fukumura et al. |
| 2004/0101965 | A1 | | 5/2004 | Griesenbach et al. |
| 2004/0121308 | A1 | | 6/2004 | Nagai et al. |
| 2006/0104950 | A1 | | 5/2006 | Okano et al. |

FOREIGN PATENT DOCUMENTS

| CN | 1357044 A | | 7/2002 |
| EP | 0 863 202 A1 | | 9/1998 |
| EP | 0 864 645 A1 | | 9/1998 |
| EP | 1 106 692 A1 | | 6/2001 |
| EP | 1 179 594 A1 | | 2/2002 |
| EP | 1179594 | * | 2/2002 |
| JP | 7-509616 A1 | | 10/1995 |
| JP | 10-506542 A1 | | 6/1998 |
| WO | WO 97/16171 A1 | | 5/1997 |
| WO | WO 97/16538 | | 5/1997 |
| WO | WO 97/16538 A1 | | 5/1997 |
| WO | WO 00/27430 A3 | | 5/2000 |
| WO | WO 00/70055 | * | 11/2000 |
| WO | WO 00/70070 A1 | | 11/2000 |
| WO | WO 01/32898 A3 | | 5/2001 |
| WO | WO 03/092738 A1 | | 11/2003 |
| WO | WO 03/093476 A1 | | 11/2003 |
| WO | WO 03/102183 A1 | | 12/2003 |
| WO | WO 2004/038029 A1 | | 6/2004 |

OTHER PUBLICATIONS

Lamb et al (In Fields Virology, 3rd edition, ed. Fields et al, Lippincott Williams & Wilkins, Philadelphia PA) p. 1181; 1996.*

(Continued)

*Primary Examiner*—Brenda Brumback
*Assistant Examiner*—Sharon Hurt
(74) *Attorney, Agent, or Firm*—Clark & Elbing LLP

(57) ABSTRACT

F gene-deficient virus virions are successfully recovered by using an F gene-deficient Sendai virus genomic cDNA. Further, F gene-deficient infectious viral particles are successfully constructed by using F-expressing cells as helper cells. Also, F gene and HN gene-deficient virus virions are successfully recovered by using a virus genomic cDNA deficient in both F gene and HN gene. Further, F gene and HN gene-deficient infectious viral particles are successfully produced by using F- and HN-expressing cells as helper cells. A virus deficient in F gene and HN gene and having F protein is constructed by using F-expressing cells as helper cells. In addition, M gene-deficient infectious virus particles were produced using helper cells expressing M protein. From cells infected with M gene-deficient viruses, release of virus-like particles was inhibited. Further, a VSV-G pseudo type virus is successfully constructed by using VSV-G-expressing cells. Techniques for constructing these deficient viruses contribute to the development of vectors of Paramyxoviridae usable in gene therapy.

16 Claims, 94 Drawing Sheets

OTHER PUBLICATIONS

Karron et al (PNAS USA 94:13961-13966, 1997).*
Speilhofer et al (Journal of Virology 72(3):2150-2159, Mar. 1998).*
Cathomen et al (EMBO Journal 17(14):3899-3980, 1998).*
Li et al (Journal of Virology 74(14): 6564-6569, Jul. 2000).*
Matsumura et al (Journal of General Virology 80:117-123, Jan. 1999).*
Leyrer et al (Journal of General Virology 79:683-687, Apr. 1998).*
Lin et al (Virology 238:460-469, 1997).*
Sakai et al (FEBS Letters 456:221-226, 1999).*
Ali and Nayak, "Assembly of Sendai Virus: M Protein Interacts with F and HN Proteins and with the Cytoplasmic Tail and Transmembrane Domain of F Protein," *Virology* 276:289-303 (2000).
Bitzer et al., "Sendai Virus Efficiently Infects Cells via the Asialoglycoprotein Receptor and Requires the Presence of Cleaved $F_0$ Precursor Proteins for this Alternative Route of Cell Entry," *J. Virol.* 71:5481-5486 (1997).
Brown and Rose, "Sorting of GPI-Anchored Proteins to Glycolipid-Enriched Membrane Subdomains during Transport to the Apical Cell Surface," *Cell* 68:533-544 (1992).
Cathomen et al., "A Matrix-Less Measles Virus Is Infectious and Elicits Extensive Cell Fusion: Consequences for Propagation in the Brain," *EMBO J.*, 17:3899-3908 (1998).
Garoff et al., "Virus Maturation by Budding," *Microbiol. Mol. Biol. Rev.*, 62:1171-1190 (1998).
Heggeness et al., "In Vitro Assembly of the Nonglycosylated Membrane Protein (M) of Sendai Virus," *Proc. Natl. Acad. Sci. USA*, 79:6232-6236 (1982).
Kido et al., "The Human Mucus Protease Inhibitor and its Mutants Are Novel Defensive Compounds Against Infection with Influenza A and Sendai Viruses," *Biopolymers (Peptide Science)* 51:79-86 (1999).
Kondo et al., "Temperature-Sensitive Phenotype of a Mutant Sendai Virus Strain Is Caused by its Insufficient Accumulation of the M Protein," *J. Biol. Chem.*, 268:21924-21930 (1993).
Li et al., "A Cytoplasmic RNA Vector Derived from Nontransmissible Sendai Virus with Efficient Gene Transfer and Expression," *J. Virol.* 74:6564-6569 (2000).
Manié et al., "Measles Virus Structural Components Are Enriched into Lipid Raft Microdomains: a Potential Cellular Location for Virus Assembly," *J. Virol.*, 74:305-311 (2000).
Mebatsion et al., "Matrix Protein of Rabies Virus Is Responsible for the Assembly and Budding of Bullet-Shaped Particles and Interacts with the Transmembrane Spike Glycoprotein G," *J. Virol.*, 73 242-250 (1999).
Morikawa et al., "Characterization of Temperature-Sensitive Mutants of Measles Virus," *Kitasato Arch. of Exp. Med.*, 64:15-30 (1991).
Sanderson et al., "Sendai Virus Assembly: M Protein Binds to Viral Glycoproteins in Transit through the Secretory Pathway," *J. Virol.*, 67:651-663 (1993).
Sanderson et al., "Sendai Virus M Protein Binds Independently to either the F or the HN Glycoprotein In Vivo," *J. Virol.*, 68:69-76 (1994).
Simons and Ikonen, "Functional Rafts in Cell Membranes," *Nature* 387:569-572 (1997).
Speilhofer et al., "Chimeric Measles Viruses with a Foreign Envelope," *J. Virol.*, 72:2150-2159 (1998).
Stricker and Roux, "The Major Glycoprotein of Sendai Virus Is Dispensable for Efficient Virus Particle Budding," *J. Gen. Virol.*, 72:1703-1707 (1991).
Thompson and Portner, "Localization of Functional Sites on the Hemagglutinin-Neuraminidase Glycoprotein of Sendai Virus by Sequence Analysis of Antigenic and Temperature-Sensitive Mutants," *Virology* 160:1-8 (1987).
Yoshida et al., "Membrane (M) Protein of HVJ (Sendai Virus): Its Role in Virus Assembly." *Virology* 71:143-161 (1976).
Yu et al., "Sendai Virus-Based Expression of HIV-1 gp120: Reinforcement by the V(-) Version," *Genes to Cells* 2:457-466 (1997).

Markwell et al., "An Alternative Route of Infection for Viruses: Entry by Means of the Asialoglycoprotein Receptor of a Sendai Virus Mutant Lacking its Attachment Protein," *Proc. Natl. Acad. Sci. USA* 82:978-982 (1985).
Barclay and Palese, "Influenza B Viruses with Site-Specific Mutations Introduced into the HA Gene," *Journal of Virology*, 69(2):1275-1279, 1995.
Conzelmann, "Nonsegmented Negative-Strand RNA Viruses: Genetics and Manipulation of Viral Genomes," *Annu. Rev. Genet.*, 32:123-162, 1998.
Huntley et al., "Phosphorylation of Sendai Virus Phosphoprotein by Cellular Protein Kinase C ζ," *The Journal of Biological Chemistry*, 272(26):16578-16584, 1997.
Kato et al., "Initiation of Sendai Virus Multiplication from Transfected cDNA or RNA with Negative or Positive Sense," *Genes Cells*, 1(6):569-579, 1996.
Nagai, "Paramyxovirus Replication and Pathogenesis. Reverse Genetics Transforms Understanding," *Reviews in Medical Virology*, 9(2):83-99, 1999.
Schwartz et al., "Synthetic DNA-Compacting Peptides Derived from Human Sequence Enhance Cationic Lipid-Mediated Gene Transfer in vitro and in vivo," *Gene Therapy*, 6(2):282-292, 1999.
Zhimov, "Solubilization of Matrix Protein M1/M from Virions Occurs at Different pH for Orthomyxo- and Paramyxoviruses," *Virology*, 176(1):274-279, 1990.
Hasan et al., "Creation of an Infectious Recombinant Sendai Virus Expressing the Firefly Luciferase Gene from the 3' Proximal First Locus," *J. Gen. Virol.*, 78(Pt 11):2813-2820, 1997.
Brenner, "Gene Transfer to Hematopoietic Cells," New England Journal of Medicine 335(5):337-339 (1996).
Inoue et al., "A New Sendai Virus Vector Deficient in the Matrix Gene Does Not Form Virus Particles and Shows Extensive Cell-to-Cell Spreading," *J. Virol.* 77(11):6419-6429 (2003).
Bagai et al., "Hemagglutinin-Neuraminidase Enhances F Protein-Mediated Membrane Fusion of Reconstituted Sendai Virus Envelopes with Cells," *J. Virol.* 67(6):3312-3318 (1993).
Douglas et al., "Targeted Gene Delivery by Tropism-Modified Adenoviral Vectors," *Nat. Biotechnol.* 14(11):1574-1578 (1996).
Gitman et al., "Use of Virus-Attached Antibodies or Insulin Molecules to Mediate Fusion Between Sendai Virus Envelopes and Neuraminidase-Treated Cells," *Biochemistry* 24(11):2762-2768 (1985).
Miura et al., "HVJ (Sendai Virus)-Induced Envelope Fusion and Cell Fusion Are Blocked by Monoclonal Anti-HN Protein Antibody That Does Not Inhibit Hemagglutination Activity of HVJ," *Exp. Cell Res.* 141(2):409-420 (1982).
Ponimaskin et al., "Sendai Virosomes Revisited: Reconstitution with Exogenous Lipids Leads to Potent Vehicles for Gene Transfer," *Virology* 269(2):391-403 (2000).
Ramani et al., "Novel Gene Delivery to Liver Cells Using Engineered Virosomes," *FEBS Lett.* 404(2-3):164-168 (1997).
Tamasi et al., "Conjugation of Specific Antibodies to Sendai Virus Particles," *FEBS Lett.* 143(2):252-256 (1982).
Tuffereau et al., "The Role of Haemagglutinin-Neuraminidase Glycoprotein Cell Surface Expression in the Survival of Sendai Virus-Infected BHK-21 Cells," *J. Gen. Virol.* 66:2313-2318 (1985).
Altenschmidt et al., "Specific Cytotoxic T Lymphocytes In Gene Therapy," *J. Mol. Med.* 75(4):259-266 (1997).
Auten et al., "Effect of Scaffold Attachment Region on Transgene Expression in Retrovirus Vector-Transduced Primary T Cells and Macrophages," *Hum. Gene Ther.* 10(8):1389-1399 (1999).
Ayuk et al., "Establishment of an Optimised Gene Transfer Protocol for Human Primary T Lymphocytes According to Clinical Requirements," *Gene Ther.* 6(10):1788-1792 (1999).
Blaese et al., "T Lymphocyte-Directed Gene Therapy for ADA⁻ SCID: Initial Trail Results After 4 Years," *Science* 270(5235):475-480 (1995).
Buchschacher and Wong-Staal, "Development of Lentiviral Vectors for Gene Therapy for Human Diseases," *Blood* 95(8):2499-2504 (2000).

Bunnell et al., "Efficient In Vivo Marking of Primary CD4+ T Lymphocytes in Nonhuman Primates Using a Gibbon Ape Leukemia Virus-Derived Retroviral Vector," *Blood* 89(6):1987-1995 (1997).

Costello et al., "Gene Transfer into Stimulated and Unstimulated T Lymphocytes by HIV-1-Derived Lentiviral Vectors," *Gene Ther.* 7(7):596-604 (2000).

Dardalhon et al., "Lentivirus-mediated Gene Transfer in Primary T Cells Is Enhanced by a Central DNA Flap," *Gene Ther.* 8(3):190-198 (2001).

Di Nicola et al., "Recombinant Adenoviral Vector-LipofectA MINE Complex for Gene Thransduction into Human T Lymphocytes," *Hum. Gene Ther.* 10(11):1875-1884 (1999).

Friedman, "Expression of Human Adenosine Deaminase Using a Transmissable Murine Retrovirus Vector System," *Proc. Natl. Acad. Sci. USA* 82(3):703-707 (1985).

Gladow et al., "MLV-10A1 Retrovirus Pseudotype Efficiently Transduces Primary Human $CD4^+$ T Lymphocytes," *J. Gene Med.* 2(6):409-415 (2000).

Hege and Roberts, "T-Cell Gene Therapy," *Curr. Opin. Biotechnol.* 7(6):629-634 (1996).

Ikeda et al., "Recombinant Sendai Virus-Mediated Gene Transfer into Adult Rat Retinal Tissue: Efficient Gene Transfer by Brief Exposure," *Exp. Eye Res.* 75(1):39-48 (2002).

Imbert et al., "Highly Efficient Retroviral Gene Transfer into Human Primary T Lymphocytes Derived from Peripheral Blood," *Cancer Gene Ther.* 1(4):259-265 (1994).

Kühlcke et al., "Highly Efficient Retroviral Gene Transfer Based on Centrifugation-Mediated Vector Preloading of Tissue Culture Vessels," *Mol. Ther.* 5(4):473-478 (2002).

Misaki et al., "Gene-Transferred Oligoclonal T Cells Predominantly Persist in Peripheral Blood From an Adenosine Deaminase-Deficient Patient During Gene Therapy," *Mol. Ther.* 3(1):24-27 (2001).

Movassagh et al., "Retrovirus-Mediated Gene Transfer into T Cells: 95% Transduction Efficiency Without Further In Vitro Selection," *Hum. Gene Ther.* 11(8):1189-1200 (2000).

Okano et al., "Recombinant Sendai Virus Vectors for Activated T Lymphocytes," *Gene Ther.* 10(16):1381-1391 (2003).

Pollok et al., "High-Efficiency Gene Transfer into Normal and Adenosine Deaminase-Deficient T Lymphocytes is Mediated by Transduction on Recombinant Fibronectin Fragments," *J. Virol.* 72(6):4882-4892 (1998).

Puls and Minchin, "Gene Transfer and Expression of a Non-Viral Polycation-Based Vector in $CD4^+$ Cells," *Gene Ther.* 6(10):1774-1778 (1999).

Rosenberg et al., "Gene Transfer Into Humans—Immunotherapy of Patients with Advanced Melanoma, Using Tumor-Infiltrating Lymphocytes Modified by Retroviral Gene Transduction," *N. Eng. J. Med.* 323(9):570-578 (1990).

Rudoll et al., "High-Efficiency Retroviral Vector Mediated Gene Transfer into Human Peripheral Blood $CD4^+$ T Lymphocytes," *Gene Ther.* 3(8):695-705 (1996).

Sakai et al. "Accommodation of Foreign Genes into the Sendai Virus Genome: Sizes of Inserted Genes and Viral Replication," *FEBS lett.* 456(2):221-226 (1999).

Shiotani et al. "Skeletal Muscle Regeneration After Insulin-Like Growth Factor I Gene Transfer by Recombinant Sendai Virus Vector," *Gene Ther.* 8(14):1043-1050 (2001).

Stockschläder et al., "Expansion and Fibronectin-Enhanced Retroviral Transduction of Primary Human T Lymphocytes for Adoptive Immunotherapy," *J. Hematother Stem Cell Res.* 8(4):401-410 (1999).

Tuohy and Mathisen, "T Cell Design for Therapy in Autoimmune Demyelinating Disease," *J. Neuroimmunol.* 107(2): 226-232 (2000).

Uchida et al., "High Efficiency Gene Transfer into Murine T Cell Clones Using a Retroviral Vector," *J. Immunol.* 136(5):1876-1879 (1986).

Wickham et al., "Targeted Adenovirus-Mediated Gene Delivery to T Cells Via CD3," *J. Virol.* 71(10):7663-7669 (1997).

Yonemitsu et al., "Efficient Gene Transfer to Airway Epithelium Using Recombinant Sendai Virus," *Nat. Biotechnol.* 18(9):970-973 (2000).

Arai et al., *J. Virol.* 72(2):1115-1121 (1998).

Bergemann et al., *Nucleic Acids Res.* 23(21):4451-4456 (1995).

U.S. Appl. No. 10/578,085, filed May 3, 2006, Okano et al.

U.S. Appl. No. 10/543,734, filed Feb. 7, 2006, Tokusumi et al.

U.S. Appl. No. 10/562,408, filed Dec. 23, 2005, You et al.

* cited by examiner

1: SeV virions
2: LLCMK2
3: LLC/F7-trypsin
4: LLC/F7+trypsin

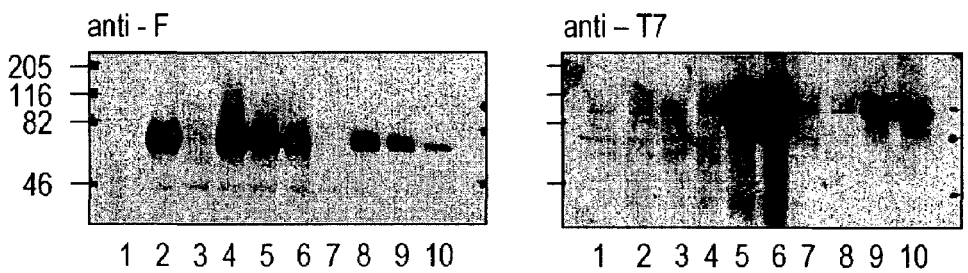

1: LLCMK2
2: LLCMK2 / F+ad 3rd
3: LLCMK2 / F-ad
4: LLCMK2 / F+ad 3d
5: LLCMK2 / F+ad 3d/Vac 1d
6: LLCMK2 / F+ad 3d/Vac 3d
7: CV-1 / F-ad
8: CV-1 / F-ad 3d
9: CV-1 / F-ad 3d/Vac 1d
10: CV-1 / F-ad 3d/Vac 3d

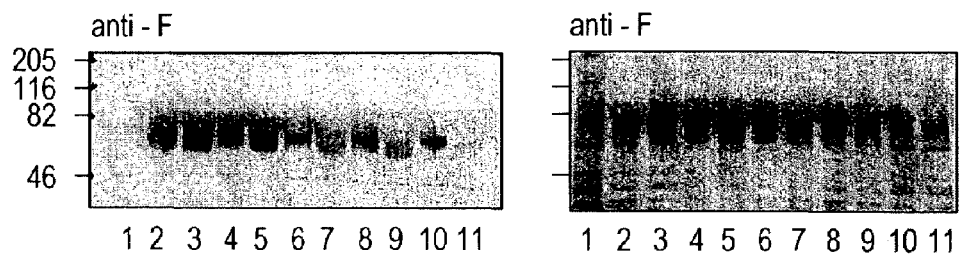

1: LLCMK2
2: LLCMK2 / F+ad 1d
3: LLCMK2 / F+ad 3d
4: LLCMK2 / F+ad 1d / AraC 1d
5: LLCMK2 / F+ad 1d / AraC 3d
6: LLCMK2 / F+ad 1d / Vac 1d
7: LLCMK2 / F+ad 1d / Vac 3d
8: LLCMK2 / F+ad 1d / AraC+Vac 1d
9: LLCMK2 / F+ad 1d / AraC+Vac 3d
10: LLCMK2 / F+ad 1d / CHX 1d
11: LLCMK2 / F+ad 1d / CHX 3d

1: CV1
2: CV1 / F+ad 1d
3: CV1 / F+ad 3d
4: CV1 / F+ad 1d / AraC 1d
5: CV1 / F+ad 1d / AraC 3d
6: CV1 / F+ad 1d / Vac 1d
7: CV1 / F+ad 1d / Vac 3d
8: CV1 / F+ad 1d / AraC+Vac 1d
9: CV1 / F+ad 1d / AraC+Vac 3d
10: CV1 / F+ad 1d / CHX 1d
11: CV1 / F+ad 1d / CHX 3d

FIG. 9
Infection with LLCMK2 / F sup
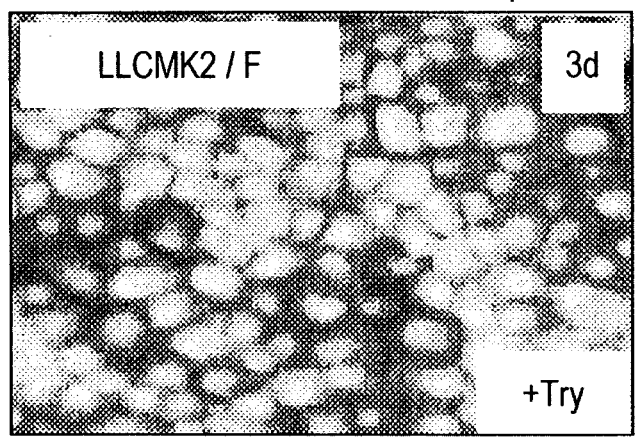
Infection with LLCMK2 sup
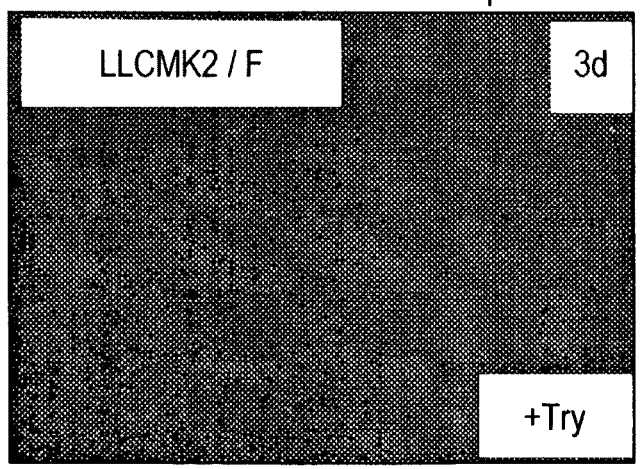

1: +18-NP, for the confirmation of the presence of +18 Not I site
2: M-GFP, for the confirmation of the presence of the GFP gene in the F gene-deficient region
3: F gene, for the confirmation of the presence of the F gene

| Primer Set | ΔFGFP | F/ΔFGFP | GFP/SeV | SeV (wt) |
|---|---|---|---|---|
| 1 | - | + | + | + |
| 2 | + | + | - | - |

FIG. 14
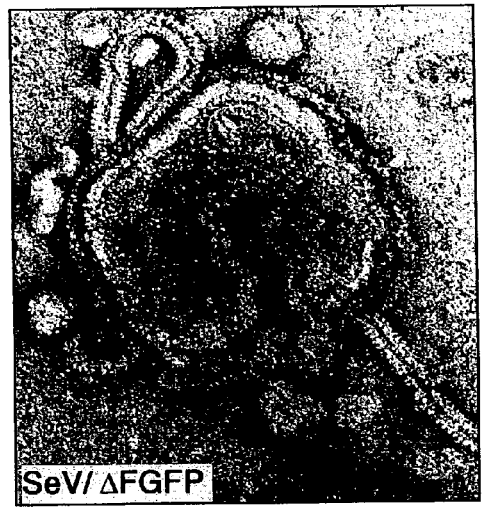

FIG. 21
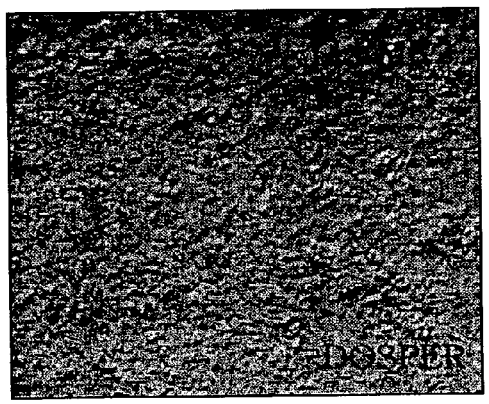
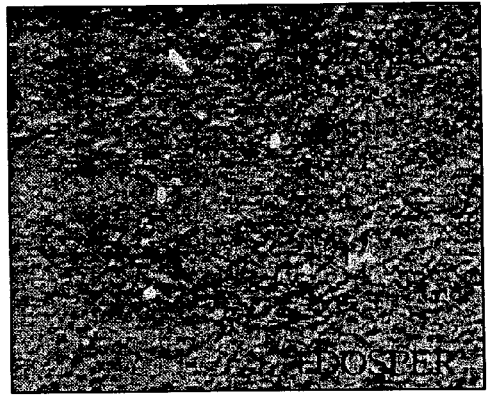
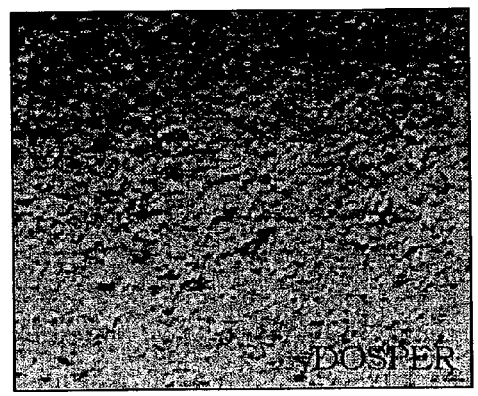
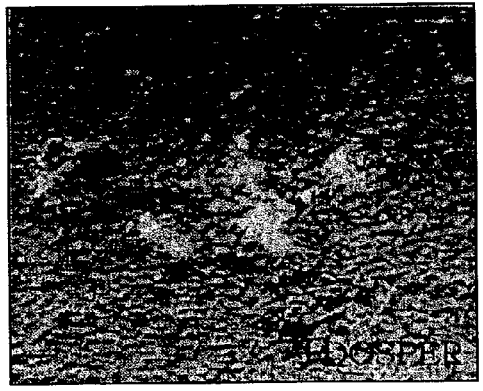

1: LLC / VacT7 / pGEM / FHN
2: LLC / VacT7
3: LLC / FHNmix
4: LLC / FHN 1-13
5: LLC / FHN 2-6
6: LLC / FHN 2-16
7: LLC / FHN 3-3
8: LLC / FHN 3-18
9: LLC / FHN 3-22
10: LLC / FHN 4-3
11: LLC / FHN 5-9

FIG. 23
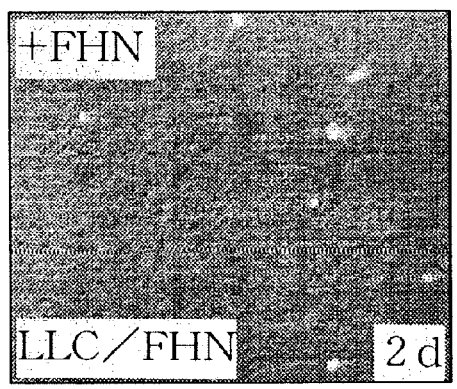
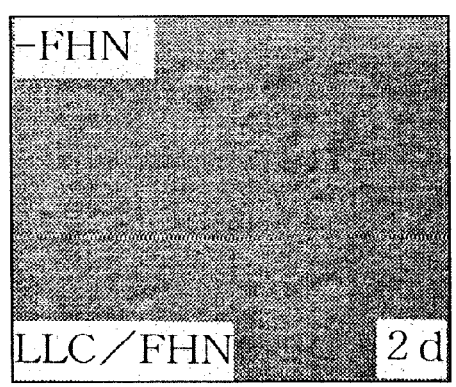
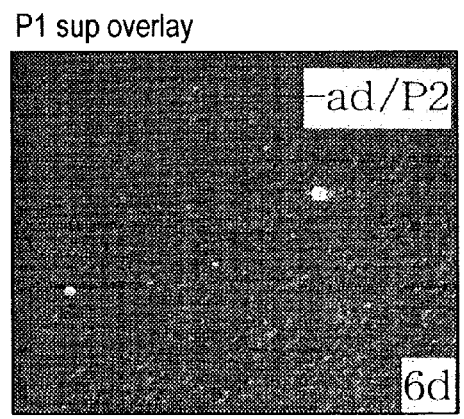
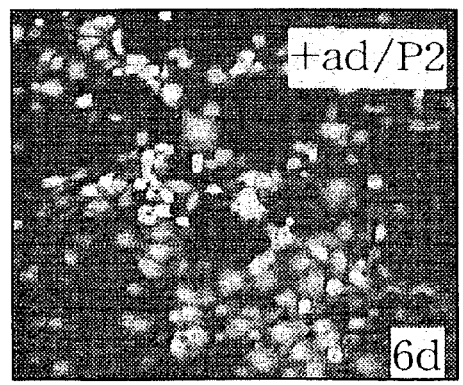

FIG. 26
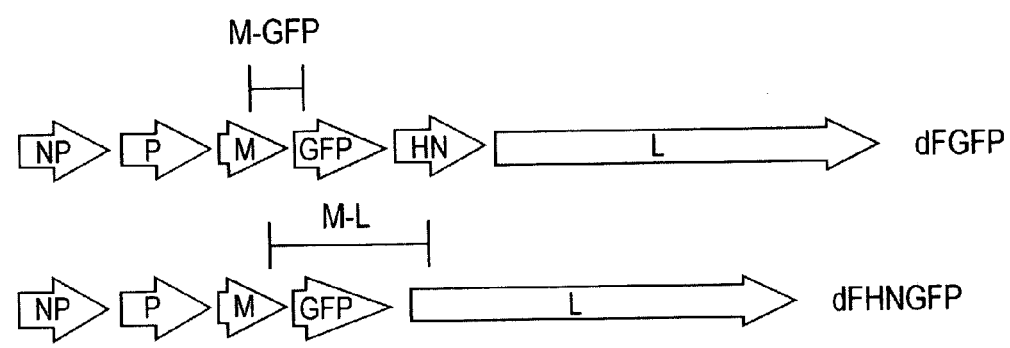
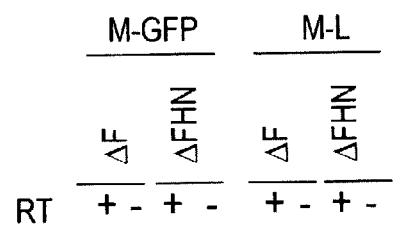
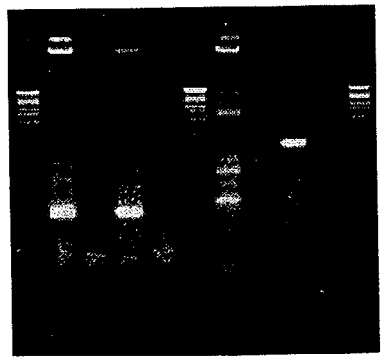

P3 virus solution: culture supernatant 7 - 8 days after infection

FIG. 39
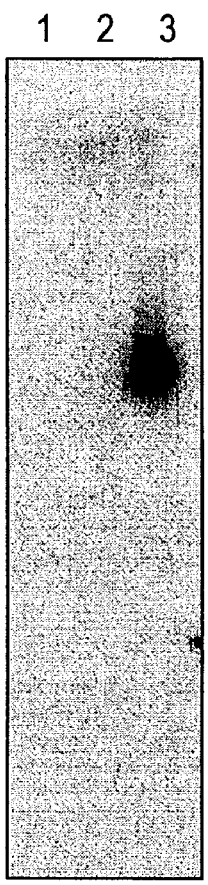
anti-F
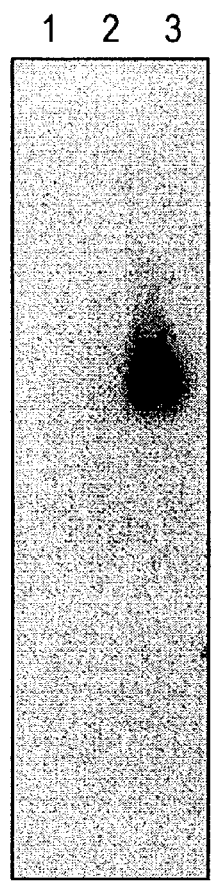
anti-HN
anti-SeV

FIG. 40
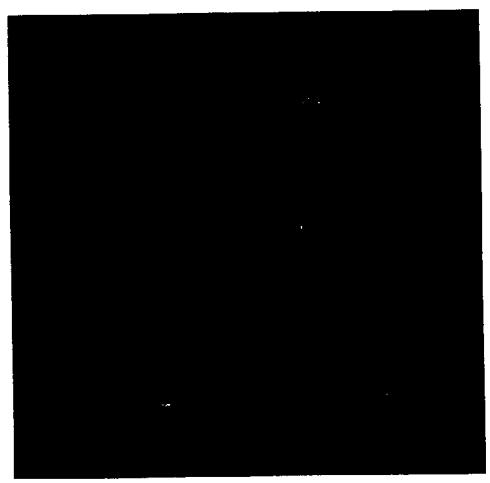
CIU measurement by using anti-SeV antibody and anti-rabbit fluorescent-labeled secondary antibody
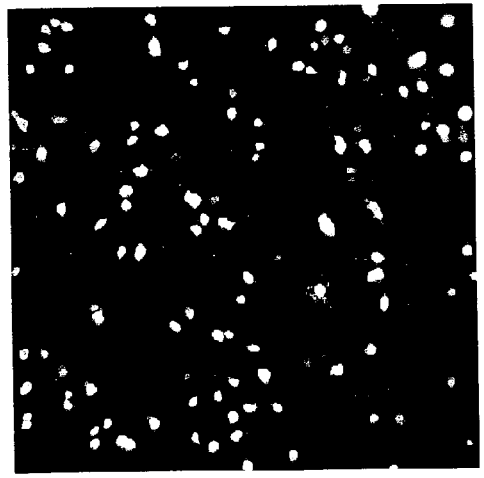
CIU measurement of GFP-expressing cells (control)

▲ New Not I site

FIG. 48

ΔFHN

FHN Cell-　　　　　　　　FHN Cell+

FIG. 51

Envelope

Antibody

| | VSV-G | F,HN |
|---|---|---|
| – | | |
| 1/20 | | |
| 1/2 | | |

Genome: SeV (+18) / ΔF-HN:GFP

Sucrose: 20 - 60% linear gradient (LLC-MK2 cells)

FIG. 54
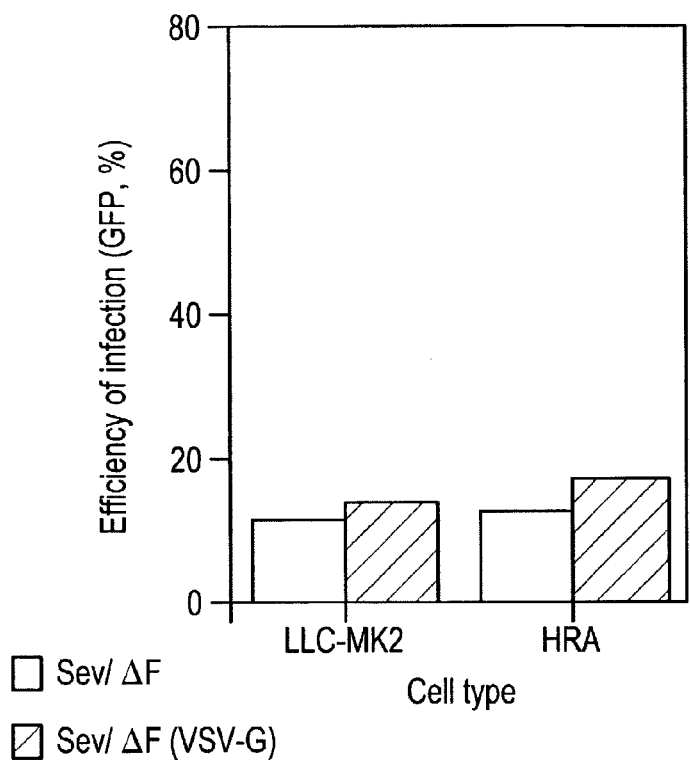
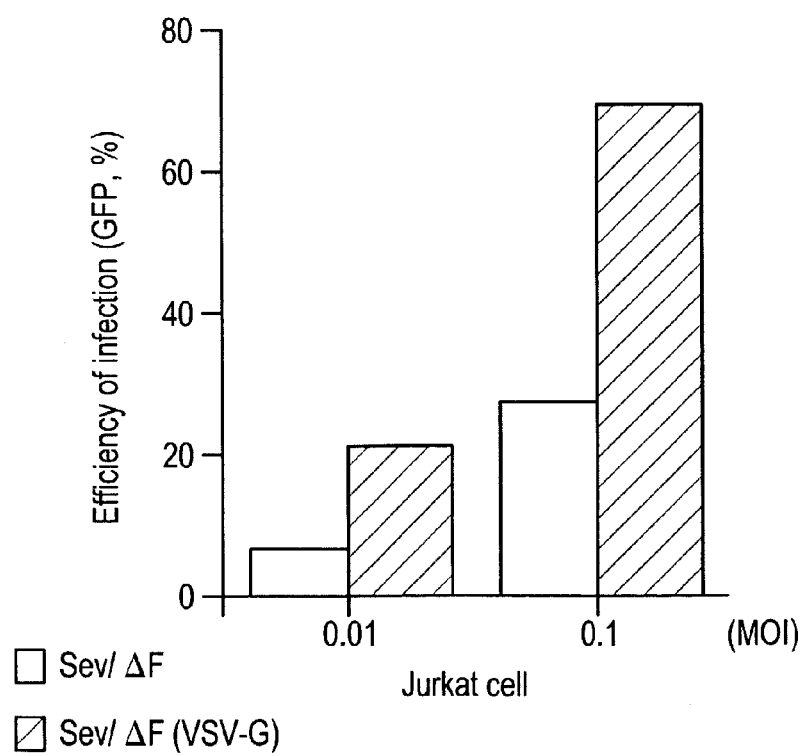

FIG. 55
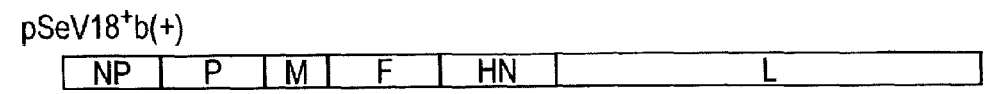
pSeV18⁺b(+)
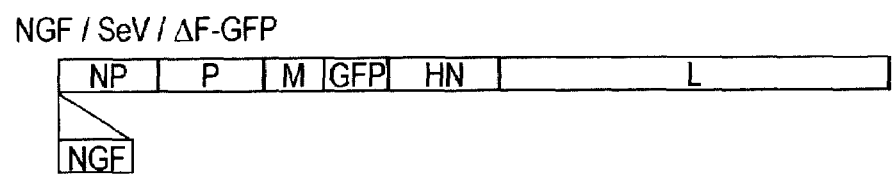
NGF / SeV / ΔF-GFP
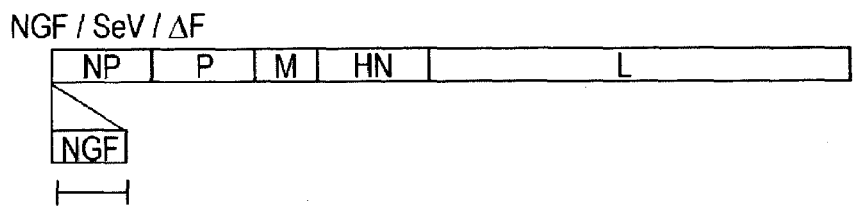
NGF / SeV / ΔF
NGF primer (NGF-N to NGF-C)
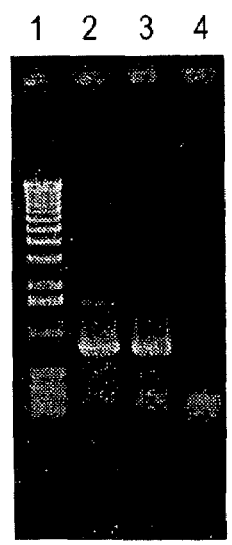
1: Marker
2: NGF / SeV / ΔF
3: NGF / SeV / ΔF-GFP
4: pSeV18⁺b(+)

1: LLCMK2 / Ad(moi=1)
2: LLCMK2 / F / Ad(moi=0)
3: LLCMK2 / F / Ad(moi=1)
4: LLCMK2 / F / Ad(moi=3)
5: LLCMK2 / F / Ad(moi=10)
6: LLCMK2 / F / Ad(moi=30)
7: LLCMK2 / F / Ad(moi=100)

1: LLC-MK2 / Ad-Cre(Negative Control)
2: LLC-MK2 / F / Ad-Cre / P0
3: LLC-MK2 / F / Ad-Cre / P1
4: LLC-MK2 / F / Ad-Cre / P2
5: LLC-MK2 / F / Ad-Cre / P3
6: LLC-MK2 / F / Ad-Cre / P4
7: LLC-MK2 / F / Ad-Cre / P5
8: LLC-MK2 / F / Ad-Cre / P6
9: LLC-MK2 / F / Ad-Cre / P7 y= 0.9157x + 0.3954
R² = 0.9835

FIG. 64
Temperature-Sensitivity (plaque assay)
SeV18+/ΔF-GFP
32 °C
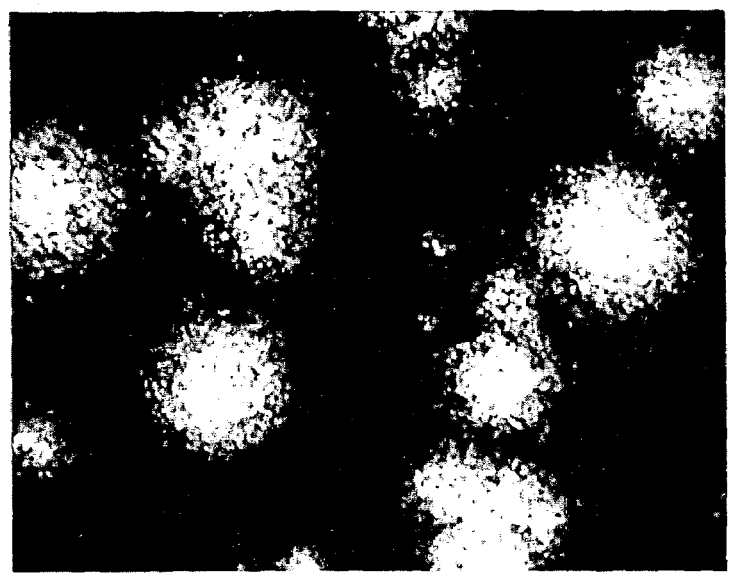
37 °C
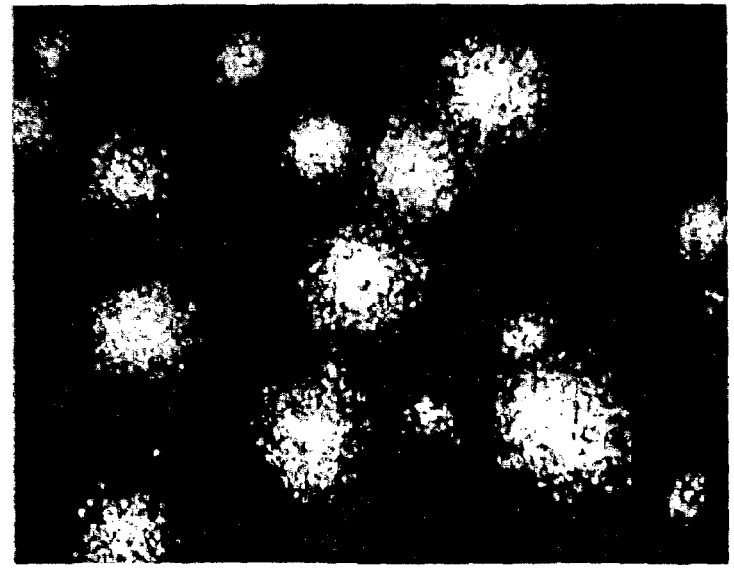

LLC-MK2/F6/A: F expression

FIG. 80
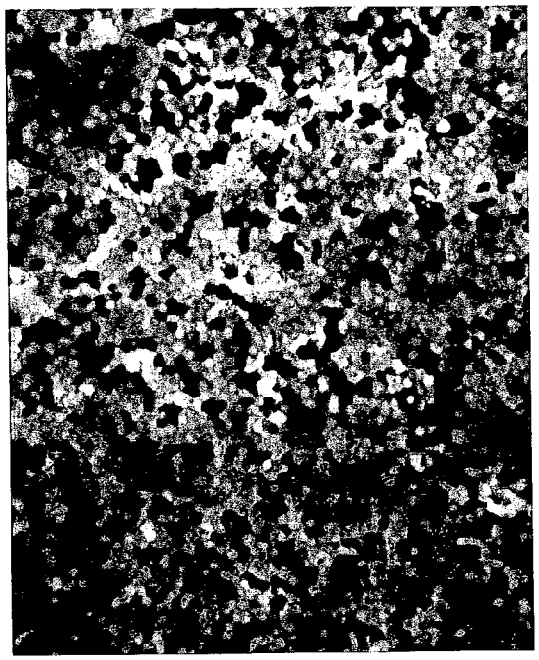
LLC-MK2
p.i. 5days
SeV18+/ΔF-GFP
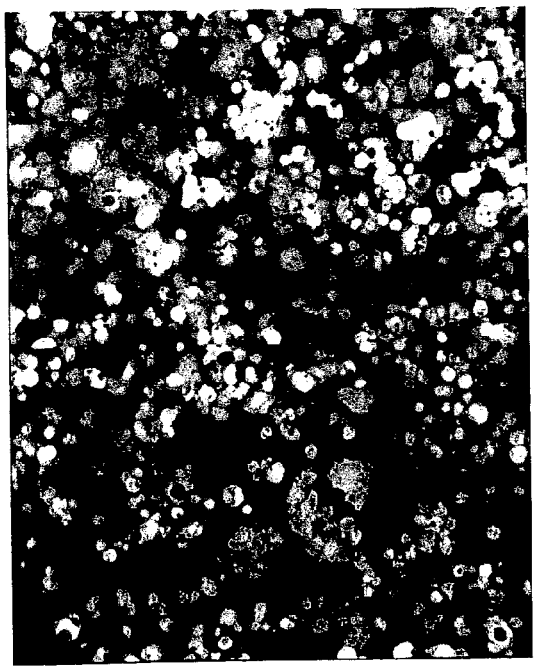
Cytotoxicity of SeV18+/ΔM-GFP
SeV18+/ΔM-GFP

FIG. 88
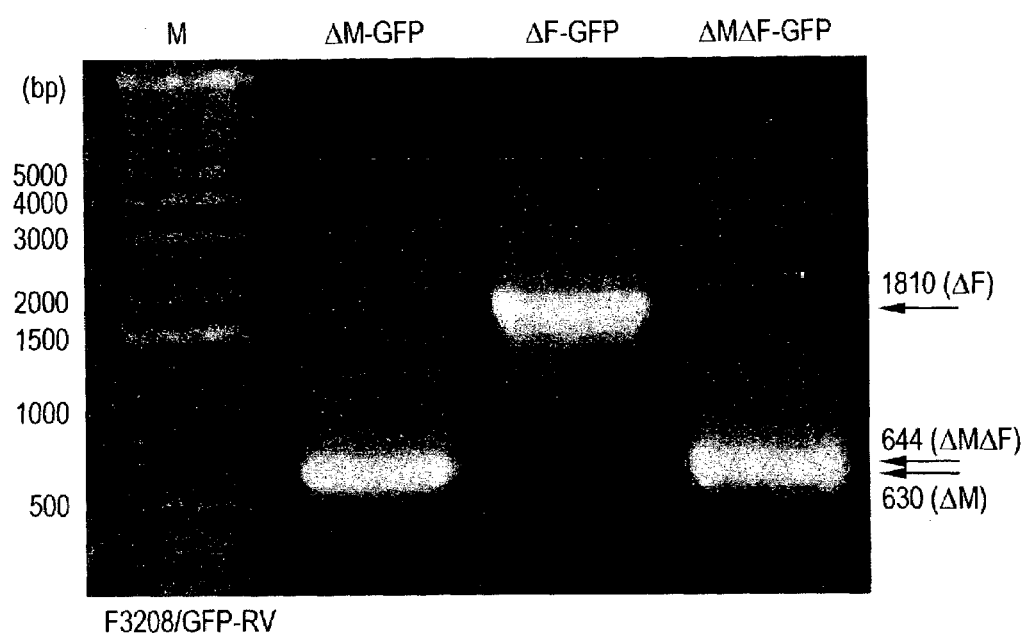
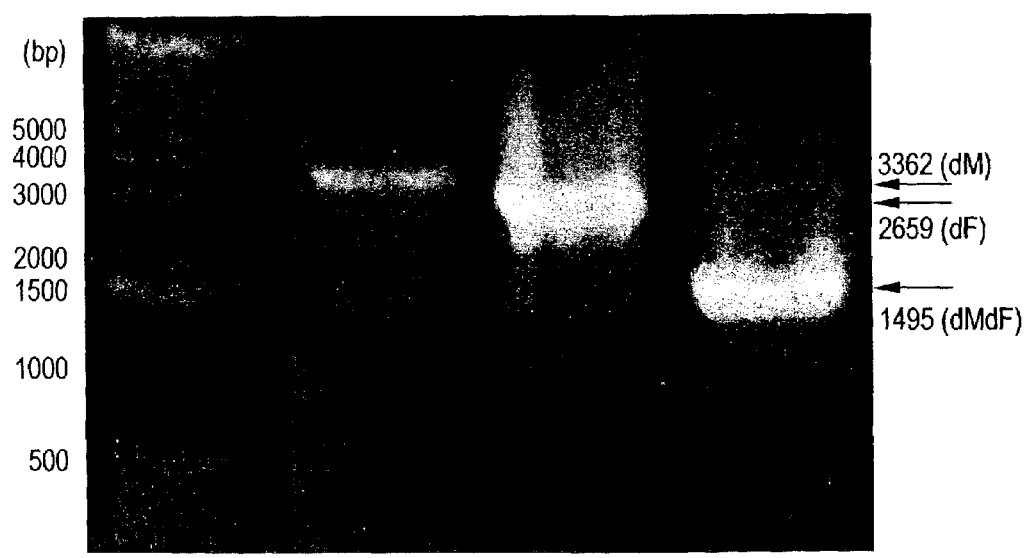

Western-blotting: 3 days post infection, LLC-MK2 cell lysate

Anti-SeV(NP)   Anti-M   Anti-F

1: No infection
2: SeV/GFP
3: SeV/ΔMΔF-GFP
4: SeV/ΔF-GFP
5: SeV/ΔM-GFP

FIG. 91
SeV/ΔF-GFP
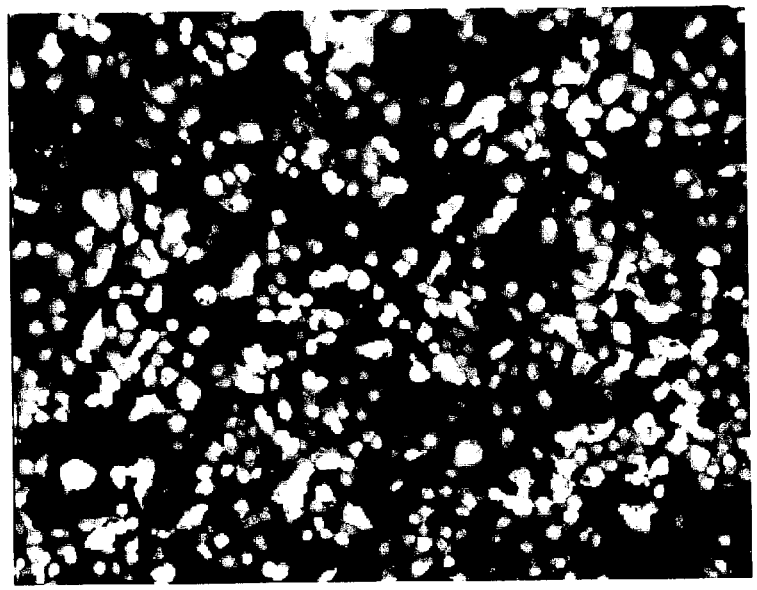
SeV/ΔMΔF-GFP

FIG. 93
SeV/ΔMΔF-GFP
SeV/ΔM-GFP
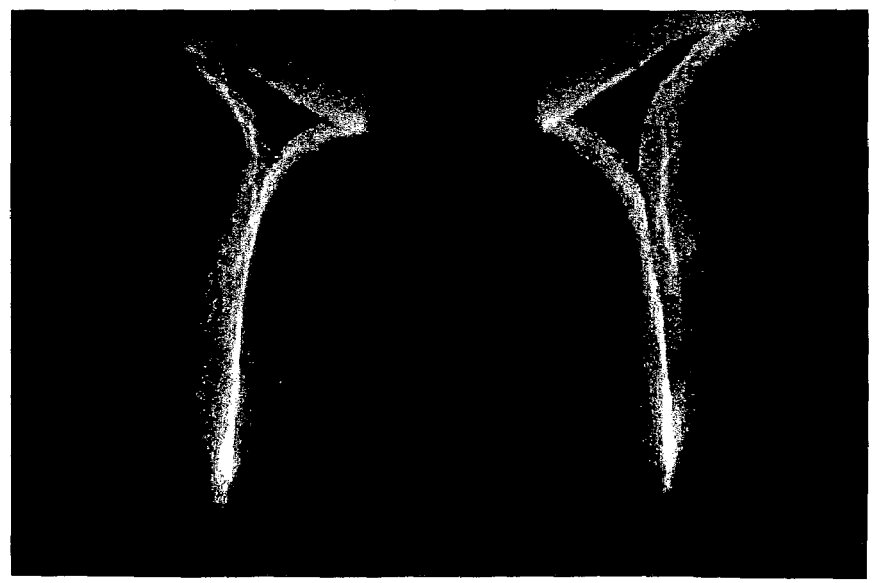

FIG. 94
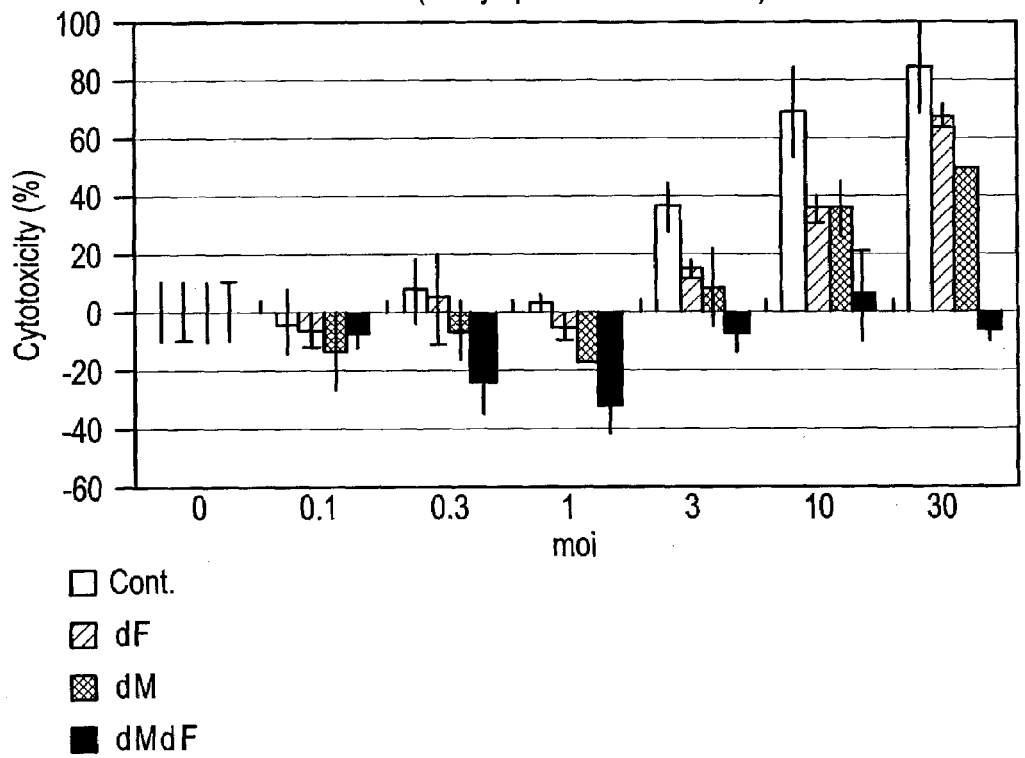
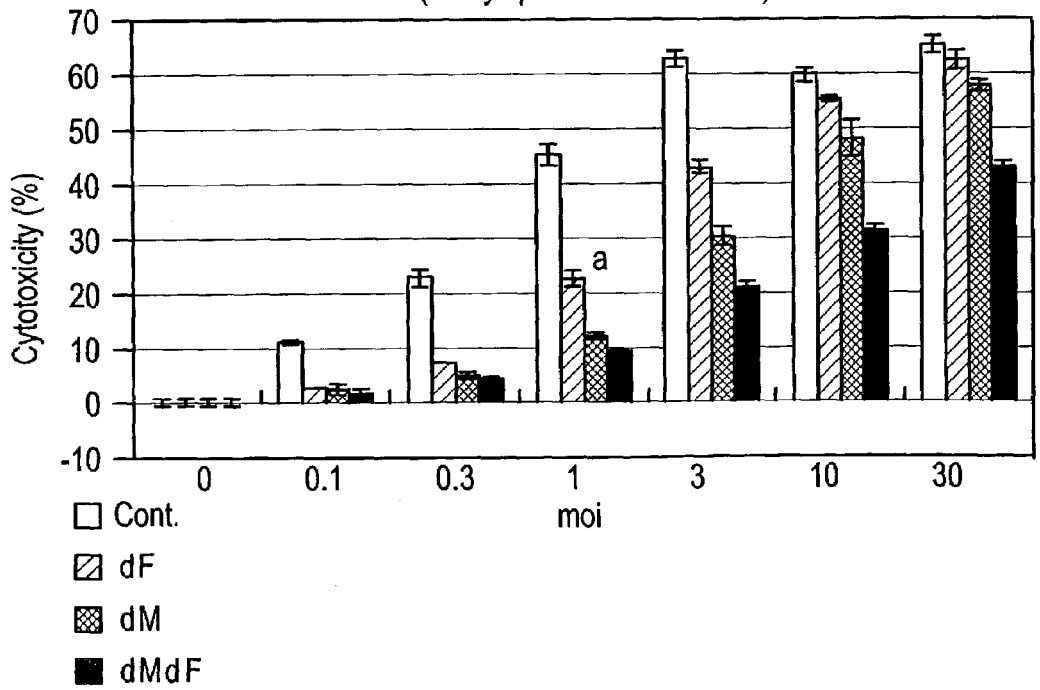

SEQUENCE LISTING

<160> NUMBER OF SEQ ID NOS: 68

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Sequence

<400> SEQUENCE: 1
atgcatgccg gcagatga                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 2
gttgagtact gcaagagc                                                        18

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 3
tttgccggca tgcatgtttc ccaaggggag agtttttgcaa cc                            42

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 4
atgcatgccg gcagatga                                                        18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 5
tgggtgaatg agagaatcag c                                                    21

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 6
atgcatatgg tgatgcggtt ttggcagtac                                           30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 7
tgccggctat tattacttgt acagctcgtc                                           30

```
<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 8
atcagagacc tgcgacaatg c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 9
aagtcgtgct gcttcatgtg g                                              21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 10
acaaccacta cctgagcacc cagtc                                          25

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 11
gcctaacaca tccagagatc g                                              21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 12
acattcatga gtcagctcgc                                                20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 13
atcagagacc tgcgacaatg c                                              21

<210> SEQ ID NO 14
```

```
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 14
aagtcgtgct gcttcatgtg g                                      21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 15
gaaaaactta gggataaagt ccc                                    23

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 16
gttatctccg ggatggtgc                                         19

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 17
gcgcggccgc cgtacggtgg caaccatgtc gtttactttg accaa            45

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 18
gcgcggccgc gatgaacttt caccctaagt ttttcttact acggcgtacg ctattacttc     60
tgacaccaga ccaactggta                                                 80

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 19
ccaccgacca cacccagcgg ccgcgacagc cacggcttcg g                 41
```

```
<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 20
ccgaagccgt ggctgtcgcg gccgctgggt gtggtcggtg g                    41

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 21
gaaatttcac ctaagcggcc gcaatggcag atatctatag                      40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 22
ctatagatat ctgccattgc ggccgcttag gtgaaatttc                      40

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 23
gggataaagt cccttgcggc cgcttggttg caaaactctc ccc                  43

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 24
ggggagagtt ttgcaaccaa gcggccgcaa gggactttat ccc                  43

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 25
ggtcgcgcgg tactttagcg gccgcctcaa acaagcacag atcatgg              47

<210> SEQ ID NO 26
```

```
<211> LENGTH: 47
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 26
ccatgatctg tgcttgtttg aggcggccgc taaagtaccg cgcgacc                    47

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 27
cctgcccatc catgacctag cggccgcttc ccattcaccc tggg                       44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 28
cccagggtga atgggaagcg gccgctaggt catggatggg cagg                       44

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 29
gcggcgcgcc atgctgctgc tgctgctgct gctgggcctg                            40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 30
gcggcgcgcc cttatcatgt ctgctcgaag cggccggccg                            40

<210> SEQ ID NO 31
<211> LENGTH: 74
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 31
gcggccgcgt ttaaacggcg cgccatttaa atccgtagta agaaaaactt agggtgaaag      60
ttcatcgcgg ccgc                                                        74
```

<210> SEQ ID NO 32
<211> LENGTH: 74
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 32
gcggccgcga tgaactttca ccctaagttt ttcttactac ggatttaaat ggcgcgccgt     60
ttaaacgcgg ccgc                                                      74

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 33
acttgcggcc gccaaagttc agtaatgtcc atgttgttct acactctg                 48

<210> SEQ ID NO 34
<211> LENGTH: 72
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 34
atccgcggcc gcgatgaact ttcaccctaa gtttttctta ctacggtcag cctcttcttg     60
tagccttcct gc                                                        72

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 35
ggagaagtct caacaccgtc cacccaagat aatcgatcag                          40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 36
ctgatcgatt atcttgggtg gacggtgttg agacttctcc                          40

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 37

```
gtatatgtgt cagttgagc ttgctgtcgg tctaaggc                              38
```

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 38

```
gccttagacc gacagcaagc tcaactgaac acatatac                             38
```

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 39

```
caatgaactc tctagagagg ctggagtcac taaagagtta cctgg                    45
```

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 40

```
ccaggtaact ctttagtgac tccagcctct ctagagagtt cattg                    45
```

<210> SEQ ID NO 41
<211> LENGTH: 52
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 41

```
gtgaaagttc atccaccgat cggctcactc gaggccacac ccaaccccac cg            52
```

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 42

```
cggtggggtt gggtgtggcc tcgagtgagc cgatcggtgg atgaactttc ac            52
```

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 43

```
cttagggtga aagaaatttc agctagcacg gcgcaatggc agatatc                  47
```

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence:
    artificially synthesized sequence

<400> SEQUENCE: 44
gatatctgcc attgcgccgt gctagctgaa atttctttca ccctaag          47

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence:
    artificially synthesized sequence

<400> SEQUENCE: 45
cttagggata aagtcccttg tgcgcgcttg gttgcaaaac tctcccc          47

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence:
    artificially synthesized sequence

<400> SEQUENCE: 46
ggggagagtt ttgcaaccaa gcgcgcacaa gggactttat ccctaag          47

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence:
    artificially synthesized sequence

<400> SEQUENCE: 47
ggtcgcgcgg tactttagtc gacacctcaa acaagcacag atcatgg          47

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence:
    artificially synthesized sequence

<400> SEQUENCE: 48
ccatgatctg tgcttgtttg aggtgtcgac taaagtaccg cgcgacc          47

<210> SEQ ID NO 49
<211> LENGTH: 49
<212> TYPE: DNA
<213> ORGANISM: Artificial Sequence
<220> FEATURE:
<223> OTHER INFORMATION: Description of Artificial Sequence:
    artificially synthesized sequence

<400> SEQUENCE: 49
cccagggtga atgggaaggg ccggccaggt catggatggg caggagtcc          49

```
<210> SEQ ID NO 50
<211> LENGTH: 49
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 50
ggactcctgc ccatccatga cctggccggc ccttcccatt caccctggg              49

<210> SEQ ID NO 51
<211> LENGTH: 72
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 51
ggccgcttaa ttaacggttt aaacgcgcgc caacagtgtt gataagaaaa acttagggtg  60
aaagttcatc ac                                                     72

<210> SEQ ID NO 52
<211> LENGTH: 72
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 52
ggccgtgatg aactttcacc ctaagttttt cttatcaaca ctgttggcgc gcgtttaaac  60
cgttaattaa gc                                                     72

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 53

Met Ala Asp Ile Tyr Arg Phe Pro Lys Phe Ser Tyr Glu
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 54

Leu Arg Thr Gly Pro Asp Lys Lys Ala Ile Pro His
 1               5                  10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence:
      artificially synthesized sequence
```

```
<400> SEQUENCE: 55

Asn Val Val Ala Lys Asn Ile Gly Arg Ile Arg Lys Leu
 1               5                  10

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 56
agagtcactg accaactaga tcgtgcacga ggcatcctac catcctca            48

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 57
tgaggatggt aggatgcctc gtgcacgatc tagttggtca gtgactct            48

<210> SEQ ID NO 58
<211> LENGTH: 55
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 58
tctcgagtcg ctcggtacga tgaaaaagcc tgaactcacc gcgacgtctg tcgag    55

<210> SEQ ID NO 59
<211> LENGTH: 83
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 59
aatgcatgat cagtaaatta caatgaacat cgaaccccag agtcccgcct attcctttgc    60
cctcggacga gtgctggggc gtc                                           83

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 60
ccaatctacc atcagcatca gc                                       22

<210> SEQ ID NO 61
<211> LENGTH: 21
<212> TYPE: DNA
<213> ORGANISM: Artificial Sequence
<220> FEATURE:
```

```
<223> OTHER INFORMATION: Description of Artificial Sequence:
      artificially synthesized sequence

<400> SEQUENCE: 61
ttcccttcat cgactatgac c                                             21

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 62
agagaacaag actaaggcta cc                                            22

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 63
ctttcaccct                                                          10

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 64
tttttcttac tacgg                                                    15

<210> SEQ ID NO 65
<211> LENGTH: 54
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 65
tctcgagtcg ctcggtacga tggccaagtt gaccagtgcc gttccggtgc tcac         54

<210> SEQ ID NO 66
<211> LENGTH: 85
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 66
aatgcatgat cagtaaatta caatgaacat cgaacccag agtcccgctc agtcctgctc    60
ctcggccacg aagtgcacgc agttg                                         85

<210> SEQ ID NO 67
<211> LENGTH: 24
<212> TYPE: DNA
<213> ORGANISM: Artificial Sequence
```

```
-continued

<220> FEATURE:
<223> OTHER INFORMATION: Description of Artificial Sequence:
      artificially synthesized sequence

<400> SEQUENCE: 67
cagatgaact tcagggtcag cttg                                              24

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 68
tgggtgaatg agagaatcag c                                                 21
```

ENVELOPE GENE-DEFICIENT PARAMYXOVIRUS VECTOR

CROSS-REFERENCE TO RELATED APPLICATIONS

This application is a continuation-in-part of U. S. patent application Ser. No. 09/966,277, filed Sep. 27, 2001 now abandoned, which claims benefit of Japanese application no. 2001/283451, filed Sep. 18, 2001, and is a continuation-in-part of International Application No. PCT/JP00/03195, filed May 18, 2000, which, in turn, claims benefit of Japanese application no. 11/200739, filed May 18, 1999, the disclosures of which are hereby incorporated by reference. The present application is also a continuation-in-part of PCT/JP02/09558, filed Sep. 18, 2002, which, in turn, claims benefit of Japanese application no. 2001/283451, filed Sep. 18, 2001, the disclosures of which are hereby incorporated by reference.

TECHNICAL FIELD

The present invention relates to an envelope gene-deficient viral vector of Paramyxoviridae.

BACKGROUND ART

In many clinical approaches of gene therapy until now, viral vectors from retroviruses, adenoviruses, and adeno-associated viruses have been used. These gene therapy vectors have limitations in gene introducing efficiency and persistent expression, and also have cell toxicity, and immunogenicity, which are crucial problems when it comes to the medical application of these vectors (Lamb, R. A. & Kolakofsky, D., Paramyxoviridae: the viruses and their replication in Fields Virology, 3rd edn, (Edited by B. N. Fields, D. M. Knipe & P. P. Howley) pp. 1177–1204 (Philadelphia, Lippincott-Raven (1996)). Novel vectors based on lentiviruses and HSV have been proposed as countermeasures, and extensive research is also being carried out to improve existing vectors. However, all of these vectors exist in the form of DNA within the nucleus throughout the life cycle. Therefore, it is difficult to fully overcome concerns of safety related to random interactions with the patient's chromosomes.

Recent rapid progress of reverse genetics technologies is making it possible to develop vectors based on RNA viruses, the development of which has been long delayed. Recombinant RNA virus vectors show high gene introduction efficiency and expression capability, and thus show a very high potentiality as vectors for gene therapy (Roberts, A. & Rose, J. K., Virology 247, 1–6 (1998); Rose, J., Proc. Natl. Acad. Sci. USA 94, 14998–15000 (1996); Palese, P. et al., Proc. Natl. Acad. Sci. USA 93, 11354–11358 (1996)). However, practically usable paramyxovirus vectors derived from deficient type genome of attenuated viruses have not been reported yet.

Paramyxovirus vectors having negative-strand RNA as the genome have several characteristics significantly different from retroviruses, DNA viruses or positive-strand RNA virus vectors. Genomes or antigenomes of negative-strand RNA viruses do not directly function as mRNA, so they cannot initiate the synthesis of viral proteins and genome replication. Both RNA genome and antigenome of these viruses always exist in the form of a ribonucleoprotein complex (RNP), so they hardly cause problems caused by antisense strands, such as interfering with the assembly of genome to RNP due to mRNA hybridizing with naked genomic RNA, as in the case of positive strand RNA viruses. These viruses comprise their own RNA polymerases, performing the transcription of viral mRNAs or replication of viral genomes using RNP complex as the template. Worthy of mentioning is that negative-strand RNA (nsRNA) viruses proliferate only in the cytoplasm of host cells, causing no integration thereof into chromosomes, because they do not go through a DNA phase. Furthermore, no homologous recombination among RNAs has been recognized. These properties are considered to contribute a great deal to the stability and safety of negative-strand RNA viruses as gene expressing vectors.

Among negative-strand RNA viruses, the present inventors have been focusing their attention on the Sendai virus (SeV). Sendai virus is a non-segmented type negative-strand RNA virus belonging to the genus Paramyxovirus, and is a type of murine parainfluenza virus. The virus attaches to the host cell membrane via envelope glycoproteins, the hemagglutinin-neuramimidase (HN) and fusion protein (F), causes membrane fusion, and efficiently releases its own RNA polymerase and the RNA genome, which exists as a ribonucleoprotein (RNP) complex, into the cytoplasm, and carries out mRNA transcription of the virus and genome replication at the site (Bitzer, M. et al., J. Virol. 71(7): 5481–5486, 1997). The viral envelope protein F is synthesized as an inactive precursor protein ($F_0$), then divided into F1 and F2 by proteolytic cleavage with trypsin-like protease such as triptase clara (Kido, H. et al., Biopolymers (Peptide Science) 51(1): 79–86, 1999), and thus becomes an active form protein to cause membrane fusion. This virus has been said to be non-pathogenic towards humans. However, wild-type SeV has been said highly cytopathic in cell culture (D. Garcin, G. Taylor, K. Tanebayashi, R. Compans and D. Kolakofsky, Virology 243, 340–353 (1998)). Therefore, we focused research on Z strain of SeV, an attenuated laboratory strain of Sendai virus, which has been isolated, and which only induces mild pneumonia in rodents, the natural hosts. This strain has been widely used as a research model for molecular level studies of the transcription-replication mechanism of paramyxoviruses and used for preparing hybridomas. In addition to the high safety mentioned above, the virus shows a high production titer of $10^{9-11}$ pfu/ml in cell lines or chicken eggs. In one recently successful recovery system of negative-strand RNA virus vector from cDNA, especially high reconstitution efficiency has been seen in the case of Sendai virus. The capability of recombinant wild type viruses introduced with exogenous genes, to efficiently and stably express introduced exogenous genes is gaining wide attention.

Thus, negative-strand RNA viruses have many advantages as gene introducing vectors. However, to apply for gene therapy, the development of highly safe vectors that do not release infectious particles when infected to cells is desired. For that purpose, a technique that mass produces viruses deficient in wild type virus production capability is necessary. However, development of an applicable vector based on an envelope gene-deficient genome has not yet been successful.

DISCLOSURE OF THE INVENTION

The aim of present invention is to provide a paramyxovirus vector deficient in an envelope gene.

To construct a paramyxovirus vector suitable for gene therapy, which completely lacks a propagation capability, the present inventors deleted F gene of SeV from the genome to establish a method to recover infectious virus particles in cells expressing F protein of Sendai virus, using cDNA in which GFP gene is introduced as a reporter. Through this F gene-deficient virus vector, a gene is introduced into rat neuronal cells in primary cultures, primitive mouse blood stem cells, human normal cells, and various other types of cells with a high efficiency, and a high expression was seen. Furthermore, high expression was obtained when administrated into rat brain in vivo. The F gene-deficient SeV vector expresses a gene relatively persistently and strongly in the infected cells without producing secondary infectious virus particles, and does not propagate within adjacent cells. Thus, the usefulness of the vector for gene therapy was suggested.

Furthermore, the present inventors produced a SeV vector cDNA deficient in both F gene and HN gene, to establish a method to recover infectious virus particles in a cell line expressing F protein and HN protein of Sendai virus. In addition, by introducing the SeV vector cDNA into F-expressing cells, the present inventors succeeded in constructing SeV vector deficient in the HN protein.

Thus, the present invention establishes an applicable novel envelope gene-deficient vector system based on a negative-strand RNA virus for the first time. The success in the recovery of infectious deficient virus particles from F gene-deficient, or FHN gene-deficient genomic cDNA using helper cells pave the way for research and development of novel vectors for gene therapy taking advantage of the remarkable characteristics of Sendai virus.

The deficient Sendai virus vector of the present invention has an extremely high gene-introducing efficiency towards various cell types and an enormous capability of expressing an exogenous gene. Furthermore, it expresses persistently in infected cells and does not release infectious virus particles, proving that it is a highly safe vector completely without virus-propagating capability.

From cells infected with F or HN gene-deficient Sendai virus vectors, non-infectious virus-like particles (VLPs, also called F-less virions or HN-less virions) are released (see Examples 7, FIG. 21, and Stricker, R. and Roux, L., J. Gen. Virol. 72: 1703–1707 (1991)). Because M protein plays central role in release of virus-like particles, virus vectors deficient in M gene lose their particle forming capability or have the capability extremely reduced, and can diffuse vectors to adjacent cells through cell fusion (WO00/09700; Mebatsion, T. et al., J. Virol. 73: 242–250 (1990); Cathomen, T. et al. EMBO J. 17: 3899–3908 (1998)). The present inventors have first established helper cells which are capable of expressing M protein stably. Using the helper cells stably expressing M proteins, the present inventors produced M gene-deficient Sendai virus vectors comprising M proteins as envelopes. Infectious M gene-deficient virus vectors are prepared in high titer (released from the producer cells into culturing medium at more than $10^7$ Cell Infectious Units (CIU)/ml), and it has been revealed from Western blot analysis and measurement of HA activity that few VLPs are released from cells infected with M gene-deficient virus vectors. Moreover, the present inventors constructed a Sendai virus cDNA deficient in both F gene and M gene and reconstituted vectors using helper cells expressing F and M proteins. In particular, virus vectors deficient in M gene in addition to F or HN gene are extremely useful as vectors for gene therapy because reinfection of virus from cells into which the vectors are introduced and cell damage and immunity induction due to secondary release are not induced. In fact, the present inventors have succeeded in producing infectious virus particles deficient in both M and F genes in the culture supernatant of virus producing cells at the titer of $10^8$ CIU/ml or more at the maximum for the first time. The virus thus obtained lost almost all the secondary virus particle forming capability. Furthermore, it was confirmed that cytotoxicity of the viral vector deficient in both M and F genes remarkably decreased compared to that of vectors deficient in either one of these two genes. This viral vector has been demonstrated to be capable of efficient gene transfer into nerve cells in vivo and in vitro and therefore would be used as a gene transfer vector having infectivity towards many types of cells including nondividing cells.

The stability of genome is pointed out as a problem when using RNA viruses. Heterologous gene expression by SeV vector showed hardly any base mutations after continual multiple passages, showing that it expresses the inserted heterologous gene stably for a long period (Yu, D. et al. Genes cells 2, 457–466 (1997)). Vectors based on negative-strand RNA virus replicons have several advantageous characteristics such as genome stability or flexibility of the size of the gene introduced or packaging, for they do not have the capsid structural protein, when compared to vectors based on replicons of Semliki forest virus, an already successful positive-strand RNA virus, or those of Sindbis virus. At least 4 kbp of exogenous DNA can be inserted into the wild type Sendai virus vector, and a much longer one can be inserted into the deficient vector. By inserting, between genes, a unit comprising a transcription initiation sequence, two or more kinds of genes can be expressed simultaneously. Persistent expression is expected in the vector based on replicon of Sendai virus since theoretically, except for human peripheral monocytes (F. Tropea et al., Exp. Cell. Res. 218(1), 63–70 (1995)), multicopied RNPs replicated in the cytoplasm are distributed into daughter cells when cell division occurs. Actually, this has been demonstrated in an in vitro study in a certain kind of blood cells. Furthermore, since the present inventors have confirmed that the Sendai virus vector is introduced with a high efficiency into blood cells, especially granulocytic cells, and also that it is introduced into c-kit positive cells, the vector is thought to be a very highly applicable vector with a very extensive tissue application range.

Thus, the present invention relates to envelope gene-deficient Sendai virus-vector, more specifically to:

(1) A paramyxovirus vector comprising a complex comprising (a) a paramyxovirus-derived negative-strand single-stranded RNA modified not to express at least one envelope protein of paramyxoviruses, and (b) proteins that bind to said negative-strand single-stranded RNA.

(2) The vector according to (1), wherein the negative-strand single-stranded RNA expresses NP protein, P protein, and L protein, and is modified not to express F, HN, or M protein, or any combination thereof.

(3) The vector according to (1), comprising at least one of the envelope proteins whose expression was suppressed in the modified negative-strand single-stranded RNA.

(4) A vector according to (1), comprising VSV-G protein.

(5) A vector according to (1), wherein the negative-strand single-stranded RNA is derived from Sendai virus.

(6) A vector according to (1), wherein the negative-strand single-stranded RNA further encodes an exogenous gene.

(7) A DNA encoding negative-strand single-stranded RNA comprised in a vector according to any one of (1) to (6), or the complementary strand thereof.

(8) A method for producing a vector according to (1), comprising the following steps of:
   (a) expressing vector DNA encoding a paramyxovirus-derived negative-strand single-stranded RNA modified not to express at least one envelope protein of paramyxoviruses, or the complementary strand, by introducing into cells expressing at least one envelope protein,
(b) culturing said cells, and, (c) recovering the virus particles from the culture supernatant.

(9) A method for producing a vector according to (1), comprising the steps of, (a) introducing, a complex comprising a paramyxovirus-derived negative-strand single-stranded RNA modified not to express at least one envelope protein of paramyxoviruses, and a protein binding to said negative-strand single-stranded RNA, into cells expressing at least one envelope protein, (b) culturing said cells, and, (c) recovering virus particles from the culture supernatant.

(10) The method according to (8) or (9), wherein the cell culture in (b) is a co-culture with cells expressing at least one envelope protein.

(11) The method according to (8) or (9), wherein cells expressing at least one envelope protein are overlaid to said cells in cell culture in (b).

(12) The method of (8) or (9), wherein the cell culture is carried out at 35° C. or less.

(13) A method according to (8) or (9), wherein at least one envelope protein expressed by the cells is identical to at least one envelope protein whose expression is suppressed in the negative-strand single-stranded RNA described above.

(14) A method according to (8) or (9), wherein at least one envelope protein expressed by the cells is VSV-G protein.

In the present invention, the term "vector" indicates virus particles in which nucleic acid molecules for expressing exogenous gene in hosts are packaged.

The term "recombinant" used herein means a compound or a composition generated by mediating a recombinant polynucleotide. A recombinant polynucleotide means a polynucleotide in which nucleotide residues are linked not naturally, namely, a polynucleotide in which nucleotide residues are not arranged in a manner found in nature. Herein, a "recombinant" paramyxovirus vector means a paramyxovirus vector constructed by genetic engineering or a paramyxovirus vector obtained by amplifying it. Recombinant paramyxovirus vectors can be generated, for example, by reconstituting recombinant paramyxovirus cDNAs.

"NP, P, M, F, HN and L genes" of viruses belonging to the family Paramyxoviridae refer to genes encoding nucleocapsid, phosphor matrix, fusion, hemagglutinin-neuramimidase and large proteins, respectively. Respective genes of viruses belonging to subfamilies of the family Paramyxoviridae are represented in general as follows. NP gene is generally described also as the "N gene".

| | | | | | | | |
|---|---|---|---|---|---|---|---|
| Genus Respirovirus | N | P/C/V | M | F | HN | — | L |
| Genus Rubulavirus | N | P/V | M | F | HN | (SH) | L |
| Genus Morbillivirus | N | P/C/V | M | F | H | — | L |

Database accession numbers for nucleotide sequences of genes of the Sendai virus classified into Respirovirus of the family Paramyxoviridae are, M29343, M30202, M30203, M30204, M51331, M55565, M69046 and X17218 for NP gene, M30202, M30203, M30204, M55565, M69046, X00583, X17007 and X17008 for P gene, D11446, K02742, M30202, M30203, M30204, M69046, U31956, X00584 and X53056 for M gene, D00152, D11446, D17334, D17335, M30202, M30203, M30204, M69046, X00152 and X02131 for F gene, D26475, M12397, M30202, M30203, M30204, M69046, X00586, X02808 and-X56131 for HN gene, and D00053, M30202, M30203, M30204, M69040, X00587 and X58886 for L gene.

Herein, the term "particle forming capability" refers to the capability of a viral vector to release infectious or noninfectious virus particles (called virus-like particles) in cells infected with said viral vector (referred to as the secondary release). Herein, that "particle forming capability is reduced or suppressed" means that particle forming capability is significantly reduced. In addition, the reduction of particle forming capability includes the complete elimination of particle forming capability.

The reduction of particle forming capability refers to, for example, a statistically significant reduction thereof (e.g. level of significance: 5% or less). Statistical examination can be performed, for example, by Student's t-test, Mann-Whitney's U-test or the like. The level of particle forming capability decreases to ½ or less, more preferably ⅕, ⅒, 1/30, 1/50, 1/100, 1/300 and 1/500 or less of the wild type virus.

The elimination of particle forming capability means that the level of VLP is below the detection limits. In such cases, VLP is $10^3$/ml or less, preferably $10^2$/ml or less, more preferably $10^1$/ml or less. The elimination of particle forming capability can be determined by means of a functional assay. For example, its elimination can be confirmed when no detectable infectivity is observed in cells transfected with a sample that may contain VLP. Moreover, virus particles can be identified with a direct observation tool such as an electron microscope, or detected and quantified from nucleic acid or protein contained in virus as an indicator. For example, genomic nucleic acid contained in virus particles may be detected and quantified by the usual method for detecting nucleic acid such as PCR. Alternatively, virus particles having a foreign gene can be quantified by transfecting cells with them and detecting the expression of said gene in the cells. Noninfectious virus particles (e.g. VLP) can be quantified by introducing these particles into cells in combination with a transfection reagent and detecting the expression of the foreign gene. The transfection can be carried out, for example, by using lipofection reagents. The following is an example of the transfection using DOSPER Liposomal Transfection Reagent (Roche, Basel, Switzerland; Cat No. 1811169). DOSPER (12.5 μl) is mixed with 100 μl of a solution with or without VLP, and the mixture is allowed to stand still at room temperature for 10 minutes. The mixed solution is used to transfect cells which have been cultured to be confluent on a 6-well plate with shaking every 15 minutes. After 2 days, the presence or absence of VLP can be determined by detecting the presence or absence of infected cells. Infective viruses can be quantified by normal CIU assay or hemagglutination activity (HA) assay (Kato, A. et al., 1996, Genes Cells 1: 569–579; Yonemitsu, Y. & Kaneda, Y., Hemaggulutinating virus of Japan-liposome-mediated gene delivery to vascular cells. Ed. by Baker A H. Molecular Biology of Vascular Diseases. Method in Molecular Medicine: Humana Press: pp. 295–306, 1999).

The term "gene" used herein means a genetic substance, which includes nucleic acids such as RNA, DNA, etc. In general, a gene may or may not encode a protein. For example, a gene may be that encoding a functional RNA such as ribozyme, antisense RNA, etc. A gene may have a naturally derived or artificially designed sequence. In addition, herein, a "DNA" includes a single-stranded DNA and a double-stranded DNA.

The present invention relates to envelope gene-deficient paramyxovirus vectors. The virus vector comprises paramyxovirus-derived negative-strand single-stranded RNA modified not to express at least one envelope protein. Paramyxovirus generally comprises a complex of RNA and protein (ribonucleoprotein; RNP) in the envelope. The RNA comprised in RNP is negative-strand (negative-strand) single-stranded RNA, which is the genome of paramyxovirus. The protein binds to the RNA to form the complex. Namely, a paramyxovirus vector according to this invention comprises a complex comprising (a) a paramyxovirus-derived negative-strand single-stranded RNA modified so as not to express at least one of the envelope proteins of paramyxoviruses and (b) proteins binding to said negative-strand single-stranded RNA. Proteins binding to a negative-strand single-stranded RNA refer to proteins binding directly and/or indirectly to the negative-strand single-stranded RNA to form an RNP complex with the negative-strand single-stranded RNA. In general, negative-strand single-stranded RNA (genomic RNA) of paramyxovirus is bound to NP, P and L proteins. RNA contained in this RNP serves as the template for transcription and replication of RNA (Lamb, R. A., and D. Kolakofsky, 1996, Paramyxoviridae: The viruses and their replication, pp. 1177–1204. In Fields Virology, $3^{rd}$ edn. Fields, B. N., D. M. Knipe, and P. M. Howley et al. (ed.), Raven Press, New York, N.Y.). Complexes of this invention include those comprising negative-strand single-stranded RNAs originating in paramyxovirus and proteins also originating in paramyxovirus which bind to the RNAs. Vectors of this invention comprise RNP comprising, for example, negative-strand single-stranded RNA of paramyxoviruses to which these proteins (NP, P and L proteins) are bound. In general, RNP complexes of paramyxovirus are capable of autonomously self-replicating in host cells. Thus, vectors transferred to cells intracellularly proliferate RNP to increase the copy number of the gene (RNA contained in complex), thereby leading to a high level expression of a foreign gene from RNP carrying the foreign gene. Vectors of this invention are preferably those capable of replicating RNA contained in complexes (RNP) in transfected cells. Herein, paramyxovirus means a virus belonging to the family Paramyxoviridae or a derivative thereof. In addition to the Sendai virus, the Paramyxoviridae virus for which the present invention can be applied is, for instance, measles virus, simian parainfluenza virus (SV5), and human parainfluenza virus 3, but is not limited to thereto. Other examples of paramyxoviruses include Newcastle disease virus, Mumps virus, Respiratory syncytial (RS) virus, rinderpest virus, distemper virus, human parainfluenza virus type 1 and 2, etc. The paramyxovirus of the present invention is preferably a virus belonging to the genus *Paramyxovirus* or a derivative thereof. Examples of viruses of the genus *Paramyxovirus* to which the present invention can be applied include human parainfluenza virus type 1 (HPIV-1), human parainfluenza virus type 3 (HPIV-3), bovine parainfluenza virus type 3 (BPIV-3), Sendai virus (also called mouse parainfluenza virus type 1), simian parainfluenza virus type 10 (SPIV-10), etc. The paramyxovirus of the present invention is most preferably Sendai virus. These viruses may be derived from natural strains, wild-type strains, mutant strains, laboratory-passaged strains, artificially constructed strains, etc. Incomplete viruses such as the DI particle (J. Virol. 68, 8413–8417 (1994)), synthesized oligonucleotides, and so on, can also be utilized as material for producing the virus vector of the present invention.

The paramyxovirus vector of the present invention is a particle separated from cells and a particle having infectivity and not having disseminative capability. The term "infectivity" used herein means capability of a vector to transfer a gene contained in the vector, to a cell by adhering to the cell. The term "not having disseminative capability" means that particles having infectivity are not released from cells infected with the virus vector.

Negative-strand single-stranded RNAs contained in viral vectors are modified, typically, so as to express NP, P and L proteins and so as not to express F, HN, or M protein, or any combination thereof. Preferably, the negative-strand single-stranded RNAs contained in the viral vectors of the present invention are modified so as not to express at least F and/or HN proteins. The present invention particularly relates to a viral vector having a negative-strand single-stranded RNA that has been modified so as not to express two or more proteins selected from F, HN, and M proteins. More specifically, this invention provides a viral vector having a negative-strand single-stranded RNA that has been modified so as not to express at least F and HN proteins, F and M proteins, or M and HN proteins. A viral vector that does not express F protein has the advantage of having no cytotoxicity such as syncytium formation. A viral vector that does not express HN protein has the advantage of not causing hemagglutination. A viral vector that does not express M protein has the advantage of not releasing VLP. Viral vectors prepared by deleting any combination of genes encoding these viral proteins have the combination of the respective advantages.

Furthermore, the present invention provides a method for attenuating cytotoxicity caused by gene transfer, the method comprising the step of transfecting cells with a viral vector deficient in genes encoding the envelope proteins (for example, F, HN or M gene, or combinations thereof) described herein. The present invention also provides a method for suppressing release of virus-like particles (VLPs) from cells transfected with a viral vector upon gene transfer, the method comprises the step of transfecting cells with the above-described viral vector. Cytotoxicity can be measured, for example, by quantifying the level of LDH release as described in Examples. Release of virus-like particles (VLPS) can be detected, for example, by measuring HA activity as described in Examples. Alternatively, VLP contained in the extracellular fluid of the transfected cells can be quantified by collecting the extracellular fluid, transfecting other cells with the fluid and measuring the expression level of the gene contained in VLP. It is preferable that cytotoxicity is attenuated and VLP release is suppressed to, for example, a statistically significant level (e.g. the significance level of 0.5% or less) compared to a viral vector without the above-described gene deletion. Statistical examination can be performed, for example, by Student's t-test, Mann-Whitney's U-test, etc. The cytotoxicity is attenuated and VLP release is suppressed to 90% or less, preferably to 80% or less, more preferably to 70% or less, still more preferably 60% or less, still further preferably to ½ or less, ⅓ or less, ⅕ or less or ⅛ or less, compared to the wild-type virus.

The term "not expressing a protein" used herein includes a case where the protein is substantially not expressed. A protein is not expressed from the genomic RNA in a virus vector by making a gene encoding the protein deficient. "Deficiency" of a gene means that any functional gene product (which is a protein if the gene encodes the protein)

of the gene is substantially not expressed. The deficiency of a gene of interest includes a case where null phenotype is indicated for the gene. The deficiency of a gene includes that the gene is deleted; that the gene is not transcribed due to mutation of a transcription initiation sequence and so on; that no functional protein is produced due to frameshift, codon mutation, or the like; that activity of the expressed protein is substantially lost [or decreased very much (for example, 1/10 or less)] due to amino acid mutation and so on; that translation into a protein does not occur [or is decreased very much (for example, 1/10 or less)]; and so on.

In the case of Sendai virus (SeV), the genome of the natural virus is approximately 15,000 nucleotides in size, and the negative-strand comprises six genes encoding NP (nucleocapsid), P (phospho), M (matrix), F (fusion), HN (hemagglutinin-neuramimidase) and L (large) proteins lined in a row following the 3'-short leader region, and a short 5'-trailer region on the other end. In this invention, this genome can be modified so as not to express envelope proteins and/or matrix proteins by designing a genome deficient in any of F, HN and M genes, or any combination thereof. Deficiency in either F gene or HN gene, or both is preferred. In addition, it is preferable that M gene is deficient. Since these proteins are unnecessary for the formation of RNP, RNPs which are components of the vectors of this invention can be manufactured by transcribing this genomic RNA (either positive or negative-strand) in the presence of NP, P and L proteins. RNP formation can be performed, for example, in LLC-MK2 cells, or the like. NP, P and L proteins can be supplied by introducing to cells expression vectors carrying the respective genes for these proteins (cf. Examples). Each gene may be also incorporated into chromosomes of host cells. NP, P and L genes to be expressed for the formation of RNP need not be completely identical to those genes encoded in the genome of the vector. That is, amino acid sequences of proteins encoded by these genes may not be identical to those of proteins encoded by RNP genome, as long as they can bind to the genomic RNA and are capable of replicating RNP in cells, and these genes may be induced with mutations or replaced with homologous genes from other viruses. Once an RNP is formed, NP, P and L genes are expressed from this RNP to autonomously replicate RNP in the cells and produce viral vectors in the presence of envelope proteins. In addition, the virus gene arrangement on the genome of the paramyxovirus of the present invention may be modified from that on the wild-type or mutant virus genome. For example, the short leader region of rSeV$^{GP42}$ (D. Garcin et al, Virology, 243, 340–353 (1998)) could be replaced with its counterpart genome sequence of SeV.

If an envelope protein is expressed in cells when a vector is reconstituted, this envelope protein will be incorporated into the vector, enabling the production of viral vectors with infectivity due to the envelope protein. Such a vector, once infected to cells, cannot produce viruses comprising an envelope protein as the initial virus can, because it does not have the envelope gene, though it can propagate RNP within the cells. Such a vector is very useful in fields such as gene therapy where exceptionally high safety is required.

Viral vectors with equivalent infection capability as the wild type virus can be produced by expressing the envelope proteins whose expression is suppressed in modified negative-strand single-stranded RNA, namely envelope genes deficient in the genome, at the time of virus reconstitution. Expressing a portion of envelope genes deficient in the genome is also conceivable. For example, when F protein alone is expressed against the genome deficient in both F and HN gene, a virus vector with F protein as envelope is produced. The virus with only F protein, but without HN protein, can be used as a vector that infects specifically to hepatocytes, mediated by asialoglycoprotein receptor (ASG-R). Thus, paramyxovirus vectors comprising at least one envelope protein whose expression is suppressed in modified negative-strand single-stranded RNA are included in the present invention.

In addition, it is also possible to reconstitute the vector of the present invention by using envelope proteins other than the above-described proteins whose expression was suppressed by modifying negative-strand single-stranded RNA. For example, virus vectors having desired envelope proteins other than those encoded by the genome of the virus which is the base of the vectors can be produced by expressing the envelope proteins in cells when the virus is reconstituted. There is no particular limitation on the type of such envelope proteins. One example of other viral envelope proteins is the G protein (VSV-G) of vesicular stomatitis virus (VSV). The paramyxovirus vector of the present invention includes pseudo-type viral vectors comprising envelope protein derived from a virus different to the virus from which the genome is derived, such as VSV-G protein, and the like.

Viral vectors of this invention can be usually prepared by (a) introducing a vector DNA encoding paramyxovirus-derived negative-strand single-stranded RNA that has been modified so as not to express at least one of the viral envelope proteins of paramyxoviruses, or a complementary strand of said RNA, into cells (helper cells) expressing one or more envelope proteins, and allowing the vector DNA to be expressed, and (b) culturing the cells to recover viral particles from the culture supernatant. By coexpressing NP, P and L proteins at the time of vector DNA expression, RNPs are formed and a virus having envelope proteins is constructed. Envelope proteins expressed in cells may be constitutively or, at the time of viral reconstitution, inducibly expressed in the cells.

By culturing the cells at low temperature in the step (b), the efficiency of virus vector production can be significantly increased. Therefore, it is preferable that the cells are cultured in the step (b) at low temperature, namely 35° C. or less, more preferably 34° C. or less, even more preferably 33° C. or less, and most preferably 32° C. or less.

Vector DNA to be expressed in helper cells encodes negative-strand single-stranded RNA contained in vectors of this invention (negative-strand) or complementary strand thereof (positive-strand). For example, DNA encoding negative-strand single-stranded RNA or complementary strand thereof is linked downstream of T7 promoter to be transcribed to RNA by T7 RNA polymerase. Desired promoters can be used except those including the recognition sequence of T7 polymerase. Alternatively, RNA transcribed in vitro may be transfected into helper cells. Vector DNAs may be cloned into plasmids to amplify in E. coli. Although the strand to be transcribed inside cells may be either positive or negative-strand, it is well known that virus reconstitution efficiency is preferably improved by arranging so as to transcribe the positive strand (A. Kato, Y. Sakai, T. Shioda, T. Kondo, M. Nakanishi, Y. Nagai, Genes to Cells, 1, 569–579 (1996))).

As helper cells, cells expressing envelope protein are used. As described above, helper cells are not limited to cells expressing all proteins of envelope genes deficient in the virus vector, for instance, for F, HN gene-deficient Sendai virus vector DNA, cells expressing F protein alone can be used as helper cells. In addition, cells expressing envelope protein different to the protein encoded by the envelope gene deficient in the virus vector may also be used. For example, as described above, an envelope protein that is not the envelope protein of paramyxovirus such as VSV-G protein can also be used as an envelope protein.

Helper cells that express the envelope proteins can be obtained by transfecting cells with an expression vector carrying the genes encoding these proteins and selecting the cells into which the genes have been stably incorporated. It is preferable that the envelope proteins can be expressed by way of induction. Examples of the cell include, for example, simian kidney-derived cell line LLC-MK2. The high level expression of the envelope proteins in helper cells is important for harvesting the virus with a high titer. For that purpose, it is preferable to perform, for example, the above-described transfection and cell selection at least twice or more. For example, cells are transfected with an envelope protein expression plasmid carrying a drug-resistance marker gene and the cells into which the envelope protein gene has been introduced are selected using the drug. Then, the selected cells are transfected with an envelope protein expression plasmid carrying a different drug-resistance marker gene and the second selection is made using this different drug resistance marker. This selection method enables to select cells capable of expressing the envelope protein at a higher level than those selected by the first transfection. Such envelope protein expressing helper cells which have been constructed via twice or more transfections can be preferably used. Such twice or more transfections are important for preparation of helper cells expressing M protein in particular. Furthermore, helper cells simultaneously expressing two or more envelope proteins, for example, M and F proteins are preferably prepared by twice or more transfections of cells with not only the M protein expression plasmid but also the F protein expression plasmid so as to enhance the induction level of F protein expression.

The helper cells thus obtained can be used to reconstitute the vector according to the present invention. For example, a viral vector can be reconstituted by transfecting a plasmid expressing a recombinant Sendai virus vector genome deficient in one or more envelope genes into host cells together with a vector expressing one or more envelope proteins, and NP, P and L protein expression vectors. Alternatively, RNP complex can be manufactured using, for example, host cells incorporated with F gene into chromosomes thereof. Amino acid sequences of these proteins supplied from outside the viral genome need not be identical to those deriving from the virus. As long as these proteins are equally active to or more active than natural type proteins in the ability of transferring nucleic acids into cells, genes encoding these proteins may be modified by inserting some mutations or replacing with homologous genes from other viruses. Since, in general, many envelope proteins, solely or in combination, show cytotoxicity (C. M. Horvath et al., J. Virology, 66, 4564–4569 (1992); X. Hu et al., J. Virology, 66, 1528–1534 (1992); R. Lamb, Virology, 197, 1–11 (1993); A. Moscona and R. W. Peluso, J. Virology, 65, 2773–2777 (1991)), and therefore, they may be arranged to be expressed only when the vector is reconstituted under the control of an inducible promoter or the expression can be induced at the time of reconstitution using other mechanism that can regulate the expression (cf. Examples).

Once RNP or virus comprising RNP is formed, virus vectors of this invention can be amplified by introducing this RNP or virus again into the aforementioned helper cells and culturing them. This process comprises the steps of (a) introducing a complex comprising negative-strand single-stranded RNA derived from paramyxovirus modified not to express at least one envelope protein of paramyxoviruses, and proteins that binds to said negative-strand single-stranded RNA to cells expressing envelope proteins, and (b) culturing the cells and recovering virus particles from the culture supernatant.

RNP may be introduced to cells as a complex formed together with, for example, lipofectamine and a polycationic liposome. Specifically, a variety of transfection reagents can be utilized. Examples thereof are DOTMA (Boehringer), Superfect (QIAGEN #301305), DOTAP, DOPE, DOSPER (Boehringer #1811169), etc. Chloroquine may be added to prevent RNP from decomposition in endosomes (Calos, M. P., 1983, Proc. Natl. Acad. Sci. USA 80: 3015).

Once a viral vector is thus constructed in host cells, it can be further amplified by coculturing these cells with cells expressing envelope proteins. As described in Example 12, a preferable example is the method of overlaying cells expressing envelope proteins over virus producing cells.

As an envelope protein, besides a viral envelope protein, for example, a chimeric protein comprising, in its extracellular region, a polypeptide derived from an adhesion molecule, ligand, receptor protein, and such that can adhere to specific cells, and in its intracellular region, polypeptides derived from virus envelope can be used. Hereby, vectors targeted to specific tissues can be produced. Viral vectors of this invention, for example, may comprise a viral gene contained in the vector that has been modified to reduce the antigenicity or enhance the RNA transcription and replication efficiency. Specifically, for example, as for paramyxovirus, it is possible to modify at least one of the NP, P/C, and L genes, which are genes of replication factors, to enhance the function of transcription or replication. In addition, the HN protein is a structural protein having both hemagglutinin activity and neuramimidase activity, and it is possible to enhance the virus stability in blood, for example, by weakening the former activity and to regulate infectivity, for example, by altering the latter activity. It is also possible to regulate the fusion ability by altering the F protein, which is implicated in membrane fusion. Furthermore, it is possible to generate a virus vector that is engineered to have weak antigenicity against these proteins through analyzing the antigen presenting epitopes and such of possible antigenic molecules on the cell surface such as the F protein and HN protein.

In addition, paramyxovirus whose accessory gene is deficient can be used as the paramyxovirus of the present invention. For example, by knocking out V gene, one of the accessory genes of SeV, pathogenicity of SeV to hosts such as mice markedly decreases without damages to the expression and replication of genes in cultured cells (Kato, A. et al., 1997, J. Virol. 71: 7266–7272; Kato, A. et al., 1997). Such attenuated vectors are particularly preferable as virus vectors for in vivo or ex vivo gene transfer.

Viral vectors of this invention may include RNA encoding a foreign gene in their negative-strand single-stranded RNA. Any gene desired to be expressed in target cells may be used as the foreign gene. For example, when gene therapy is intended, a gene for treating an objective disease is inserted into the viral vector DNA. In the case where a foreign gene is inserted into the viral vector DNA, for example, Sendai viral vector DNA, it is preferable, to insert a sequence comprising a nucleotide number of a multiple of six between the transcription termination sequence (E) and transcription initiation sequence (S), etc. (Calain, P. and Roux, L., Journal of Virology, Vol. 67, No. 8, 1993, p. 4822–4830). Foreign gene may be inserted before or after each of the virus genes (NP, P, M, F, HN and L genes) (cf. Examples). E-I-S sequence (transcription termination sequence-intervening sequence-transcription initiation sequence) or portion thereof is appropriately inserted before or after a foreign gene and a unit of E-I-S sequence is located between each gene so as not to interfere with the expression of genes before or after the foreign gene. Expression level of the inserted foreign gene can be regulated by the type of transcription initiation sequence added upstream of the foreign gene, as well as the site of gene insertion and nucleotide sequences before and after the gene. For example, in Sendai virus, the nearer the insertion site is to the 3'-end of negative-strand RNA (in the gene arrangement on the wild type viral genome, the nearer to NP gene), the higher the expression level of the inserted gene is. To secure a high expression level of a foreign gene, it is preferable to insert the foreign gene into upstream region, namely at the 3'-side in negative-strand genome such as upstream of NP gene (the 3'-side in negative-strand) or between NP and P genes. Conversely, the nearer the insertion position is to the 5'-end of negative-strand RNA (in the gene arrangement on the wild type viral genome, the nearer to L gene), the lower the expression level of the inserted gene is. To suppress the expression of a foreign gene to a low level, the foreign gene is inserted, for example, to the far most 5'-side of the negative-strand, that is, downstream of L gene in the wild type viral genome (the 5'-side adjacent to L gene in negative-strand) or upstream of L gene (the 3'-side adjacent to L gene in negative-strand) Thus, the insertion position of a foreign gene can be properly adjusted so as to obtain a desired expression level of the gene or so as to optimize the combination of it and the virus protein-encoding genes before and after it. For instance, if the overexpression of a gene introduced by inoculating a high titer virus vector may cause toxicity, it is possible not only to limit the titer of the virus to be inoculated, but also to reduce the expression level from individual virus vectors, for example, by designing the insertion position on the vector as closely to the 5'-terminus of the negative-strand as possible, or replacing the transcription initiation sequence with one having lower efficiency so as to obtain an appropriate therapeutic effect.

Because, in general, it is advantageous to obtain high expression of an foreign gene as long as cytotoxicity is not raised, it is preferable to ligate the foreign gene with a highly efficient transcription initiation sequence and to insert the gene into the vicinity of the 3'-terminus of the negative-strand genome. Examples of preferable vectors include a vector in which the foreign gene is located at the 3'-side of any virus protein-genes of paramyxovirus in the negative-strand genome of paramyxovirus vector. For example, a vector in which the foreign gene is inserted upstream (at the 3'-side of the negative-strand) of N gene is preferable. Alternatively, the foreign gene may be inserted immediately downstream of N gene.

To facilitate the insertion of a foreign gene, a cloning site may be designed at the inserting position in the vector DNA encoding the genome. The cloning site can be arranged to be, for example, the recognition sequence for restriction enzymes. Foreign gene fragments can be inserted into the restriction enzyme site in the vector DNA encoding the genome. Cloning site may be arranged to be a so-called multi-cloning site comprising a plurality of restriction enzyme recognition sequences. Vectors of this invention may harbor other foreign genes at the sites other than those described above.

Recombinant Sendai virus vectors comprising a foreign gene can be constructed as follows according to, for example, the description in "Hasan, M. K. et al., J. Gen. Virol. 78: 2813–2820, 1997", "Kato, A. et al., 1997, EMBO J. 16: 578–587" and "Yu, D. et al., 1997, Genes Cells 2: 457–466".

First, a DNA sample comprising the cDNA nucleotide sequence of a desired foreign gene is prepared. It is preferable that the DNA sample can be electrophoretically identified as a single plasmid at concentrations of 25 ng/µl or more. Below, a case where a foreign gene is inserted to DNA encoding viral genome utilizing NotI site will be described as an example. When NotI recognition site is included in the objective cDNA nucleotide sequence, it is preferable to delete the NotI site beforehand by modifying the nucleotide sequence using site-specific mutagenesis and such method so as not to alter the amino acid sequence encoded by the cDNA. From this DNA sample, the desired gene fragment is amplified and recovered by PCR. To have NotI sites on the both ends of amplified DNA fragment and further add a copy of transcription termination sequence (E), intervening sequence (I) and transcription initiation sequence (S) (EIS sequence) of Sendai virus to one end, a forward side synthetic DNA sequence (sense strand) and reverse side synthetic DNA sequence (antisense strand) are prepared as a pair of primers containing NotI restriction enzyme cleavage site sequence, transcription termination sequence (E), intervening sequence (I), transcription initiation sequence (S) and a partial sequence of the objective gene.

For example, to secure cleavage by NotI, the forward side synthetic DNA sequence is arranged in a form in which any two or more nucleotides (preferably 4 nucleotides excluding GCG and GCC, sequences originating in NotI recognition site, more preferably ACTT) are selected on the 5'-side of the synthetic DNA, NotI recognition site "gcggccgc" is added to its 3'-side, and to the 3'-side thereof, any desired 9 nucleotides or nucleotides of 9 plus a multiple of 6 nucleotides are added as the spacer sequence, and to the 3'-side thereof, about 25 nucleotide-equivalent ORF including the initiation codon ATG of the desired cDNA is added. It is preferable to select about 25 nucleotides from the desired cDNA as the forward side synthetic DNA sequence so as to have G or C as the final nucleotide on its 3'-end.

In the reverse side synthetic DNA sequence, any two or more nucleotides (preferably 4 nucleotides excluding GCG and GCC, sequences originating in the NotI recognition site, more preferably ACTT) are selected from the 5'-side of the synthetic DNA, NotI recognition site "gcggccgc" is added to its 3'-side, and to its further 3'-side, an oligo DNA is added as the insertion fragment to adjust the length. This oligo DNA is designed so that the total nucleotide number including the NotI recognition site "gcggccgc", complementary sequence of cDNA and EIS nucleotide sequence of Sendai virus genome originating in the virus described below becomes a multiple of six (so-called "rule of six"; Kolakofski, D. et al., J. Virol. 72: 891–899, 1998; Calain, P. and Roux, L., J. Virol. 67: 4822–4830, 1993). Further to the 3'-side of inserted fragment, a sequence complementary to S sequence of Sendai virus, preferably 5'-CTTTCACCCT-3' (SEQ ID NO: 63), I sequence, preferably 5'-AAG-3', and a sequence complementary to E sequence, preferably 5'-TTTTTCTTACTACGG-3' (SEQ ID NO: 64), is added, and further to the 3'-side thereof, about 25 nucleotide-equivalent complementary sequence counted in the reverse direction from the termination codon of the desired cDNA sequence the length of which is adjusted to have G or C as the final nucleotide, is selected and added as the 3'-end of the reverse side synthetic DNA.

PCR can be done according to the usual method with, for example, ExTaq polymerase (Takara Shuzo). Preferably, PCR is performed using Vent polymerase (NEB), and desired fragments thus amplified are digested with NotI, then inserted to NotI site of the plasmid vector pBluescript. Nucleotide sequences of PCR products thus obtained are confirmed with a sequencer to select a plasmid having the right sequence. The inserted fragment is excised from the plasmid using NotI, and cloned to the NotI site of the plasmid carrying the genomic cDNA deficient in one or more envelope genes. Alternatively, it is also possible to obtain the recombinant Sendai virus cDNA by directly inserting the fragment to the NotI site without the mediation of the plasmid vector pBluescript.

It is also possible to transcribe a viral vector DNA of the present invention in test tubes or cells, reconstitute RNP with viral L, P and NP proteins, and produce the virus vector comprising this RNP. Reconstitution of virus from the viral vector DNA can be carried out according to methods known in the art using cells expressing envelope proteins (WO97/16539 and 97/16538: Durbin, A. P. et al., 1997, Virology 235: 323–332; Whelan, S. P. et al., 1995, Proc. Natl. Acad. Sci. USA 92: 8388–8392; Schnell, M. J. et al., 1994, EMBO J. 13:4195–4203; Radecke, F. et al., 1995, EMBO J. 14:5773–5784; Lawson, N. D. et al., Proc. Natl. Acad. Sci. USA 92: 4477–4481; Garcin, D. et al., 1995, EMBO J. 14: 6087–6094; Kato, A. et al., 1996, Genes Cells 1: 569–579; Baron, M. D. and Barrett, T., 1997, J. Virol. 71: 1265–1271; Bridgen, A. and Elliott, R. M., 1996, Proc. Natl. Acad. Sci. USA 93:15400–15404). These methods enable reconstituting, from DNA, desired paramyxovirus vectors including the parainfluenza virus, vesicular stomatitis virus, rabies virus, measles virus, rinderpest virus, Sendai virus vectors, etc. When a viral vector DNA is made deficient in F, HN and/or M genes, infectious virus particles are not formed with such a defective vector by itself. However, it is possible to form infectious virus particles by separately transferring these deficient genes, genes encoding other viral envelope proteins, and such, to host cells and expressing them therein.

Methods for transferring viral vector DNA into cells include the following: 1) the method of preparing DNA precipitates that can be taken up by objective cells; 2) the method of preparing a DNA comprising complex which is suitable for being taken up by objective cells and which is also not very cytotoxic and has a positive charge, and 3) the method of instantaneously boring on the objective cellular membrane pores wide enough to allow DNA molecules to pass through by electric pulse.

In Method 2), a variety of transfection reagents can be utilized, examples being DOTMA (Boehringer), Superfect (QIAGEN #301305), DOTAP, DOPE, DOSPER (Boehringer #1811169), etc. An example of Method 1) is a transfection method using calcium phosphate, in which DNA that entered cells are incorporated into phagosomes, and a sufficient amount is incorporated into the nuclei as well (Graham, F. L. and Van Der Eb, J., 1973, Virology 52: 456; Wigler, M. and Silverstein, S., 1977, Cell 11: 223). Chen and Okayama have investigated the optimization of the transfer technique, reporting that optimal DNA precipitates can be obtained under the conditions where 1) cells are incubated with DNA in an atmosphere of 2 to 4% $CO_2$ at 35° C. for 15 to 24 h, 2) cyclic DNA with a higher precipitate-forming activity than linear DNA is used, and 3) DNA concentration in the precipitate mixture is 20 to 30 μg/ml (Chen, C. and Okayama, H., 1987, Mol. Cell. Biol. 7: 2745). Method 2) is suitable for a transient transfection. An old method is known in the art in which a DEAE-dextran (Sigma #D-9885, M.W. $5\times10^5$) mixture is prepared in a desired DNA concentration ratio to perform the transfection. Since most of the complexes are decomposed inside endosomes, chloroquine may be added to enhance transfection effects (Calos, M. P., 1983, Proc. Natl. Acad. Sci. USA 80: 3015). Method 3) is referred to as electroporation, and is more versatile compared to methods 1) and 2) because it doesn't have cell selectivity. Method 3) is said to be efficient under optimal conditions for pulse electric current duration, pulse shape, electric field potency (gap between electrodes, voltage), conductivity of buffers, DNA concentration, and cell density.

Among the above-described three categories, transfection reagents (method 2)) are suitable in the case where nucleic acids or RNPs are introduced into cells for vector reconstitution in this invention, because method 2) is easily operable, and facilitates the examining of many test samples using a large amount of cells. Preferably, Superfect Transfection Reagent (QIAGEN, Cat. No. 301305) or DOSPER Liposomal Transfection Reagent (Boehringer Mannheim, Cat. No. 1811169) is used, but the transfection reagents are not limited thereto.

Specifically, the reconstitution of the viral vector from cDNA can be performed as follows.

Simian kidney-derived LLC-MK2 cells are cultured in 24-well to 6-well plastic culture plates or 100 mm diameter culture dish and such using a minimum essential medium (MEM) containing 10% fetal calf serum (FCS) and antibiotics (100 units/ml penicillin G and 100 μg/ml streptomycin) to 70 to 80% confluency, and infected, for example, with recombinant vaccinia virus vTF7-3 expressing T7 polymerase at 2 PFU/cell. This virus has been inactivated by a UV irradiation treatment for 20 min in the presence of 1 μg/ml psoralen (Fuerst, T. R. et al., Proc. Natl. Acad. Sci. USA 83: 8122–8126, 1986; Kato, A. et al., Genes Cells 1: 569–579, 1996). Amount of psoralen added and UV irradiation time can be appropriately adjusted. One hour after the infection, the cells are transfected with 2 to 60 μg, more preferably 3 to 5 μg, of the above-described recombinant Sendai virus cDNA by the lipofection method and such using plasmids (24 to 0.5 μg of pGEM-N, 12 to 0.25 μg of pGEM-P and 24 to 0.5 μg of pGEM-L, more preferably 1 μg of pGEM-N, 0.5 μg of pGEM-P and 1 μg of pGEM-L) (Kato, A. et al., Genes Cells 1: 569–579, 1996) expressing trans-acting viral proteins required for the production of full-length Sendai viral genome together with Superfect (QIAGEN). The transfected cells are cultured in a serum-free MEM containing 100 μg/ml each of rifampicin (Sigma) and cytosine arabinoside (AraC) if desired, more preferably only containing 40 μg/ml of cytosine arabinoside (AraC) (Sigma), and concentrations of reagents are set at optima so as to minimize cytotoxicity due to the vaccinia virus and maximize the recovery rate of the virus (Kato, A. et al., 1996, Genes Cells 1, 569–579). After culturing for about 48 to 72 h following the transfection, the cells are recovered, disrupted by repeating three cycles of freezing and thawing, transfected to LLC-MK2 cells expressing envelope proteins, and cultured. After culturing the cells for 3 to 7 days, the culture solution is collected. Alternatively, infectious virus vectors can be obtained more efficiently by transfecting LLC-MK2 cells already expressing envelope proteins with plasmids expressing NP, L and P proteins, or transfecting together with an envelope-expressing plasmid. When plasmids expressing F and HN proteins is used for the envelope protein expression, the quantity ratios of plasmids expressing the genomic RNA, N, P, L, F and HN proteins may be set, for example, at 6:2:1:2:2:2 (in terms of the copy number of transcriptional unit). When a plasmid expressing M protein is co-transfected, it can used in the same amount as that of the F protein expression plasmid. Conditions of transfection are not limited thereto, however, and can be appropriately optimized. Viral vectors can be amplified by culturing these cells overlaid on LLC-MK2 cells expressing envelope proteins (cf. Examples). Virus titer contained in the culture supernatant can be determined by measuring the hemagglutination activity (HA), which can be assayed by "endo-point dilution method" (Kato, A. et al., 1996, Genes Cells 1, 569–579). Virus stock thus obtained can be stored at −80° C.

According to the method of the present invention, it is possible to release the viral vector of this invention into the extracellular fluid (culture supernatant) of the virus producing cells at the titer, for example, of $1\times10^5$ CIU/ml or more, preferably $1\times10^6$ CIU/ml or more, $5\times10^6$ CIU/ml or more, $1\times10^7$ CIU/ml or more, $5\times10^7$ CIU/ml or more, $1\times10^8$ CIU/ml or more, and $5\times10^8$ CIU/ml or more. Furthermore, the present invention relates to a mammalian cell containing genes encoding envelope proteins of paramyxovirus integrated into its chromosome, which cell is capable of producing an infectious paramyxoviral vector deficient in said genes. This cell is capable of releasing said vector into the extracellular fluid at the titer of, for example, $1\times10^5$ CIU/ml or more, preferably $1\times10^6$ CIU/ml or more, $5\times10^6$ CIU/ml or more, $1\times10^7$ CIU/ml or more, $5\times10^7$ CIU/ml or more, $1\times10^8$ CIU/ml or more, and $5\times10^8$ CIU/ml or more. Virus production can be carried out by the method described herein. Preferably, the cell maintains the genes encoding the envelope proteins in such a manner as to inducibly express the proteins. Inducible expression refers to the expression induced by a specific stimulus or under specific conditions, and such an expression system can be constituted using, for example, an inductive promoter, Cre/lox P, and such. The cell may maintain two or more genes encoding paramyxovirus envelope proteins. For example, a combination of the genes encoding F and HN proteins, F and M proeins, or HN and M proteins, are integrated into chromosome of the cell.

A preferred embodiment for reconstituting viral vectors of the present invention is a method comprising the steps of: (a) transcribing the vector DNA encoding the negative strand RNA or the complementary strand thereof (positive strand) deficient in genes encoding envelope proteins derived from the negative-strand RNA virus in cells expressing viral proteins that are required for formation of infectious viral particles (that is, NP, P and L proteins as well as products of envelope protein genes deficient in the above-described genome) and (b) co-culturing said cells with cells that contains the envelope protein genes deficient in the above-described genome incorporated in their chromosomes and are capable of expressing said proteins. The virus can be harvested from the culture supernatant of these cells. Preferably, the method further comprises, after the step (b), the steps of: (c) preparing cell extracts from the culture medium of (b), (d) introducing said extracts into cells containing envelope protein genes deficient in the above-described genome integrated into their chromosomes and culturing the cells, and (e) harvesting viral particles from the culture supernatant. The step (d), in particular, is peferably performed under the aforementioned lower temperature conditions. Virus particles thus obtained can be amplified by allowing them to infect the envelope protein expressing cells (preferably at low temperature). Specifically, the virus can be reconstituted as described in Examples. Envelope protein genes are not limited to those deficient in the genome, but any desired envelope protein genes capable of conferring infectivity on virus, such as VSV-G, may be used.

Recombinant Sendai virus vectors of this invention can be appropriately diluted, for example, with physiological saline and phosphate-buffered physiological saline (PBS) to prepare a composition. When recombinant Sendai virus vectors of this invention are proliferated in chicken eggs and such, the composition can include chorioallantoic fluid. Compositions comprising recombinant Sendai virus vectors of this invention may contain physiologically acceptable media such as deionized water, 5% dextrose aqueous solution, and so on, and, furthermore, other stabilizers and antibiotics may also be contained.

The type of host cells used for virus reconstitution is not particularly limited, so long as viral vector can be reconstituted therein. For example, in the reconstitution of Sendai virus vector or RNP complex, culture cells such as simian kidney-derived CV-1 cells and LLC-MK2 cells, hamster kidney-derived BHK cells, human-derived cells, and so on can be used. Infectious virus particles having the envelope can be also obtained by expressing appropriate envelope proteins in these cells. To obtain Sendai virus vector in a large quantity, the vector can be amplified, for example, by infecting virus vector obtained from the above-described host cells into embryonated chicken eggs together with vectors expressing envelope genes. Alternatively, viral vectors can be produced using transgenic chicken eggs in which envelope protein genes have been introduced. Methods for manufacturing viral fluid using chicken eggs have been already developed (Nakanishi, et al. (eds.), 1993, "Shinkei-kagaku Kenkyu-no Sentan-gijutu Protocol III (High Technology Protocol III of Neuroscience Research), Molecular Neurocyte Physiology, Koseisha, Osaka, pp. 153–172). Specifically, for example, fertilized eggs are placed in an incubator and incubated for 9 to 12 days at 37 to 38° C. to grow embryos. Sendai virus vector is inoculated together with vectors expressing envelope proteins into chorioallantoic cavity of eggs, and cultured for several days to proliferate the virus. Conditions such as culture duration may be varied depending on the type of recombinant Sendai virus used. Subsequently, chorioallantoic fluid comprising the virus is recovered. Separation and purification of Sendai virus vector can be performed according to the standard methods (Tashiro, M., "Virus Experiment Protocols", Nagai and Ishihama (eds.), Medicalview, pp. 68–73 (1995)).

As a vector to express envelope proteins, viral vectors themselves of this invention may be used. For example, when two types of vectors in which a different envelope gene is deficient in the viral genome are transferred to the same cell, the envelope protein deficient in one vector is supplied by the expression of the other vector to complement each other, thereby leading to the formation of infectious virus particles and completion of replication cycle to amplify the viral vectors. That is, when two or more types of vectors are inoculated to cells in combinations so as to complement each other's envelope proteins, mixtures of virus vectors deficient in respective envelope proteins can be produced on a large scale and at a low cost. Mixed viruses thus produced are useful for the production of vaccines and such. Due to the deficiency of envelope genes, these viruses have a smaller genome size compared to the complete virus, so they can harbor a long foreign gene. Also, since these originally non-infectious viruses are extracellularly diluted, and it's difficult to retain their coinfection, they become sterile, which is advantageous in managing their release to the environment.

Recovered paramyxovirus can be purified so as to be substantially pure. Purification can be performed by known purification and separation methods including filtration, centrifugation, column chromatographic purification, and such or by combination thereof. The term "substantially pure" used herein means that virus occupies the main ratio as a component of the sample in which the virus exists. Typically, substantially pure virus vectors can be detected by confirming that the ratio of the virus-derived proteins to the total proteins including in the sample occupies 50% or more, preferably 70% or more, more preferably 80% or more, and even more preferably 90% or more. Specifically, paramyxovirus can be purified, for example, by a method in which cellulose sulfate ester or crosslinked polysaccharide sulfate ester is used (Examined Published Japanese Patent Application (JP-B) No. Sho 62-30752; JP-B Sho 62-33879; JP-B Sho 62-30753), a method in which adsorption to fucose sulfate-containing polysaccharide and/or a decomposition product thereof is used (WO97/32010), etc.

Gene therapy is enabled by administering viral vectors when the viral vectors are prepared by using a therapeutic gene as the foreign gene. In the application of viral vectors of this invention to gene therapy, it is possible to express a foreign gene with which treatment effects are expected or an endogenous gene the supply of which is insufficient in the patient's body, by either direct or indirect (ex vivo) administration of the vector. There is no particular limitation on the type of foreign gene, and in addition to nucleic acids encoding proteins, they may be nucleic acids encoding no proteins, such as an antisense or ribozyme. In addition, when genes encoding antigens of bacteria or viruses involved in infectious diseases are used as foreign genes, immunity can be induced in animals by administering these genes to the animals. That is, vectors carrying these genes can be used as vaccines.

When using as vaccines, viral vectors of the present invention may be applicable for, for example, cancers, infectious diseases and other general disorders. For example, as cancer a treatment, it is possible to express genes with therapeutic effects on tumor cells or antigen presenting cells (APC) such as dendritic cells (DCs) by using the vectors of the invention. Examples of such genes are those encoding the tumor antigen Muc-1 or Muc-1 like mutin tandem repeat peptide (U.S. Pat. No. 5,744,144), melanoma gp100 antigen, etc. Such treatments with genes have been widely applied to cancers in the mammary gland, colon, pancreas, prostate, lung, etc. Combination with cytokines to enhance adjuvant effects is also effective in gene therapy. Examples of such genes are i) single-chain IL-12 in combination with IL-2 (Proc. Natl. Acad. Sci. USA 96 (15): 8591–8596, ii) interferon-γ in combination with IL-2 (U.S. Pat. No. 5,798,100), iii) granulocyte colony-stimulating factor (GM-CSF) used alone, and iv) GM-CSF aiming at the treatment of brain tumor in combination with IL-4 (J. Neurosurgery, 90 (6), 1115–1124 (1999)), etc.

Examples of genes used for the treatment of infectious diseases are those encoding the envelope protein of the virulent strain H5N1 type of influenza virus, the envelope chimera protein of Japanese encephalitis virus (Vaccine, vol. 17, No. 15–16, 1869–1882 (1999)) the HIV gag or SIV gag protein of AIDS virus (J. Immunology (2000), vol. 164, 4968–4978), the HIV envelope protein, which is incorporated as a oral vaccine encapsulated in polylactate-glycol copolymer microparticles for administration (Kaneko, H. et al., Virology 267, 8–16 (2000)), the B subunit (CTB) of cholera toxin (Arakawa, T. et al., Nature Biotechnology (1998) 16 (10): 934–8; Arakawa, T. et al., Nature Biotechnology (1998) 16 (3): 292–297), the glycoprotein of rabies virus (Lodmell, D. L. et al., 1998, Nature Medicine 4 (8): 949–52), and the capsid protein L1 of human papilloma virus 6 causing cervical cancer (J. Med. Virol., 60, 200–204 (2000).

Gene therapy may also be applied to general disorders. For example, in the case of diabetes, the expression of insulin peptide fragment by inoculation of plasmid DNA encoding the peptide has been performed in type I diabetes model animals (Coon, B. et al., J. Clin. Invest., 1999, 104 (2): 189–94).

Compositions containing paramyxovirus vectors are useful as reagents and pharmaceuticals. Dose of the vectors may vary depending on a disease, body weight, age, sex, symptom, administration purpose, form of a composition to be inoculated, administration method, gene to be introduced, and so on, but it can be properly determined by one skilled in the art. It is preferable to inoculate, with pharmaceutically acceptable carriers, the vectors whose concentration is within the range of preferably about $10^5$ pfu/ml to about $10^{11}$ pfu/ml, more preferably about $10^7$ pfu/ml to about $10^9$ pfu/ml, and most preferably about $1 \times 10^8$ pfu/ml to about $5 \times 10^8$ pfu/ml. The dosage for humans is preferably in the range of $2 \times 10^5$ CIU to $2 \times 10^{10}$ CIU and may be administered once or several times within the range of clinically acceptable side effects. Number of administration per day is similarly determined within the above-described range. The dosage to animals other than humans can be determined by, for example, multiplying the aforementioned human dosage value by the body weight ratio or volume ratio (e.g. values on the average) of targeted administration parts between animals of interest and humans. The subject of inoculation of the compositions containing paramyxovirus vectors includes all mammals such as humans, monkeys, mice, rats, rabbits, sheep, bovines, dogs, etc.

BRIEF DESCRIPTION OF THE DRAWINGS

FIG. 5 indicates photographs showing the result obtained by an attempt to harvest the deficient viruses by using cells expressing the deficient protein. It was revealed that the expression of F protein by the helper cell line was stopped rapidly by the vaccinia viruses used in the reconstitution of F-deficient SeV.

1. LLC-MK2 and CV-1 represent cell lysates from the respective cell types alone.
2. LLC-MK2/F+ad and CV-1/F+ad represent cell lysates from the respective cells that have been subjected to the induction of expression and to which adenovirus AxCAN-Cre has been added.
3. LLC-MK2/F−ad and CV-1/F−ad represent cell lysates from the respective cell lines in which the F gene but no adenovirus AxCANCre has been introduced.

4. LLC-MK2/F+ad 3rd represents a cell lysate from cells in which the expression was induced by adenovirus AxCANCre and which were then further passaged 3 times.
5. 1d and 3d respectively indicate one day and three days after the induction of expression.
6. Vac1d and Vac3d respectively indicate cells one day and three days after the infection of vaccinia virus.
7. AraC1d and AraC3d respectively indicate cells one day and three days after the addition of AraC.
8. CHX 1d and CHX 3d respectively indicate cells one day and three days after the addition of protein synthesis inhibitor cycloheximide.

Figure 6:
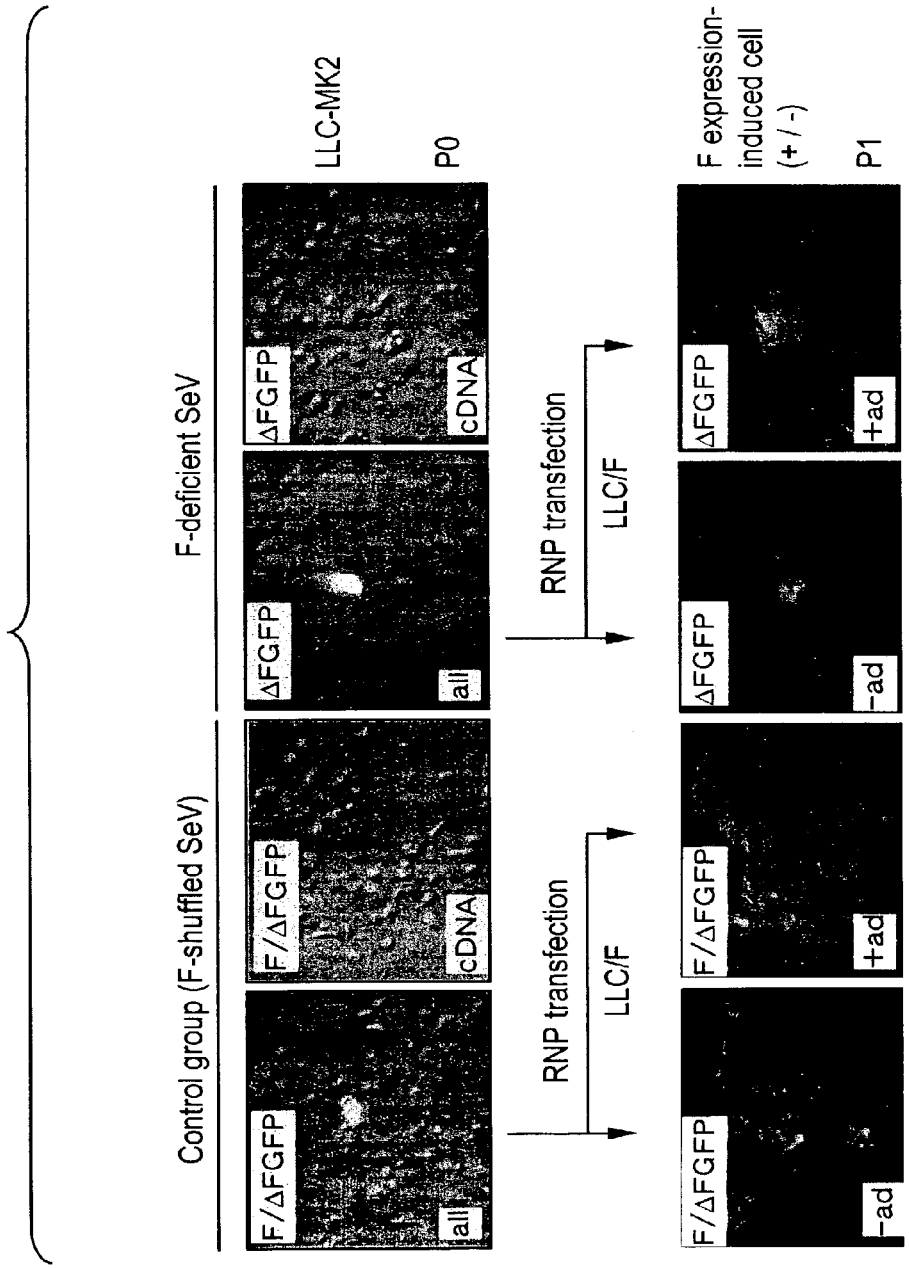

FIG. 6 indicates photographs showing the result that was obtained by observing GFP expression after GFP-comprising F-deficient SeV cDNA (pSeV18+/ΔF-GFP) was transfected into LLC-MK2 cells in which F was not expressed (detection of RNP). In a control group, the F gene was shuffled with the NP gene at the 3' end, and then, SeV cDNA (F-shuffled SeV), in which GFP had been introduced into the F-deficient site, was used. The mark "all" indicates cells transfected with plasmids directing the expression of the NP gene, P gene, and L gene (pGEM/NP, pGEM/P, and pGEM/L) together with SeV cDNA at the same time; "cDNA" indicates cells transfected with cDNA (pSeV18+/ΔF-GFP) alone. For RNP transfection, P0 cells expressing GFP were collected; the cells ($10^7$ cells/ml) were suspended in Opti-MEM (GIBCO BRL); 100 μl of lysate prepared after treating three times with freeze-thaw cycles was mixed with 25 μl of cationic liposome DOSPER (Boehringer Mannheim) and allowed to stand still at room temperature for 15 minutes; and the mixture was added to cells (+ad) in which the expression of F had been induced to achieve the RNP transfection. Cells expressing Cre DNA recombinase, in which no recombinant adenovirus had been introduced, were used as a control group of cells (−ad). The result showed that GFP was expressed depending on the RNP formation of SeV in P0 in LLC-MK2 cells; and the F-deficient virus was amplified depending on the induction of expression of F in P1.

Figure 7:
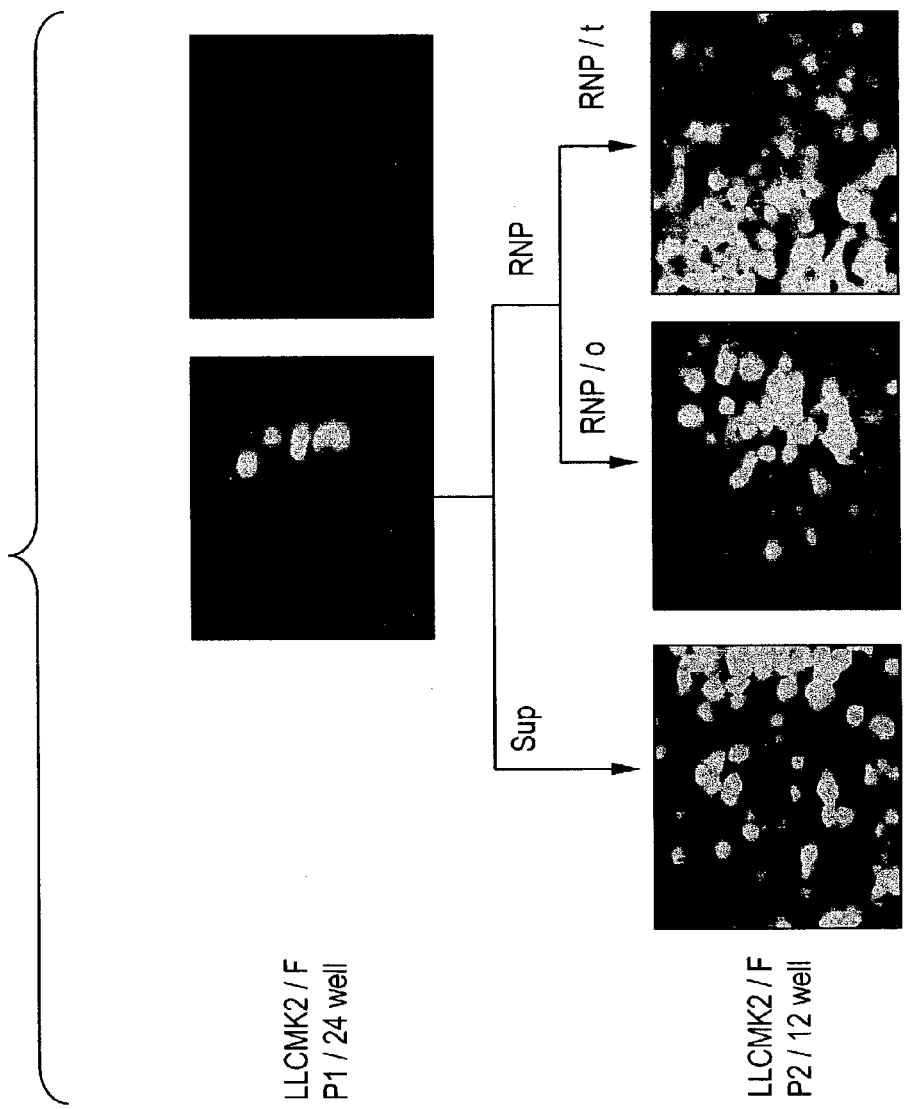

FIG. 7 indicates photographs showing the result that was obtained by studying whether functional RNP reconstituted with F-deficient genomic cDNA could be rescued by the F-expressing helper cells and form the infective virion of the deficient virus. RNP/o represents cells overlaid with RNP; RNP/t represents cells that was transfected with RNP.

Figure 8:
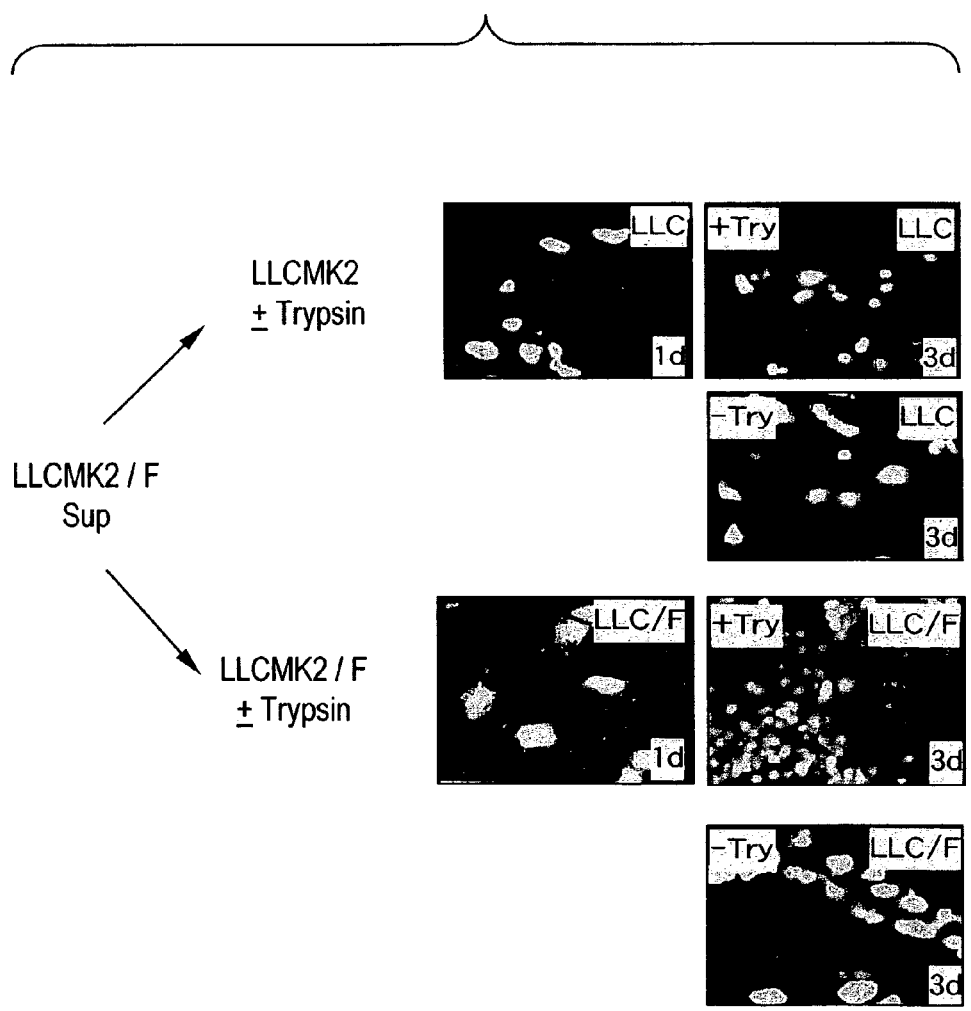

FIG. 8 indicates photographs showing the evidence for the F-expressing cell-specific growth of the F-deficient virus. The lysate comprising functional-RNP constructed from the genome lacking the gene was lipofected to the F-expressing cells as described in Example 2; and the culture supernatant was then recovered. This culture supernatant was added to the medium of the F-expressing cells to achieve the infection; on the third day, the culture supernatant was recovered and concurrently added to both F-expressing cells and cells that had not expressed F; and then the cells were cultured in the presence or absence of trypsin for three days. The result is shown here. The viruses were amplified only in the presence of trypsin in the F-expressing cells.

FIG. 9 indicates photographs showing evidence for specific release of the F-deficient viruses to the culture supernatant after the introduction into F-expressing cells. The lysate comprising functional RNP constructed from the genome lacking the gene was lipofected to the F-expressing cells as described in Example 2 and then the culture supernatant was recovered. This culture supernatant was added to the medium of the F-expressing cells to achieve the infection; on the third day, the culture supernatant was recovered and concurrently added to both F-expressing cells and cells that did not express F; and then the cells were cultured in the presence or absence of trypsin for three days. The bottom panel shows the result with supernatant of the cells that did not express F.

Figure 10:
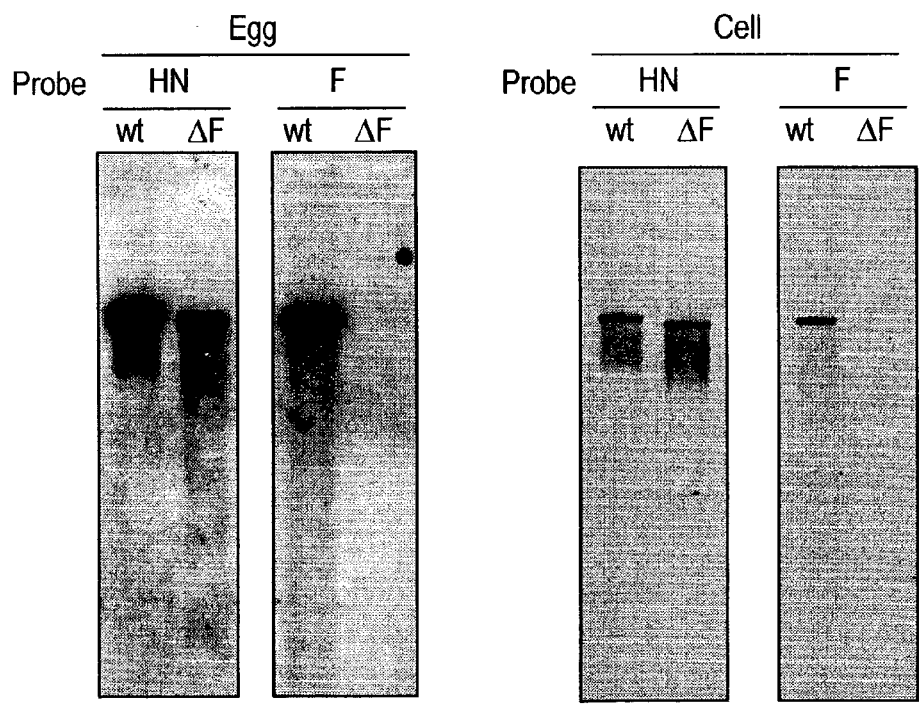

FIG. 10 indicates photographs showing the result obtained by recovering viruses from the culture supernatant of the F-expressing cells, extracting the total RNA and performing Northern blot analysis using F and HN as probes to verify the genomic structure of virion recovered from the F-deficient cDNA. In the viruses recovered from the F-expressing cells, the HN gene was detected but the F gene was not detectable; and thus it was clarified that the F gene was not present in the viral genome.

Figure 11:
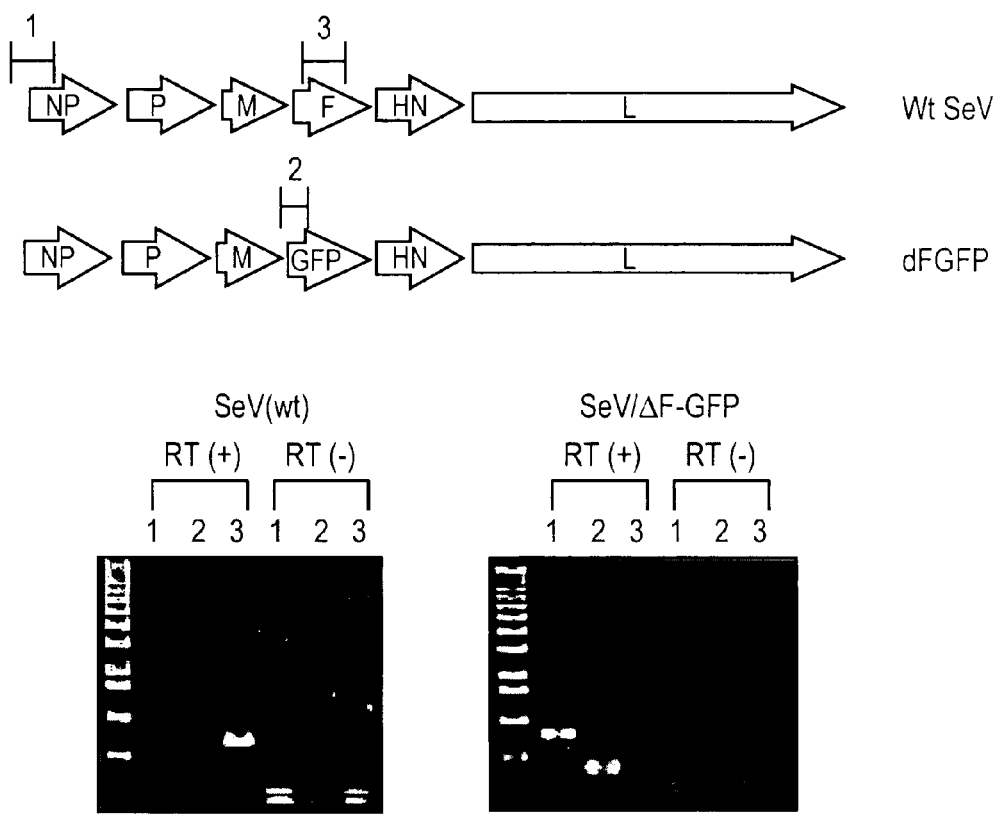

FIG. 11 indicates photographs showing the result of RT-PCR, which demonstrates that the GFP gene is present in the locus where F had been deleted, as in the construct of the cDNA. 1: +18-NP, for the confirmation of the presence of +18 NotI site. 2: M-GFP, for the confirmation of the presence of the GFP gene in the F gene-deficient region. 3: F gene, for the confirmation of the presence of the F gene. The genomic structures of wild type SeV and F-deficient GFP-expressing SeV are shown in the top panel. It was verified that the GFP gene was present in the F-deficient locus, +18-derived NotI site was present at the 3' end of NP and the F gene was absent in any part of the RNA genome.

Figure 12:
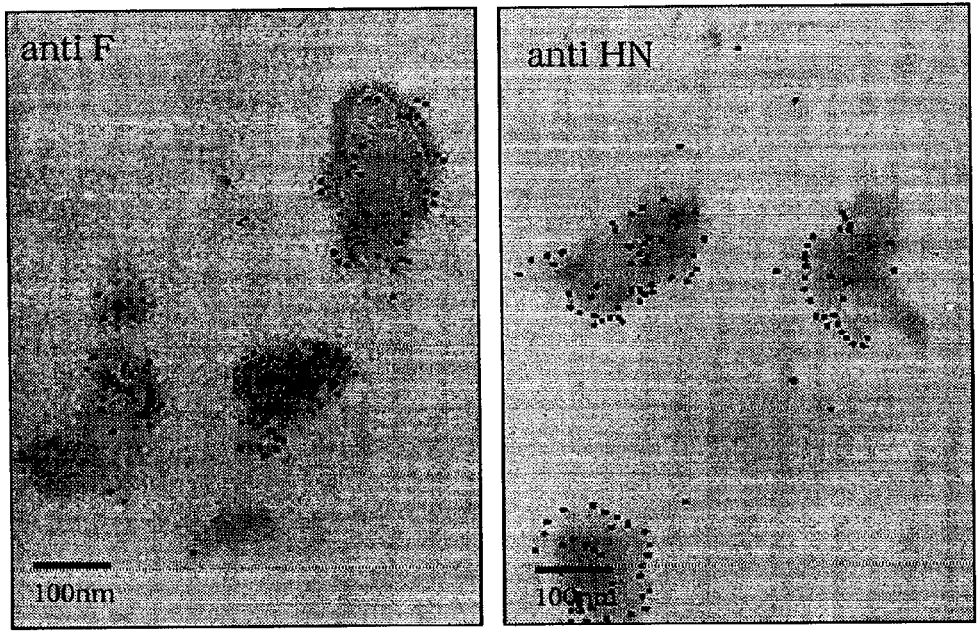

FIG. 12 indicates photographs that were obtained by the immuno-electron microscopic examination with gold colloid-bound IgG (anti-F, anti-HN) specifically reacting to F or HN of the virus. It was clarified that the spike-like structure of the virus envelope comprised F and HN proteins.

Figure 13:
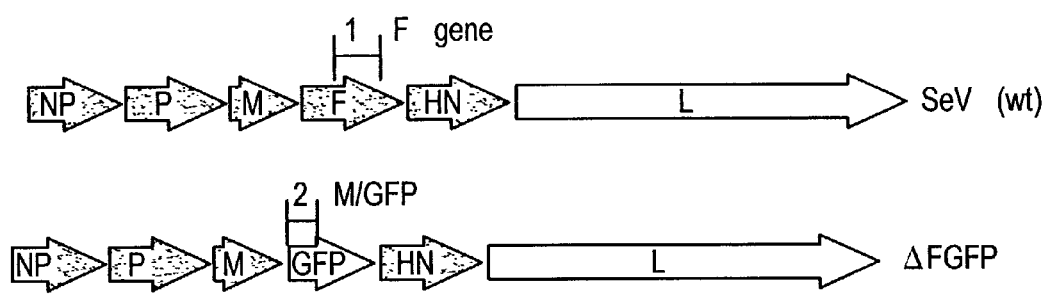

FIG. 13 indicates diagrams showing the result of RT-PCR, which demonstrates that the structures of genes except the GFP gene were the same as those from the wild type.

FIG. 14 indicates photographs showing the result obtained by examining the F-deficient virus particle morphology by electron microscopy. Like the wild-type virus particles, the F-deficient virus particles had helical RNP structure and spike-like structure inside.

Figure 15:
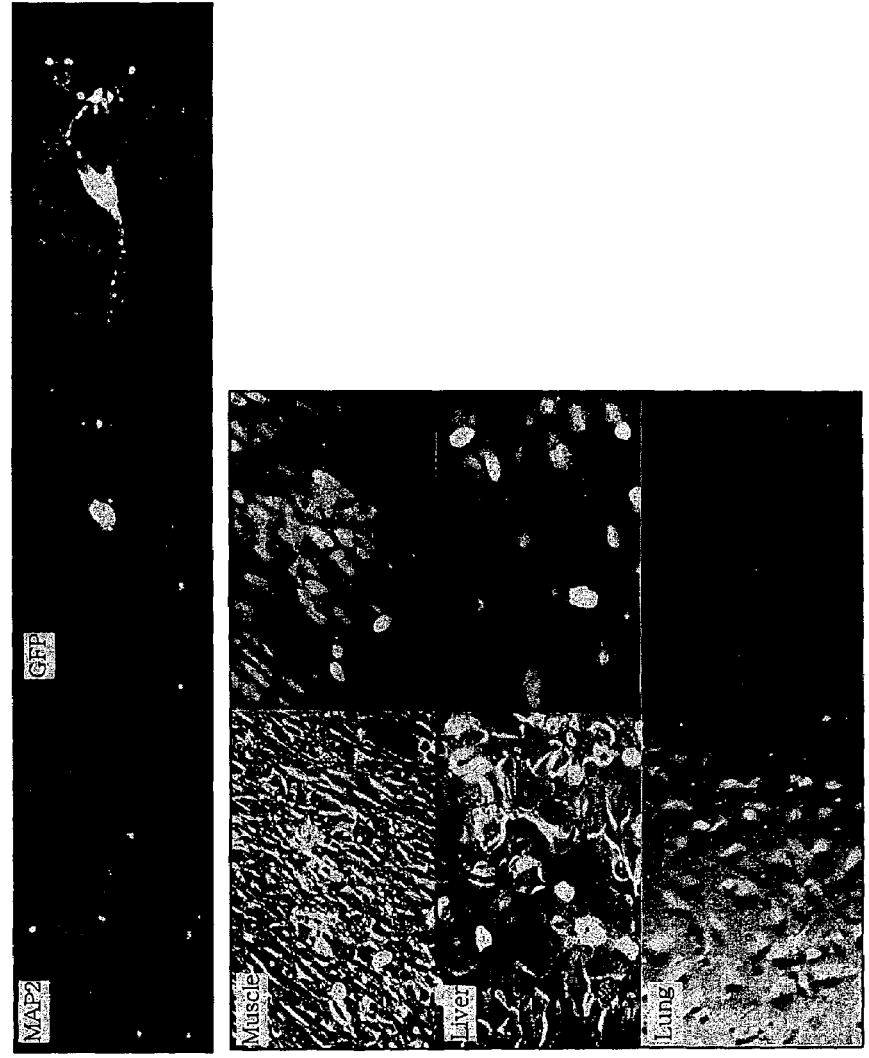

FIG. 15 indicates photographs showing the result of in vitro gene transfer to a variety of cells using an F-deficient SeV vector with a high efficiency.

Figure 16:
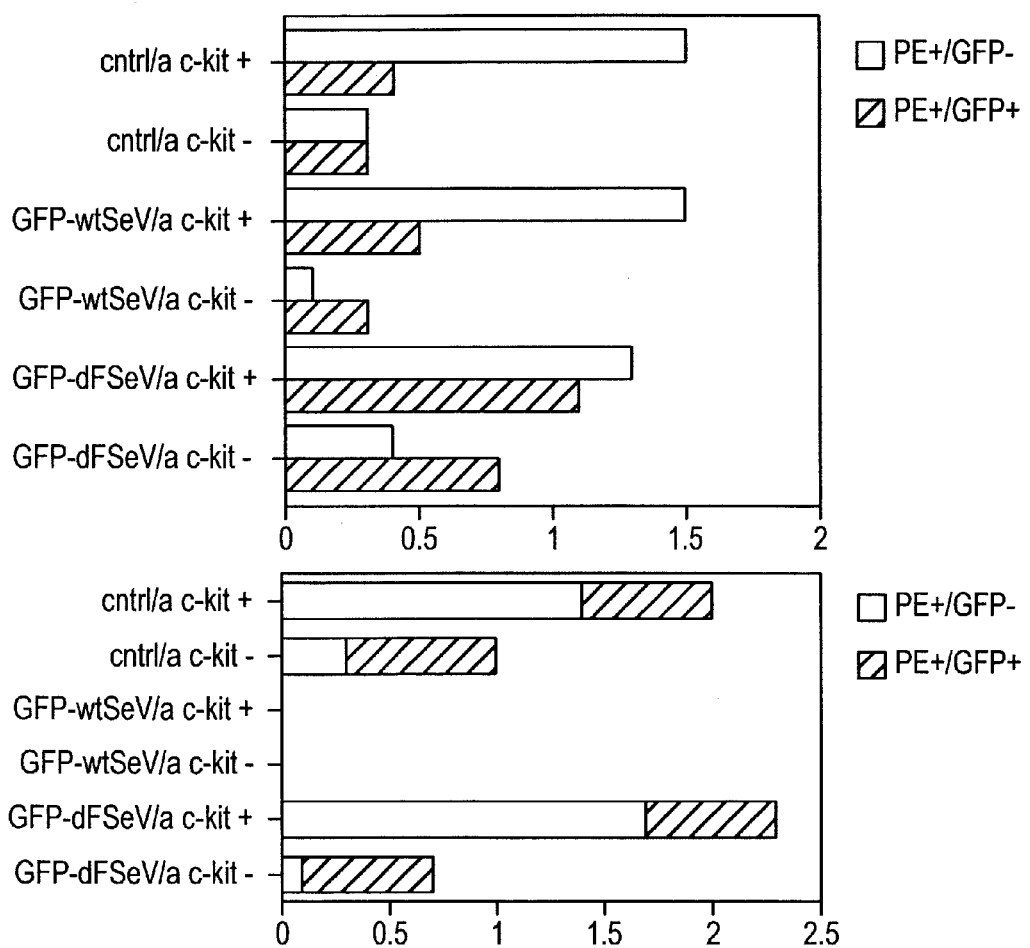

FIG. 16 indicates diagrams showing the analytical result obtained after the introduction of the F-deficient SeV vector into primary bone marrow cells from mouse (BM c-kit+/−). Open bars represent PE-positive/GFP-negative; closed bars represent PE-positive/GFP-positive.

Figure 17:
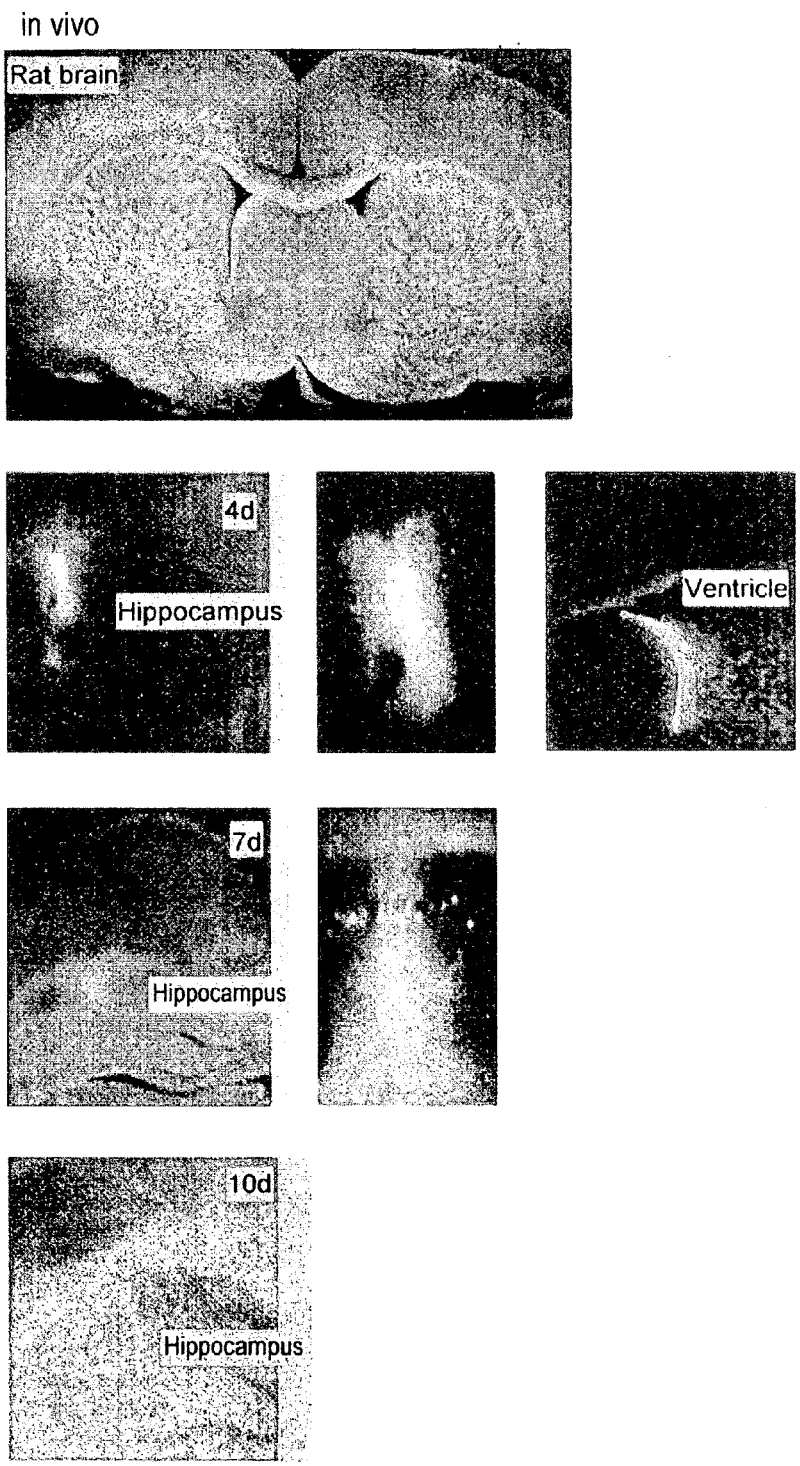

FIG. 17 indicates photographs showing the result of in vivo administration of the vector into the rat cerebral ventricle.

FIG. 18 indicates photographs showing the result obtained by using the culture supernatant comprising F-deficient SeV viruses recovered from the F-expressing cells to infect LLC-MK2 cells that do not express F, culturing the cells in the presence or absence of trypsin for three days to confirm the presence of viruses in the supernatant by HA assay.

Figure 18A:
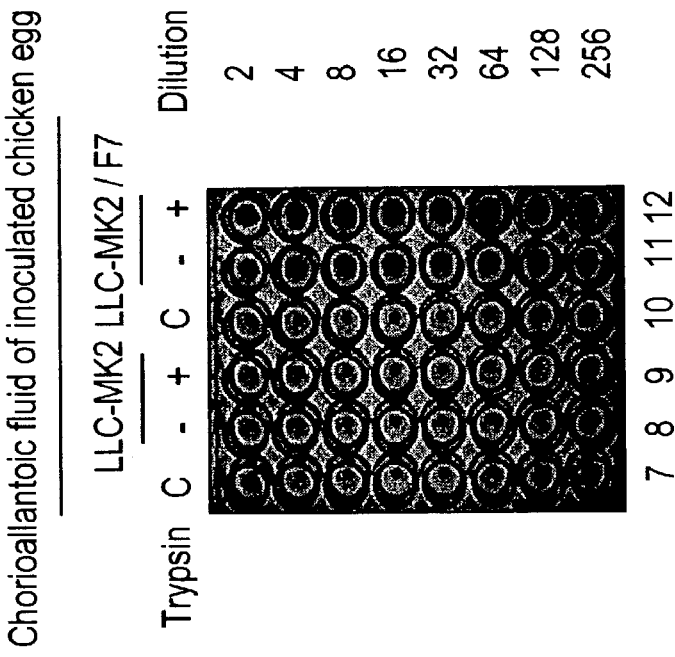
Figure 18B:
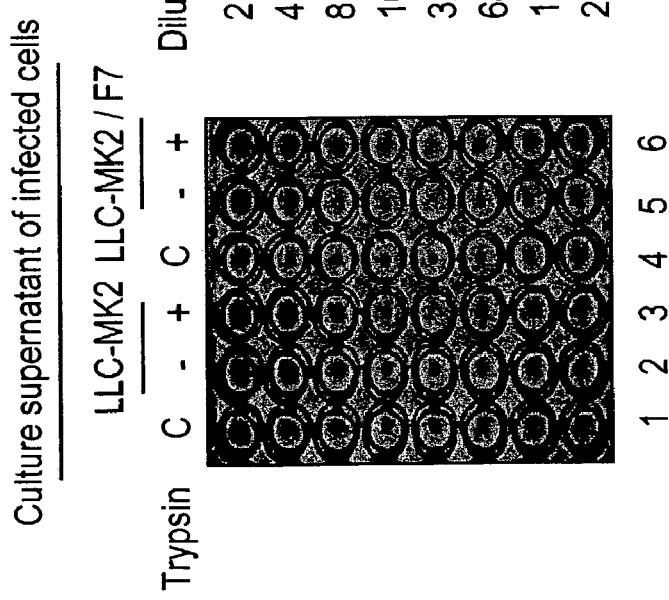
Figure 19:
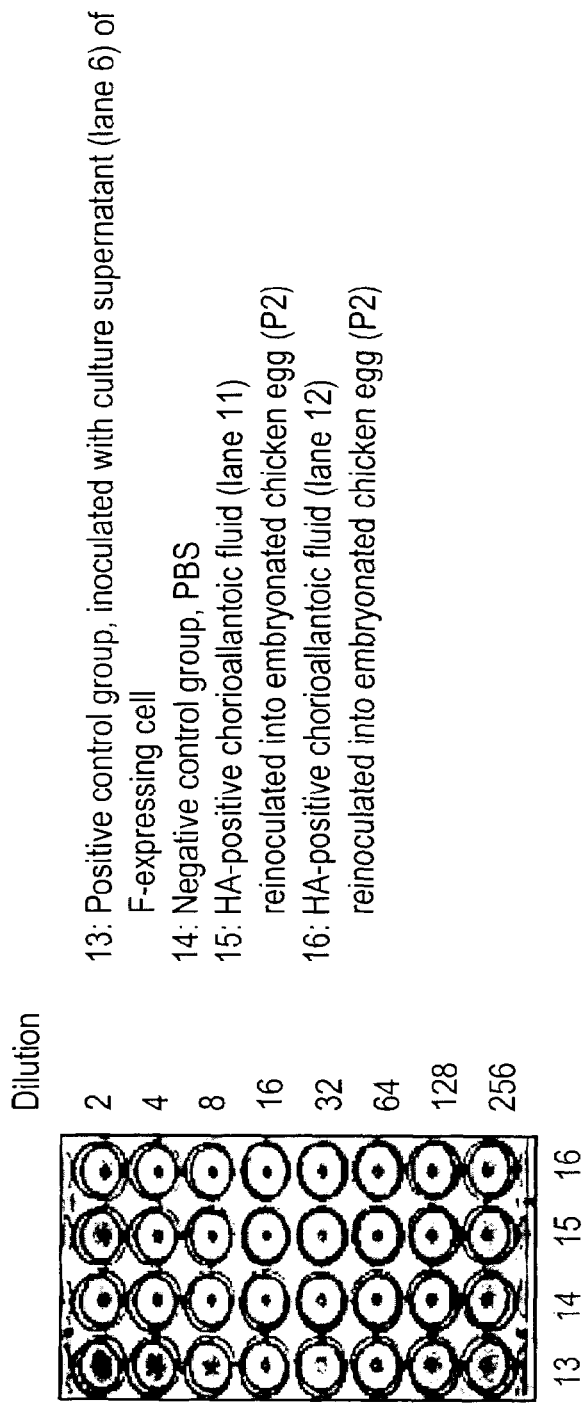

FIG. 19 is a photograph showing the result obtained by conducting HA assay of chorioallantoic fluids after a 2-day incubation of embryonated chicken egg that had been inoculated with chorioallantoic fluid (lanes 11 and 12) from HA-positive embryonated eggs in FIG. 18B.

Figure 20:
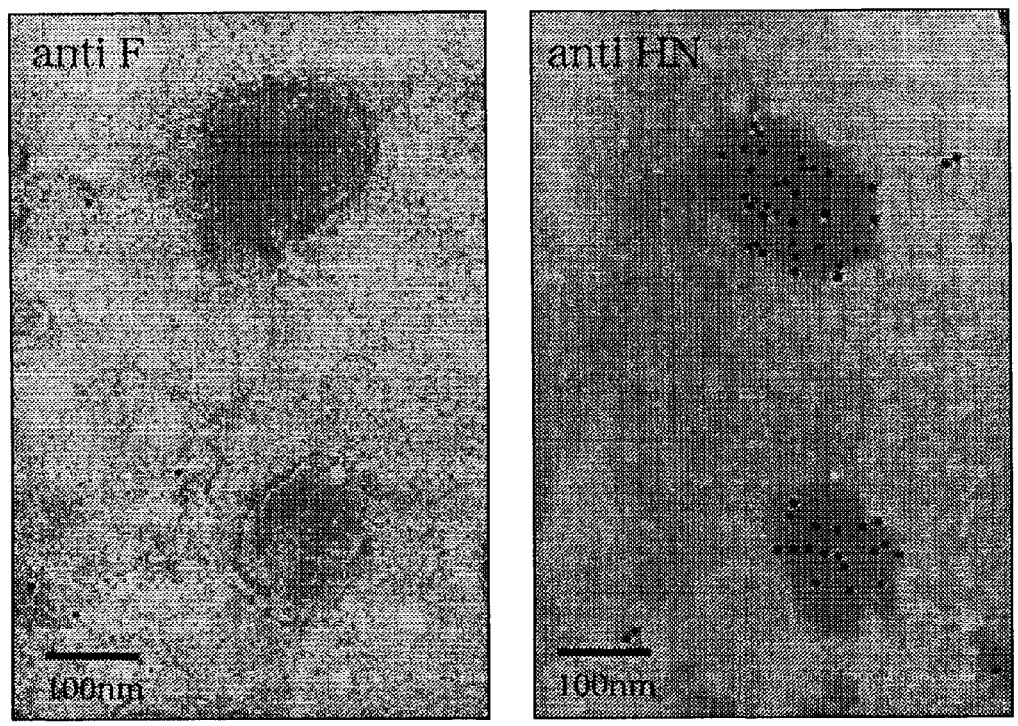

FIG. 20 indicates photographs showing the result obtained by examining the virus liquid, which is HA-positive and has no infectivity, by immuno-electron microscopy. The presence of the virus particles was verified and it was found that the virion envelope was reactive to antibody recognizing HN protein labeled with gold colloid, but not reactive to antibody recognizing F protein labeled with gold colloid.

FIG. 21 indicates photographs showing the result of transfection of F-deficient virus particles into cells.

Figure 22:
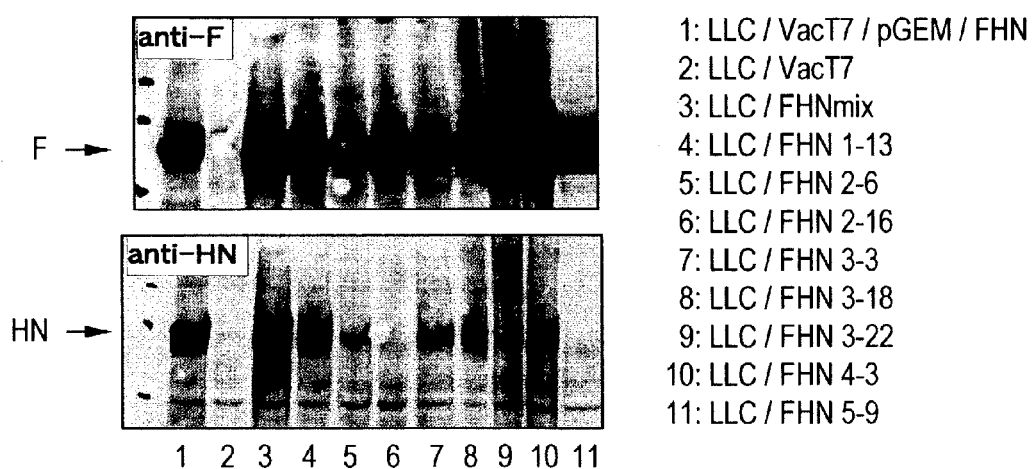

FIG. 22 indicates photographs showing the result of creation of cells co-expressing F and HN, which were evaluated by Western blotting. LLC/VacT7/pGEM/FHN represents cells obtained by transfecting vaccinia-infected LLC-MK2 cells with pGEM/FHN plasmid; LLC/VacT7 represents vaccinia-infected LLC-MK2 cells. LLCMK2/FHNmix represents LLC-MK2 cells in which the F and HN genes were introduced but not cloned. LLC/FHN represents LLC-MK2 cells in which the F and HN genes were introduced and the expression was induced by adenovirus AxCAVCre (after 3 days); 1-13, 2-6, 2-16, 3-3, 3-18, 3-22, 4-3 and 5-9 are cell-line numbers (names) in the cloning.

FIG. 23 indicates photographs showing the result for the confirmation of virus generation depending on the presence or absence pGEM/FHN. FHN-deficient GFP-expressing SeV cDNA, pGEM/NP, pGEM/P, pGEM/L, and pGEM/FHN were mixed and introduced into LLC-MK2 cells. 3 hours after the gene transfer, the medium was changed with MEM containing AraC and trypsin and then the cells were further cultured for three days. 2 days after the gene transfer, observation was carried out with a stereoscopic fluorescence microscope to evaluate the difference depending on the presence or absence of pGEM/FHN, and the virus generation was verified based on the spread of GFP-expressing cells. The result is shown here. When pGEM/FHN was added at the time of reconstitution, the spread of GFP-expressing cells was recognized; but when no pGEM/FHN was added, the GFP expression was observable merely in a single cell.

Figure 24:
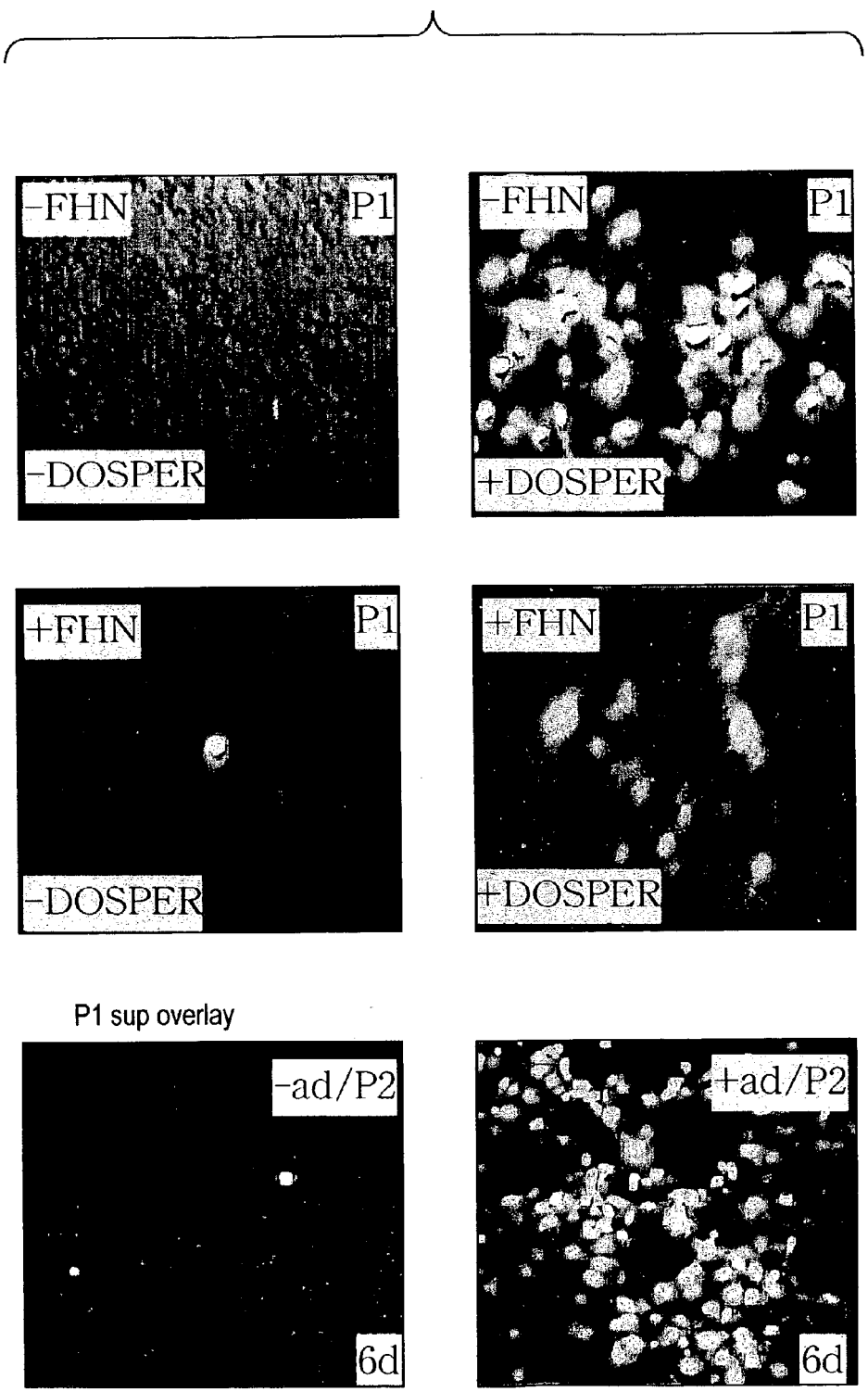

FIG. 24 indicates photographs showing the result of reconstitution by RNP transfection and growth of FHN-deficient viruses. On the third day after the induction of expression, cells co-expressing FHN (12 wells) were lipofected by using P0 RNP overlay or DOSPER, and then GFP was observed after 4 days. When RNP transfection was conducted, the harvest of viruses was successful for P1 FHN-expressing cells as was for the F-deficient ones (top). The growth of the FHN-deficient viruses was verified after inoculating a liquid comprising the viruses to cells in which the expression of FHN protein was induced 6 hours or more after the infection with AxCANCre (bottom panel).

Figure 25:
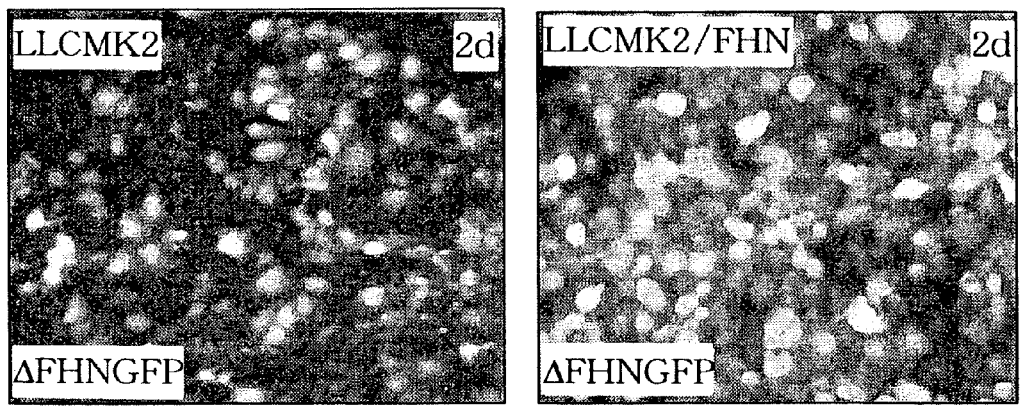

FIG. 25 indicates photographs showing the result obtained after inoculating the liquid comprising viruses reconstituted from FHN-deficient GFP-expressing cDNA to LLC-MK2, LLC-MK2/F, LLC-MK2/HN, and LLC-MK2/FHN and culturing them in the presence or absence of the trypsin. The spread of cells expressing GFP protein was verified 3 days after the culture. The result is shown here. The expansion of GFP was observed only with LLC-MK2/FHN, and thus it was verified that the virus contained in the liquid was grown in a manner specific to FHN co-expression and dependent on trypsin.

FIG. 26 is a photograph showing the result where the confirmation was carried out for the genomic structure of RNA derived from supernatant of the FHN-expressing cells.

Figure 27:
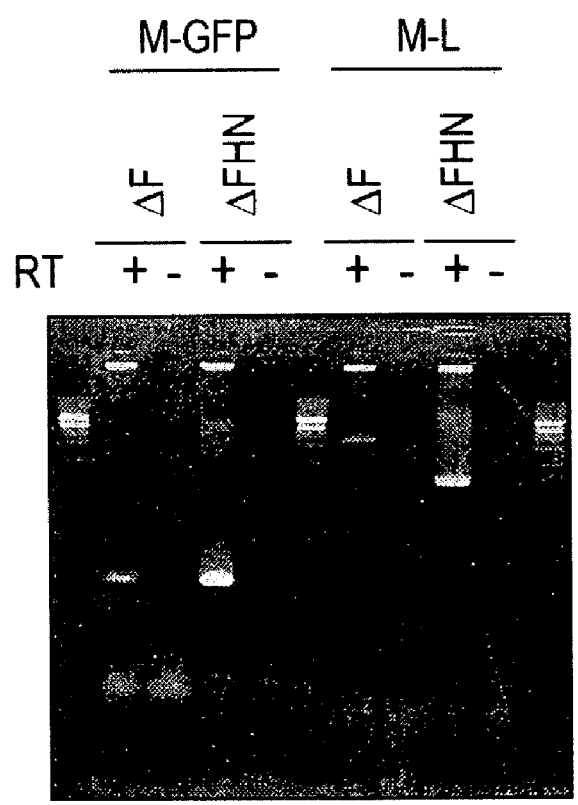

FIG. 27 is a photograph showing the result where the confirmation was carried out for the genomic structure of RNA derived from supernatant of the F-expressing cells infected with the FHN-deficient viruses.

Figure 28:
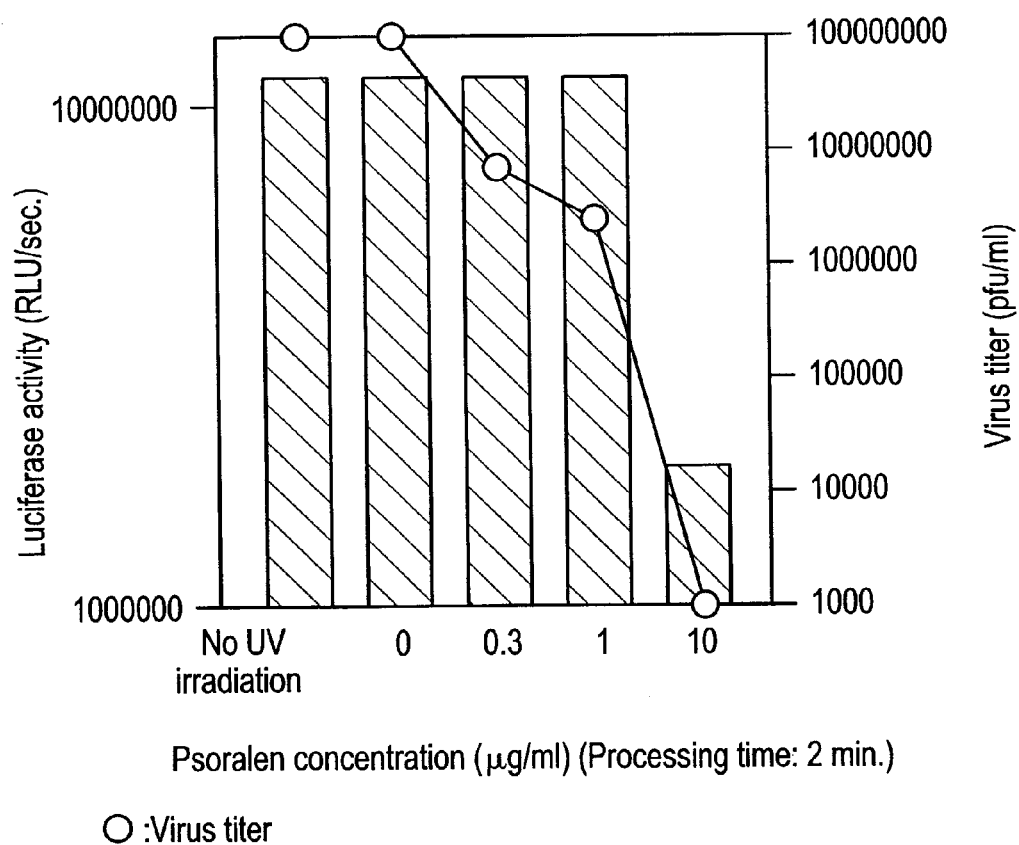

FIG. 28 is a diagram showing inactivation of vaccinia virus and T7 activity when psoralen concentration was varied in psoralen/UV irradiation.

Figure 29:
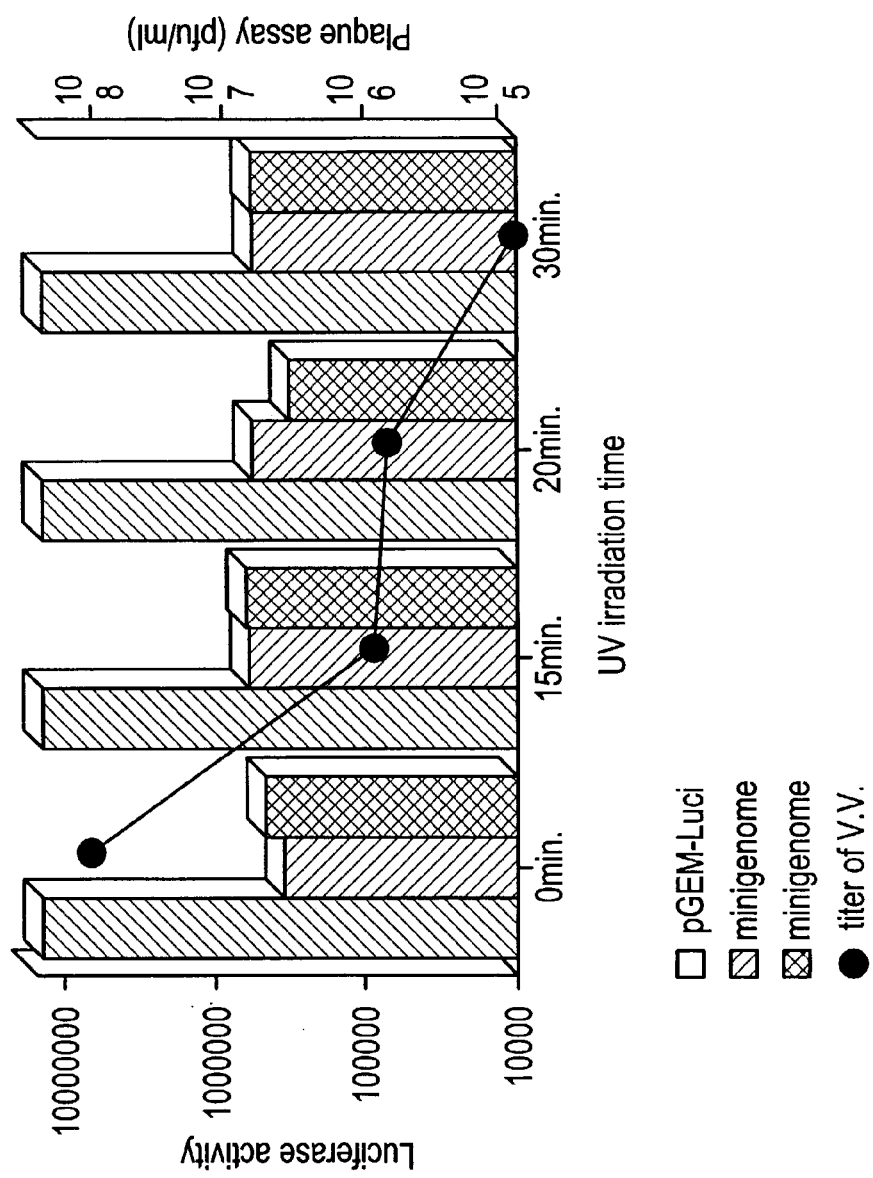
Figure 30A:
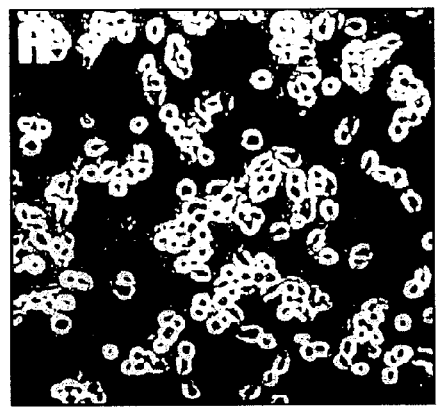
Figure 30C:
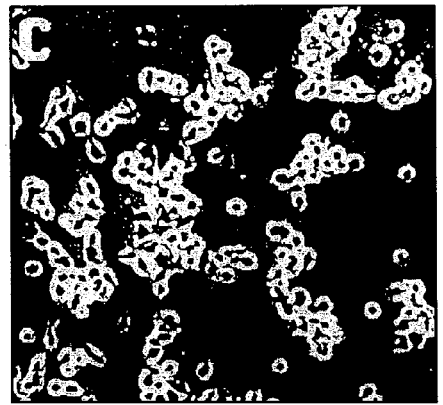
Figure 30B:
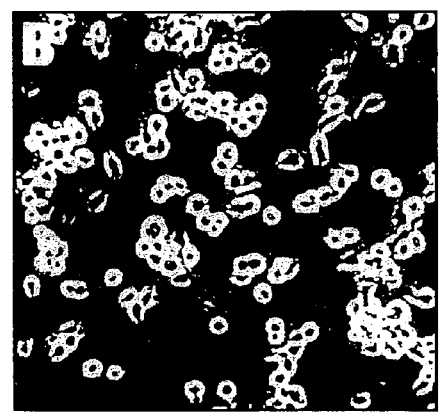
Figure 30D:
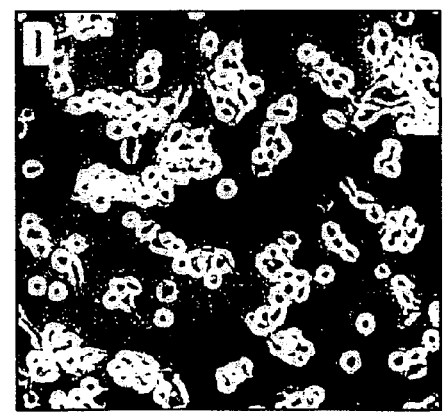

FIG. 29 is a diagram showing inactivation of vaccinia virus and T7 RNA polymerase activity when the duration of UV irradiation was varied in psoralen/UV irradiation.

FIG. 30 indicates photographs showing a cytotoxicity (CPE) of vaccinia virus after psoralen/UV irradiation. $3 \times 10^5$ LLC-MK2 cells were plated on a 6-well plate. After culturing overnight, the cells were infected with vaccinia virus at moi=2. After 24 hours, CPE was determined. The result of CPE with mock-treatment of vaccinia virus is shown in A; CPE after the treatment with vaccinia virus for 15, 20, or 30 minutes are shown in B, C, and D, respectively.

Figure 31:
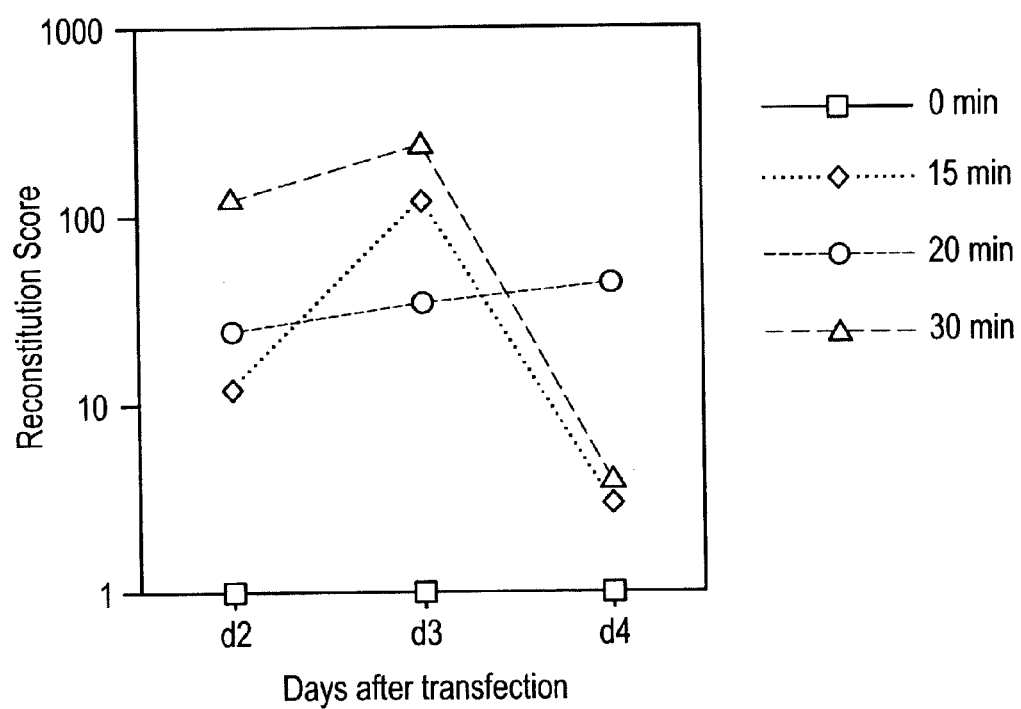

FIG. 31 is a diagram indicating the influence of duration of UV treatment of vaccinia virus on the reconstitution efficiency of Sendai virus.

Figure 32:
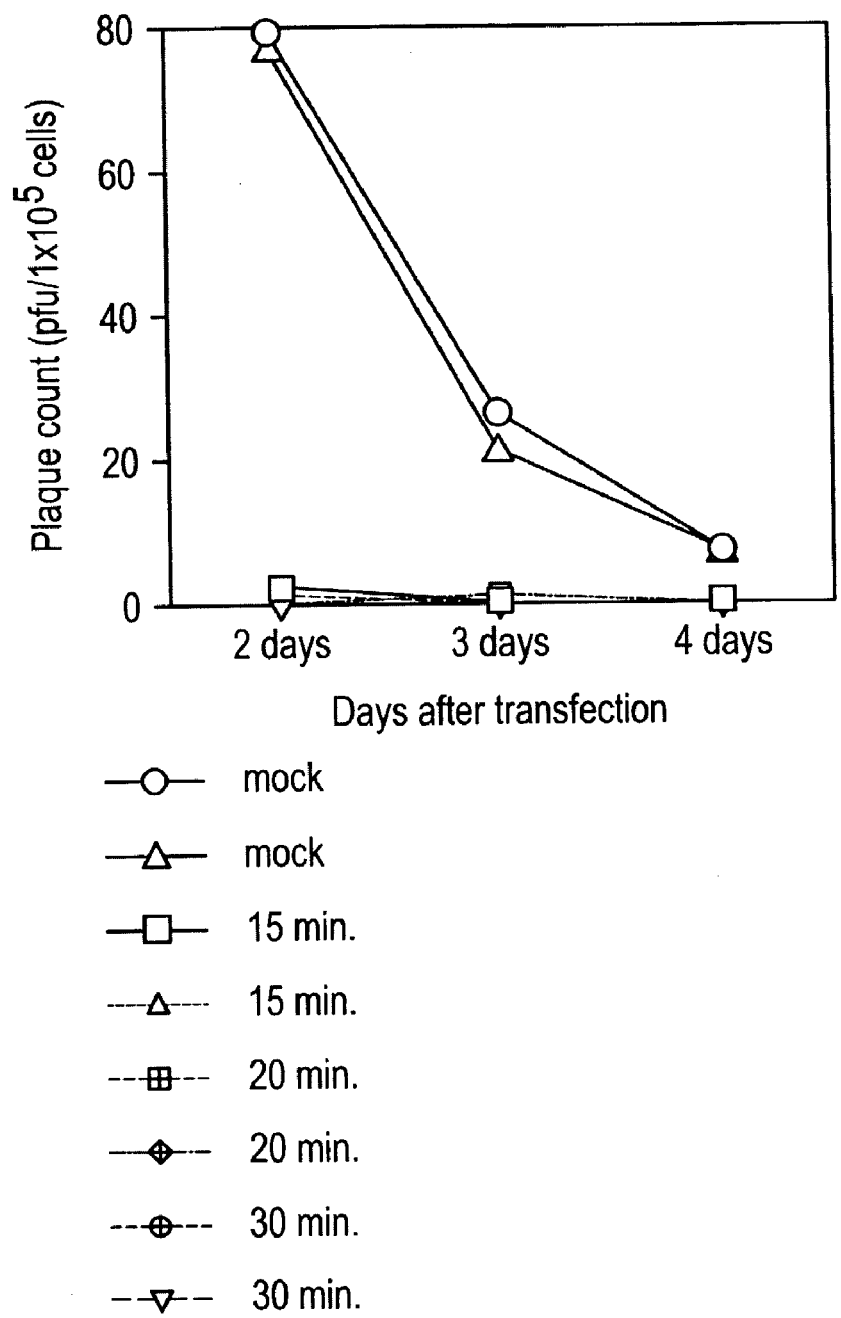

FIG. 32 is a diagram indicating the titer of vaccinia virus capable of replicating that remained in the cells after the reconstitution experiment of Sendai virus.

Figure 33:
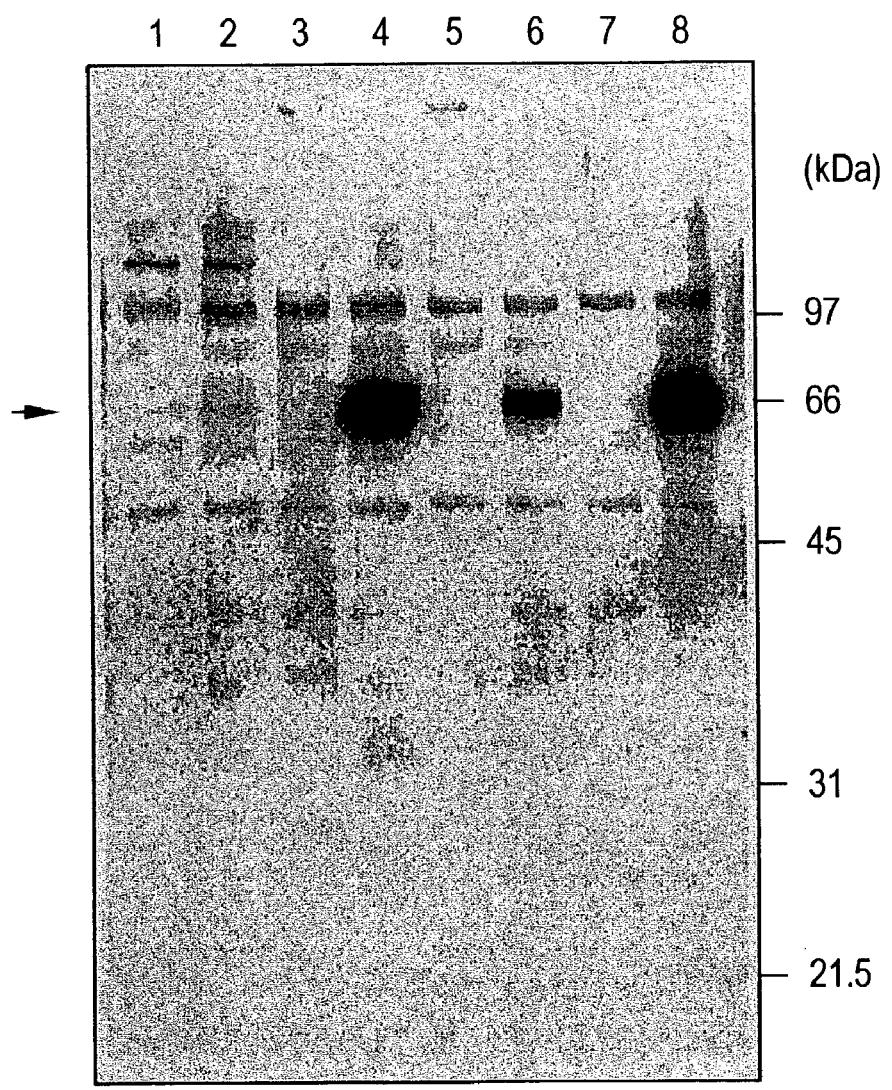

FIG. 33 is a photograph showing a result of Western blot analysis using anti-VSV-G antibody.

Figure 34:
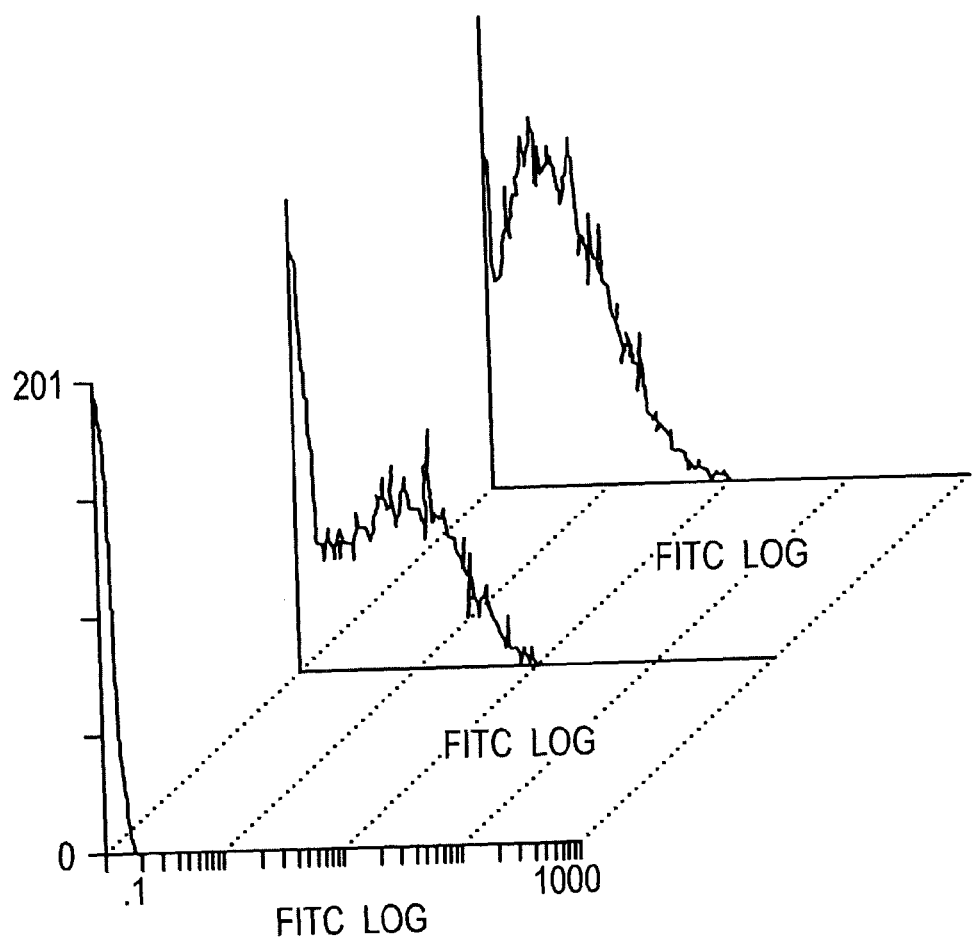

FIG. 34 indicates a diagram showing results of flow cytometry analysis using anti-VSV-G antibody. It shows the result of analysis of LLC-MK2 cell line (L1) for the induction of VSV-G expression on the fourth day after AxCANCre infection (moi=0, 2.5, 5). Primary antibody used was anti-VSV-G antibody (MoAb I-1); secondary antibody was FITC-labeled anti-mouse Ig.

Figure 35:
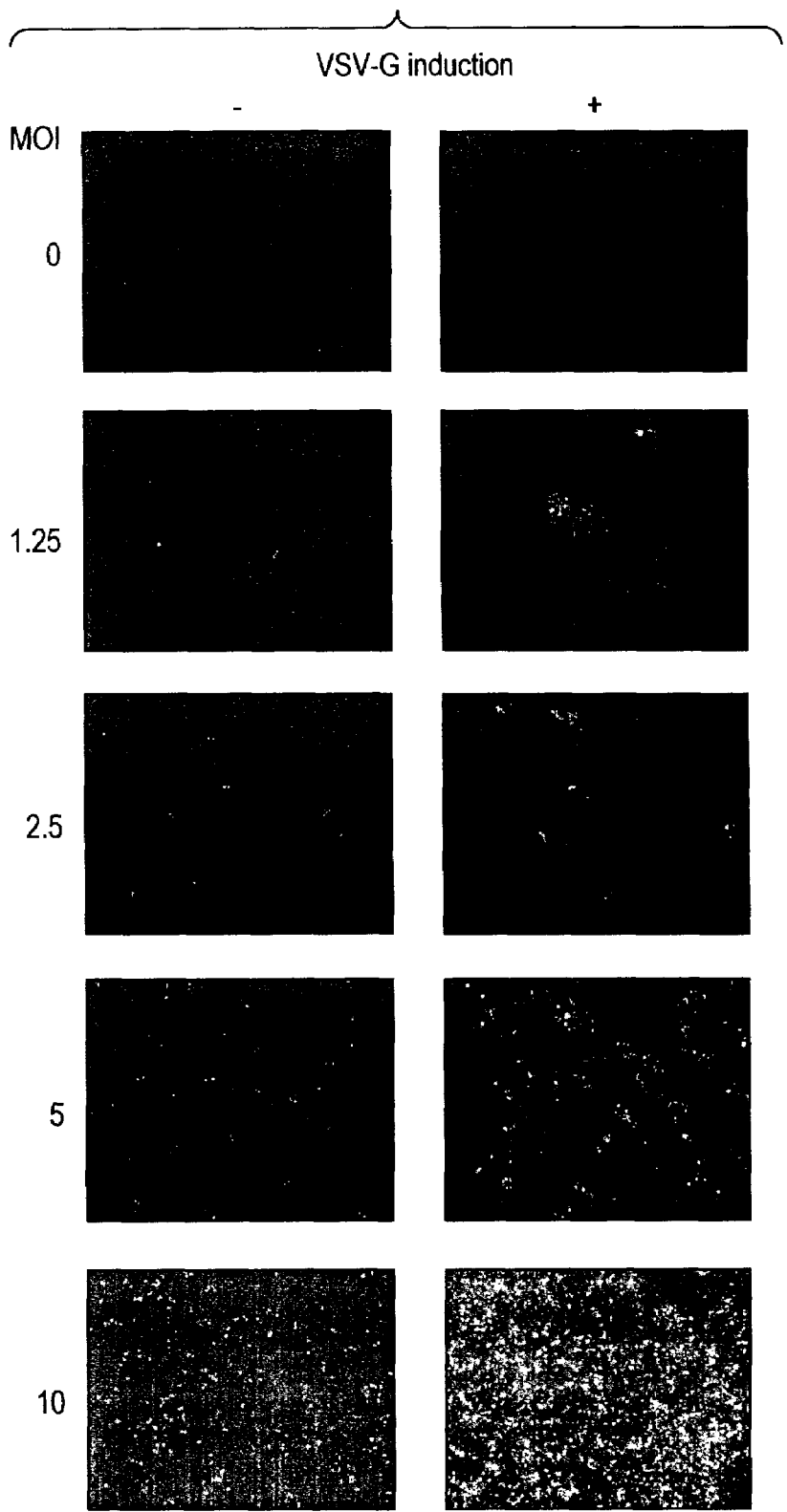

FIG. 35 indicates photographs showing a result where supernatants were recovered after the infection with altered amounts of AxCANCre (MOI=0, 1.25, 2.5, 5, 10) and a constant amount of pseudo-type Sendai virus having a F gene-deficient genome, and further the supernatants were used to infect cells before VSV-G induction (−) and after induction (+), and cells expressing GFP were observed after 5 days.

Figure 36:
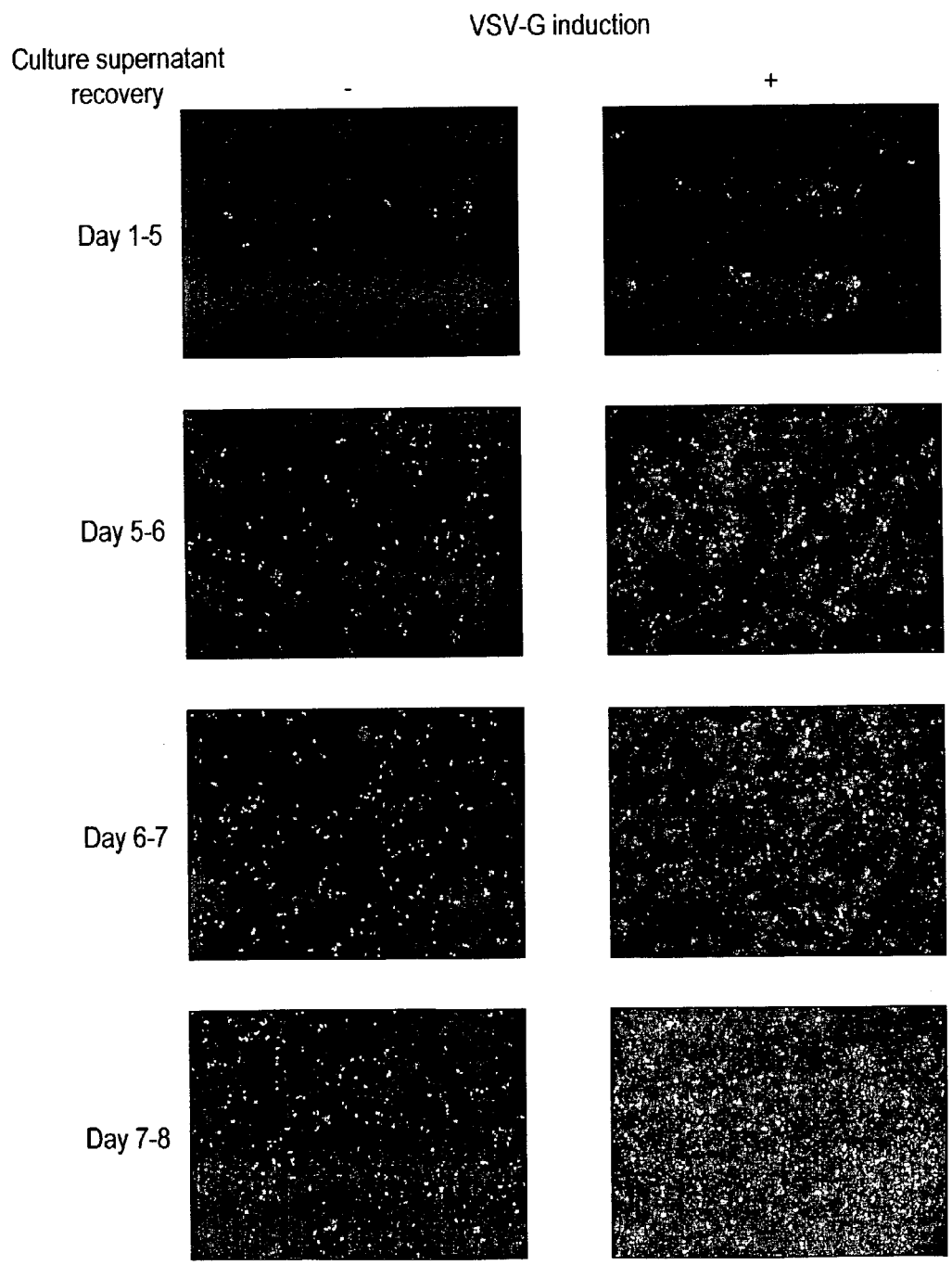

FIG. 36 indicates photographs showing the result obtained for the time course of virus production amount.

Figure 37:
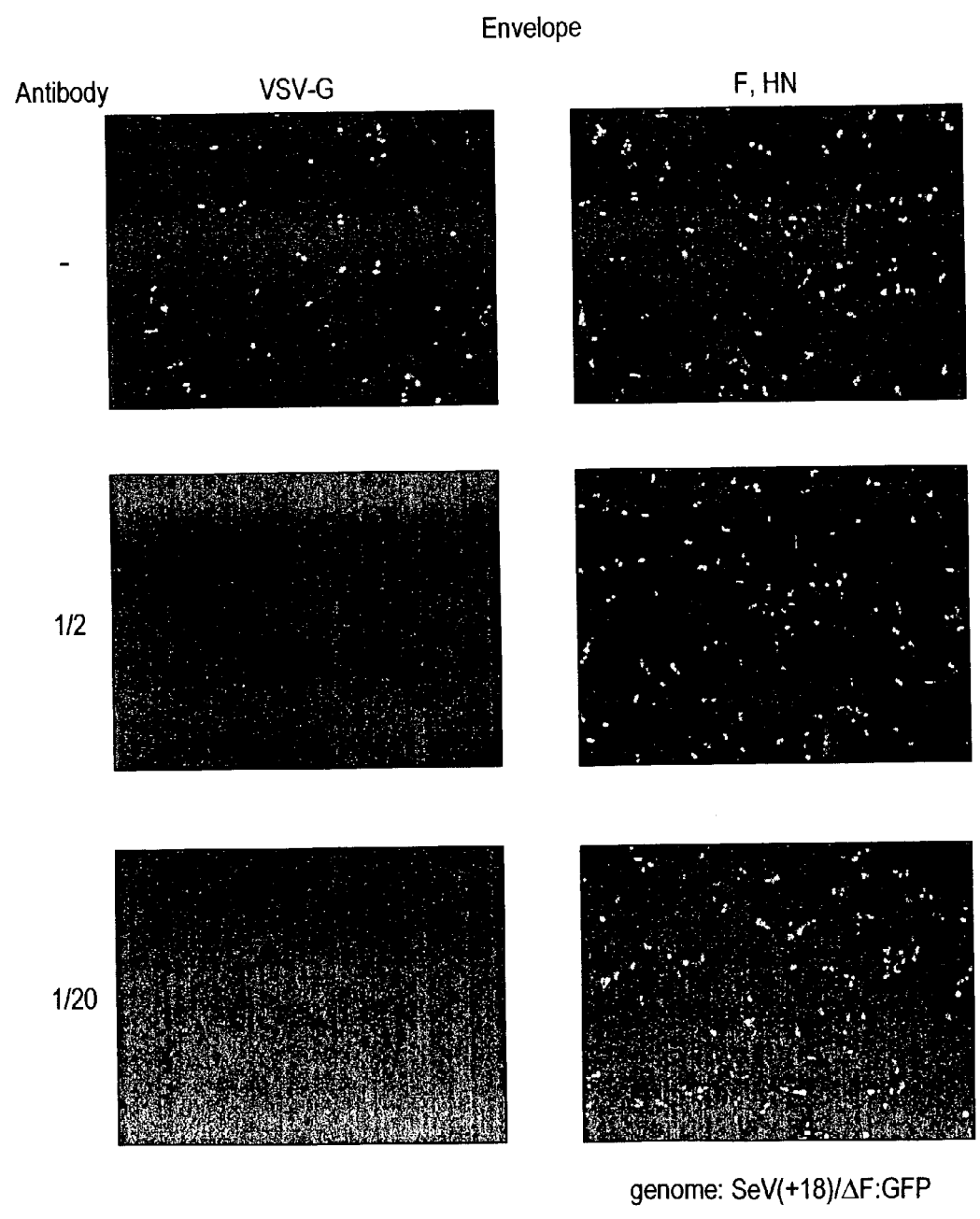

FIG. 37 indicates photographs showing the result obtained by examining whether the infectivity is influenced by the treatment of pseudo-type Sendai virus having the F gene-deficient genome, which was established with the VSV-G-expressing cell line, and FHN-deficient Sendai virus treated with anti-VSV antibody.

Figure 38:
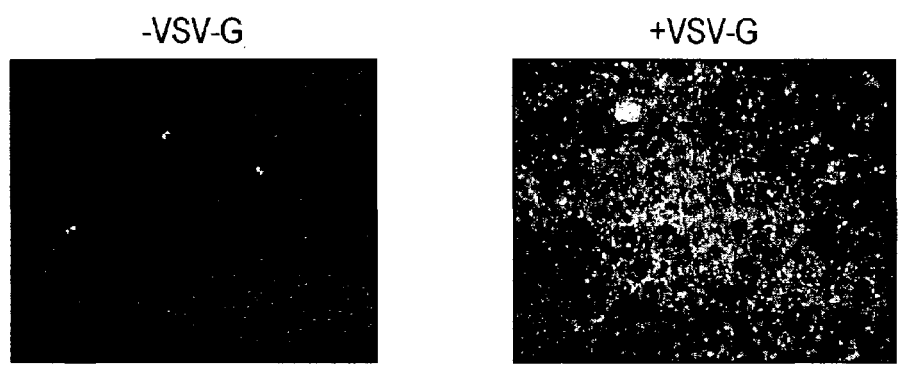

FIG. 38 indicates photographs showing the result where the expression of the GFP gene was tested as an index to determine the presence of production of the pseudo-type virus having VSV-G in its capsid after the infection of VSV-G gene-expressing cells LLCG-L1 with F and HN-deficient Sendai virus comprising the GFP gene.

FIG. 39 indicates photographs showing the result confirming that viruses grown in the VSV-G gene-expressing cells were deficient in F and HN genes by Western analysis of protein in the extract of infected cells.

FIG. 40 indicates photographs showing the result for the observation of GFP-expressing cells under a fluorescence microscope.

Figure 41:
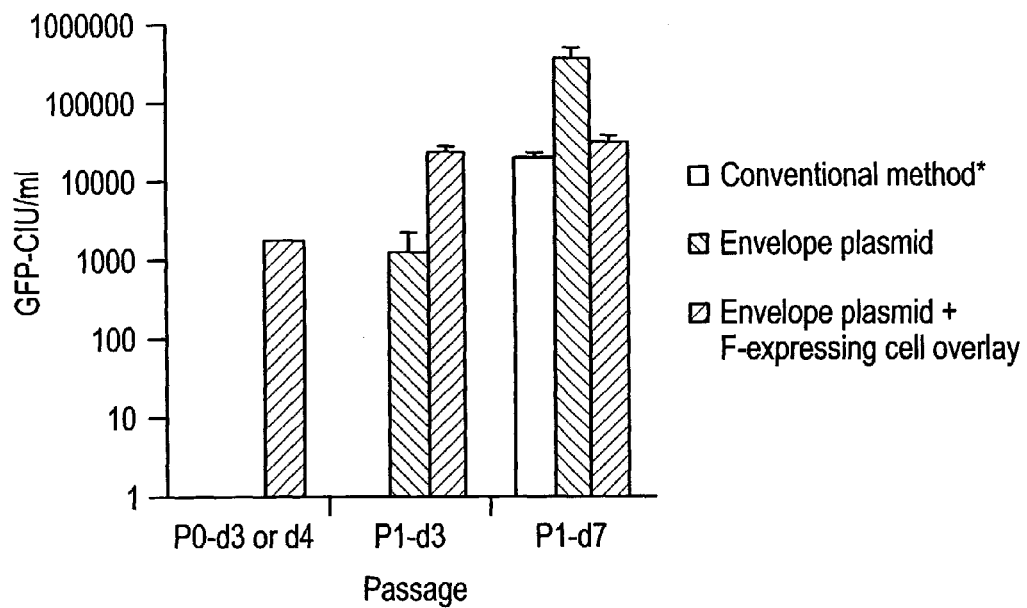

FIG. 41 is a diagram showing the improvement in efficiency for the reconstitution of SeV/ΔF-GFP by the combined used of the envelope-expressing plasmid and cell overlay. Considerable improvement was recognized at d3 to d4 (day 3 to day 4) of P0 (prior to passaging).

Figure 42:
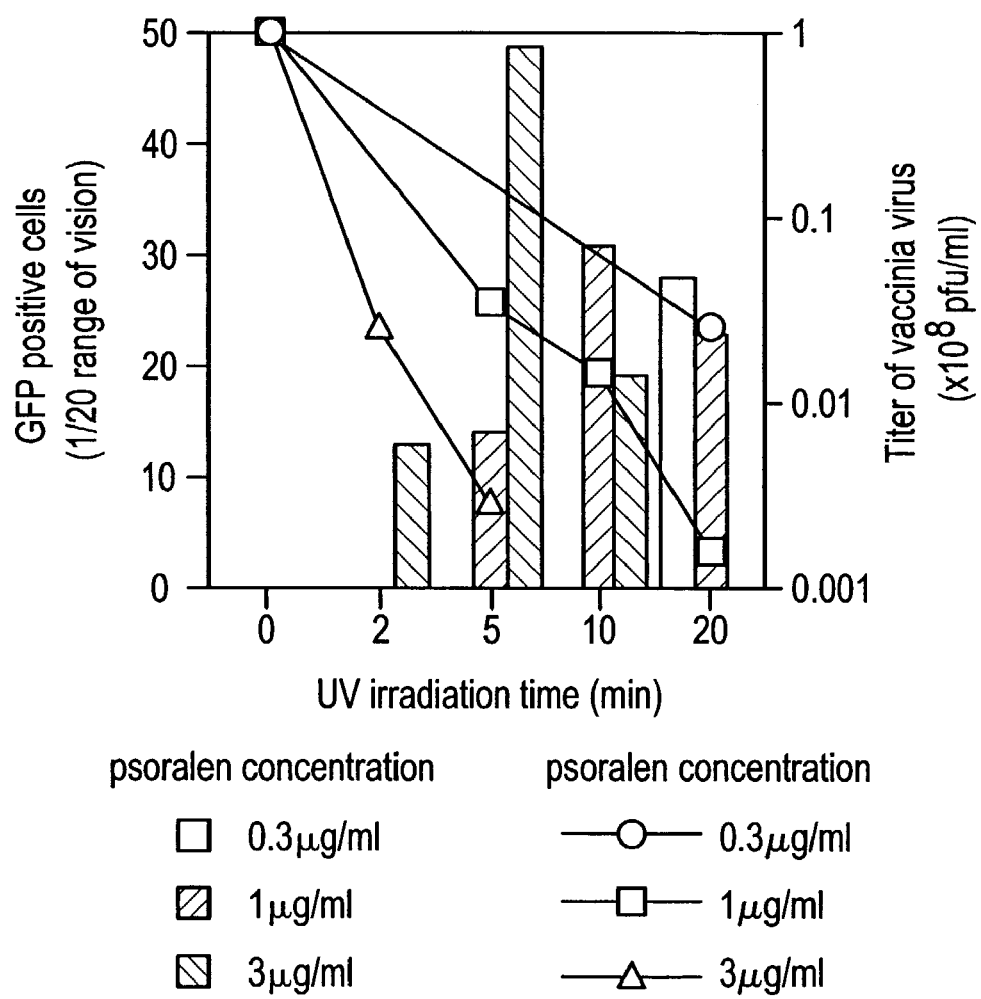

FIG. 42 is a diagram showing the result where treatment conditions were evaluated for the reconstitution of SeV/ΔF-GFP by the combined used of the envelope-expressing plasmid and cell overlay. GFP-positive cells represent the amount of virus reconstituted.

Figure 43:
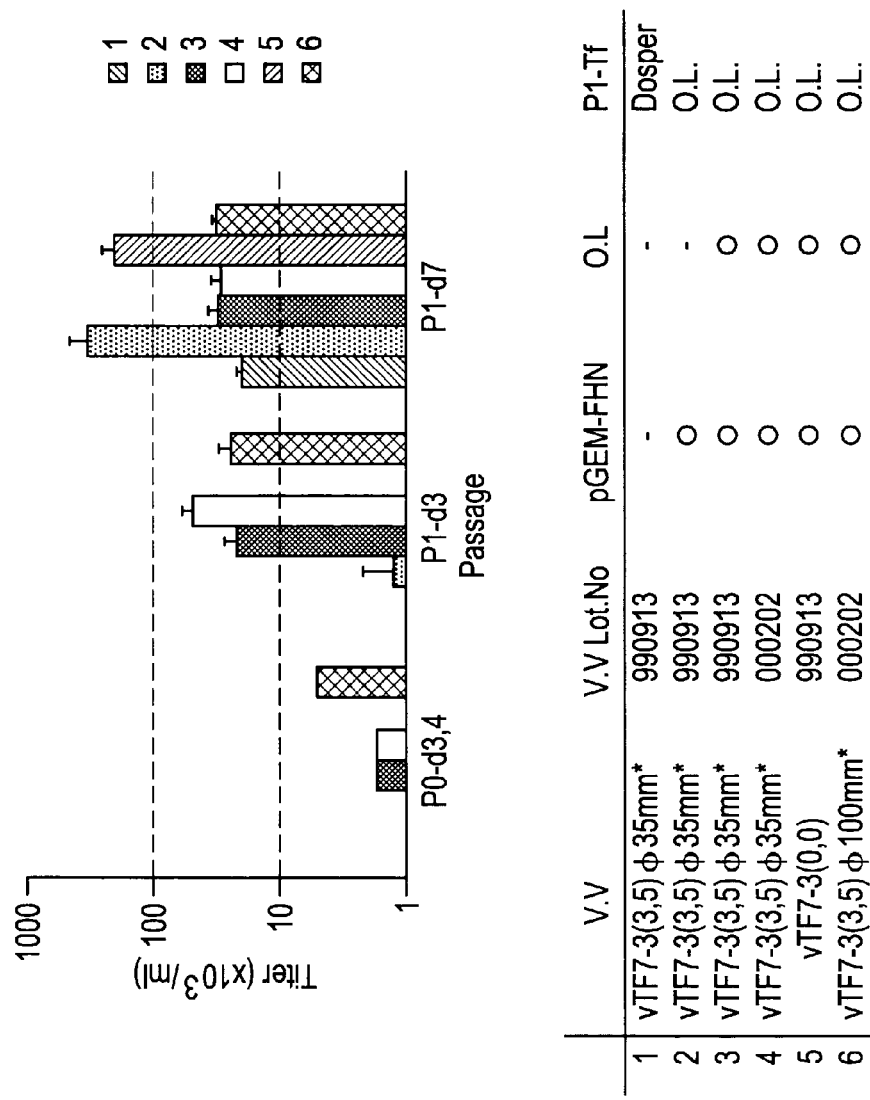

FIG. 43 is a diagram showing the result where the rescue of F-deficient Sendai viruses from cDNA was tested. It shows the improvement in efficiency for the reconstitution of SeV/ΔF-GFP by the combined used of the envelope-expressing plasmid and cell overlay. All the tests were positive on the seventh day. However, the efficiency was evaluated on the third day where the probability of success was midrange.

Figure 44:
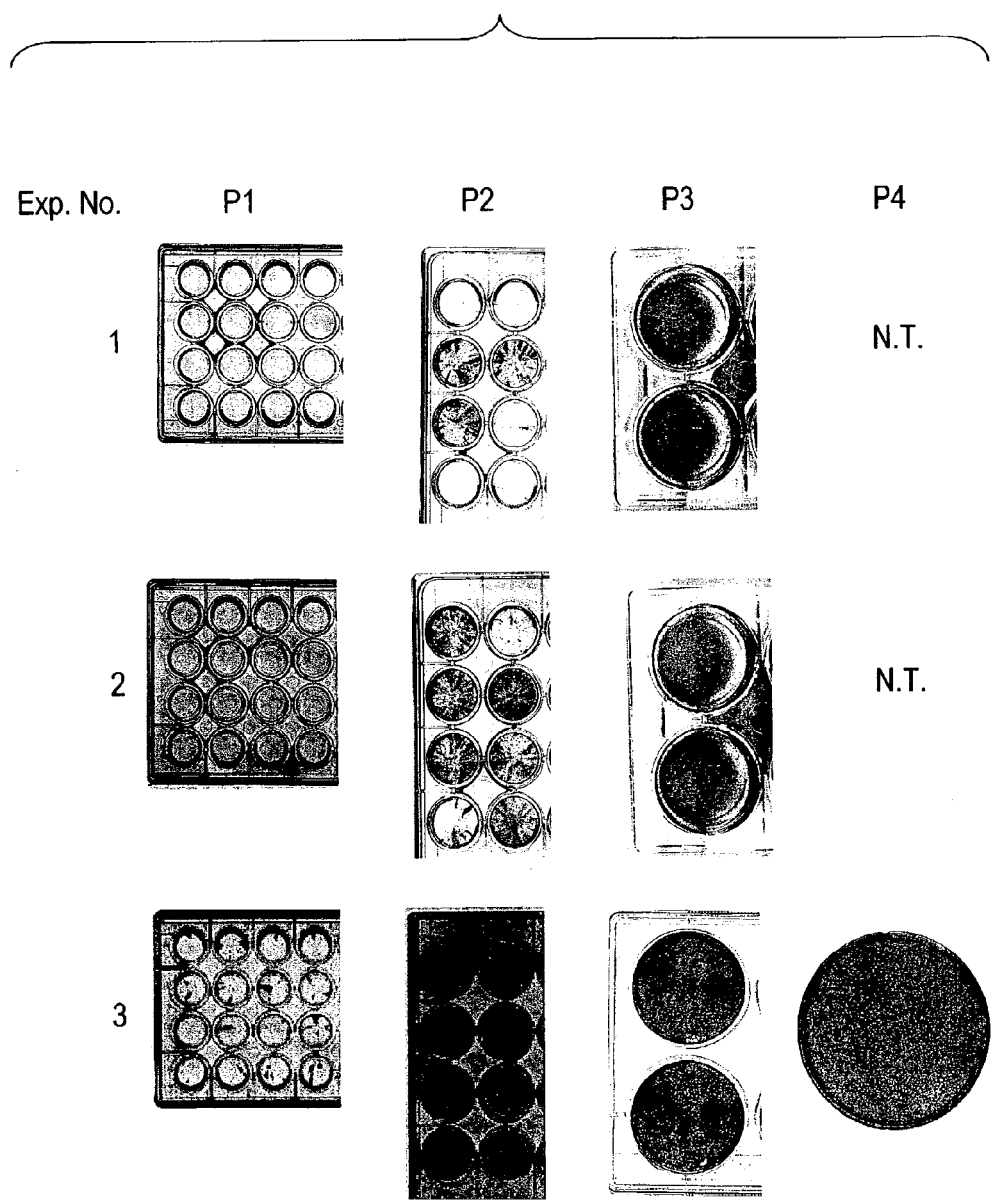

FIG. 44 indicates photographs showing the result of lacZ expression by LacZ-comprising F-deficient Sendai virus vector comprising no GFP.

FIG. 45 indicates diagrams showing subcloning of Sendai virus genomic cDNA fragment (A) and structures of 5 Sendai virus genomic cDNAs constructed with newly introduced NotI site (B).

Figure 46:
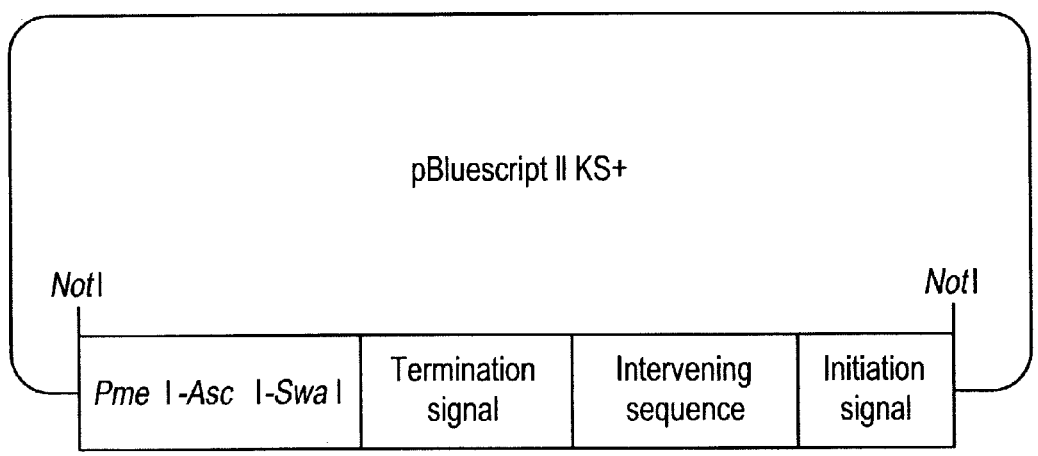

FIG. 46 is a diagram showing structures of plasmids to be used for cloning to add NotI site, transcription initiation signal, intervening sequence, and transcription termination signal into SEAP.

Figure 47:
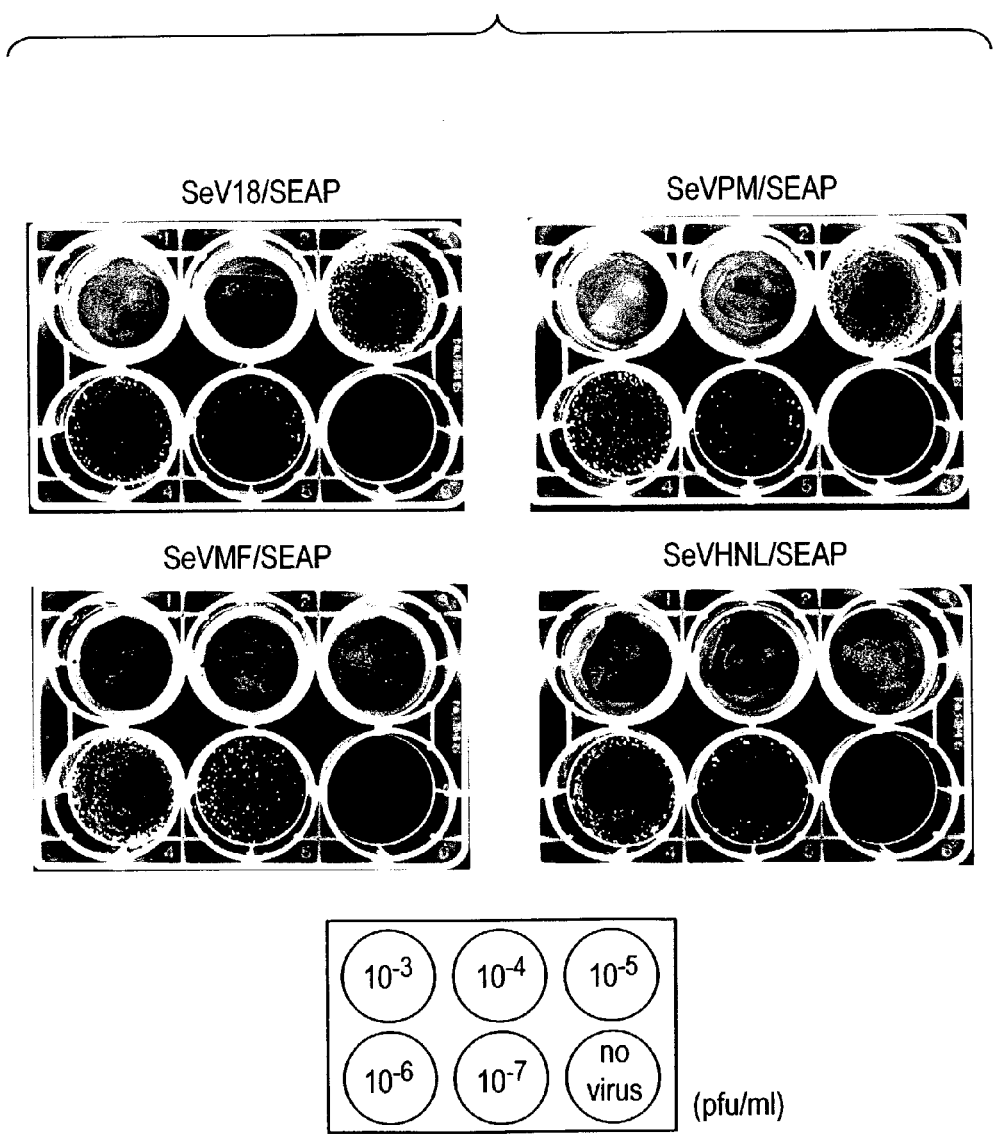

FIG. 47 indicates photographs showing the result of plaque assay of each Sendai virus vector. It shows partial fluorescence image in the plaque assay obtained by LAS1000.

Figure 48:
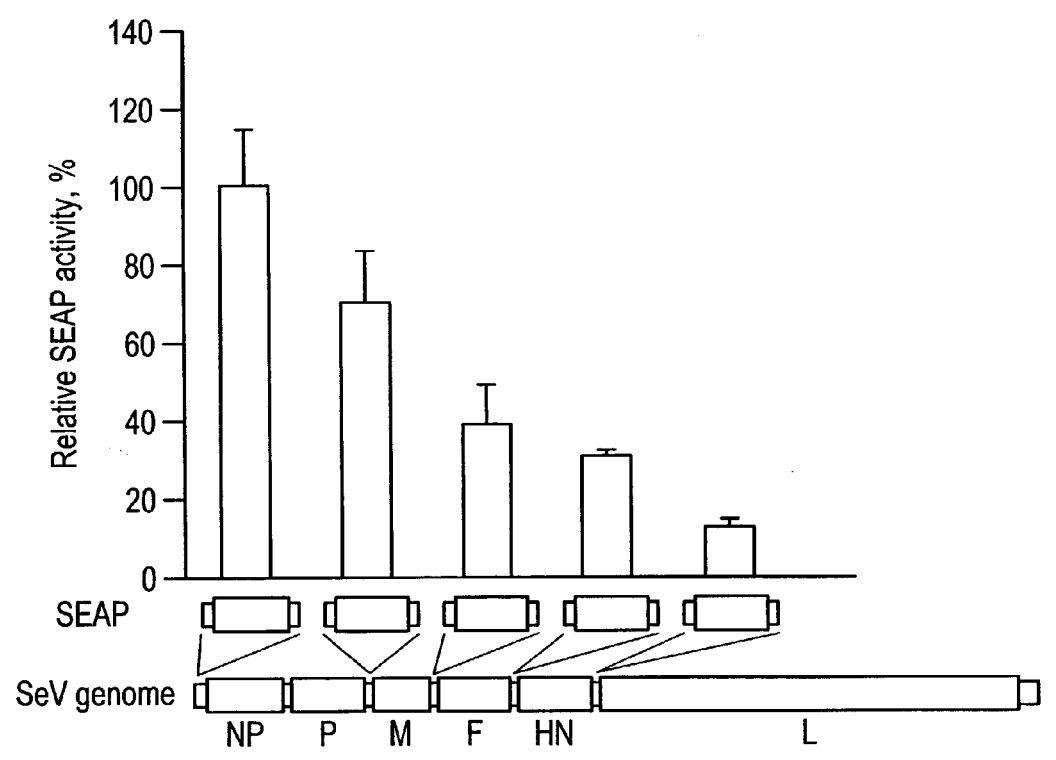

FIG. 48 is a diagram showing the result where altered expression levels of reporter gene (SEAP) were compared with one another among the respective Sendai virus vectors. The data of SeV18+/SEAP was taken as 100 and the respective values were indicated relative to it. It was found that the activity, namely the expression level, was decreased as the SEAP gene was placed more downstream.

Figure 49:
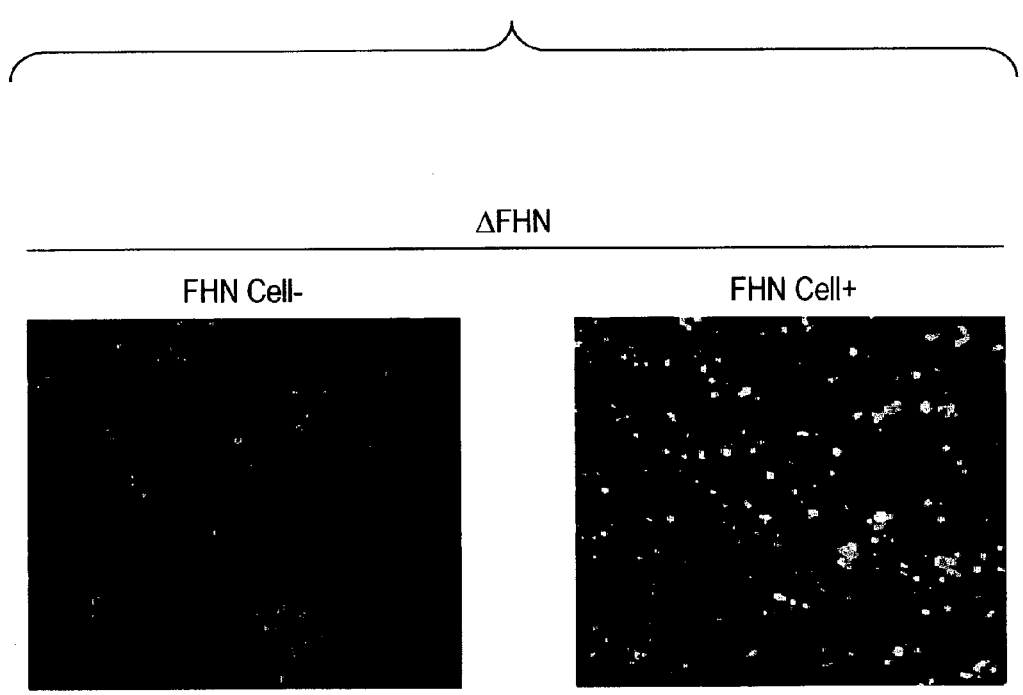

FIG. 49 indicates microscopic photographs showing the expression of GFP in P1 cells co-expressing FHN.

Figure 50:
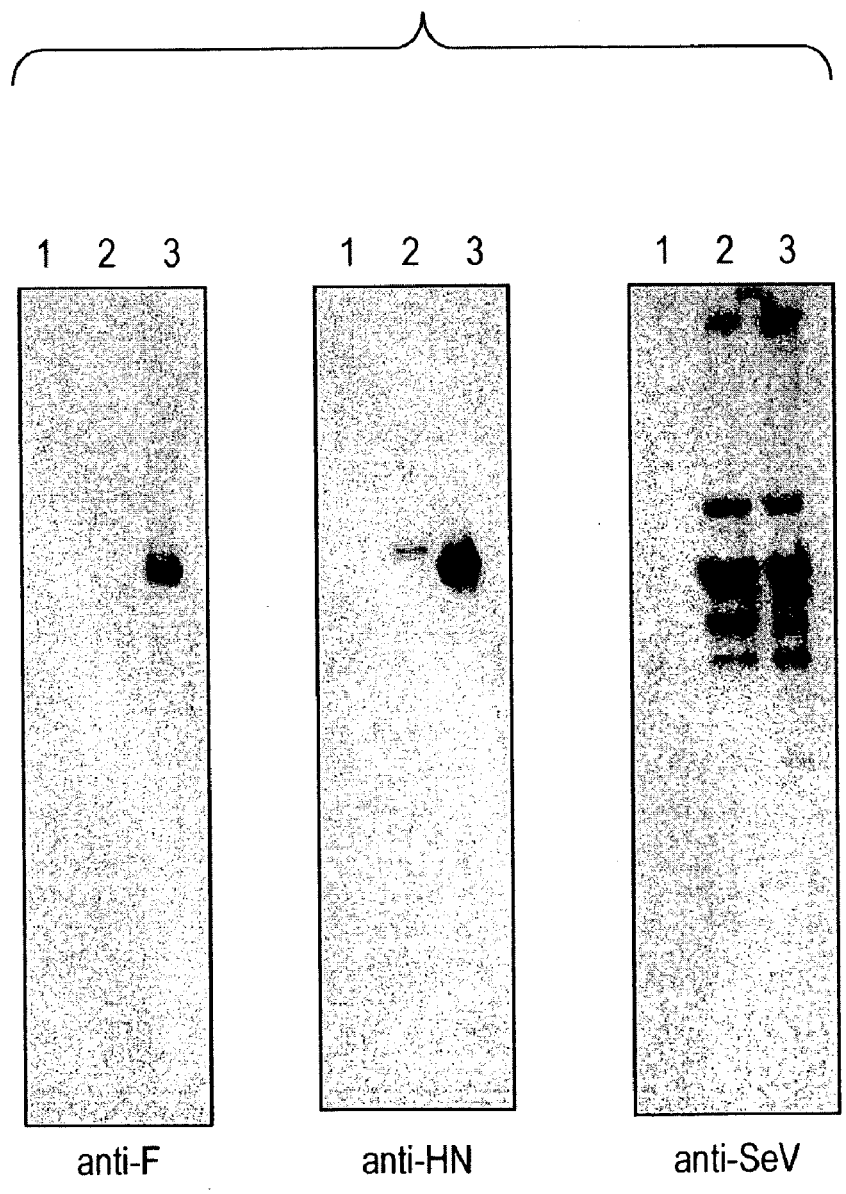

FIG. 50 indicates photographs showing the result of Western blot analysis of the extracts from cells infected with VSV-G pseudo-type SeV/ΔF:GFP using anti-F antibody (anti-F), anti-HN antibody (anti-HN), and anti-Sendai virus antibody (anti-SeV).

FIG. 51 indicates photographs showing GFP fluorescence from F- and HN-deficient cells infected with VSV-G pseudo-type SeV in the presence or absence of a neutralizing antibody (VGV antibody).

Figure 52:
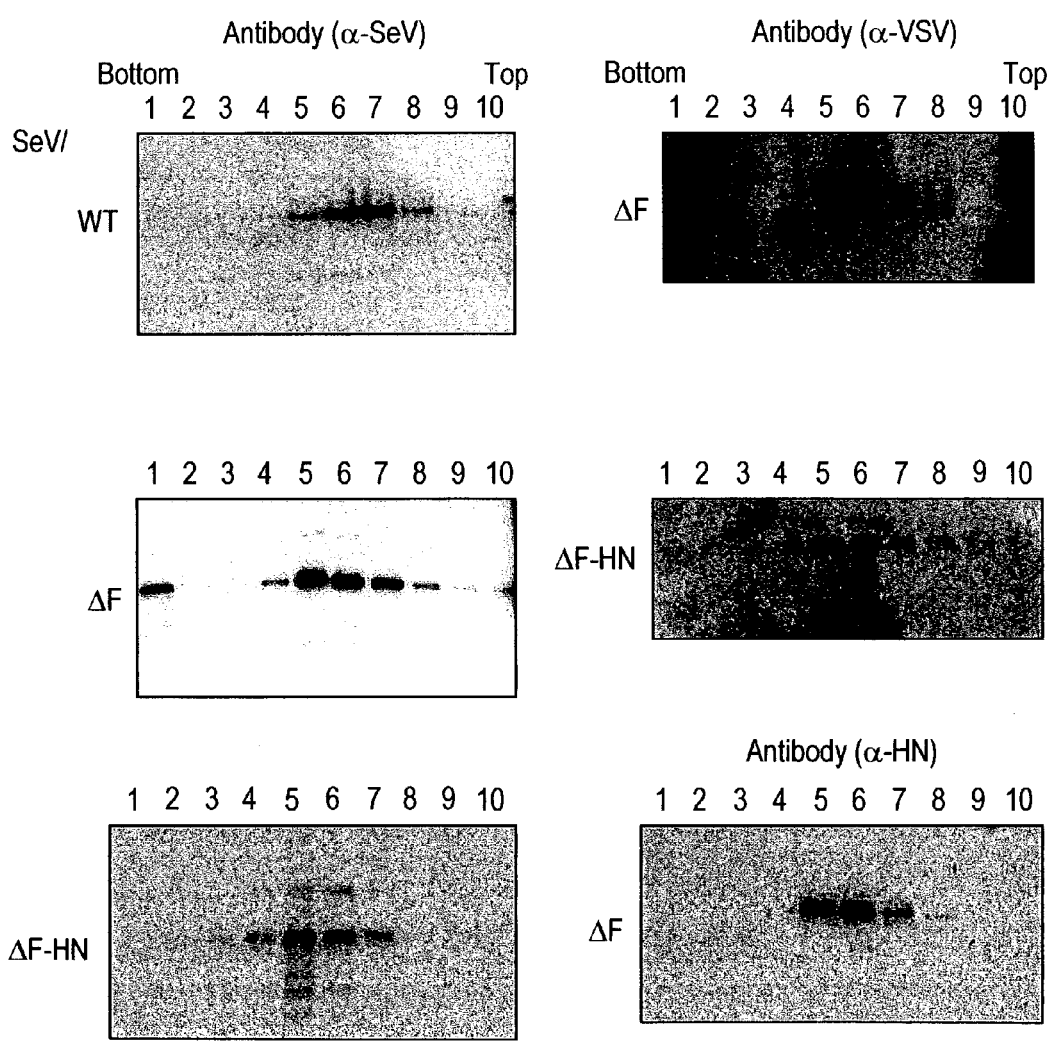

FIG. 52 indicates photographs showing results of Western analysis for VSV-G pseudo-type Sendai viruses having F gene-deficient or F gene- and HN gene-deficient genome, which were fractionated by density gradient ultracentrifugation.

Figure 53:
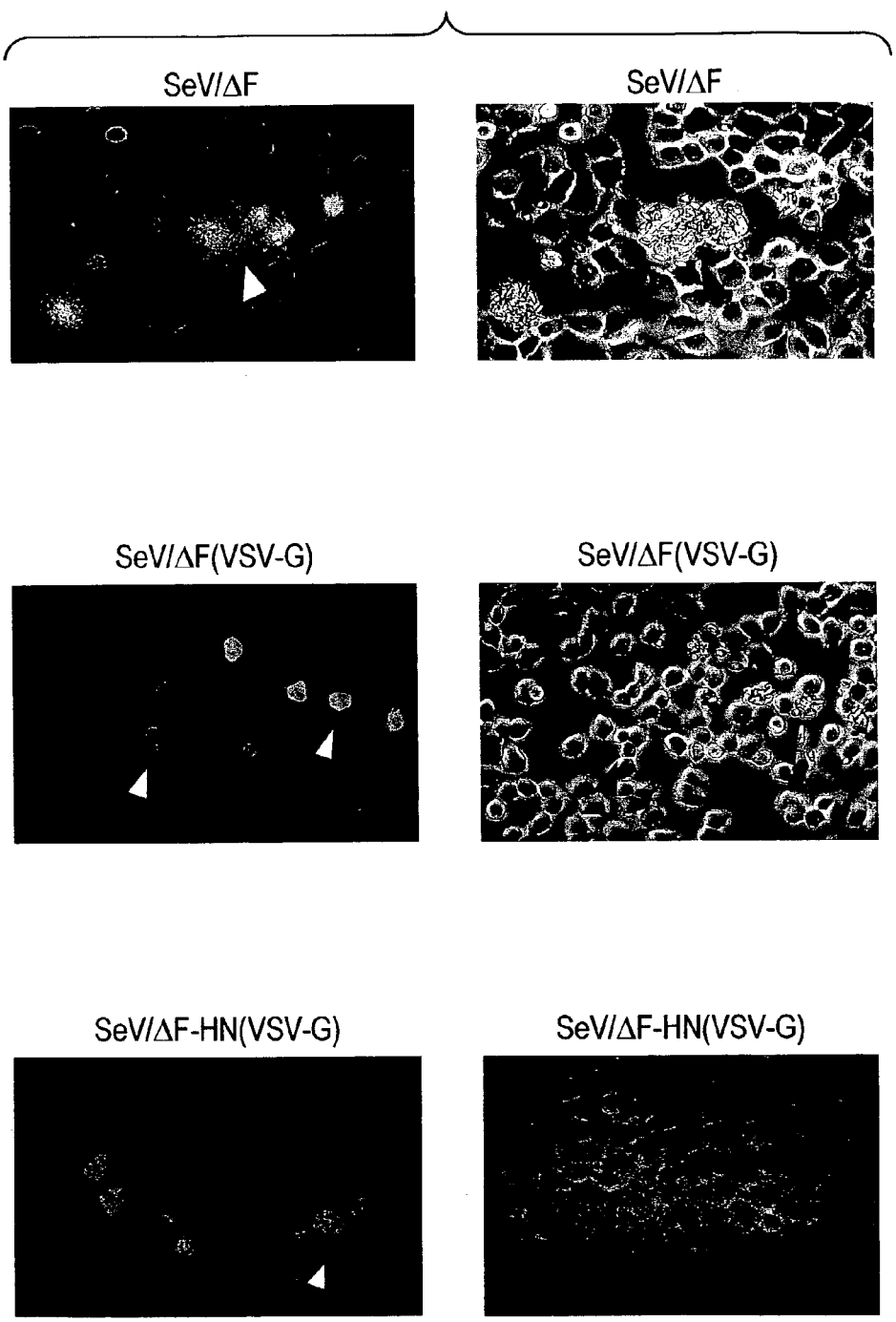

FIG. 53 indicates photographs showing hematoadsorption test mediated with Sendai viruses having F gene-deficient genome, or VSV-G pseudo-type Sendai viruses having F gene-deficient or F gene- and HN gene-deficient genome.

FIG. 54 indicates diagrams showing the specificity of infection to culture cells of Sendai virus having F gene-deficient genome or VSV-G pseudo-type Sendai virus.

FIG. 55 indicates photographs showing the confirmation of the structures of NGF-expressing F-deficient Sendai virus (NGF/SeV/ΔF).

Figure 56:
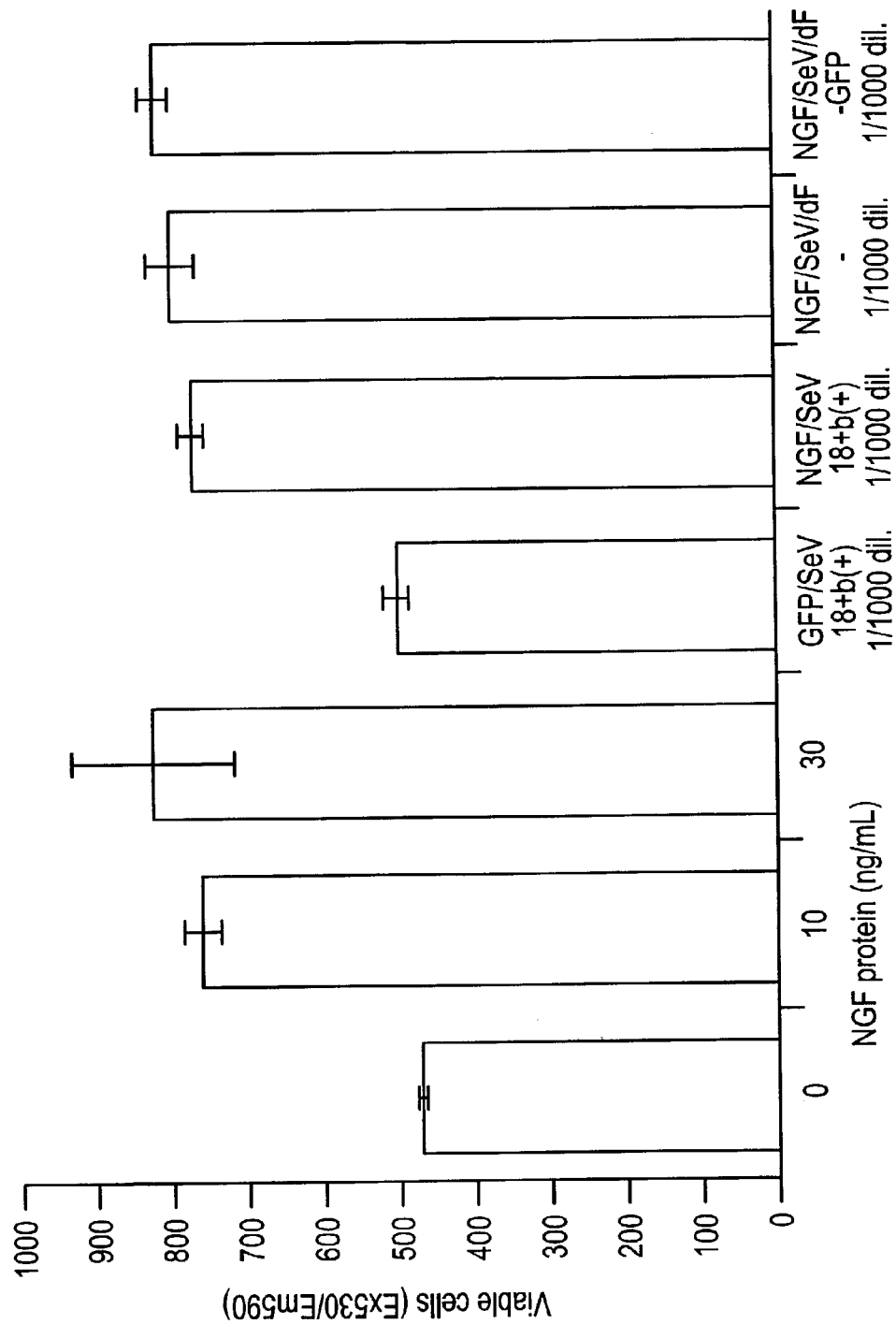
Figure 57A:
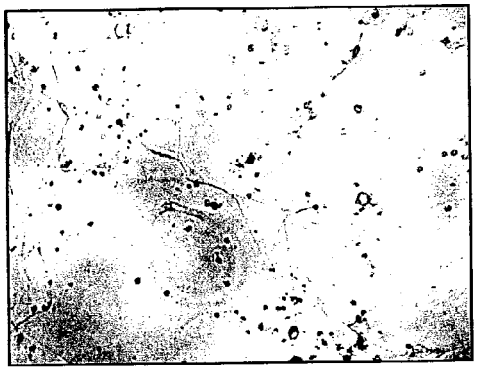
Figure 57B:
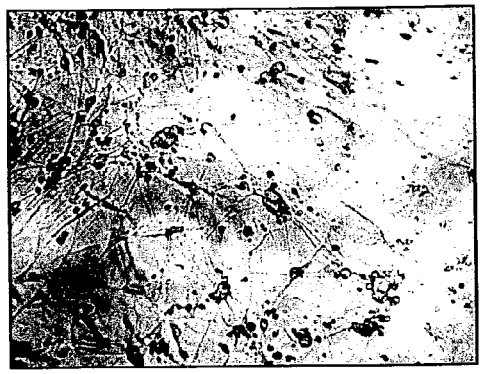
Figure 57C:
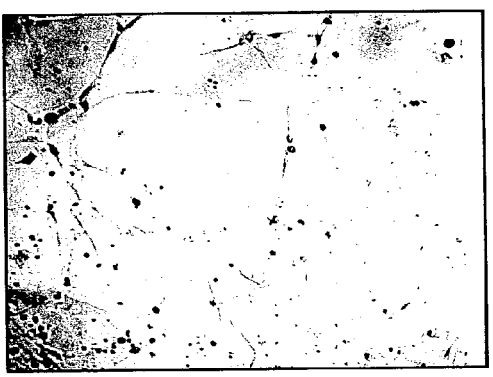
Figure 57D:
Figure 57E:
Figure 57F:

FIG. 56 is a diagram showing the activity of NGF expressed by the NGF-comprising cells infected with F-deficient SeV. With the initiation of culture, diluted supernatant of SeV-infected cells or NGF protein (control) was added to a dissociated culture of primary chicken dorsal root ganglion (DRG)neurons. After three days, the viable cells were counted by using mitochondrial reduction activity as an index (n=3). The quantity of culture supernatant added corresponded to 1000-fold dilution.

FIG. 57 indicates photographs showing the activity of NGF expressed by the NGF-comprising cells infected with F-deficient SeV. With the initiation of culture, diluted supernatant of SeV-infected cells or NGF protein (control) was added to a dissociated culture of primary chicken dorsal root ganglion (DRG) neurons. After three days, the samples were observed under a microscope, A) control (without NGF);
B) addition of NGF protein (10 ng/mL);
C) addition of culture supernatant (100-fold diluted) of NGF/SeV infected cells;
D) addition of culture supernatant (100-fold diluted) of NGF/SeV infected cells;
E) addition of culture supernatant (100-fold diluted) of NGF/SeV/ΔF infected cells, and;
F) addition of culture supernatant (100-fold diluted) of NGF/SeV/ΔF-GFP infected cells.

Figure 58:
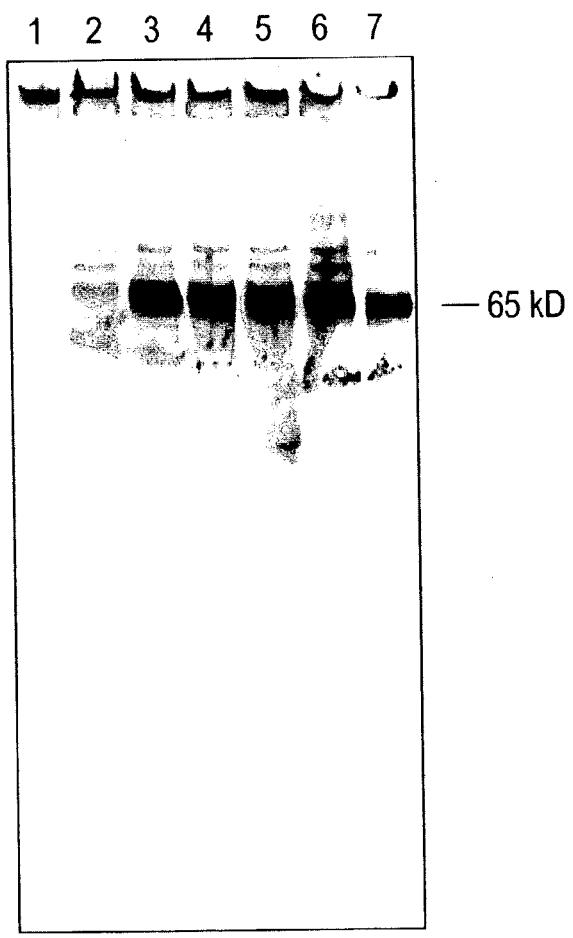

FIG. 58 is a photograph showing moi of AxCANCre and the expression level of F protein.

Figure 59:
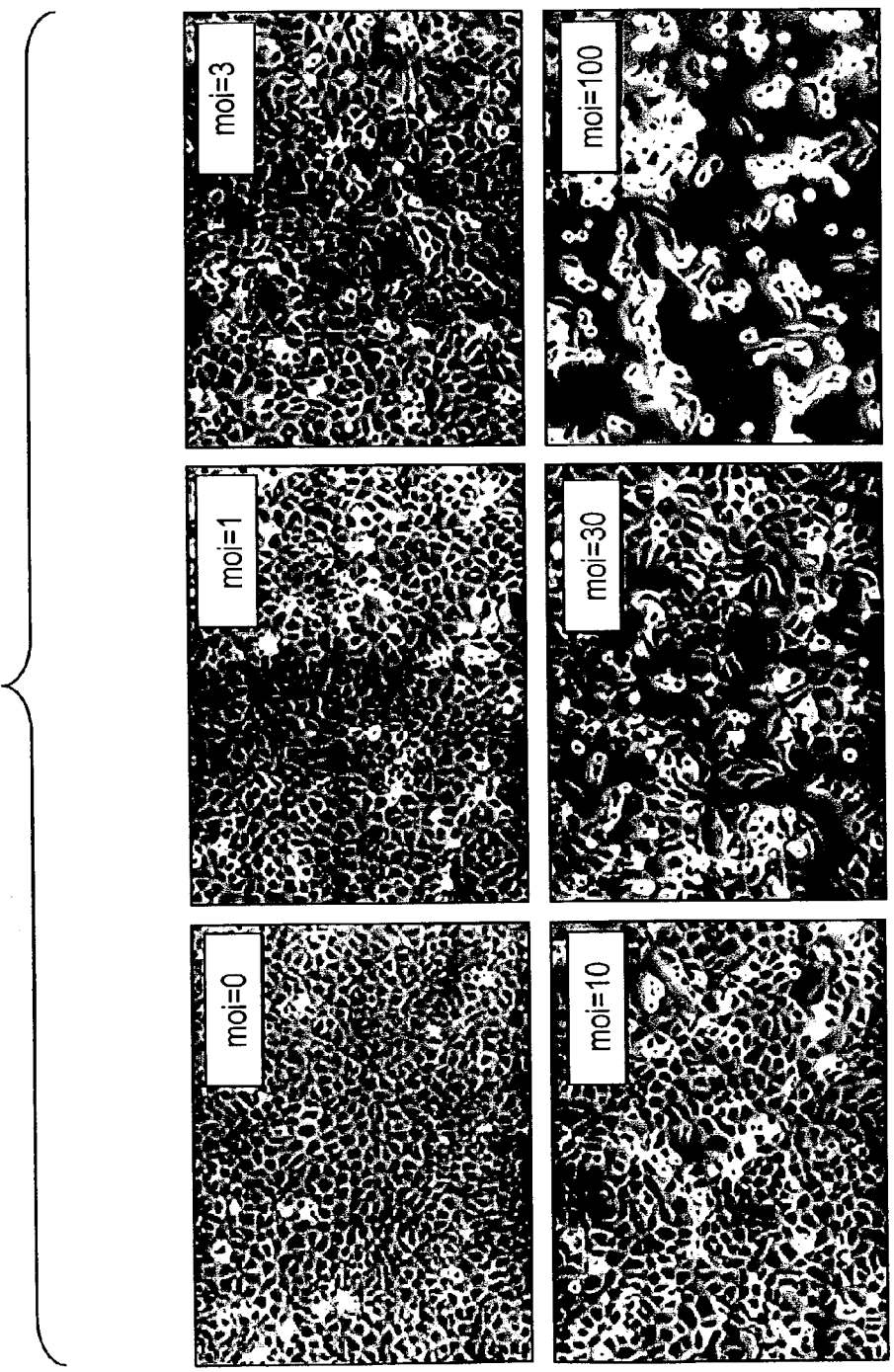

FIG. 59 indicates photographs showing the expression of LLC-MK2/F by AxCANCre.

Figure 60:

FIG. 60 is a photograph showing the durability of expression over the passages.

Figure 61:
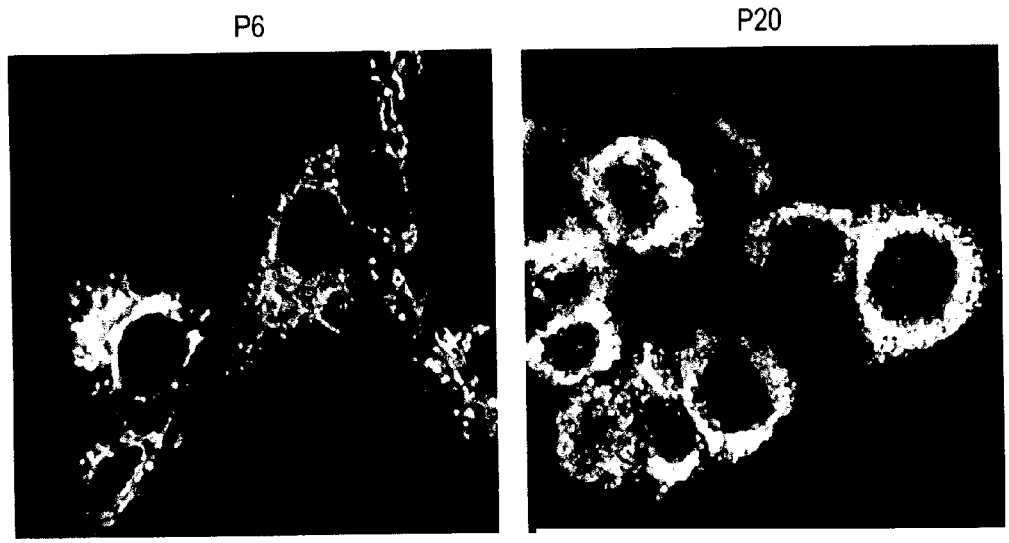

FIG. 61 indicates photographs showing the localization of F protein over the passages.

Figure 62:
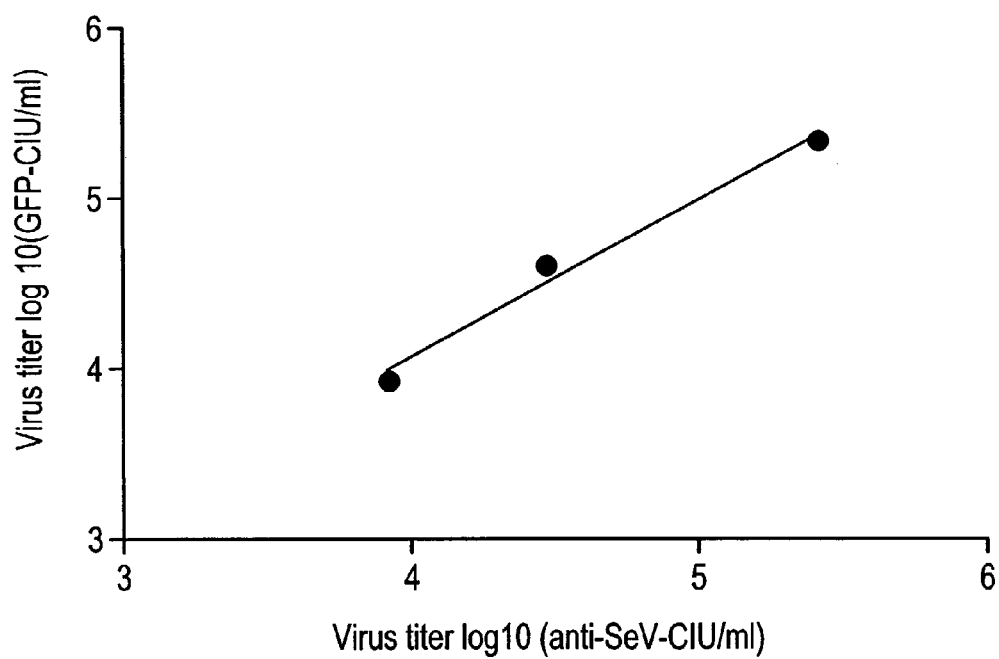

FIG. 62 is a diagram showing the correlation between GFP-CIU and anti-SeV-CIU.

Figure 63:
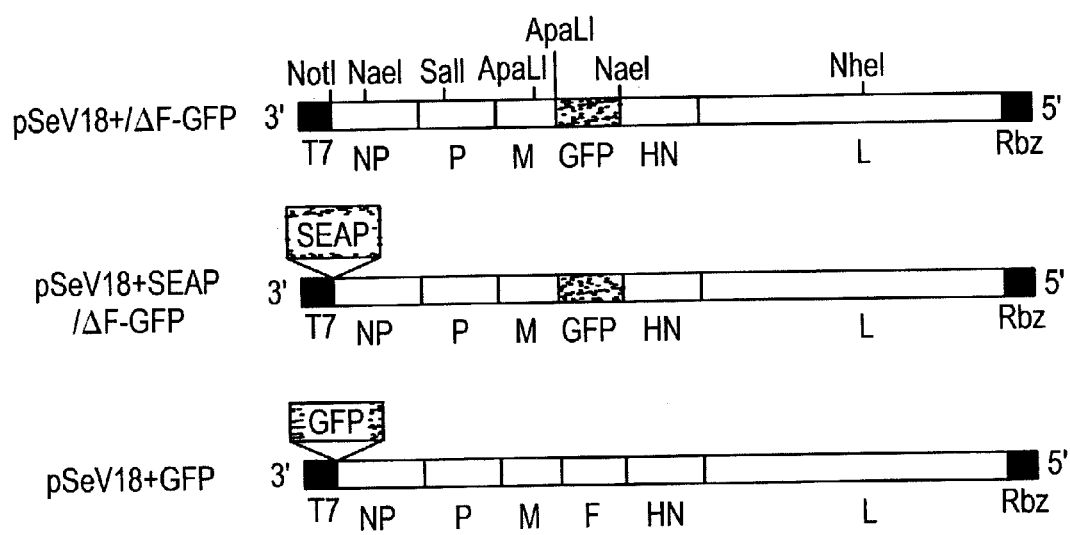

FIG. 63 indicates a diagram showing structures of genes encoding F-deficient SeV and additional type SeV genomes having GFP and/or SEAP genes.

FIG. 64 indicates photographs showing micrographs showing the expression of GFP after cells continuously expressing F protein (LLC-MK2/F7/A) were infected with SeV18+/ΔF-GFP and cultured for 6 days at 32° C. or 37° C.

Figure 65:
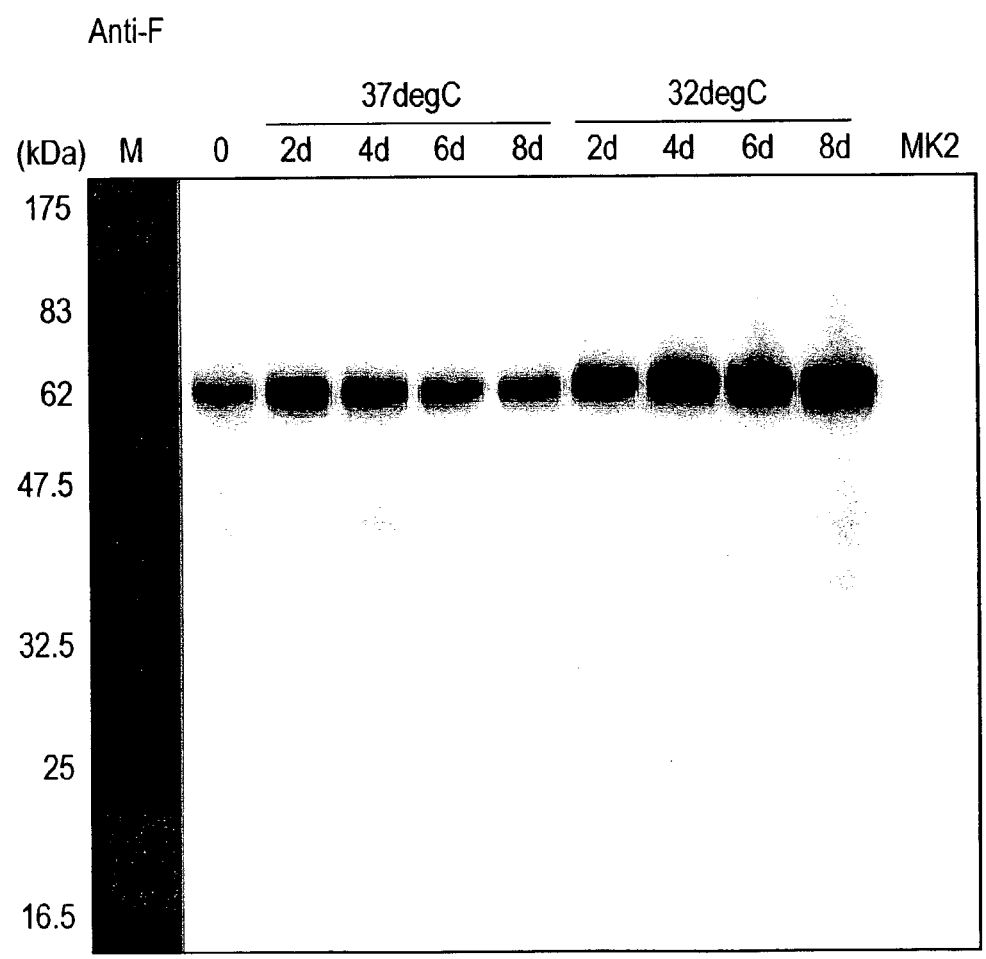

FIG. 65 indicates a photograph showing the result that was obtained by culturing, at 32° C. or 37° C. in serum-free MEM containing trypsin, cells continuously expressing SeV-F protein (LLC-MK2/F7/A) and by semi-quantitatively measuring the expression level of F protein by Western-blotting over time.

Figure 66:
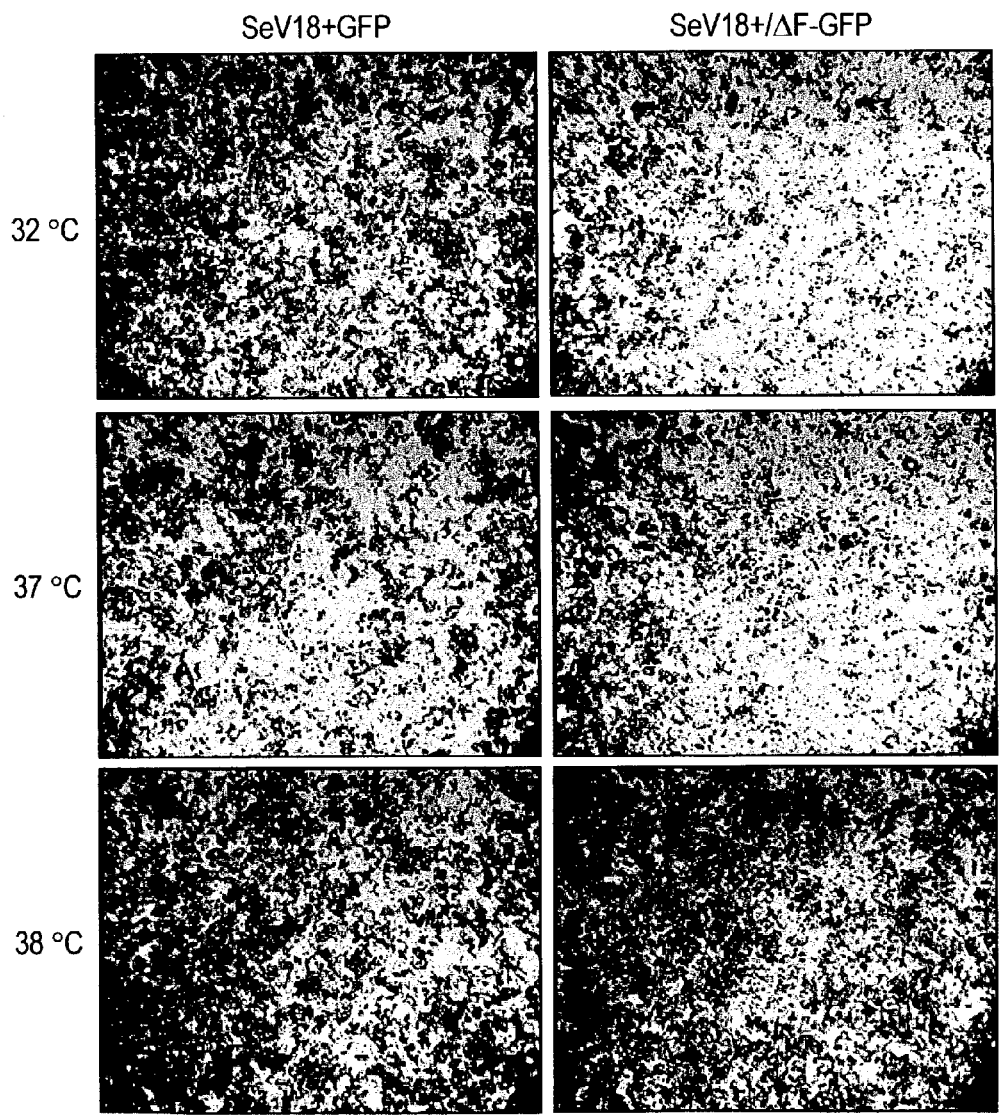

FIG. 66 indicates photographs showing micrographs showing the expression of GFP after LLC-MK2 cells were infected with SeV18+GFP or SeV18+/ΔF-GFP at m.o.i.=3 and cultured for 3 days at 32° C., 37° C., or 38° C.

Figure 67:
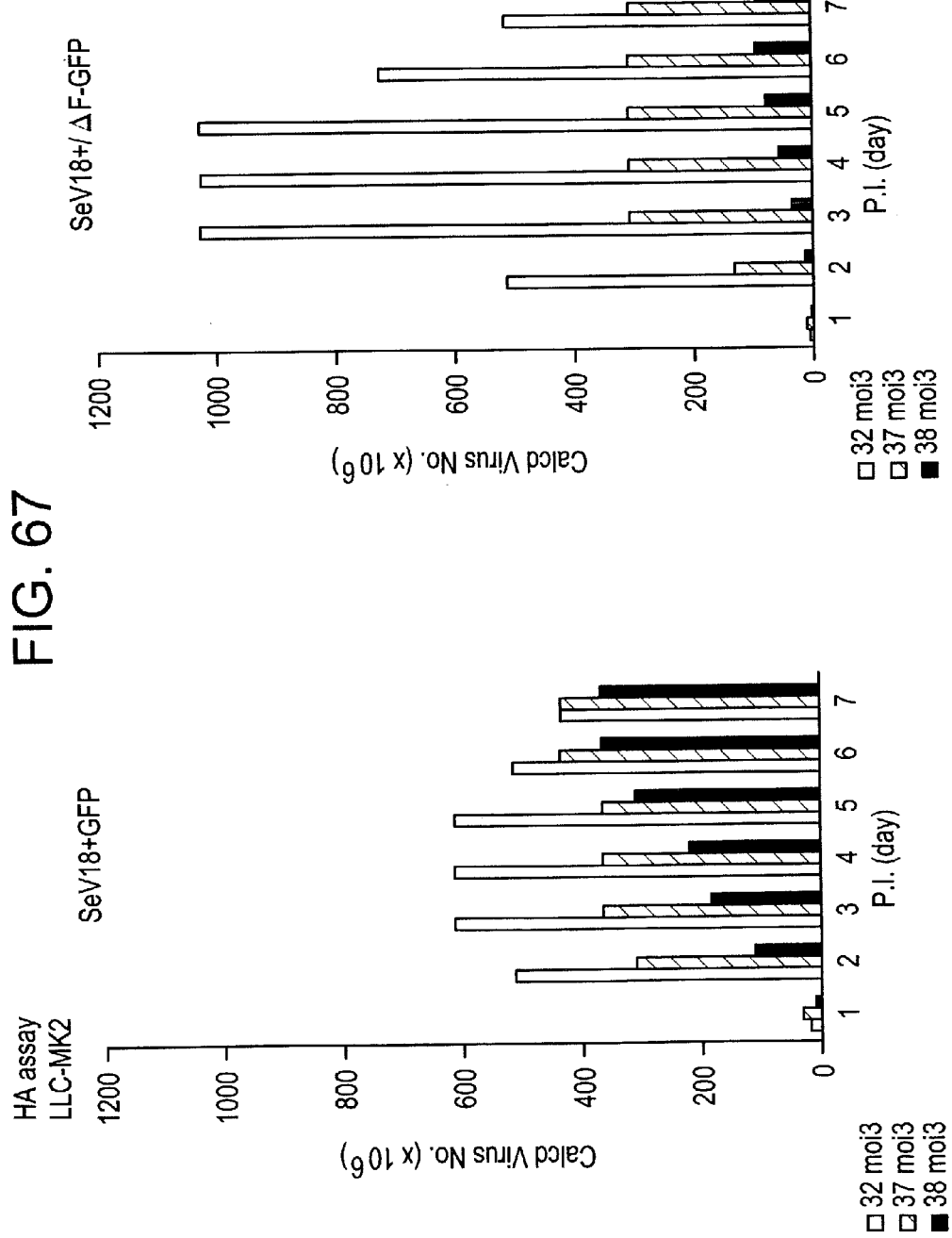

FIG. 67 indicates diagrams showing hemagglutination activity (HA activity) of the culture supernatants that were sampled over time (the media were exchanged for new ones at the same time) after LLC-MK2 cells were infected with SeV18+GFP or SeV18+/ΔF-GFP at m.o.i.=3 and cultured at 32° C., 37° C., or 38° C.

Figure 68:
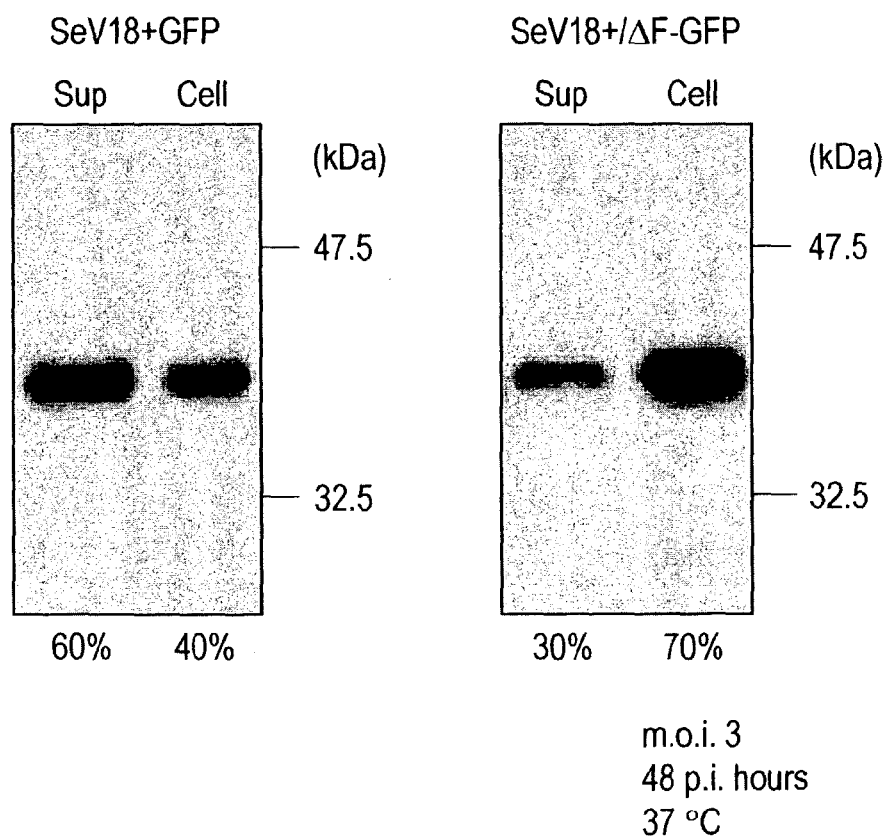

FIG. 68 indicates photographs showing ratios of M protein in cells to that in virus-like particles. The rations were measured by Western-blotting with anti-M protein antibody by recovering the culture supernatants and the cells that were obtained after LLC-MK2 cells were infected with SeV18+GFP or SeV18+/ΔF-GFP at m.o.i.=3 and cultured for 2 days at 37° C. and by using 1/10 equivalents of 1 well of 6-well-plate culture per lane.

Figure 69:
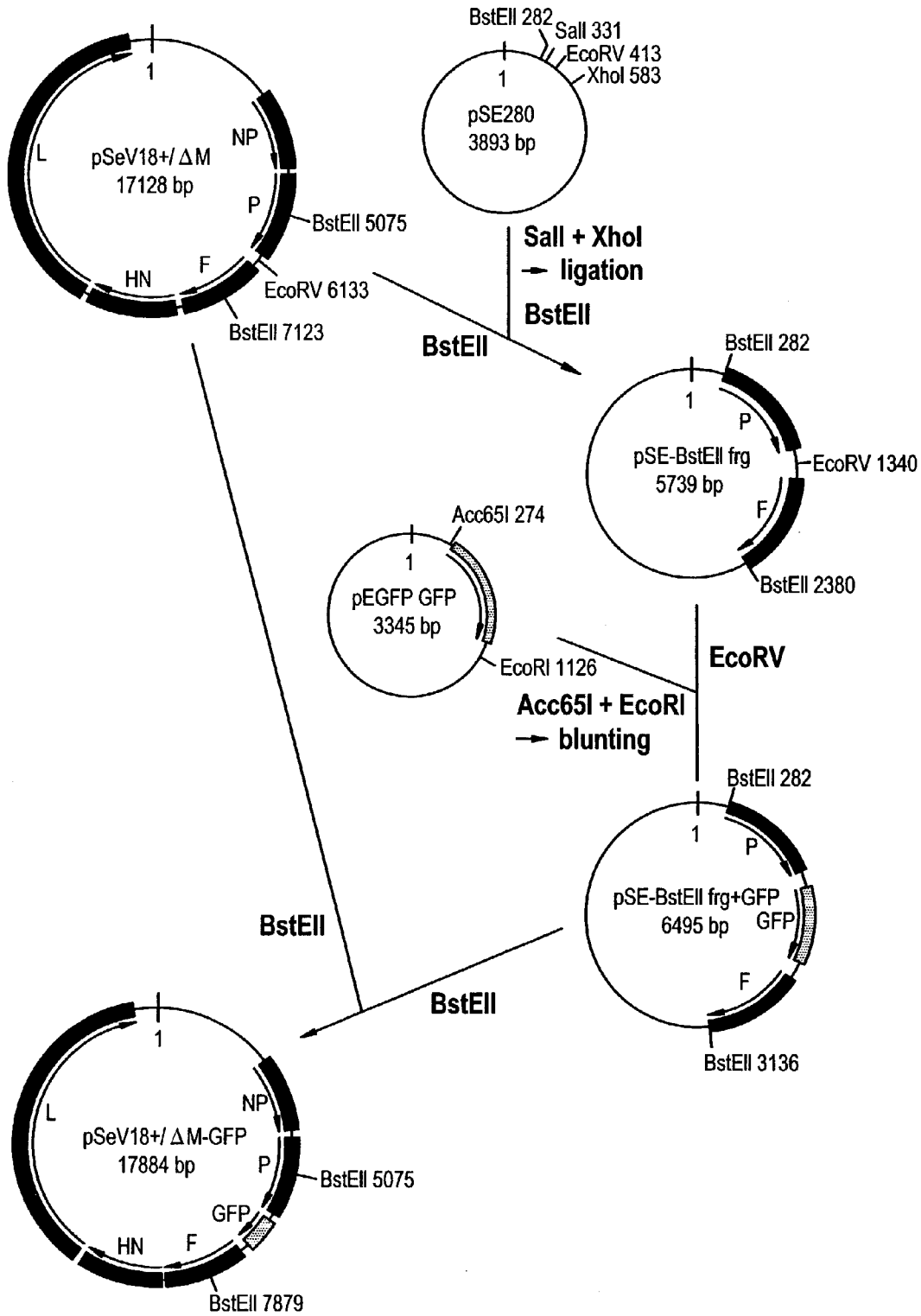

FIG. 69 indicates a diagram showing the construction scheme for M-deficient SeV genome cDNA having an EGFP gene.

Figure 70:
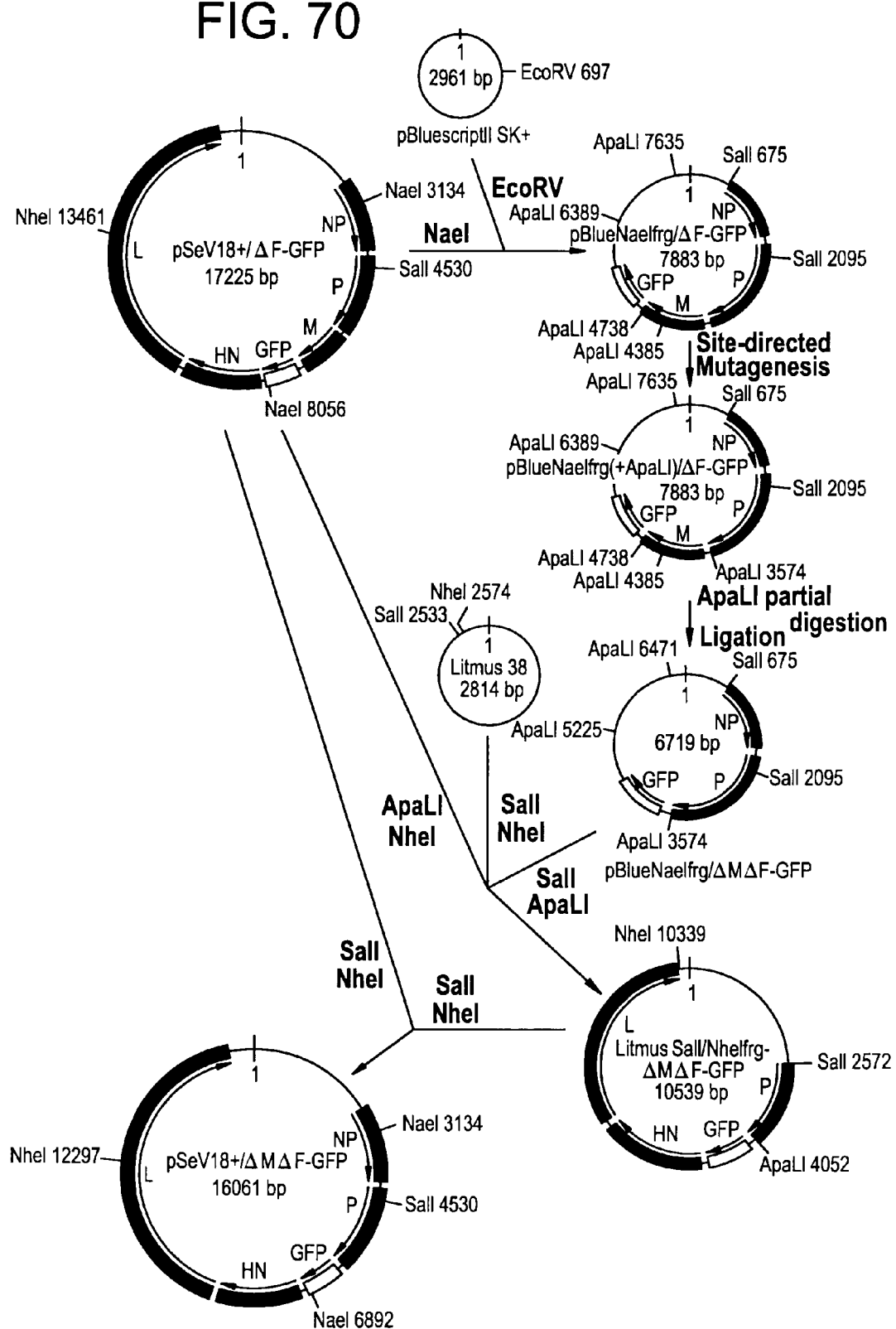

FIG. 70 indicates a diagram showing the construction scheme for both F- and M-deficient SeV genome cDNA.

Figure 71:
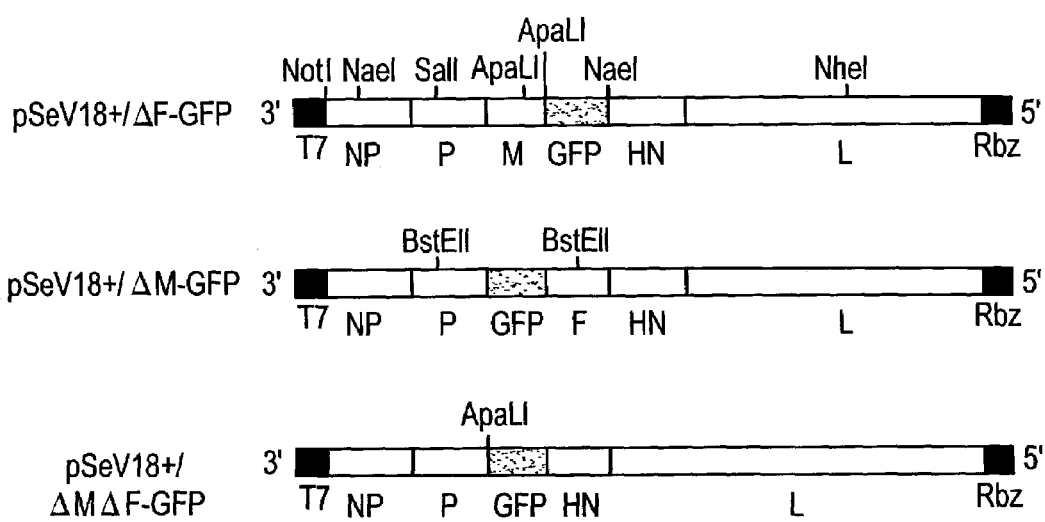

FIG. 71 indicates a diagram showing structures of the constructed F- and/or M-deficient SeV genes.

Figure 72:
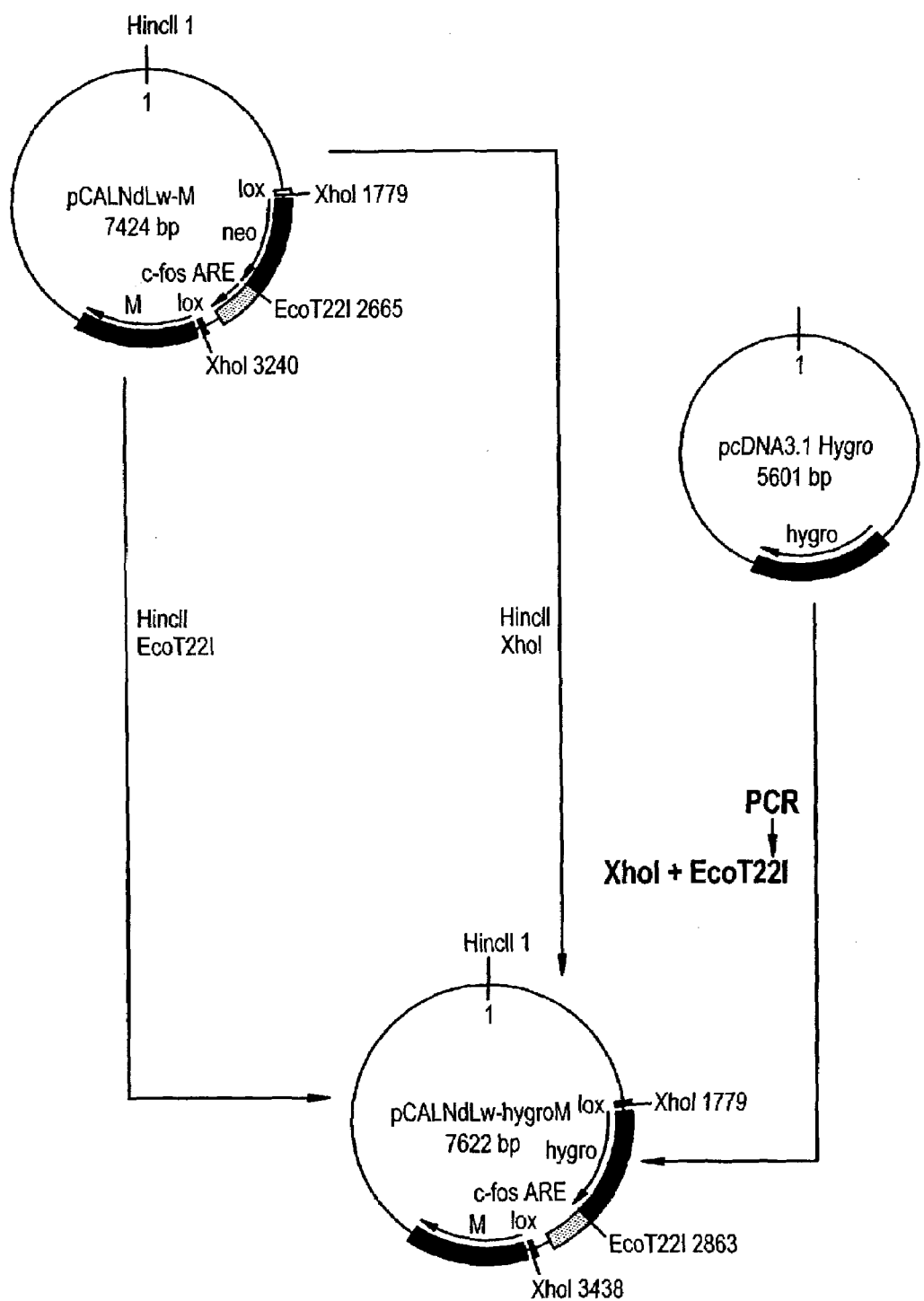

FIG. 72 indicates a diagram showing the construction scheme for the M gene-expressing plasmid having a hygromycin resistance gene.

Figure 73:
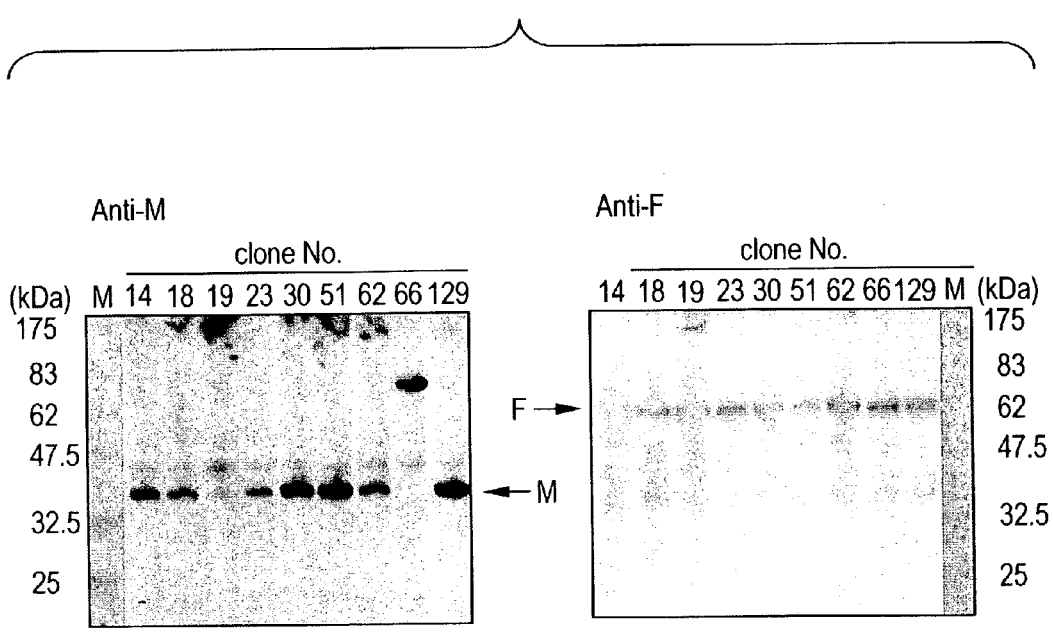

FIG. 73 indicates photographs showing the result that was obtained by semi-quantitatively comparing the expression of M and F proteins by Western-blotting after cells inducibly expressing the cloned M (and F) proteins were infected with Cre DNA recombinase-expressing recombinant adenovirus (AxCANCre).

Figure 74:
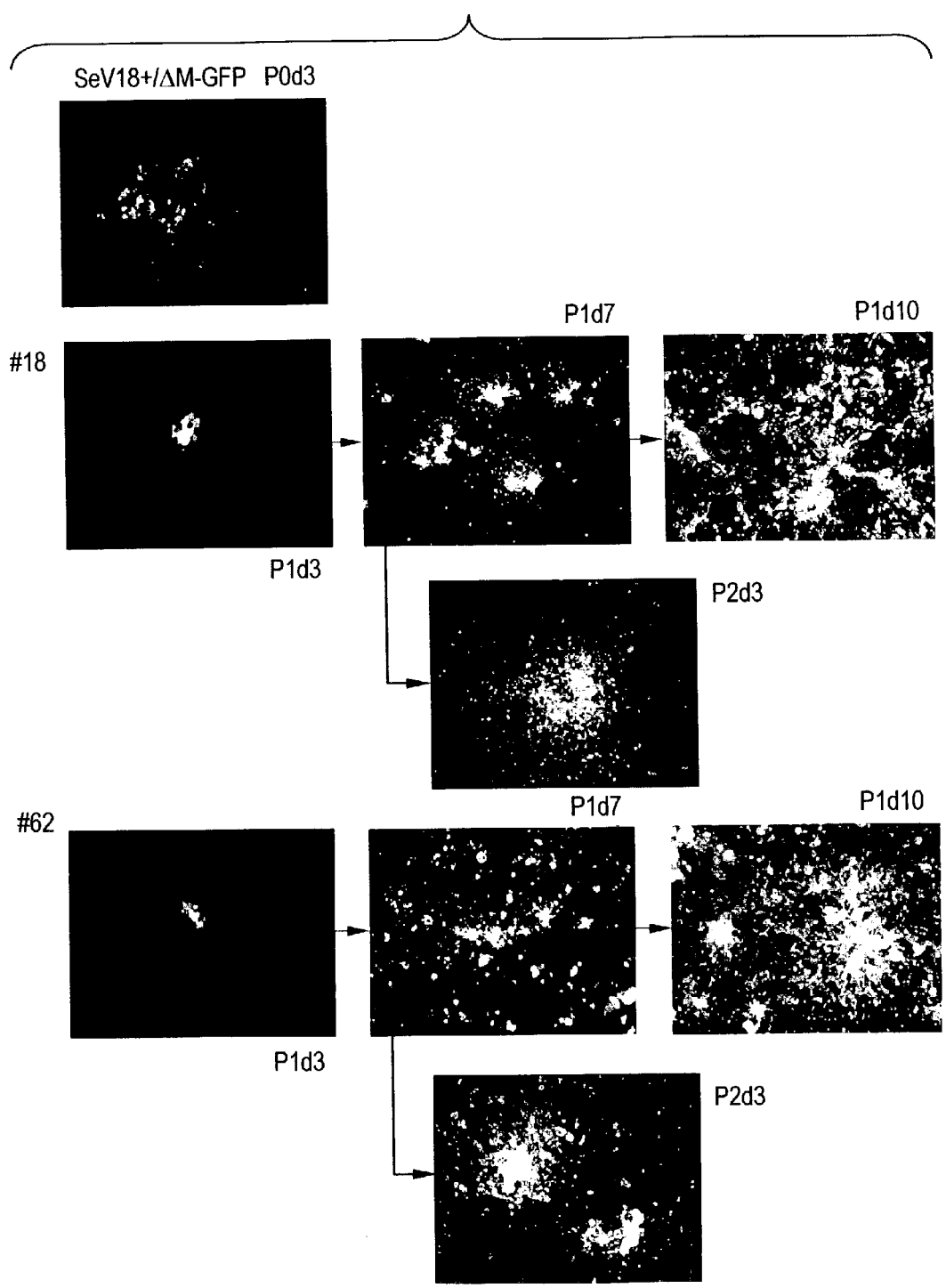

FIG. 74 indicates photographs showing viral reconstitution of M-deficient SeV (SeV18+/ΔM-GFP) using helper cell (LLC-MK2/F7/M) clones #18 and #62.

Figure 75:
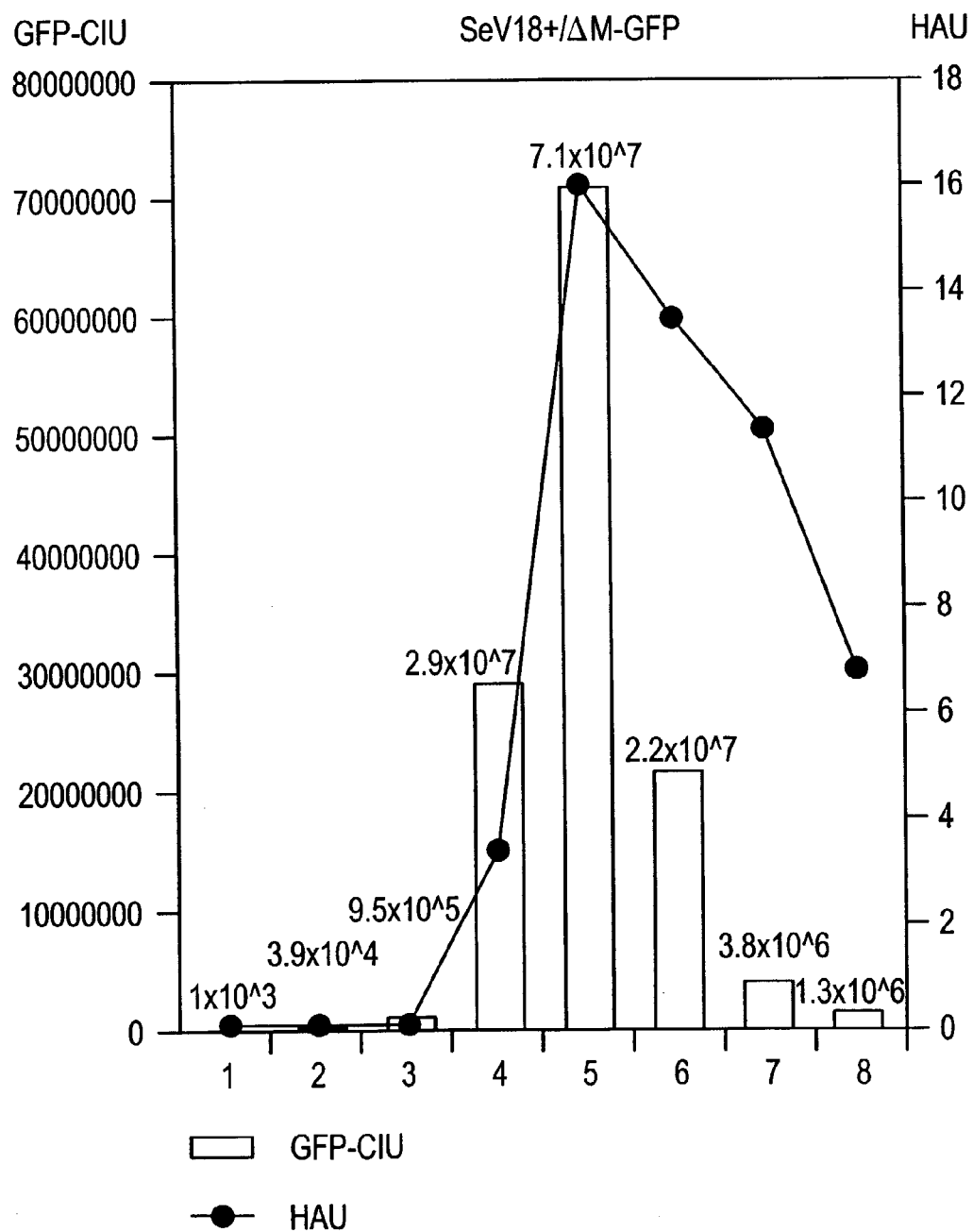

FIG. 75 indicates a diagram showing the virus productivity of SeV18+/ΔM-GFP (time courses of CIU and HAU).

Figure 76:
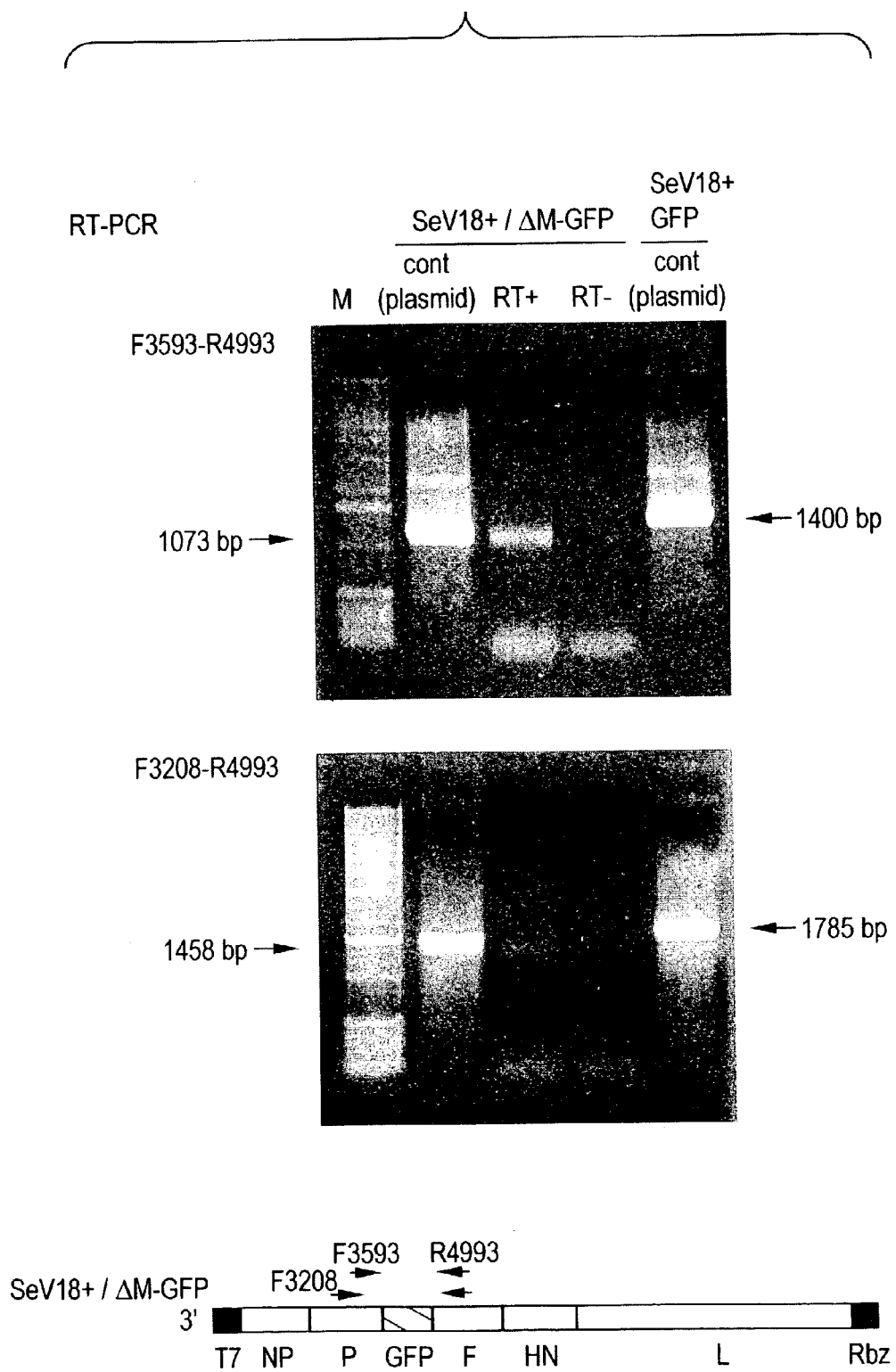

FIG. 76 indicates photographs and a diagram showing the result of RT-PCR for confirming the gene structure in virions of SeV18+/ΔM-GFP.

Figure 77:
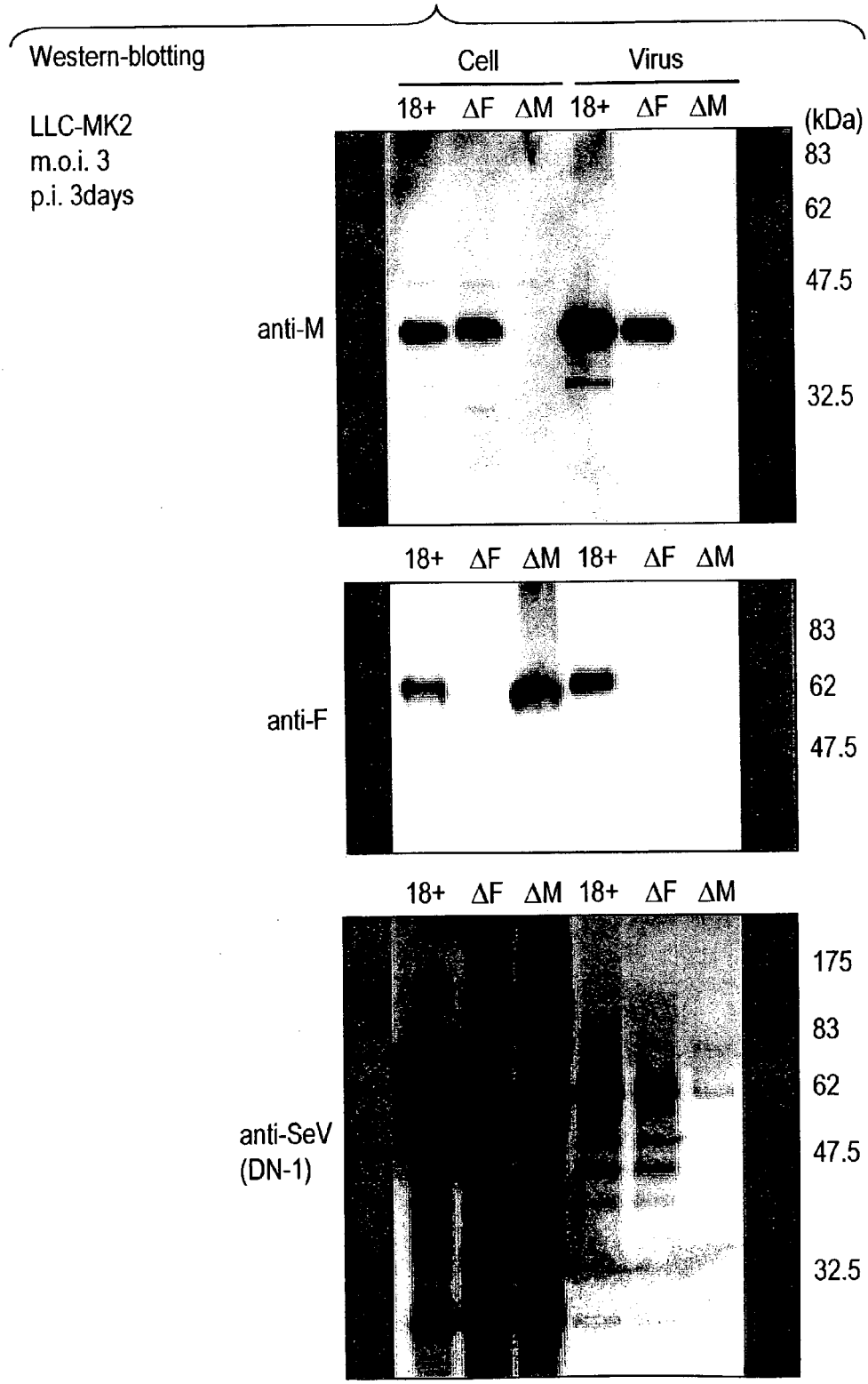

FIG. 77 indicates photographs showing the result of comparison between SeV18+GFP and SeV18+/ΔF-GFP that was obtained, to confirm the virus structure of SeV18+/ΔM-GFP, by carrying out Western-blotting for virus proteins in infected LLC-MK2 cells and the culture supernatants.

Figure 78:
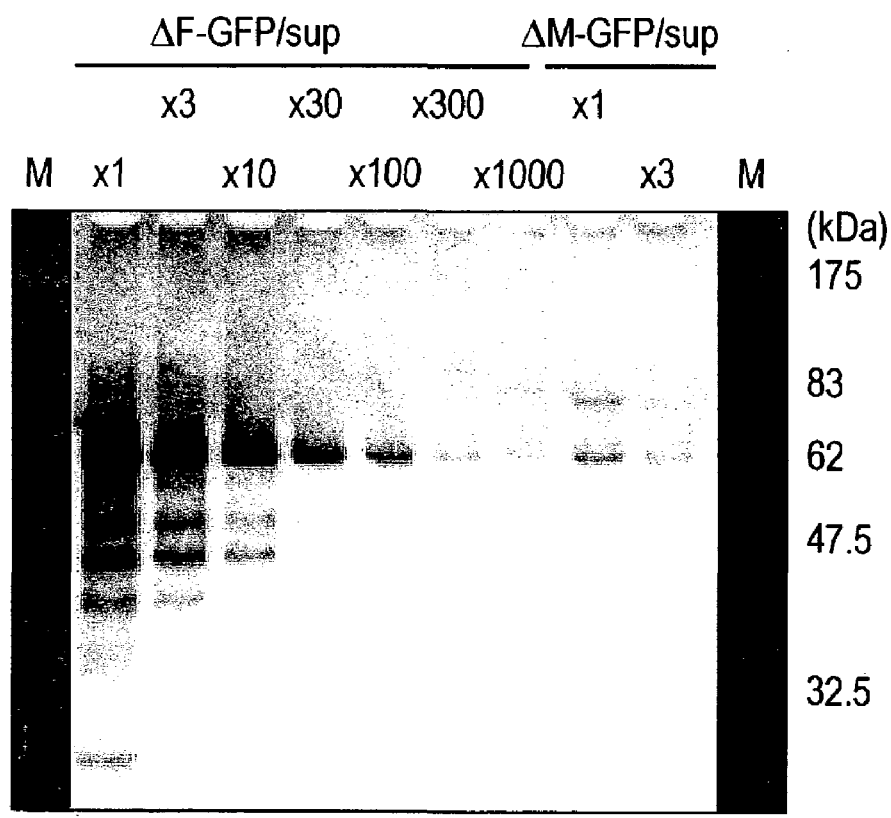

FIG. 78 indicates a photograph showing the quantitative comparison (by preparing dilution series and by carrying out Western-blotting) of virus-derived proteins in the culture supernatants of LLC-MK2 cells infected with SeV18+/ΔM-GFP and SeV18+/ΔF-GFP.

Figure 79:
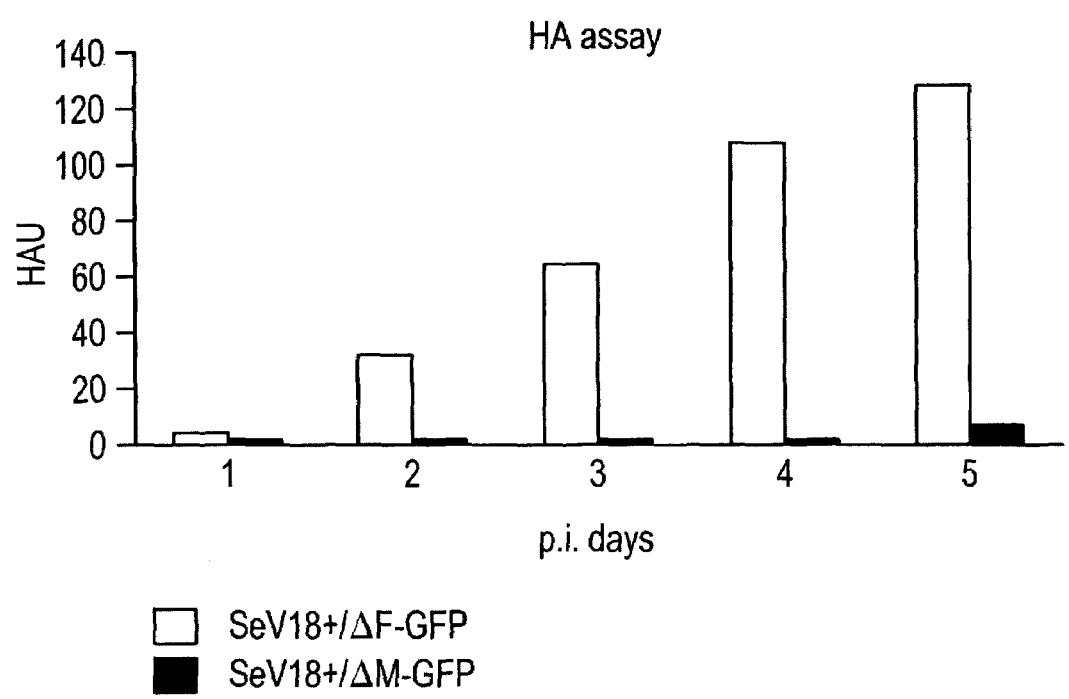

FIG. 79 indicates a diagram showing HA activity of the culture supernatants that were recovered over time after LLC-MK2 cells were infected with SeV18+/ΔM-GFP or SeV18+/ΔF-GFP at m.o.i.=3.

FIG. 80 indicates photographs showing fluorescence micrographs 4 days after LLC-MK2 cells were infected with SeV18+/ΔM-GFP or SeV18+/ΔF-GFP at m.o.i.=3.

Figure 81:
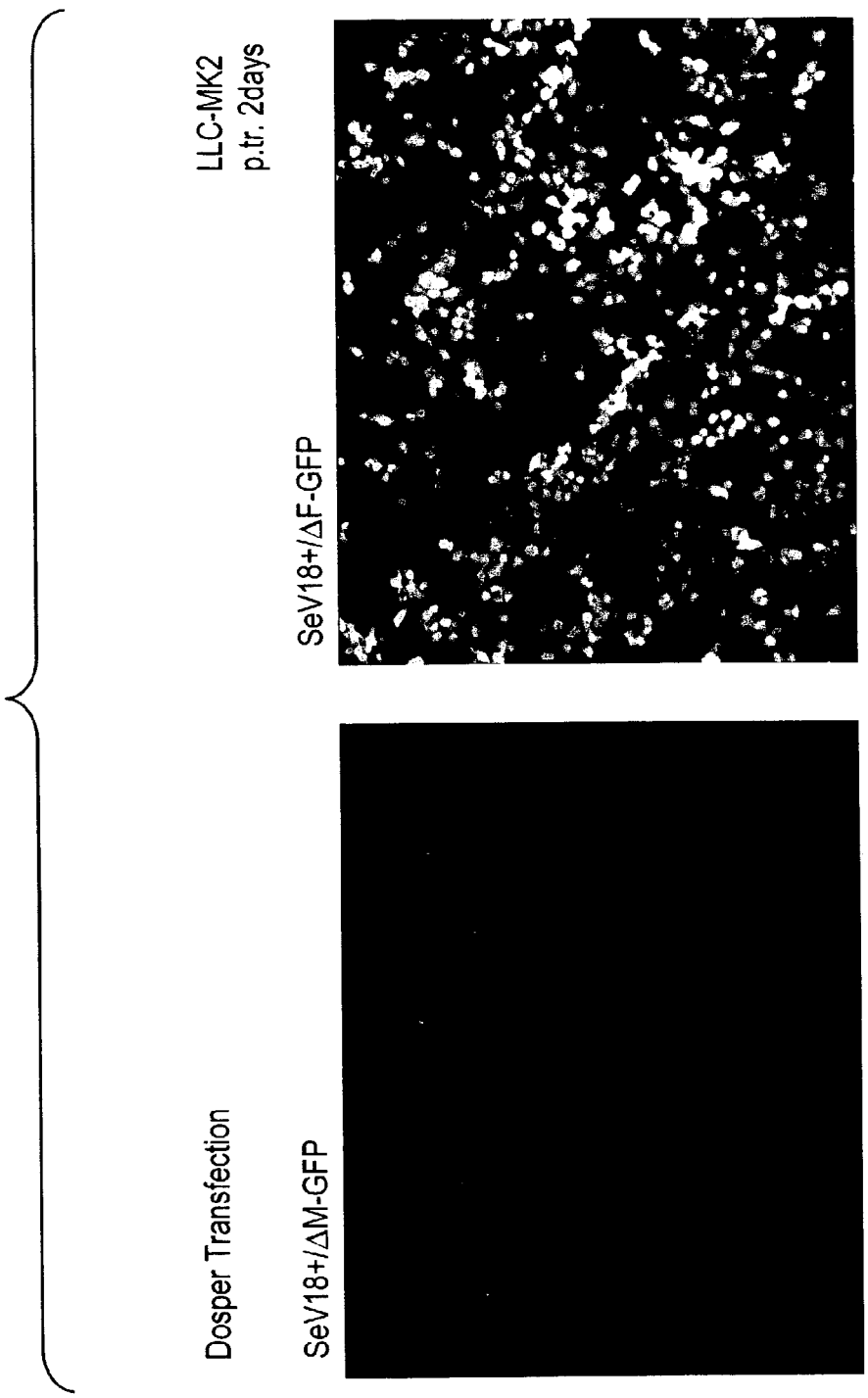

FIG. 81 indicates photographs showing fluorescence micrographs 2 days after LLC-MK2 cells were infected using cationic liposomes (Dosper) with the culture supernatants that were recovered 5 days after LLC-MK2 cells were infected with SeV18+/ΔM-GFP or. SeV18+/ΔF-GFP at m.o.i.=3.

Figure 82:
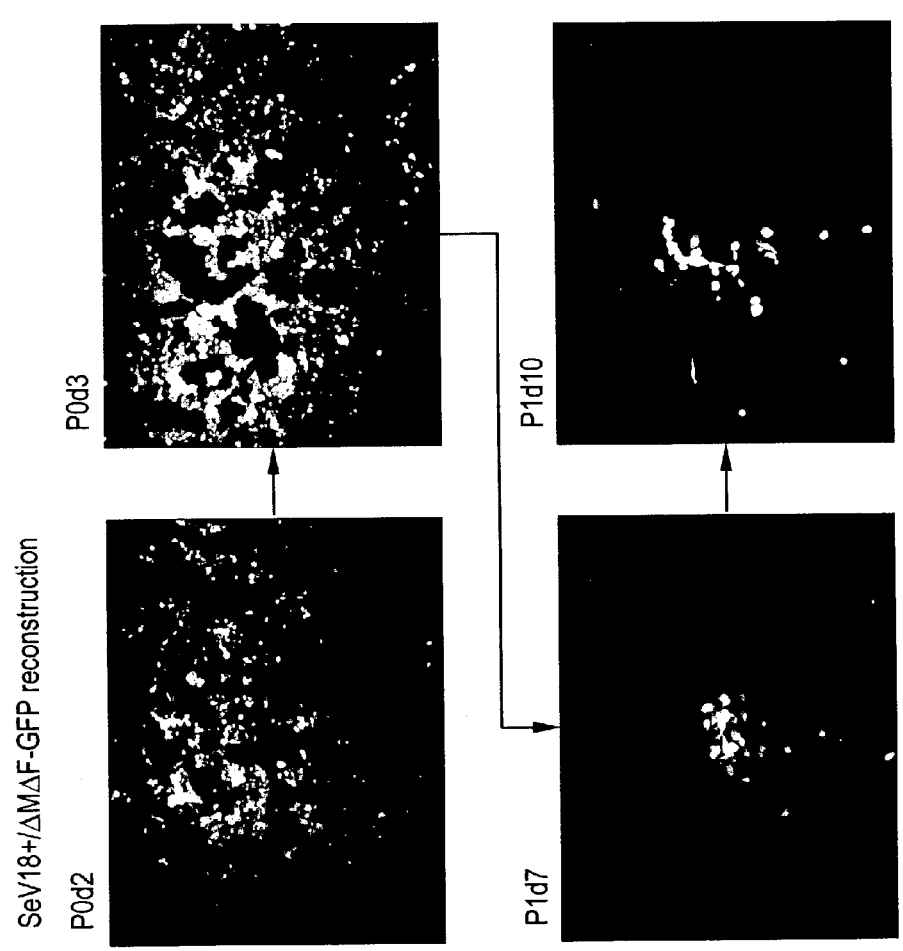

FIG. 82 indicates photographs showing viral reconstitution of F- and M-deficient SeV (SeV18+/ΔMΔF-GFP).

Figure 83:
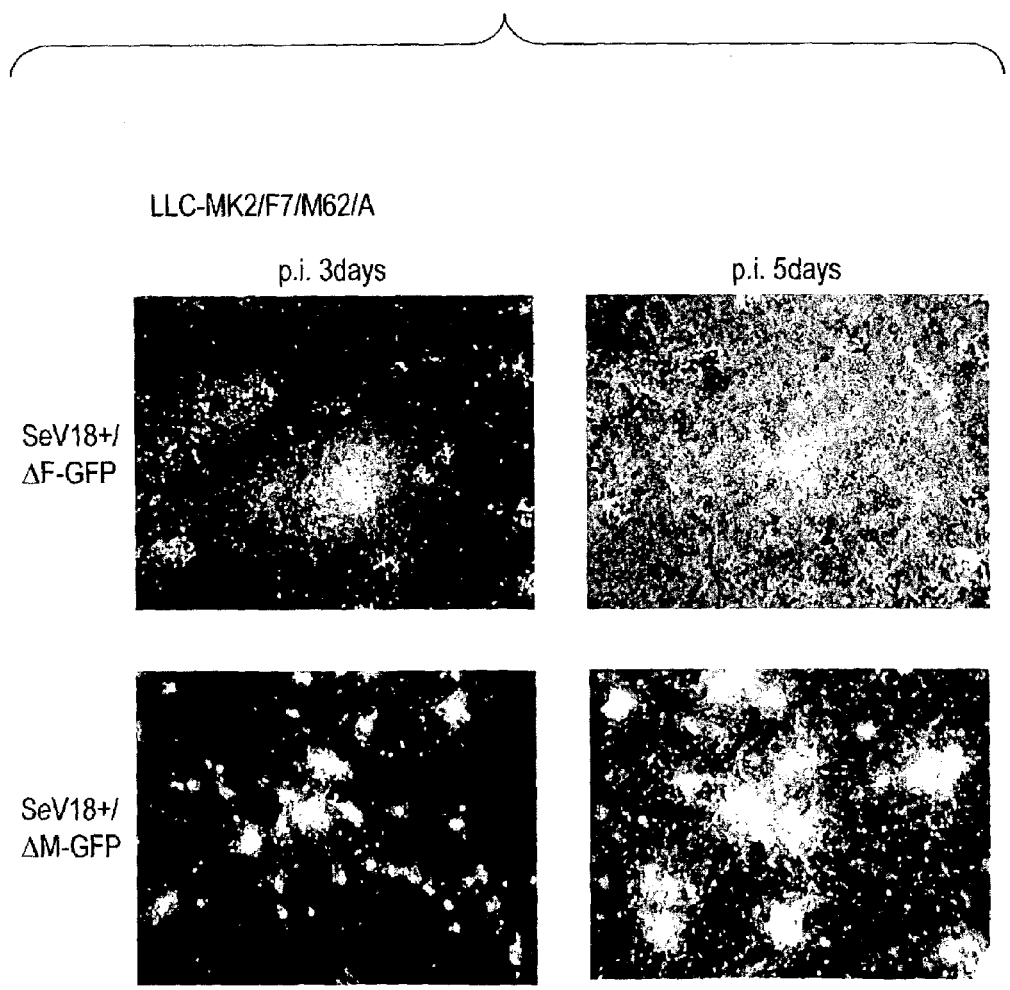

FIG. 83 indicates photographs showing fluorescence micrographs 3 days and 5 days after both M- and F-expressing cells (LLC-MK2/F7/M62/A) were infected with SeV18+/ΔM-GFP or SeV18+/ΔF-GFP.

Figure 84:
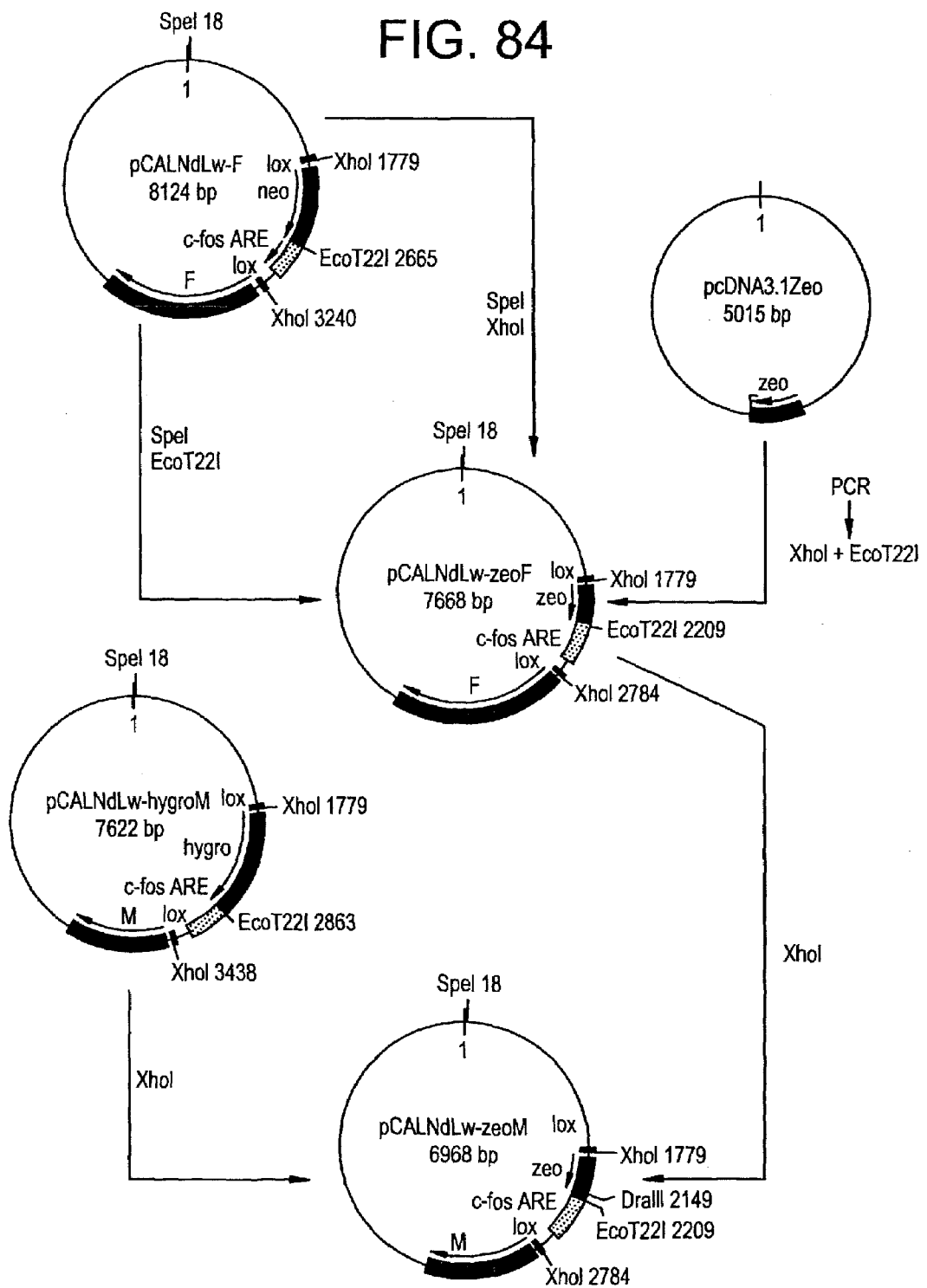

FIG. 84 represents a construction scheme for the vector that induces the M or F gene expression and has the Zeocin selection marker.

Figure 85:
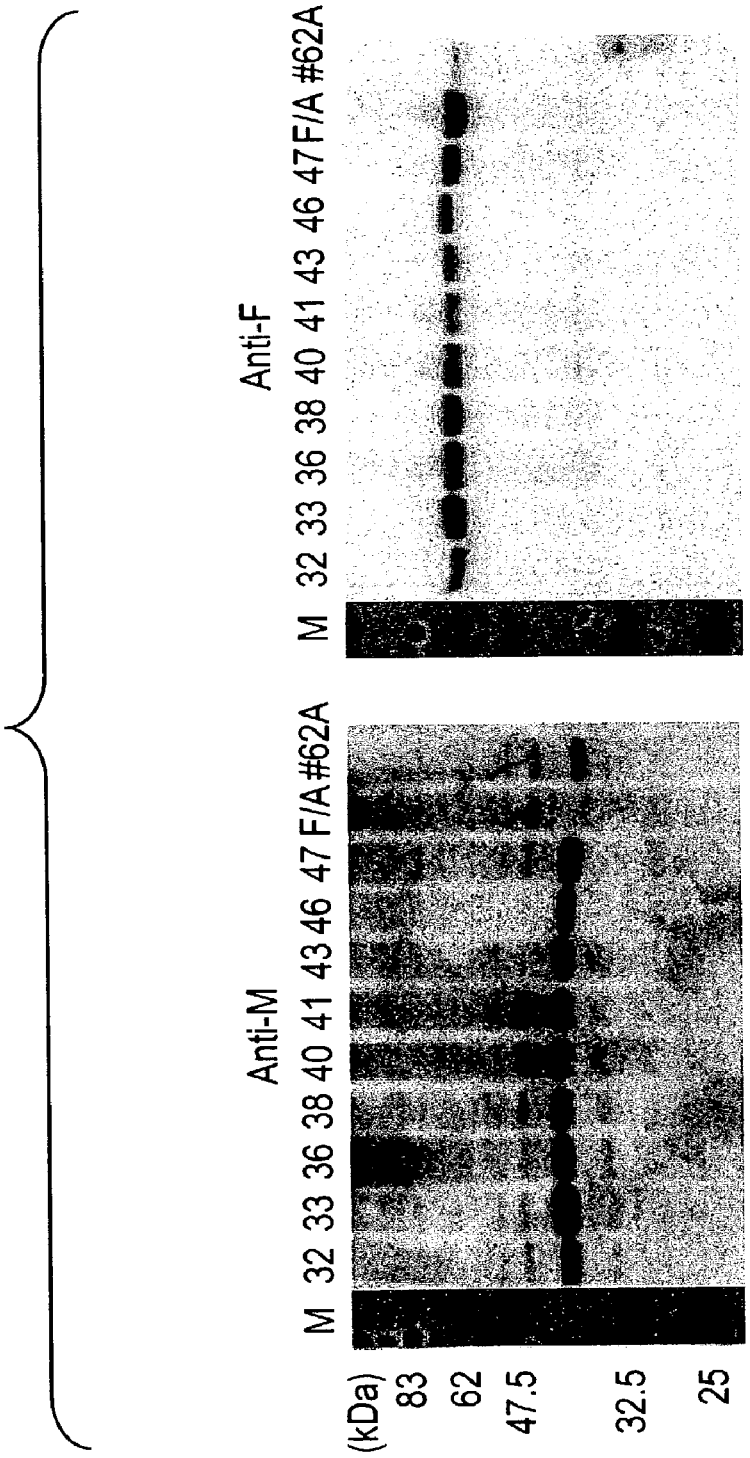

FIG. 85 shows the expression of M and F proteins in M and F expressing helper cells.

Figure 86:
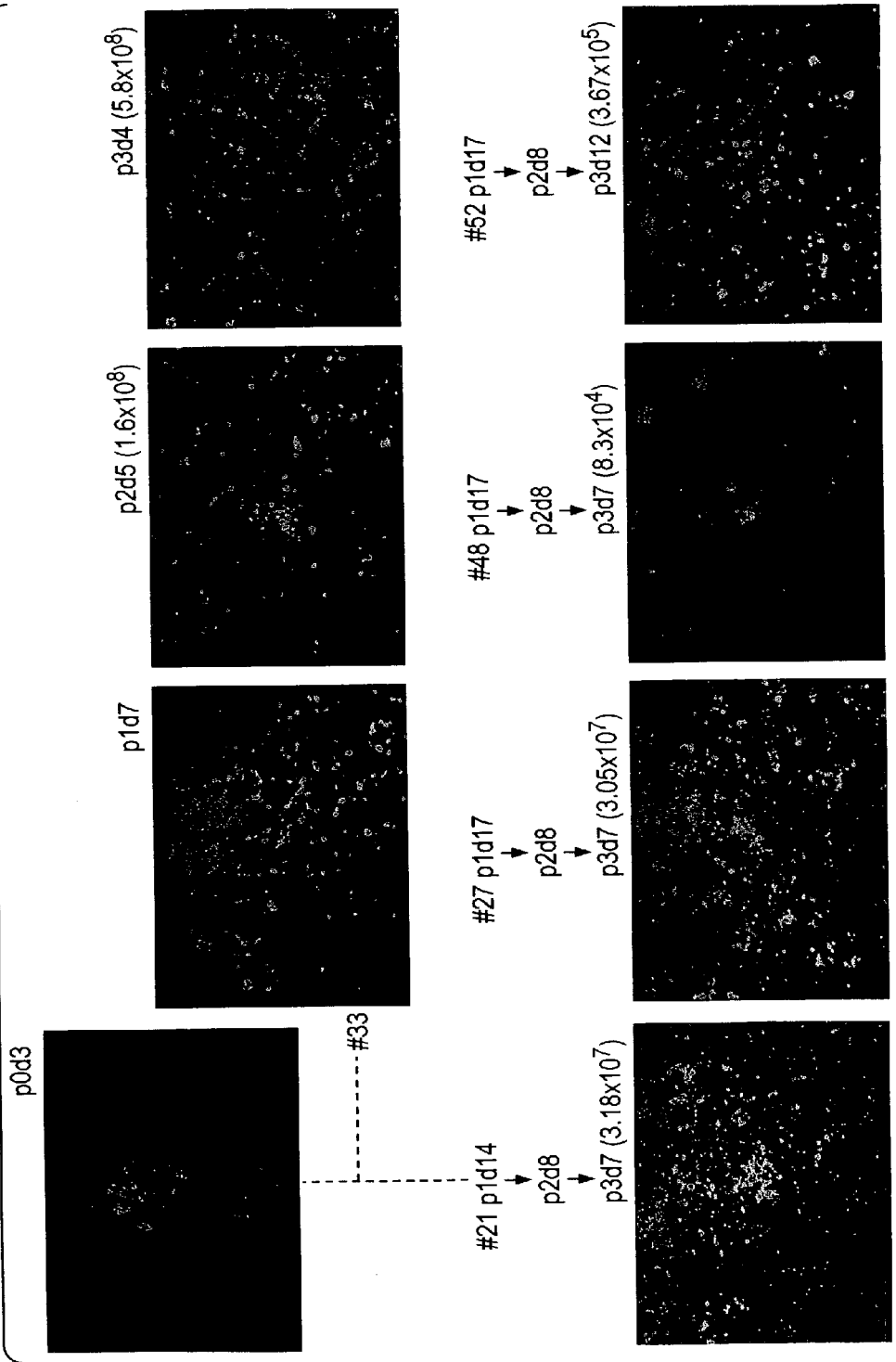

FIG. 86 represents photographs showing the GFP expression in cells transfected with M and F-deficient SeV having GFP gene.

Figure 87:
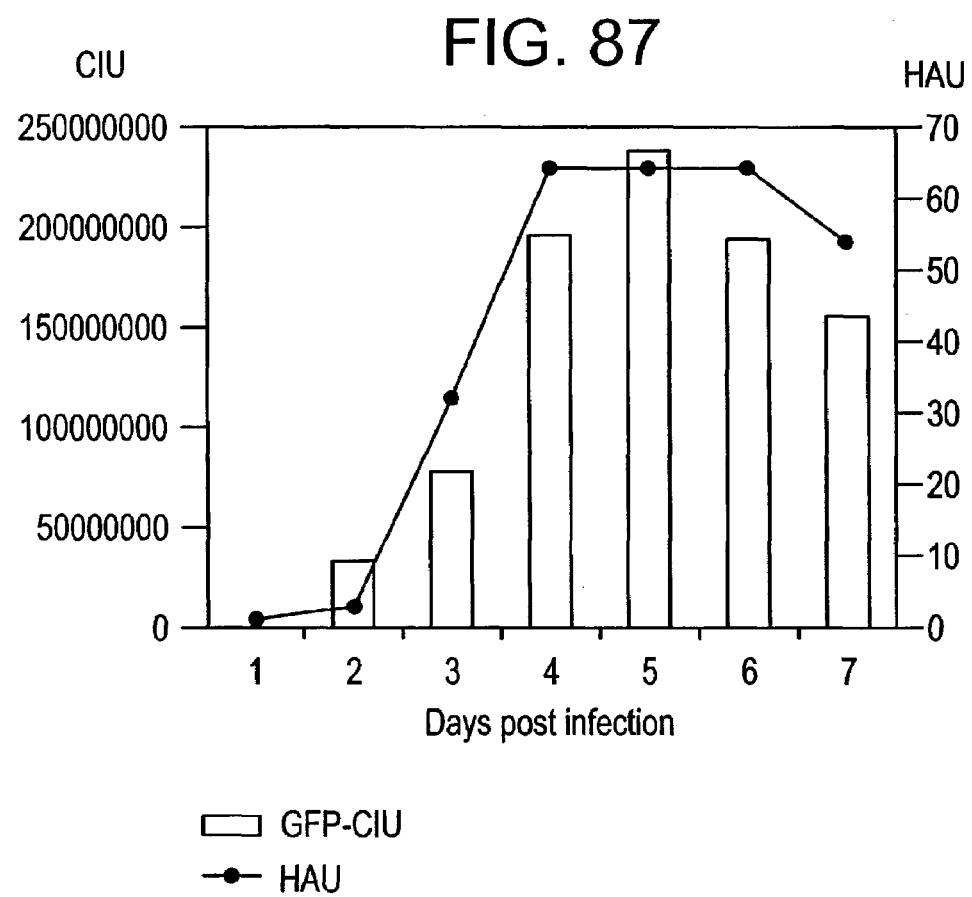

FIG. 87 is a graph showing the virus production from cells producing M and F-deficient SeV having GFP gene.

FIG. 88 represents the genome structure of M and F-deficient SeV confirmed by RT-PCR. "dF" represents SeV18+/ΔF-GFP, "dM" SeV18+/ΔM-GFP, and "dMdF" SeV18+/ΔMΔF-GFP, respectively.

Figure 89:
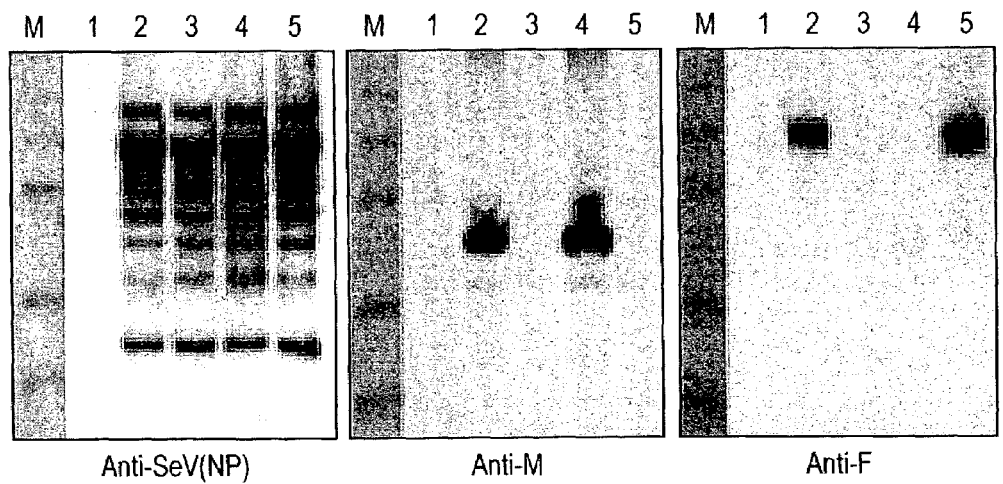

FIG. 89 represents the results of Western blot analyses confirming deficiency of the expression of M and F proteins in cells transfected with M and F-deficient SeV.

Figure 90:
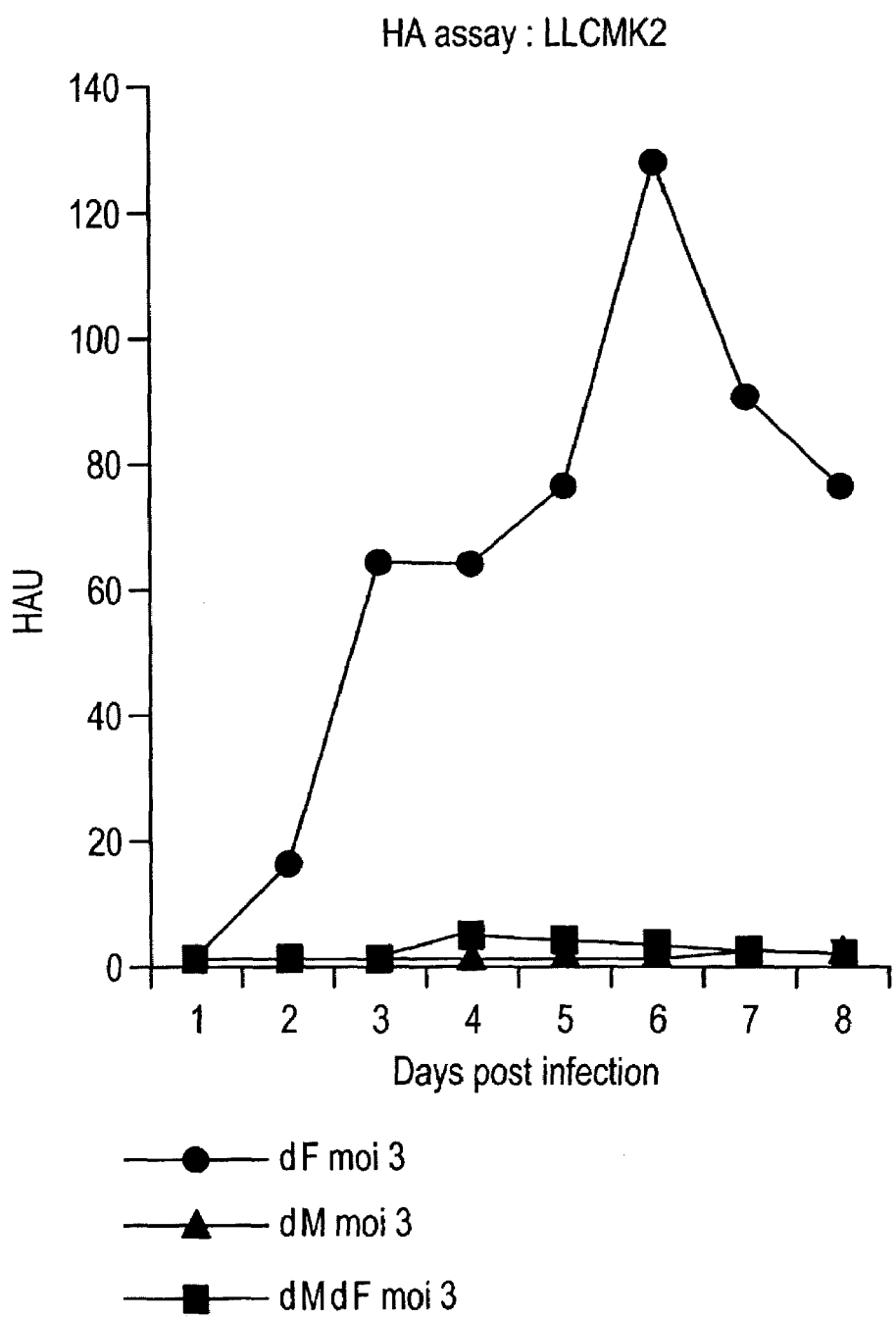

FIG. 90 is a graph showing the results of HA assay for examining the presence or absense of the secondarily released virus particles from cells transfected with M and F-deficient SeV.

FIG. 91 represents photographs showing the results of examining the presence or absense of the secondarily released virus particles from cells transfected with M and F-deficient SeV. The examination was performed by transfecting cells with the culture supernatant of the M and F-deficient SeV-transfected cells.

Figure 92:
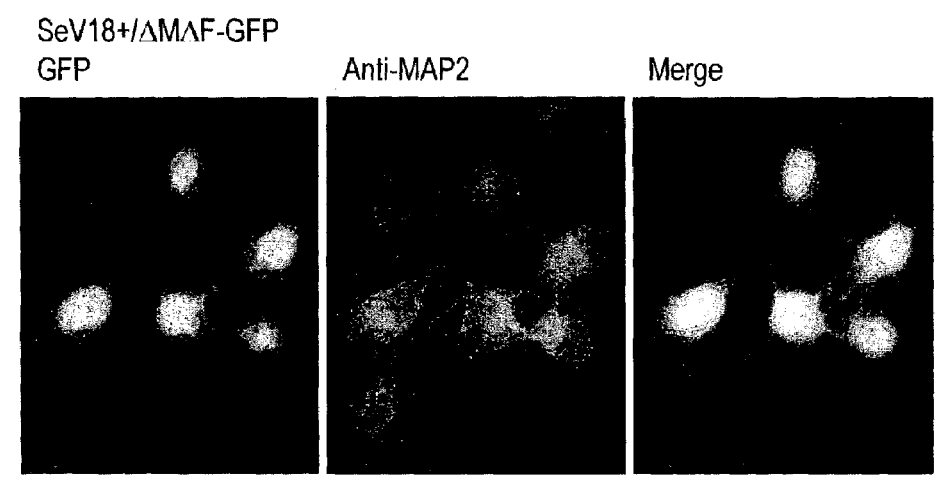

FIG. 92 represents photographs showing the infectivity of M and F-deficient SeV and M-deficient SeV against cerebral cortex nerve cells.

FIG. 93 represents photographs showing the expression of the transferred gene after the in vivo administration of M and F-deficient SeV and M-deficient SeV into the gerbil brain.

FIG. 94 is a series of graphs showing the moi-dependent cytotoxicity of M and F-deficient SeV and M-deficient SeV. "Cont." represents SeV having the replication ability (SeV18+GFP), "dF" SeV18+/ΔF-GFP, "dM" SeV18+/ΔM-GFP, and "dMdF" SeV18+/ΔMΔF-GFP.

BEST MODE FOR CARRYING OUT THE INVENTION

The present invention is illustrated in detail below with reference to Examples, but is not to be construed as being limited thereto. All the references cited herein are incorporated by reference.

EXAMPLE 1

Construction of F-Deficient Sendai Virus

<1> Construction of F-deficient SeV Genomic cDNA and F-expressing Plasmid

The full-length genomic cDNA of Sendai virus (SeV), pSeV18+ b(+) (Hasan, M. K. et al., 1997, J. General Virology 78: 2813–2820) ("pSeV18+ b(+)" is also referred to as "pSeV18+") was digested with SphI/KpnI, and the resulting fragment (14673 bp) was recovered and cloned into plasmid pUC18 to generate pUC18/KS. The F-disrupted site was constructed on this pUC18/KS. The F gene disruption was performed by the combined use of PCR-ligation method, and as a result, the ORF for the F gene (ATG-TGA=1698 bp) was removed; thus atgcatgccggcagatga (SEQ ID NO: 1) was ligated to it to construct the F-deficient SeV genomic cDNA (pSeV18+/ΔF). In PCR, a PCR product generated by using a primer pair (forward: 5'-gttgagtactgcaagagc/SEQ ID NO: 2, reverse: 5'-tttgccggcatgcatgtttcccaagggagagttttgcaacc/SEQ ID NO: 3) was ligated upstream of F and another PCR product generated by using a primer pair (forward: 5'-atgcatgccggcagatga/SEQ ID NO: 4, reverse: 5'-tgggtgaatgagagaatcagc/SEQ ID NO: 5) was ligated downstream of the F gene at EcoT22I site. The resulting plasmid was digested with SacI and SalI, and then the fragment (4931 bp) spanning the region comprising the site where F is disrupted was recovered and cloned into pUC18 to generate pUC18/dFSS. This pUC18/dFSS was digested with DraIII. The resulting fragment was recovered and substituted with a DraIII fragment from the region comprising the F gene of pSeV18+; and the ligation was carried out to generate plasmid pSeV18+/ΔF.

Further, in order to construct a cDNA (pSeV18+/ΔF-GFP) in which the EGFP gene has been introduced at the site where F was disrupted, the EGFP gene was amplified by PCR. To set the EGFP gene with a multiple of 6 (Hausmann, S. et al., RNA 2, 1033–1045 (1996)), PCR was carried out with an NsiI-tailed primer (5'-atgcatatggtgatgcggttttggcagtac: SEQ ID NO: 6) for the 5' end and an NgoMIV-tailed primer (5'-Tgccggctattattacttgtacagctcgtc: SEQ ID NO: 7) for the 3' end. The PCR products were digested with restriction enzymes NsiI and NgoMIV, and then the fragment was recovered from the gel; the fragment was ligated at the site of pUC18/dFSS between NsiI and NgoMIV restriction enzyme sites where the disrupted F is located and the sequence was determined. A DraIII fragment comprising the EGFP gene was removed and recovered from the site, and substituted for a DraIII fragment in the region comprising the F gene of pSeV18+; then ligation was carried out to obtain plasmid pSeV18+/ΔF-GFP.

On the other hand, Cre-loxP-inducible expression plasmid for F gene expression was constructed by amplifying the SeV F gene by PCR, confirming the sequence, and inserting into the unique site SwaI of plasmid pCALNdLw (Arai et al., J. Virology 72, 1998, p1115–1121) in which the expression of gene products has been designed to be induced by Cre DNA recombinase, to obtain plasmid pCALNdLw/F.

<2> Preparation of Helper Cells Inducing the Expression of SeV-F Protein

To recover infectious virus particles from F-deficient genome, a helper cell strain expressing SeV-F protein was established. The cell utilized was LLC-MK2 cell that is commonly used for the growth of SeV and is a cell strain derived from monkey kidney. The LLC-MK2 cells were cultured in MEM containing 10% heat-treated inactivated fetal bovine serum (FBS), sodium penicillin G (50 units/ml), and streptomycin (50 μg/ml) at 37° C. under 5% $CO_2$ gas. Because SeV-F gene product is cytotoxic, the above-mentioned plasmid pCALNdLw/F designed to induce the expression of F gene product through Cre DNA recombinase was introduced into LLC-MK2 cells by calcium phosphate method (mammalian transfection kit (Stratagene)) according to the gene transfer protocol.

10 μg of plasmid pCALNdLw/F was introduced into LLC-MK2 cells grown to be 40% confluent in a 10-cm plate, and the cells were cultured in 10 ml of MEM containing 10% FBS at 37° C. under 5% $CO_2$ for 24 hours in an incubator. After 24 hours, the cells were scraped off, and suspended in 10 ml medium; then the cells were plated on 5 dishes with 10-cm diameter (one plate with 5 ml; 2 plates with 2 ml; 2 plates with 0.2 ml) in MEM containing 10 ml of 10% FBS and 1200 μg/ml G418 (GIBCO-BRL) for the cultivation. The culture was continued for 14 days while the medium was changed at 2-day intervals, to select cell lines in which the gene has been introduced stably. 30 cell strains were recovered as G418-resistant cells grown in the medium by using cloning rings. Each clone was cultured to be confluent in 10-cm plates.

After the infection of each clone with recombinant adenovirus AxCANCre expressing Cre DNA recombinase, the cells were tested for the expression of SeV-F protein by Western blotting using anti-SeV-F protein monoclonal IgG (f236; J. Biochem. 123: 1064–1072) as follows.

After grown to be confluent in a 6-cm dish, each clone was infected with adenovirus AxCANCre at moi=3 according to the method of Saito et al., (Saito et al., Nucl. Acids Res. 23: 3816–3821 (1995); Arai, T. et al., J Virol 72, 1115–1121 (1998)). After the infection, the cells were cultured for 3 days. The culture supernatant was discarded and the cells were washed twice with PBS buffer, scraped off with a scraper and were collected by centrifugation at 1500×g for five minutes.

The cells are kept at −80° C. and can be thawed when used. The cells collected were suspended in 150 μl PBS buffer, and equal amount of 2×Tris-SDS-BME sample loading buffer (0.625 M Tris, pH 6.8, 5% SDS, 25% 2-ME, 50% glycerol, 0.025% BPB; Owl) was added thereto. The mixture was heat-treated at 98° C. for 3 minutes and then used as a sample for electrophoresis. The sample ($1\times10^5$ cells/lane) was fractionated by electrophoresis in an SDS-polyacrylamide gel (Multi Gel 10/20, Daiichi Pure Chemicals). The fractionated proteins were transferred onto a PVDF transfer membrane (Immobilon-P transfer membranes; Millipore) by semi-dry blotting. The transfer was carried out under a constant current of 1 $mA/cm^2$ for 1 hour onto the transfer membrane that had been soaked in 100% methanol for 30 seconds and then in water for 30 minutes.

The transfer membrane was shaken in a blocking solution containing 0.05% Tween20 and 1% BSA (BlockAce; Snow Brand Milk Products) for one hour, and then it was incubated at room temperature for 2 hours with an anti-SeV-F antibody (f236) which had been diluted 1000-folds with a blocking solution containing 0.05% Tween 20 and 1% BSA. The transfer membrane was washed 3 times in 20 ml of PBS-0.1% Tween20 while being shaken for 5 minutes and then it was washed in PBS buffer while being shaken for 5 minutes. The transfer membrane was incubated at room temperature for one hour in 10 ml of peroxidase-conjugated anti-mouse IgG antibody (Goat anti-mouse IgG; Zymed) diluted 2000-fold with the blocking solution containing 0.05% Tween 20 and 1% BSA. The transfer membrane was washed 3 times with 20 ml of PBS-0.1% Tween20 while being shaken for 5 minutes, and then it was washed in PBS buffer while being shaken for 5 minutes.

Figure 1:
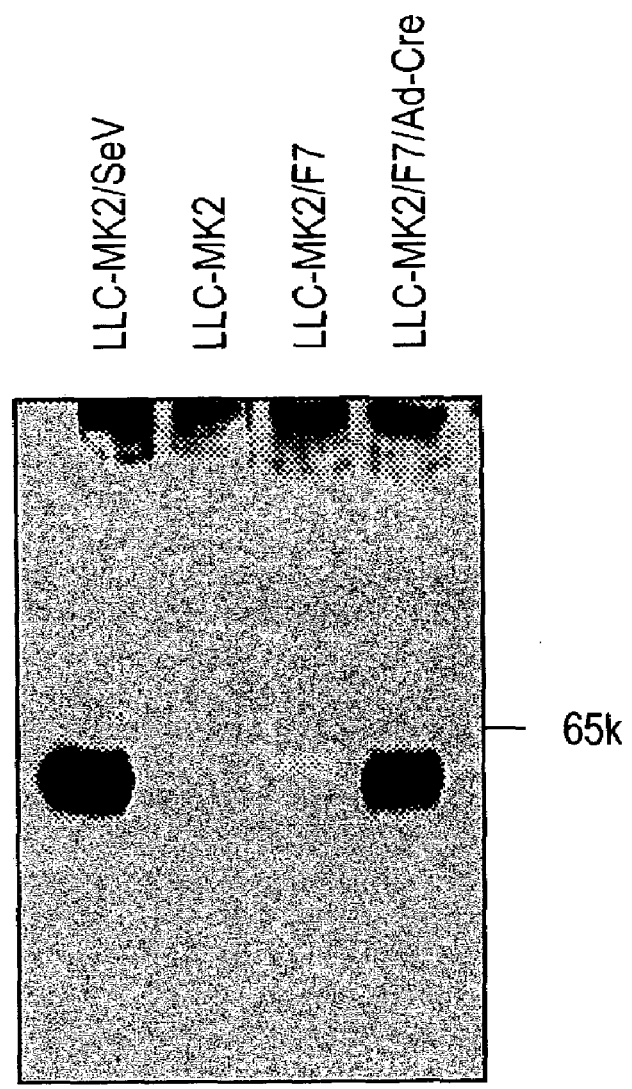
FIG. 1 is a photograph showing an analytical result of the expression of F protein via a Cre-loxP-inducible expression system by Western blotting. It shows the result of detecting proteins on a transfer membrane cross-reacting to the anti-SeV-F antibody by chemiluminescence method.

Detections were carried out for proteins cross-reacting to the anti-SeV-F antibody on the transfer membrane by chemiluminescence method (ECL western blotting detection reagents; Amersham). The result is shown in FIG. 1. The SeV-F expression specific to AxCANCre infection was detected to confirm the generation of LLC-MK2 cells that induce expression of a SeV-F gene product.

Figure 2:
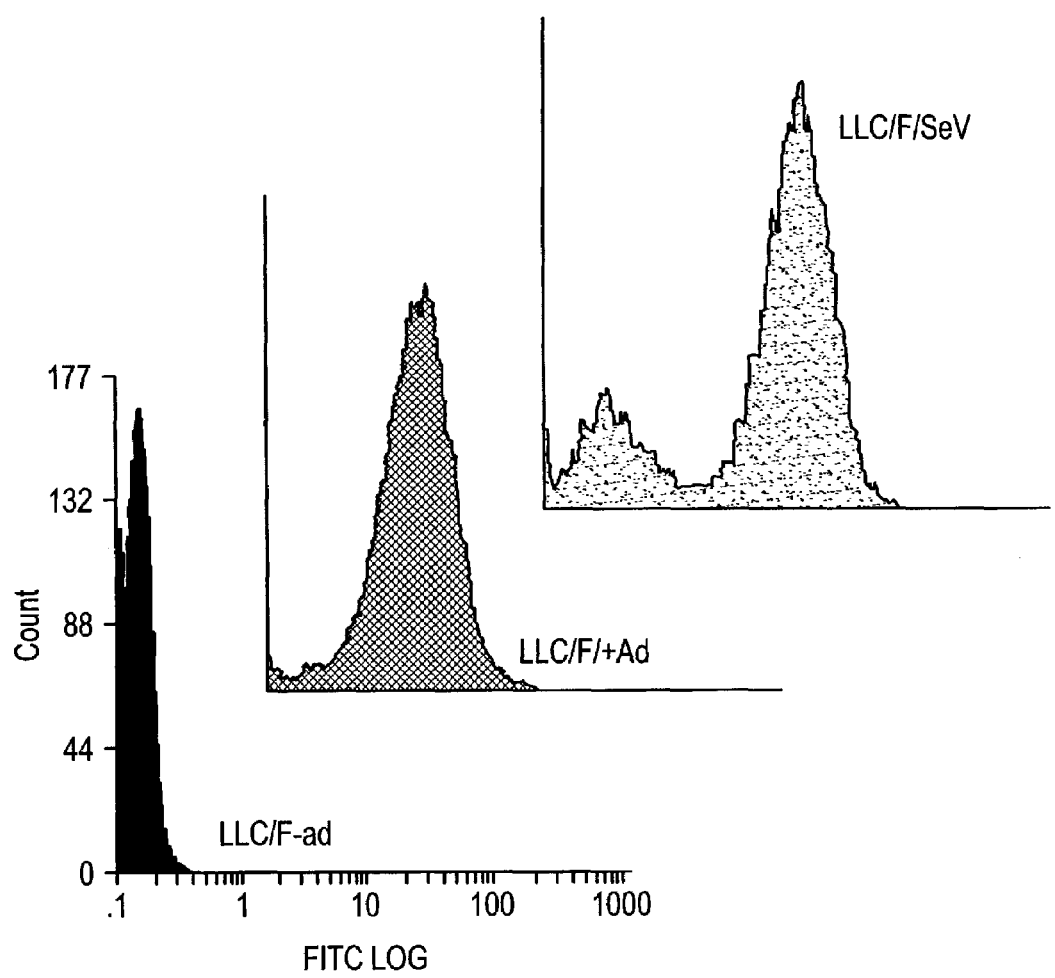
FIG. 2 indicates a diagram showing an analytical result of cell-surface display of F protein the expression of which was induced by the Cre-loxP system. It shows results of flow cytometry analysis for LLC-MK2/F7 with the anti-SeV-F antibody.

One of the several resulting cell lines, LLC-MK2/F7 cell, was analyzed by flow cytometry with an anti-SeV-F antibody (FIG. 2). Specifically, $1\times10^5$ cells were precipitated by centrifugation at 15,000 rpm at 4° C. for 5 minutes, washed with 200 μl PBS, and allowed to react in PBS for FACS (NIKKEN CHEMICALS) containing 100-fold diluted anti-F monoclonal antibody (f236), 0.05% sodium azide, 2% FCS at 4° C. for 1 hour in a dark place. The cells were again precipitated at 15,000 rpm at 4° C. for 5 minutes, washed with 200 μl PBS, and then allowed to react to FITC-labeled anti-mouse IgG (CAPPEL) of 1 μg/ml on ice for 30 minutes. Then the cells were again washed with 200 μl PBS, and then precipitated by centrifugation at 15,000 rpm at 4° C. for 5 minutes. The cells were suspended in 1 ml of PBS for FACS and then analyzed by using EPICS ELITE (Coulter) argon laser at an excitation wavelength of 488 nm and at a fluorescence wavelength of 525 nm. The result showed that LLC-MK2/F7 exhibited a high reactivity to the antibody in a manner specific to the induction of SeV-F gene expression, and thus it was verified that SeV-F protein was expressed on the cell surface.

EXAMPLE 2

Confirmation of Function of SeV-F Protein Expressed by Helper Cells

It was tested whether or not SeV-F protein, of which expression was induced by helper cells, retained the original protein function.

After plating on a 6-cm dish and grown to be confluent, LLC-MK2/F7 cells were infected with adenovirus AxCAN-Cre at moi=3 according to the method of Saito et al. (described above). Then, the cells were cultured in MEM (serum free) containing trypsin (7.5 µg/ml; GIBCO-BRL) at 37° C. under 5% $CO_2$ in an incubator for three days.

Figure 3:
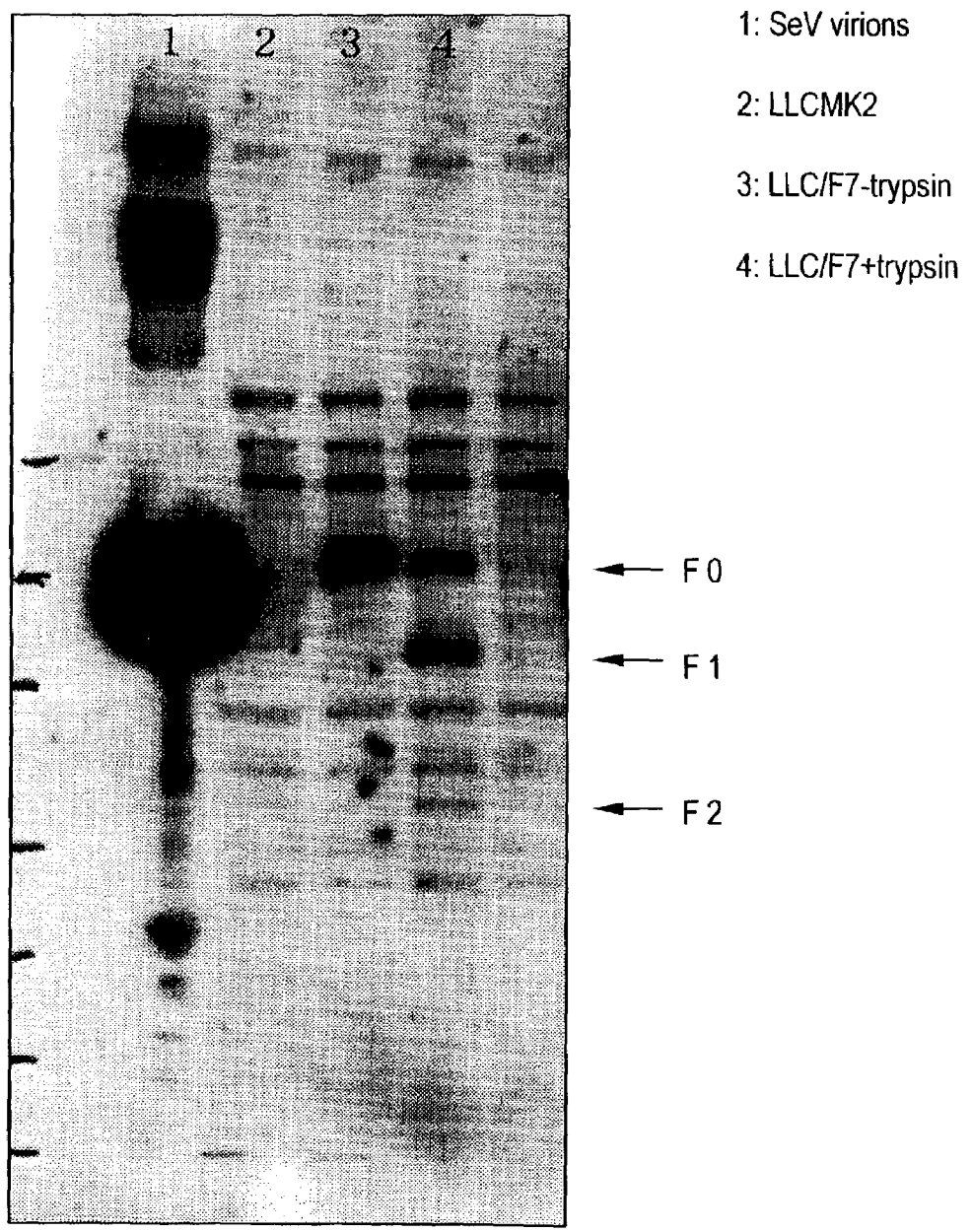
FIG. 3 indicates a photograph showing the result confirming cleavage of the expressed F protein by trypsin using Western blotting.
Figure 4:
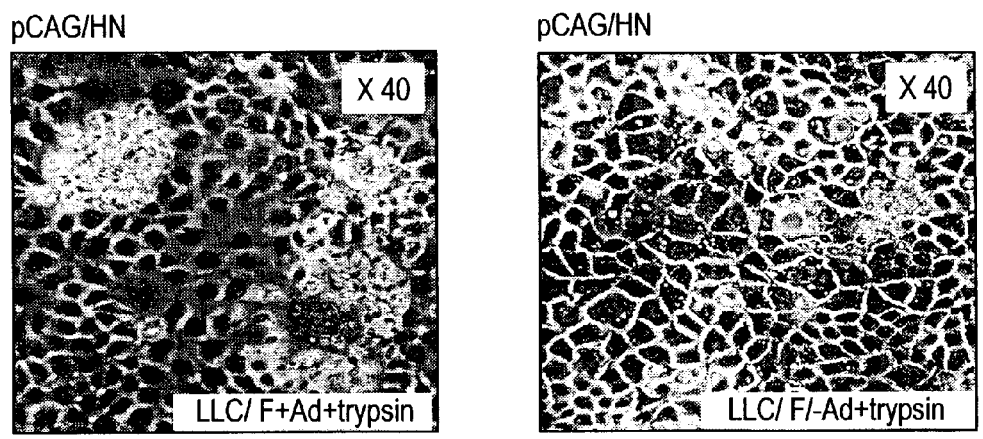
FIG. 4 indicates photographs showing the result confirming cell-surface expression of HN in an experiment of cell-surface adsorption onto erythrocytes.

The culture supernatant was discarded and the cells were washed twice with PBS buffer, scraped off with a scraper, and collected by centrifugation at 1500×g for five minutes. The cleavage of expressed F protein by trypsin was verified by Western blotting as described above (FIG. 3). SeV-F protein is synthesized as F0 that is a non-active protein precursor, and then the precursor is activated after being digested into two subunits F1 and F2 by proteolysis with trypsin. LLC-MK2/F7 cells after the induction of F protein expression thus, like ordinary cells, continues to express F protein, even after being passaged, and no cytotoxicity mediated by the expressed F protein was observed as well as no cell fusion of F protein-expressing cells was observed. However, when SeV-HN expression plasmid (pCAG/SeV-HN) was transfected into the F-expressing cells and the cells were cultured in MEM containing trypsin for 3 days, cell fusion was frequently observed. The expression of HN on the cell surface was confirmed in an experiment using erythrocyte adsorption onto the cell surface (Hematoadsorption assay; Had assay) (FIG. 4). Specifically, 1% chicken erythrocytes were added to the culture cells at a concentration of 1 ml/dish and the mixture was allowed to stand still at 4° C. for 10 minutes. The cells were washed 3 times with PBS buffer, and then colonies of erythrocytes on the cell surface were observed. Cell fusion was recognized for cells on which erythrocytes aggregated; cell fusion was found to be induced through the interaction of F protein with HN; and thus it was demonstrated that F protein, the expression of which was sustained in LLC-MK2/F7, retained the original function thereof.

EXAMPLE 3

Functional RNP Having F-deficient Genome and Formation of Virions

To recover virions from the deficient viruses, it is necessary to use cells expressing the deficient protein. Thus, the recovery of the deficient viruses was attempted with cells expressing the deficient protein, but it was revealed that the expression of F protein by the helper cell line stopped rapidly due to the vaccinia viruses used in the reconstitution of F-deficient SeV (FIG. 5) and thus the virus reconstitution based on the direct supply of F protein from the helper cell line failed. It has been reported that replication capability of vaccinia virus is inactivated, but the activity of T7 expression is not impaired by the treatment of vaccinia virus with ultraviolet light of long wavelengths (long-wave UV) in the presence of added psoralen (PLWUV treatment) (Tsung et al., J Virol 70, 165–171, 1996). Thus, virus reconstitution was attempted by using PLWUV-treated vaccinia virus (PLWUV-VacT7). UV Stratalinker 2400 (Catalog NO. 400676 (100V); Stratagene, La Jolla, Calif., USA) equipped with five 15-Watt bulbs was used for ultraviolet light irradiation. The result showed that the expression of F protein was inhibited from the F-expressing cells used in the reconstitution, but vaccinia viruses were hardly grown in the presence of AraC after lysate from the cells reconstituted with this PLWUV-VacT7 was infected to the helper cells, and it was also found that the expression of F protein by the helper cell line was hardly influenced. Further, this reconstitution of wild type SeV using this PLWUV-VacT7 enables the recovery of viruses from even $10^3$ cells, whereas by previous methods, this was not possible unless $10^5$ or more cells were there, and thus the efficiency of virus reconstitution was greatly improved. Thus, reconstitution of F-deficient SeV virus was attempted by using this method.

<Reconstitution and Amplification of F-deficient SeV Virus>

The expression of GFP was observed after transfecting LLC-MK2 cells with the above-mentioned pSeV18$^+$/ΔF-GFP in which the enhanced green fluorescent protein (EGFP) gene had been introduced as a reporter into the site where F had been disrupted according to the 6n rule in the manner as described below. It was also tested for the influence of the presence of virus-derived genes NP, P, and L that are three components required for the formation of RNP.

LLC-MK2 cells were plated on a 100-mm Petri-dish at a concentration of $5×10^6$ cells/dish and were cultured for 24 hours. After the culture was completed, the cells were treated with psoralen and ultraviolet light of long wavelengths (365 nm) for 20 minutes, and the cells were infected with recombinant vaccinia virus expressing T7 RNA polymerase (Fuerst, T. R. et al., Proc. Natl. Acad. Sci. USA 83, 8122–8126 (1986)) at room temperature for one hour (moi=2) (moi=2 to 3; preferably moi=2). After the cells were washed 3 times, plasmids pSeV18$^+$/ΔF-GFP, pGEM/NP, pGEM/P, and pGEM/L (Kato, A. et al., Genes cells 1, 569–579 (1996)) were respectively suspended in quantities of 12 µg, 4 µg, 2 µg, and 4 µg/dish in OptiMEM (GIBCO); SuperFect transfection reagent (1 µg DNA/5 µl SuperFect; QIAGEN) was added thereto; the mixtures were allowed to stand still at room temperature for 10 minutes; then they are added to 3 ml of OptiMEM containing 3% FBS; cells were added thereto and cultured. The same experiment was carried out using wild-type SeV genomic cDNA (pSeV(+)) (Kato, A. et al., Genes cells 1, 569–579 (1996)) as a control instead of pSeV18$^+$/ΔF-GFP. After culturing for 3 hours, the cells were washed twice with MEM containing no serum, and then cultured in MEM containing cytosine β-D-arabinofuranoside (AraC, 40 µg/ml; Sigma) and trypsin (7.5 µg/ml; GIBCO) for 70 hours. These cells were harvested, and the pellet was suspended in OptiMEM ($10^7$ cells/ml). After freeze-and-thaw treatment was repeated 3 times, the cells were mixed with lipofection reagent DOSPER (Boehringer Mannheim) ($10^6$ cells/25 µl DOSPER) and allowed to stand still at room temperature for 15 minutes. Then F-expressing LLC-MK2/F7 cell line ($10^6$ cells/well in 12-well plate) was transfected, and the cells were cultured in MEM containing no serum (containing 40 µg/ml AraC and 7.5 µg/ml trypsin).

The result showed that the expression of GFP was recognized only when all the three components, NP, P, and L derived from the virus are present and the deficient virus RNP expressing foreign genes can be generated (FIG. 6).

<Confirmation of F-deficient Virions>

It was tested whether the functional RNP reconstituted by F-deficient genomic cDNA by the method as described above could be rescued by the F-expressing helper cells and form infective virions of F-deficient virus. Cell lysates were mixed with cationic liposome; the lysates were prepared by freeze/thaw from cells reconstituted under conditions in which functional RNP is formed (condition where pSeV18$^+$/ΔF-GFP, pGEM/NP, pGEM/P, and pGEM/L are transfected at the same time) or conditions under which functional RNP is not formed (conditions in which two plasmids, pSeV18$^+$/ΔF-GFP and pGEM/NP, are transfected) as described above;

the lysates were lipofected into F-expressing cells and non-expressing cells; the generation of virus particles was observed based on the expansion of the distribution of GFP-expressing cells. The result showed that the expansion of distribution of GFP-expressing cells was recognized only when the introduction to the F-expressing cells was carried out by using a lysate obtained under condition in which functional RNP is reconstituted (FIG. 7). Furthermore, even in plaque assay, the plaque formation was seen only under the same conditions. From these results, it was revealed that functional RNPs generated from F-deficient virus genome were further converted into infective virus particles in the presence of F protein derived from F-expressing cells and the particles were released from the cells.

The demonstration of the presence of infective F-deficient virions in the culture supernatant was carried out by the following experiment. The lysate comprising the functional RNP constructed from the F gene deficient genome was lipofected to F-expressing cells as described in Example 2, and the culture supernatant was recovered. This culture supernatant was added to the medium of F-expressing cells to achieve the infection; on the third day, the culture supernatant was recovered and concurrently added to both F-expressing cells and cells that did not express F; and then the cells were cultured in the presence or absence of trypsin for three days. In F-expressing cells, viruses were amplified only in the presence of trypsin (FIG. 8). It was also revealed that non-infectious virus particles were released into the supernatant of cells that do not express F (in the bottom panel of FIG. 9) or from F-expressing cells cultured in the absence of trypsin. A summary of the descriptions above is as follows: the growth of F-deficient GFP-expressing viruses is specific to F-expressing cells and depends on the proteolysis with trypsin. The titer of infective F-deficient Sendai virus thus grown ranged from $0.5 \times 10^7$ to $1 \times 10^7$ CIU/ml.

EXAMPLE 4

Analysis of F-deficient GFP-expressing Virus

In order to confirm the genomic structure of virions recovered from F-deficient cDNA, viruses were recovered from the culture supernatant of the F-expressing cells, the total RNA was extracted and then Northern blot analysis was conducted by using F and HN as probes. The result showed that the HN gene was detectable, but the F gene was not detectable in the viruses harvested from the F-expressing cells, and it was clarified that the F gene was not present in the viral genome (FIG. 10). Further, by RT-PCR, it was confirmed that the GFP gene was present in the deleted locus for F as shown in the construction of the cDNA (FIG. 11) and that the structures of other genes were the same as those from the wild type. Based on the findings above, it was shown that no rearrangement of the genome had occurred during the virus reconstitution. In addition, the morphology of recovered F-deficient virus particles was examined by electron microscopy. Like the wild type virus, F-deficient virus particles had the helical RNP structure and spike-like structure inside (FIG. 14). Further, the viruses were examined by immuno-electron microscopy with gold colloid-conjugated IgG (anti-F, anti-HN) specifically reacting to F or HN. The result showed that the spike-like structure of the envelope of the virus comprised F and HN proteins (FIG. 12), which demonstrated that F protein produced by the helper cells was efficiently incorporated into the virions. The result will be described below in detail.

<Extraction of Total RNA, Northern Blot Analysis, and RT-PCR>

Total RNA was extracted from culture supernatant obtained 3 days after the infection of F-expressing cell LLC-MK2/F7 with the viruses by using QIAamp Viral RNA mini kit (QIAGEN) according to the protocol. The purified total RNA (5 µg) was separated by electrophoresis in a 1% denaturing agarose gel containing formaldehyde, and then transferred onto a Hybond-N+ membrane in a vacuum blotting device (Amersham-Pharmacia). The prepared membrane was fixed with 0.05 M NaOH, rinsed with 2-fold diluted SSC buffer (Nacalai tesque), and then was subjected to pre-hybridization in a hybridization solution (Boehringrer Mannheim) for 30 minutes; a probe for the F or HN gene prepared by random prime DNA labeling (DIG DNA Labeling Kit; Boehringer Mannheim) using digoxigenin (DIG)-dUTP (alkaline sensitive) was added thereto and then hybridization was performed for 16 hours. Then, the membrane was washed, and allowed to react to alkaline phosphatase-conjugated anti-DIG antibody (anti-digoxigenin-AP) the analysis was carried out by using a DIG detection kit. The result showed that the HN gene was detectable but the F gene was not detectable in the viruses harvested from the F-expressing cells, and it was clarified that the F gene was not present in the viral genome (FIG. 10).

Further, detailed analysis was carried out by RT-PCR. In the RT-PCR, first strand cDNA was synthesized from the purified virus RNA by using SUPERSCRIPTII Preamplification System (GIBCO-BRL) according to the protocol; the following PCR condition was employed with LA PCR kit (TAKARA ver2.1): 94° C./3 min; 30 cycles for the amplification of 94° C./45 sec, 55° C./45 sec, 72° C./90 sec; incubation at 72° C. for 10 minutes; then the sample was electrophoresed in a 2% agarose gel at 100 v for 30 minutes, the gel was stained with ethidium bromide for a photographic image. Primers used to confirm the M gene and EGFP inserted into the F-deficient site were forward 1: 5'-atcagagacctgcgacaatgc (SEQ ID NO: 8) and reverse 1: 5'-aagtcgtgctgcttcatgtgg (SEQ ID NO: 9); primers used to confirm EGFP inserted into the F-deficient site and the HN gene were forward 2: 5'-acaaccactacctgagcacccagtc (SEQ ID NO: 10) and reverse 2: 5'-gcctaacacatccagagatcg (SEQ ID NO: 11); and the junction between the M gene and HN gene was confirmed by using forward 3: 5'-acattcatgagt-cagctcgc (SEQ ID NO: 12) and reverse 2 primer (SEQ ID NO: 11). The result showed that the GFP gene was present in the deficient locus for F as shown in the construction of the cDNA (FIG. 11) and that the structures of other genes were the same as those from the wild type (FIG. 13). From the findings shown above, it is clarified that no rearrangement of the genome had resulted during the virus reconstitution.

<Electron Microscopic Analysis with Gold Colloid-conjugated Immunoglobulin>

The morphology of recovered F-deficient virus particles were examined by electron microscopy. First, culture supernatant of cells infected with the deficient viruses was centrifuged at 28,000 rpm for 30 minutes to obtain a virus pellet; then the pellet was re-suspended in 10-fold diluted PBS at a concentration of $1 \times 10^9$ HAU/ml; one drop of the suspension was dropped on a microgrid with a supporting filter and then the grid was dried at room temperature; the grid was treated with PBS containing 3.7% formalin for 15 minutes for fixation and then pre-treated with PBS solution containing 0.1% BSA for 30 minutes; further, anti-F monoclonal antibody (f236) or anti-HN monoclonal antibody (Miura, N. et al., Exp. Cell Res. (1982) 141: 409–420) diluted 200-folds with the same solution was dropped on the grid and allowed to react under a moist condition for 60 minutes. Subsequently, the grid was washed with PBS, and then gold colloid-conjugated anti-mouse IgG antibody diluted 200-folds was dropped and allowed to react under a moist condition for 60 minutes. Subsequently, the grid was washed with PBS and then with distilled sterile water, and air-dried at room temperature; 4% uranium acetate solution was placed on the grid for the staining for 2 minutes and the grid was dried; the sample was observed and photographed in a JEM-1200EXII electron microscope (JEOL.). The result showed that the spike-like structure of the envelope of the virus comprised F and HN proteins (FIG. 12), which demonstrated that F protein produced by the helper cells was efficiently incorporated into the virions. In addition, like the wild type virus, F-deficient virus particles had a helical RNP structure and a spike-like structure inside (FIG. 14).

EXAMPLE 5

High-efficiency Gene Transfer to a Variety of Cells Via F-deficient SeV Vector in Vitro <Introduction into Primary Culture Cells of Rat Cerebral Cortex Nerve Cells>

Primary culture cells of rat cerebral cortex neurons were prepared and cultured as follows: an SD rat (SPF/VAF Crj: CD, female, 332 g, up to 9-week old; Charles River) on the eighteenth day of pregnancy was deeply anesthetized by diethyl ether, and then euthanized by bloodletting from axillary arteries. The fetuses were removed from the uterus after abdominal section. The cranial skin and bones were cut and the brains were taken out. The cerebral hemispheres were transferred under a stereoscopic microscope to a working solution DMEM (containing 5% horse serum, 5% calf serum and 10% DMSO); they were sliced and an ice-cold papain solution (1.5 U, 0.2 mg of cysteine, 0.2 mg of bovine serum albumin, 5 mg glucose, DNase of 0.1 mg/ml) was added thereto; the solution containing the sliced tissues was incubated for 15 minutes while shaking by inverting the vial every 5 minutes at 32° C. After it was verified that the suspension became turbid enough and the tissue sections became translucent, the tissue sections were crushed into small pieces by pipetting. The suspension was centrifuged at 1200 rpm at 32° C. for 5 minutes, and then the cells were re-suspended in B27-supplemented neural basal medium (GIBCO-BRL, Burlington, Ontario, Canada). The cells were plated on a plate coated with poly-D-lysine (Becton Dickinson Labware, Bedford, Mass., U.S.A.) at a density of $1 \times 10^5$ cells/dish and then cultured at 37° C. under 5% $CO_2$.

After the primary culture of nerve cells from cerebral cortex ($5 \times 10^5$/well) were cultured for 5 days, the cells were infected with F-deficient SeV vector (moi=5) and further cultured for three days. The cells were fixed in a fixing solution containing 1% paraformaldehyde, 5% goat serum, and 0.5% Triton-X at room temperature for five minutes. Blocking reaction was carried out for the cells by using BlockAce (Snow Brand Milk Products) at room temperature for 2 hours, and then incubated with 500-fold diluted goat anti-rat microtubule-associated protein 2 (MAP-2) (Boehringer) IgG at room temperature for one hour. Further, the cells were washed three times with PBS(–) every 15 minutes and then were incubated with cys3-conjugated anti-mouse IgG diluted 100-folds with 5% goat serum/PBS at room temperature for one hour. Further, after the cells were washed three times with PBS(–) every 15 minutes, Vectashield mounting medium (Vector Laboratories, Burlingame, U.S.A.) was added to the cells; the cells, which had been double-stained with MAP-2 immuno staining and GFP fluorescence, were fluorescently observed by using a confocal microscope (Nippon Bio-Rad MRC 1024, Japan) and an inverted microscope Nikon Diaphot 300 equipped with excitation band-pass filter of 470–500-nm or 510–550-nm. The result showed that GFP had been introduced in nearly 100% nerve cells that were MAP2-positive (FIG. 15).

<Introduction into Normal Human Cells>

Normal human smooth-muscle cells, normal human hepatic cells, and normal human pulmonary capillary endothelial cells (Cell Systems) were purchased from DAINIPPON PHARMACEUTICAL and were cultured with SFM CS-C medium kit (Cell Systems) at 37° C. under 5% $CO_2$ gas.

Human normal cells, such as normal human smooth-muscle cells (FIG. 15, Muscle), normal human hepatic cells (FIG. 15, Liver), and normal human pulmonary capillary endothelial cells (FIG. 15, Lung), were infected with F-deficient SeV vector (m.o.i=5), and then the expression of GFP was observed. It was verified that the introduction efficiency was nearly 100% and the GFP gene was expressed at very high levels in all the cells (FIG. 15).

<Introduction into Mouse Primary Bone Marrow Cells>

Further, an experiment was conducted, in which mouse primary bone marrow cells were separated by utilizing lineage markers and were infected with F-deficient SeV vector. First, 5-fluorouracil (5-FU, Wako Pure Chemical Industries) was given to C57BL mouse (6-week old male) at a dose of 150 mg/kg by intraperitoneal injection (IP injection); 2 days after the administration, bone marrow cells were collected from the thighbone. The mononuclear cells were separated by density gradient centrifugation using Lympholyte-M (Cedarlane) A mixture ($3 \times 10^7$) of Streptavidin-magnetic beads (Pharmingen; Funakoshi), which had been coated with biotin-labeled anti-CD45R (B220), anti-Ly6G (Gr-1), anti-Ly-76 (TER-119), anti-1 (Thy1.2), and anti-Mac-1, were added to the mononuclear cells ($3 \times 10^6$ cells), and the resulting mixture was allowed to react at 4° C. for 1 hour; a fraction, from which Lin$^+$ cells had been removed by a magnet, was recovered (Lin$^-$ cells) (Erlich, S. et al., Blood 1999. 93 (1), 80–86). SeV of $2 \times 10^7$ HAU/ml was added to $4 \times 10^5$ cells of Lin$^-$ cell, and further recombinant rat SCF (100 ng/ml, BRL) and recombinant human IL-6 (100 U/ml) were added thereto. In addition, F-deficient SeV of $4 \times 10^7$ CIU/ml was added to $8 \times 10^5$ of total bone marrow cells, and GFP-SeV of $5 \times 10^7$ CIU/ml was added to $1 \times 10^6$ cells. GFP-SeV was prepared by inserting a PCR-amplified NotI fragment, which contains the green fluorescence protein (GFP) gene (the length of the structural gene is 717 bp) to which a transcription initiation (R1), a termination (R2) signal and an intervening (IG) sequence are added, at the restriction enzyme NotI-cleavage site of SeV transcription unit pSeV18+b(+) (Hasan, M. et al, J. Gen. Virol., 1997, 78:2813–2820). The reconstitution of viruses comprising the GFP gene was performed according to a known method (Genes Cells, 1996, 1: 569–579), using LLC-MK2 cells and embryonated egg, and then the viruses comprising the gene of interest were recovered. After a 48-hour culture following the infection with GFP-SeV, the cells were divided into two groups; one of them was allowed to react to phycoerythrin (PE)-labeled anti-CD117 (c-kit; Pharmingen) for 1 hour; the other was a control group. The cells were washed 3 times with PBS then were analyzed in a flow cytometer (EPICS Elite ESP; Coulter, Miami, Fla.).

The result showed that F-deficient SeV vector was also infected to bone marrow cells enriched by anti-c-kit antibody that has been utilized as a marker for blood primitive stem cells and the expression of the GFP gene was observed (FIG. 16). The presence of infective particles in the culture supernatant was confirmed by determining the presence of GFP-expressing cells three days after the addition of cell culture supernatant treated with trypsin to LLC-MK2 cells. It was clarified that none of these cells released infective virus particles.

EXAMPLE 6

Vector Administration into Rat Cerebral Ventricle

Rats (F334/Du Crj, 6 week old, female, Charles River) were anesthetized by intraperitoneal injection of Nembutal sodium solution (Dainabot) diluted 10 folds (5 mg/ml) with physiological saline (Otsuka Pharmaceutical Co., Ltd.). Virus was administrated using brain stereotaxic apparatus for small animals (DAVID KOPF). 20 μl ($10^8$ CIU) were injected at the point 5.2 mm toward bregma from interaural line, 2.0 mm toward right ear from lambda, 2.4 mm beneath the brain surface, using 30G exchangeable needles (Hamilton). A high level expression of GFP protein was observed in ventricle ependymal cells (FIG. 17). Furthermore, in the case of F deficient SeV vector, the expression of GFP protein was observed only in ependymal cells or nerve cells around the injection site, which come into contact with the virus, and no lesion was found in this region. Abnormality in behavior or changes in body weight were not observed in the administered rats until dissection. After dissection, no lesion was found in the brain or in any of the tissues and organs analyzed, such as liver, lung, kidney, heart, spleen, stomach, intestine, and so forth.

EXAMPLE 7

Formation of F-less Virus Particles from F Deficient SeV Genome

<1>

F non-expressing LLC-MK2 cells and F expressing LLC-MK2 cells (LC-MK2/F7) were infected with F deficient SeV virus and cultured with (+) and without (−) trypsin. The result of HA assay of cell culture supernatant after 3 days is shown in FIG. 18A. The culture supernatants were inoculated to embryonated chicken eggs, and the result of HA assay of chorioallantoic fluids after a 2 day-culture is shown in FIG. 18B. "C" on top of panel indicates PBS used as the control group. The numbers indicated under "Dilution" indicates the dilution fold of the virus solution. Further, HA-positive chorioallantoic fluids in embryonated chicken eggs (lanes 11 and 12) was reinoculated into embryonated chicken eggs, and after culturing for two days, the chorioallantoic fluid was examined with HA assay (FIG. 19C). As a result, F non-expressing cells or embryonated chicken eggs infected with F deficient SeV virus were found to be HA-positive. However, viruses had not propagated after re-inoculation to embryonated chicken eggs, proving that the HA-positive virus solution does not have secondary infectivity.

<2>

The non-infectious virus solution amplified in F non-expressing cells was examined for the existence of virus particles. Northern blot analysis was performed for total RNA prepared from the culture supernatant of F expressing cells, HA-positive, non-infectious chorioallantoic fluid, and wildtype SeV by QIAamp viral RNA mini kit (QIAGEN), using the F gene and HN gene as probes. As a result, bands were detected for RNA-derived from chorioallantoic fluid or virus in culture supernatant of F expressing cells when the HN gene was used as the probe, whereas no bands were detected when using the F gene probe (FIG. 10). It was proven that the HA-positive, non-infectious fluid has non-infectious virus-like particles with an F deficient genome. Further, analysis of the HA-positive, non-infectious virus solution by an immunoelectron microscopy revealed the existence of virus particles, and the envelope of virion reacted to the antibody recognizing gold colloid-labeled HN protein, but not to the antibody recognizing gold colloid-labeled F protein (FIG. 20). This result showed the existence of F-less virions, proving that the virus can be formed as a virion with HN protein alone, even without the existence of the F protein. It has been shown that SeV virion can form with F alone (Leyer, S. et al., J. Gen. Virol 79, 683–687 (1998)), and the present result proved for the first time that SeV virion can be formed with HN protein alone. Thus, the fact that F-less virions can be transiently produced in bulk in embryonated chicken eggs shows that virions packaging SeV F deficient RNP can be produced in bulk.

<3>

As described above, F-less virions transiently amplified in embryonated chicken eggs are not at all infective towards cells infected by the Sendai virus. To confirm that functional RNP structures are packaged in envelopes, F expressing cells and non-expressing cells were, mixed with cationic liposome (DOSPER, Boehringer mannheim) and transfected by incubation for 15 minutes at room temperature. As a result, GFP-expressing cells were not observed at all when the cells are not mixed with the cationic liposome, whereas all cells expressed GFP when mixed with cationic liposome. In F non-expressing cells, GFP expression was seen only in individual cells and did not extend to adjacent cells, whereas in F expressing cells, GFP-expressing cells extended to form colonies (FIG. 21) Therefore, it became clear that non-infectious virions transiently amplified in embryonated chicken eggs could express a gene when they are introduced into cells by methods such as transfection.

EXAMPLE 8

Reconstitution and Amplification of the Virus from FHN-deficient SeV Genome

<Construction of FHN-deficient Genomic cDNA>

To construct FHN-deficient SeV genomic cDNA (pSeV18⁺/ΔFHN) pUC18/KS was first digested with EcoRI to construct pUC18/Eco, and then whole sequence from start codon of F gene to stop codon of HN gene (4866–8419) was deleted, then it was ligated at BsiWI site (cgtacg). After the sequence of FHN deleted region was confirmed by base sequencing, EcoRI fragment (4057 bp) was recovered from gels to substitute for EcoRI fragment of pUC18/KS to accomplish the construction. A KpnI/SphI fragment (14673 bp) comprising the FHN deleted region was recovered from gels to substitute for KpnI/SphI fragment of pSeV18⁺ to obtain plasmid pSeV18⁺/ΔFHN.

On the other hand, the construction of FHN-deficient SeV cDNA introduced with GFP was accomplished as follows. SalI/XhoI fragment (7842 bp) was recovered from pSeV18+/ΔFHN, and cloned into pGEM11Z (Promega). The resultant plasmid was named as pGEM11Z/SXdFHN. To the FHN-deficient site of pGEM11Z/SXdFHN, PCR product with BsixI sites at both ends of ATG-TAA (846 bp) of d2EGFP (Clontech) was ligated by digesting with BsiXI enzyme. The resultant plasmid was named as pSeV18+/ΔFHN-d2GFP.

<Establishment of FHN-deficient, Protein Co-expressing Cell Line>

The plasmid expressing F gene is identical to the one used for establishment of F deficient, protein co-expressing cell line, and plasmid expressing HN gene was similarly constructed, and the fragment comprising ORF of HN was inserted to unique SwaI site of pCALNdLw (Arai et al., described above) to obtain plasmid named pCALNdLw/HN.

LLC-MK2 cells were mixed with same amount or different ratio of pCALNdLw/F and pCALNdLw/HN, to introduce genes using mammalian transfection kit (Stratagene), according to the manufacture's protocol. Cells were cloned after a three week-selection with G418. Drug resistant clones obtained were infected with a recombinant adenovirus (Ade/Cre, Saito et al., described above) (moi=10), which expresses Cre DNA recombinase. Then the cells were collected 3 days after inducing expression of F and HN protein after washing 3 times with PBS(−), and they were probed with monoclonal IgG of anti-SeV F protein and anti-SeV HN protein by using Western blotting method (FIG. 22).

<Construction of pGEM/FHN>

F and HN fragments used for the construction of pCALNdLw/F and pCALNdLw/HN were cloned into pGEM4Z and pGEM3 (Promega) to obtain pGEM4Z/F and pGEM3Z/HN, respectively. A fragment obtained by PvuII digestion of the region comprising T7 promoter and HN of pGEM3Z/HN was recovered, and ligated into the blunted site cut at the SacI unique site at the downstream of F gene of pGEM4Z/F. F and HN proteins were confirmed by Western blotting using anti-F or anti-HN monoclonal antibodies to be expressed simultaneously when they were aligned in the same direction.

<Reconstitution of FHN-deficient Virus>

The reconstitution of FHN-deficient viruses (P0) was done in two ways. One was using the RNP transfection method as used in the reconstitution of F deficient virus, and the other was using T7 to supply co-expressing plasmids. Namely, under the regulation of T7 promoter, plasmids expressing F and HN proteins were constructed separately, and using those plasmids F and HN proteins were supplied for the reconstitution. In both methods, reconstituted viruses were amplified by FHN coexpressing cells. FHN-deficient, GFP-expressing SeV cDNA (pSeV18+/ΔFHN-d2GFP), pGEM/NP, pGEM/P, pGEM/L, and pGEM/FHN were mixed in the ratio of 12 μg/10 cm dish, 4 μg/10 cm dish, 2 μg/10 cm dish, 4 μg/10 cm dish, and 4 μg/10 cm dish (final total volume, 3 ml/10 cm dish) for gene introduction into LLC-MK2 cells in the same way as F deficient SeV reconstitution described above. Three hours after the gene introduction, media was changed to MEM containing AraC (40 μg/ml, SIGMA) and trypsin (7.5 μg/ml, GIBCO), and cultured further for 3 days. Observation was carried out by fluorescence stereoscopic microscope 2 days after gene introduction. The effect of pGEM/FHN addition was analyzed, and the virus formation was confirmed by the spread of GFP-expressing cells. As a result, a spread of GFP-expressing cells was observed when pGEM/FHN was added at reconstitution, whereas the spread was not observed when pGEM/FHN was not added, and the GFP expression was observed only in a single cell (FIG. 23). It is demonstrated that the addition at FHN protein reconstitution caused virus virion formation. On the other hand, in the case of RNP transfection, virus recovery was successfully accomplished in FHN expressing cells of P1, as in the case of F deficiency (FIG. 24, upper panel).

Virus amplification was confirmed after infection of FHN-deficient virus solution to cells induced to express FHN protein 6 hours or more after Ade/Cre infection (FIG. 24, lower panel).

Solution of viruses reconstituted from FHN-deficient GFP-expressing SeV cDNA was infected to LLC-MK2, LLC-MK2/F, LLC-MK2/HN and LLC-MK2/FHN cells, and cultured with or without the addition of trypsin. After 3 days of culture, spread of GFP protein expressing cells was analyzed. As a result, spread of GFP was observed only in LLC-MK2/FHN, confirming that the virus solution can be amplified specifically by FHN co-expression and in a trypsin dependent manner (FIG. 25).

To confirm FHN-deficient viral genome, culture supernatant recovered from LLC-MK2/FHN cells was centrifuged, and RNA was extracted using QIAamp Viral RNA mini kit (QIAGEN), according to manufacturer's protocol. The RNA was used for template synthesis of RT-PCR using Superscript Preamplification System for first Strand Synthesis (GIBCO BRL), and PCR was performed using TAKARA Z-Taq (Takara). F-deficient virus was used as a control group. PCR primer sets were selected as combination of M gene and GFP gene, or combination of M gene and L gene (for combination of M gene and GFP gene (M-GFP), forward: 5'-atcagagacctgcgacaatgc/SEQ ID NO: 13, reverse: 5'-aagtcgtgctgcttcatgtgg/SEQ ID NO: 14; for combination of M gene and L gene (M-L), forward: 5'-gaaaaacttagg-gataaagtccc/SEQ ID NO: 15, reverse: 5'-gttatctccgggatg-gtgc/SEQ ID NO: 16). As a result, specific bands were obtained for both F-deficient and FHN-deficient viruses at RT conditions when using M and GFP genes as primers. In the case of using M and L genes as primers, the bands with given size comprising GFP were detected for FHN deficient sample, and lengthened bands with the size comprising HN gene were detected for F deficient one. Thus, FHN deficiency in genome structure was proven (FIG. 26).

On the other hand, FHN-deficient virus was infected to F expressing cells similarly as when using the F-deficient virus, and culture supernatant was recovered after 4 days to perform infection experiment toward LLC-MK2, LLC-MK2/F, and LLC-MK2/FHN. As a result, GFP expression cell was not observed in any infected cell, showing that the virus has no infectiousness to these cells. However, it has been already reported that F protein alone is enough to form virus particles (Leyer, S. et al, J. Gen. Virol. 79, 683–687 (1998)) and that asialoglycoprotein receptor (ASG-R) mediates specific infection to hepatocytes (Spiegel et al., J. Virol 72, 5296–5302, 1998). Thus, virions comprising FHN-deficient RNA genome, with virus envelope configured with only F protein may be released to culture supernatant of F expressing cells. Therefore, culture supernatant of F expressing cells infected with FHN-deficient virus was recovered, and after centrifugation, RNA was extracted as described above and analyzed by RT-PCR by the method described above. As a result, the existence of RNA comprising FHN-deficient genome was proved as shown in FIG. 27.

Western blotting analysis of virus virion turned into pseudotype with VSV-G clearly shows that F and HN proteins are not expressed. It could be said that herein, the production system of FHN-deficient virus virions was established.

Moreover, virions released from F protein expressing cells were overlaid on FHN expressing or non-expressing LLC-MK2 cells with or without mixing with a cationic liposome (50 μl DOSPER/500 μl/well) As a result, spread of GFP-expressing cells was observed when overlaid as mixture with DOSPER, while HN-less virion only has no infectiousness at all, not showing GFP-expressing cells, as was seen in the case of F-less particles described above. In FHN non-expressing cells GFP expressing cell was observed, but no evidence of virus re-formation and spread was found.

These virus-like particles recovered from F expressing cells can infect cells continuously expressing ASG-R gene, ASG-R non-expressing cells, or hepatocytes, and whether the infection is liver-specific or ASG-R specific can be examined by the method of Spiegel et al.

EXAMPLE 9

Application of Deficient Genome RNA Virus Vector

1. F-deficient RNP amplified in the system described above is enclosed by the F-less virus envelope. The envelope can be introduced into cells by adding any desired cell-introducing capability to the envelope by chemical modification methods and such, or by gene introducing reagents or gene guns or the like (RNP transfection, or RNP injection), and the recombinant RNA genome can replicate and produce proteins autonomously and continuously in the cells.
2. A vector capable of specific targeting can be produced, when intracellular domain of HN is left as-is, and the extracellular domain of HN is fused with ligands capable of targeting other receptors in a specific manner, and recombinant gene capable of producing chimeric protein is incorporated into viral-genome. In addition, the vector can be prepared in cells producing the recombinant protein. These vectors can be applicable to gene therapy, as vaccines, or such.
3. Since the reconstitution of SeV virus deficient in both FHN has been successfully accomplished, targeting vector can be produced by introducing targeting-capable envelope chimeric protein gene into FHN deletion site instead of the GFP gene, reconstituting it by the same method as in the case of FHN-deficient vector, amplifying the resultant once in FHN-expressing cells, infecting the resultant to non-expressing cells, and recovering virions formed with only the targeting-capable chimeric envelope protein transcribed from the viral-genome.
4. A mini-genome of Sendai virus and a virion formed with only F protein packaging mini-genome by introducing NP, P, L and F gene to cells have been reported (Leyer et al., J Gen. Virol 79, 683–687, 1998). A vector in which murine leukemia virus is turned into pseudotype by Sendai F protein has also been reported (Spiegel et al., J. Virol 72, 5296–5302, 1998). Also reported so far is the specific targeting of trypsin-cleaved F-protein to hepatocytes mediated by ASG-R (Bitzer et al., J. Virol. 71, 5481–5486, 1997). The systems in former reports are transient particle-forming systems, which make it difficult to continuously recover vector particles. Although Spiegel et al. has reported retrovirus vector turned into pseudo-type by Sendai F protein, this method carries intrinsic problems like the retrovirus being able to introduce genes to only mitotic cells. The virus particles recovered in the present invention with a FHN co-deficient SeV viral-genome and only the F protein as the envelope protein are efficient RNA vectors capable of autonomous replication in the cytoplasm irrespective of cell mitosis. They are novel virus particles, and is a practical system facilitating mass production.

EXAMPLE 10

Virus Reconstitution and Amplification from FHN-deficient SeV Genome

The techniques of reconstitution of infectious virus particles from cDNA that cloned the viral genome has been established for many single-strand minus strand RNA viruses such as the Sendai virus, measles virus.

In most of the systems, reconstitution is carried out by introducing plasmids introduced with cDNA, NP, P, and L genes at the downstream of T7 promoter into cells and expressing cDNA and each gene using T7 polymerase. To supply T7 polymerase, recombinant vaccinia virus expressing T7 polymerase is mainly used.

T7 expressing vaccinia virus can express T7 polymerase efficiently in most cells. Although, because of vaccinia virus-induced cytotoxicity, infected cells can live for only 2 or 3 days. Inmost cases, rifampicin is used as an anti-vaccinia reagent. In the system of Kato et al. (Kato, A. et al., Genes cells 1, 569–579 (1996)), AraC was used together with rifampicin for inhibiting vaccinia virus growth to a minimum level, and efficient reconstitution of Sendai virus.

However, the reconstitution efficiency of minus strand RNA virus represented by Sendai virus is several particles or less in $1 \times 10^5$ cells, far lower than other viruses such as retroviruses. Cytotoxicity due to the vaccinia virus and the complex reconstitution process (transcribed and translated protein separately attaches to bare RNA to form RNP-like structure, and after that, transcription and translation occurs by a polymerase) can be given as reasons for this low reconstitution efficiency.

In addition to the vaccinia virus, an adeno virus system was examined as a means for supplying T7 polymerase, but no good result was obtained. Vaccinia virus encodes RNA capping enzyme functioning in cytoplasm as the enzyme of itself in addition to T7 polymerase and it is thought that the enzyme enhances the translational efficiency by capping the RNA transcribed by T7 promoter in the cytoplasm. The present invention tried to enhance the reconstitution efficiency of Sendai virus by treating vaccinia virus with Psoralen-Long-Wave-UV method to avoid cytotoxicity due to the vaccinia virus.

By DNA cross-linking with Psoralen and long-wave ultraviolet light, the state in which the replication of virus with DNA genome is inhibited, without effecting early gene expression in particular, can be obtained. The notable effect seen by inactivation of the virus in the system may be attributed to that vaccinia virus having a long genome (Tsung, K. et al., J Virol 70, 165–171 (1996)).

In the case of wildtype virus that can propagate autonomously, even a single particle of virus formed by reconstitution makes it possible for Sendai virus to be propagated by inoculating transfected cells to embryonated chicken eggs.

Therefore, one does not have to consider of the efficiency of reconstitution and the residual vaccinia virus seriously.

However, in the case of reconstitution of various mutant viruses for researching viral replication, particle formation mechanism, and so on, one may be obligated to use cell lines expressing a protein derived from virus and such, not embryonated chicken eggs, for propagation of the virus. Further, it may greatly possible that the mutant virus or deficient virus propagates markedly slower than the wild type virus.

To propagate Sendai virus with such mutations, transfected cells should be overlaid onto cells of the next generation and cultured for a long period. In such cases, the reconstitution efficiency and residual titer of vaccinia virus may be problematic. In the present method, titer of surviving vaccinia virus was successfully decreased while increasing reconstitution efficiency.

Using the present method, a mutant virus that could have not been ever obtained in the former system using a non-treated vaccinia virus was successfully obtained by reconstitution (F, FHN-deficient virus). The present system would be a great tool for the reconstitution of a mutant virus, which would be done more in the future. Therefore, the present inventors examined the amount of Psoralen and ultraviolet light (UV), and the conditions of vaccinia virus inactivation.

<Experiment>

First, Psoralen concentration was tested with a fixed irradiation time of 2 min. Inactivation was tested by measuring the titer of vaccinia virus by plaque formation, and by measuring T7 polymerase activity by pGEM-luci plasmid under the control of T7 promoter and mini-genome of Sendai virus. The measurement of T7 polymerase activity of mini-genome of Sendai virus is a system in which cells are transfected concomitantly with plasmid of mini-genome of Sendai virus and pGEM/NP, pGEM/P, and pGEM/L plasmids, which express NP-, P-, and L-protein of Sendai virus by T7, to examine transcription of the RNA encoding luciferase enzyme protein by RNA polymerase of Sendai virus after the formation of ribonucleoprotein complex.

After the 2 min UV irradiation, decrease in titer of vaccinia virus depending on psoralen concentration was seen. However, T7 polymerase activity was unchanged for a Psoralen concentration up to 0, 0.3, and 1 µg/ml, but decreased approximately to one tenth at 10 µg/ml (FIG. 28).

Furthermore, by fixing Psoralen concentration to 0.3 µg/ml, UV irradiation time was examined. In accordance with the increase of irradiation time, the titer of vaccinia virus was decreased, although no effect on T7 polymerase activity was found up to a 30 min irradiation. In this case, under the conditions of 0.3 µg/ml and 30 min irradiation, titer could be decreased down to $1/1000$ without affecting T7 polymerase activity (FIG. 29).

However, in vaccinia virus with a decreased titer of $1/1000$, CPE24 hours after infection at moi=2 calibrated to pretreatment titer (moi=0.002 as residual titer after treatment) was not different from that of non-treated virus infected at moi=2 (FIG. 30).

Using vaccinia virus treated under the conditions described above, the efficiency of reconstitution of Sendai virus was examined. Reconstitution was carried out by the procedure described below, modifying the method of Kato et al. mentioned above. LLC-MK2 cells were seeded onto 6-well microplates at $3 \times 10^5$ cells/well, and after an overnight culture, vaccinia virus was diluted to the titer of $6 \times 10^5$ pfu/100 µl calibrated before PLWUV treatment, and infected to PBS-washed cells. One hour after infection, 100 µl of OPTI-MEM added with 1, 0.5, 1, and 4 µg of plasmid pGEM-NP, P, L, and cDNA, respectively, was further added with 10 µl Superfect (QIAGEN) and left standing for 15 min at room temperature, and after adding 1 ml OPTI-MEM (GIBCO) (containing Rif and AraC), was overlaid onto the cells.

Two, three and four days after transfection, cells were recovered, centrifuged, and suspended in 300 µl/well of PBS. 100 µl of cell containing solution made from the suspension itself, or by diluting the suspension by 10 or 100 folds, was inoculated to embryonated chicken eggs at day 10 following fertilization, 4 eggs for each dilution ($1 \times 10^5$, $1 \times 10^4$, and $1 \times 10^3$ cells, respectively). After 3 days, allantoic fluid was recovered from the eggs and the reconstitution of virus was examined by HA test (Table 1). Eggs with HA activity was scored as 1 point, 10 points and 100 points for eggs inoculated with $1 \times 10^5$, $1 \times 10^4$, and $1 \times 10^3$ cells, respectively, to calculate the Reconstitution Score (FIG. 31). The formula is as shown in Table 1.

TABLE 1

Effect of the duration of UV treatment of vaccinia virus on reconstitution efficiency of Sendai virus

| The number of inoculated cells | Score (a) | The number of HA -positive eggs (b) | | | | | | | | | | | |
|---|---|---|---|---|---|---|---|---|---|---|---|---|---|
| | | 2d | | | | 3d | | | | 4d | | | |
| | | 0' | 15' | 20' | 30' | 0' | 15' | 20' | 30' | 0' | 15' | 20' | 30' |
| $10^5$ | 1 (a1) | 1 | 2 | 4 | 4 | 0 | 2 | 4 | 4 | 1 | 3 | 4 | 4 |
| $10^4$ | 10 (a2) | 0 | 1 | 3 | 2 | 0 | 2 | 3 | 4 | 0 | 0 | 4 | 0 |
| $10^3$ | 100 (a3) | 0 | 0 | 0 | 1 | 0 | 1 | 0 | 2 | 0 | 0 | 0 | 0 |
| Reconstitution Score | (a1 + a2 + a3) × b | 1 | 12 | 24 | 124 | 0 | 122 | 34 | 244 | 1 | 3 | 44 | 4 |

Reconstitution Score = (a1 + a2 + a3) × b

Also, residual titers of vaccinia virus measured at 2, 3, and 4 days after transfection within cells were smaller in the treated group in proportion to the titer given before transfection (FIG. 32).

By inactivating vaccinia virus by PLWUV, titer could be decreased down to $1/1000$ without affecting T7 polymerase activity. However, CPE derived from vaccinia virus did not differ from that of non-treated virus with a 1000 fold higher titer as revealed by microscopic observations.

Using vaccinia virus treated with the condition described above for reconstitution of Sendai virus, reconstitution efficiency increased from ten to hundred folds (FIG. 31). At the same time, residual titer of vaccinia virus after transfection was not 5 pfu/$10^5$ cells or more. Thus, the survival of replicable vaccinia virus was kept at 0.005% or less.

EXAMPLE 11

Construction of Pseudotype Sendai Virus

<1> Preparation of Helper Cells in Which VSV-G Gene Product is Induced

Because VSV-G gene product has a cytotoxicity, stable transformant was created in LLC-MK2 cells using plasmid pCALNdLG (Arai T. et al., J. Virology 72 (1998) p1115–1121) in which VSV-G gene product can be induced by Cre recombinase. Introduction of plasmid into LLC-MK2 cells was accomplished by calcium phosphate method (CalPhosTMMammalian Transfection Kit, Clontech), according to accompanying manual.

Ten micrograms of plasmid pCALNdLG was introduced into LLC-MK2 cells grown to 60% confluency in a 10 cm culture dish. Cells were cultured for 24 hours with 10 ml MEM-FCS 10% medium in a 5% $CO_2$ incubator at 37° C. After 24 hours, cells were scraped off and suspended in 10 ml of medium, and then using five 10 cm culture dishes, 1, 2 and 2 dishes were seeded with 5 ml, 2 ml and 0.5 ml, respectively. Then they were cultured for 14 days in 10 ml MEM-FCS 10% medium containing 1200 µg/ml G418 (GIBCO-BRL) with a medium change on every other day to select stable transformants. Twenty-eight clones resistant to G418 grown in the culture were recovered using cloning rings. Each clone was expanded to confluency in a 10 cm culture dish.

For each clone, the expression of VSV-G was examined by Western blotting described below using anti-VSV-G monoclonal antibody, after infection with recombinant adenovirus AxCANCre containing Cre recombinase.

Each clone was grown in a 6 cm culture dish to confluency, and after that, adenovirus AxCANCre was infected at MOI=10 by the method of Saito et al. (see above), and cultured for 3 days. After removing the culture supernatant, the cells were washed with PBS, and detached from the culture dish by adding 0.5 ml PBS containing 0.05% trypsin and 0.02% EDTA (ethylenediaminetetraacetic acid) and incubating at 37° C., 5 min. After suspending in 3 ml PBS, the cells were collected by centrifugation at 1500×g, 5 min. The cells obtained were resuspended in 2 ml PBS, and then centrifuged again at 1500×g, 5 min to collect cells.

The cells can be stored at −20° C., and can be used by thawing according to needs. The collected cells were lysed in 100 µl cell lysis solution (RIPA buffer, Boehringer Mannheim), and using whole protein of the cells ($1 \times 10^5$ cells per lane) Western blotting was performed. Cell lysates were dissolved in SDS-polyacrylamide gel electrophoresis sample buffer (buffer comprising 6 mM Tris-HCl (pH 6.8), 2% SDS, 10% glycerol, 5% 2-mercaptoethanol) and subjected as samples for electrophoresis after heating at 95° C., 5 min. The samples were separated by electrophoresis using SDS-polyacrylamide gel (Multigel 10/20, Daiichi Pure Chemicals Co., Ltd), and the separated protein was then transferred to transfer membrane (Immobilon-P Transfer-Membranes, Millipore) by semi-dry blotting method. Transfer was carried out using transfer membrane soaked with 100% methanol for 20 sec and with water for 1 hour, at a 1 mA/$cm^2$ constant current for 1 hour.

The transfer membrane was shaken in 40 ml of blocking solution (Block-Ace, Snow Brand Milk Products Co., Ltd.) for 1 hour, and washed once in PBS.

The transfer membrane and 5 ml anti-VSV-G antibody (clone P4D4, Sigma) diluted 1/1000 by PBS containing 10% blocking solution were sealed in a vinyl-bag and left to stand at 4° C.

The transfer membrane was soaked twice in 40 ml of PBS-0.1% Tween 20 for 5 min, and after the washing, soaked in PBS for 5 min for washing.

The transfer membrane and 5 ml of anti-mouse IgG antibody labeled with peroxidase (anti-mouse immunoglobulin, Amersham) diluted to 1/2500 in PBS containing 10% blocking solution were sealed in vinyl-bag and were shaken at room temperature for 1 hour.

After shaking, the transfer membrane was soaked twice in PBS-0.1% Tween 20 for 5 min, and after the washing, soaked in PBS for 5 min for washing.

The detection of proteins on the membrane crossreacting with anti-VSV-G antibody was carried out by the luminescence method (ECL Western blotting detection reagents, Amersham). The result is shown in FIG. 33. Three clones showed AxCANCre infection specific VSV-G expression, confirming the establishment of LLC-MK2 cells in which VSV-G gene product can be induced.

One clone among the clones obtained, named as LLCG-L1, was subjected to flow cytometry analysis using anti-VSV antibody (FIG. 34). As a result, reactivity with antibody specific to VSV-G gene induction was detected in LLCG-L1, confirming that VSV-G protein is expressed on the cell surface.

<2> Preparation of Pseudotype Sendai Virus Comprising a Genome Deficient in the F Gene Using Helper Cells Sendai virus comprising a genome deficient in F gene was infected to VSV-G gene expressing cells, and whether production of pseudotype virus-with VSV-G as capsid can be seen-or not was examined using F-deficient Sendai virus comprising GFP gene described in the examples above, and the expression of GFP gene as an index. As a result, in LLCG-L1 without infection of recombinant adenovirus AxCANCre comprising Cre recombinase, viral gene was introduced by F-deficient Sendai virus infection and GFP-expressing cells were detected, although the number of expressing cells was not increased. In VSV-G induced cells, chronological increase of GFP-expressing cells was found. When 1/5 of supernatants were further added to newly VSV-G induced cells, no gene introduction was seen in the former supernatant, while the increase of GFP-expressing cells as well as gene introduction were found in the latter supernatant. Also, in the case that supernatant from latter is added to LLCG-L1 cells without induction of VSV-G, gene was introduced, but increase of GFP-expressing cells was not seen. Taken together, virus propagation specific to VSV-G expressing cells was found, and pseudotype F-deficient virus formation with VSV-G was found.

<3> Evaluation of Conditions for Producing Pseudotype Sendai Virus with F Gene-deficient Genome A certain amount of pseudotype Sendai viruses with F gene-deficient genomes was infected changing the amount of AxCANCre infection (MOI=0, 1.25, 2.5, 5, and 10) and culture supernatant was recovered at day 7 or day 8. Then, the supernatant was infected to the cells before and after induction of VSV-G, and after 5 days, number of cells expressing GFP was compared to see the effect of amount of VSV-G gene expression. As a result, no virus production was found at MOI=0 and maximum production was found at MOI=10 (FIG. 35). In addition, when time course of virus production was analyzed, the production level started to increase from day 5 or after, persisting to day 8 (FIG. 36).

The measurement of virus titer was accomplished by calculating the number of particles infected to cells in the virus solution (CIU), by counting GFP-expressing cells 5 days after infection of serially (10 fold each) diluted virus solutions to cells not yet induced with VSV-G. As a result, the maximal virus production was found to be $5 \times 10^5$ CIU/ml.

<4> Effect of Anti-VSV Antibody on Infectiousness of Pseudotype Sendai Virus with F Gene-deficient Genome As to whether pseudotype Sendai virus with F gene-deficient genome obtained by using VSV-G expressing cells comprises VSV-G protein in the capsid, the neutralizing activity of whether infectiousness will be affected was evaluated using anti-VSV antibody. Virus solution and antibody were mixed and lest standing at room temperature for 30 min, and then infected to LLCG-L1 cells without VSV-G induction. On day 5, gene-introducing capability was examined by the existence of GFP-expressing cells. As a result, perfect inhibition of infectiousness was seen by the anti-VSV antibody, whereas in Sendai virus with F gene-deficient genome having the original capsid, the inhibition was not seen (FIG. 37). Therefore, it was clearly shown that the present virus obtained is a pseudotype Sendai virus comprising VSV-G protein in its capsid, in which infectiousness of the virus can be specifically inhibited by an antibody.

<5> Confirmation of Pseudotype Sendai Virus's Possession of F-deficient Genome

Western blotting analysis of cell extract of infected cells was carried out to examine if the present virus propagated in cells expressing VSV-G gene is the F-deficient type. Western analysis was accomplished by the method described above. As the primary antibodies, anti-Sendai virus polyclonal antibody prepared from rabbit, anti-F protein monoclonal antibody prepared from mouse, and anti-HN protein monoclonal antibody prepared from mouse were used. As the secondary antibodies, anti-rabbit IgG antibody labeled with peroxidase in the case of anti-Sendai virus polyclonal antibody, and anti-mouse IgG antibody labeled with peroxidase in the case of anti-F protein monoclonal antibody and anti-HN protein monoclonal antibody, were used. As a result, F protein was not detected, whereas protein derived from Sendai virus and HN protein were detected, confirming it is F-deficient type.

<6> Preparation of Pseudotype Sendai Virus with F and HN Gene-deficient Genome by Using Helper Cells Whether the production of pseudotype virus with VSV-G in its capsid is observed after the infection of Sendai virus with F and HN gene-deficient genome to LLCG-L1 cells expressing VSV-G gene was analyzed using GFP gene expression as the indicator and F and HN gene-deficient Sendai virus comprising GFP gene described in examples above, by a similar method as described in examples above. As a result, virus propagation specific to VSV-G expressing cells was observed, and the production of F and HN deficient Sendai virus that is a pseudotype with VSV-G was observed (FIG. 38). The measurement of virus titer was accomplished by calculating the number of particles infected to cells in the virus solution (CIU), by counting GFP-expressing cells 5 days after infection of serially (10 fold each) diluted virus solutions to cells not yet induced with VSV-G. As a result, the maximal virus production was $1 \times 10^6$ CIU/ml.

<7> Confirmation of Pseudotype Sendai Virus's Possession of F and HN Deficient Genome Western blotting of proteins in cell extract of infected cells was carried out to analyze whether the present virus propagated in VSV-G expressing cells are the F and HN deficient type. As a result, F and HN proteins were not detected, whereas proteins derived from Sendai virus were detected, confirming that it is F and HN deficient type (FIG. 39).

EXAMPLE 12

Analysis of Virus Reconstitution Method

<Conventional Method>

LLC-MK2 cells were seeded onto 100 mm culture dishes at $5 \times 10^6$ cells/dish. After a 24 hour culture, the cells were washed once with MEM medium without serum, and then infected with recombinant vaccinia virus expressing T7 RNA polymerase (Fuerst, T. R. et al., Proc. Natl. Acad. Sci. USA 83, 8122–8126 1986) (vTF7-3) at room temperature for 1 hour (moi=2) (moi=2 to 3, preferably moi=2 is used). The virus used herein, was pretreated with 3 µg/ml psoralen and long-wave ultraviolet light (365 nm) for 5 min. Plasmids pSeV18$^+$/ΔF-GFP, pGEM/NP, pGEM/P, and pGEM/L (Kato, A. et al., Genes cells 1, 569–579(1996)) were suspended in Opti-MEM medium (GIBCO) at ratio of 12 µg, 4 µg, 2 µg, and 4 µg/dish, respectively. Then, SuperFect transfection reagent (1 µg DNA/5 µl, QIAGEN) was added and left to stand at room temperature for 15 min and 3 ml Opti-MEM medium containing 3% FBS was added. Thereafter, the cells were washed twice with MEM medium without serum, and DNA-SuperFect mixture was added. After a 3 hr culture, cells were washed twice with MEM medium without serum, and cultured 70 hours in MEM medium containing 40 µg/ml cytosine β-D-arabinofuranoside (AraC, Sigma). Cells and culture supernatant were collected as P0-d3 samples. Pellets of P0-d3 were suspended in Opti-MEM medium ($10^7$ cells/ml). They were freeze-thawed three times and then mixed with lipofection reagent DOSPER (Boehringer Mannheim) ($10^6$ cells/25 µl DOSPER) and left to stand at room temperature for 15 min. Then, F expressing LLC-MK2/F7 cells were transfected with the mixture ($10^6$ cells/well in 24-well plate) and cultured with MEM medium without serum (containing 40 µg/ml AraC and 7.5 µg/ml trypsin). Culture supernatants were recovered on day 3 and day 7 and were designated as P1-d3 and P1-d7 samples.

<Envelope Plasmid+F Expressing Cells Overlaying Method>

Transfection was carried out similarly as described above, except that 4 µg/dish envelope plasmid pGEM/FHN was added. After a 3 hr culture, cells were washed twice with MEM medium without serum, and cultured 48 hours in MEM medium containing 40 µg/ml cytosine β-D-arabinofuranoside (AraC, Sigma) and 7.5 µg/ml trypsin. After removing the culture supernatant, cells were overlaid with 5 ml cell suspension solution of a 100 mm dish of F expressing LLC-MK2/F7 cells suspended with MEM medium without serum (containing 40 µg/ml AraC and 7.5 µg/ml trypsin). After a 48 hr culture, cells and supernatants were recovered and designated as P0-d4 samples. Pellets of P0-d4 samples were suspended in Opti-MEM medium ($2 \times 10^7$ cells/ml) and freeze-thawed three times. Then F expressing LLC-MK2/F7 cells were overlaid with the suspension ($2 \times 10^6$ cells/well, 24-well plate) and cultured in MEM medium without serum (containing 40 µg/ml AraC and 7.5 µg/ml trypsin). Culture supernatants were recovered on day 3 and day 7 of the culture, designated as P1-d3 and P1-d7 samples, respectively. As a control, experiment was carried out using the same method as described above, but without overlaying and adding only the envelope plasmid.

<CIU (Cell Infectious Units) Measurement by Counting GFP-expressing Cells (GFP-CIU)>

LLC-MK2 cells were seeded onto a 12-well plate at $2 \times 10^5$ cells/well, and after 24 hr culture the wells were washed once with MEM medium without serum. Then, the cells were infected with 100 μl/well of appropriately diluted samples described above (P0-d3 or P0-d4, P1-d3, and P1-d7), in which the samples were diluted as containing 10 to 100 positive cells in 10 $cm^2$. After 15 min, 1 ml/well of serum-free MEM medium was added, and after a further 24 hr culture, cells were observed under fluorescence microscopy to count GFP-expressing cells.

<Measurement of CIU (Cell Infectious Units)>

LLC-MK2 cells were seeded onto a 12-well plate at $2 \times 10^5$ cells/dish and after a 24 hr culture, cells were washed once with MEM medium without serum. Then, the cells were infected with 100 μl/well of samples described above, in which the virus vector contained is designated as SeV/ΔF-GFP. After 15 min, 1 ml/well of MEM medium without serum was added and cultured for a further 24 hours. After the culture, cells were washed with PBS (−) three times and were dried up by leaving standing at room temperature for approximately 10 min to 15 min. To fix cells, 1 ml/well acetone was added and immediately removed, and then the cells were dried up again by leaving to stand at room temperature for approximately 10 min to 15 min. 300 μl/well of anti-SeV polyclonal antibody (DN-1) prepared from rabbit, 100-fold diluted with PBS (−) was added to cells were and incubated for 45 min at 37° C. Then, they were washed three times with PBS (−) and 300 μl/well of anti-rabbit IgG (H+L) fluorescence-labeled second antibody (Alexa™568, Molecular Probes), 200-fold diluted with PBS (−) was added and incubated for 45 min at 37° C. After washing with PBS (−) three times, the cells were observed under fluorescence microscopy (Emission: 560 nm, Absorption: 645 nm filters, Leica) to find florescent cells (FIG. 40).

As controls, samples described above (SeV/ΔF-GFP) were infected at 100 μl/well, and after 15 min 1 ml/well of MEM without serum was added, and after a 24 hr culture, cells were observed under fluorescence microscopy (Emission: 360 nm, Absorption: 470 nm filters, Leica) to find GFP-expressing cells, without the process after the culture.

EXAMPLE 13

Evaluation of the Most Suitable PLWUV (Psoralen and Long-wave UV light) Treatment Conditions for Vaccinia Virus (vTF7-3) for Increasing Reconstitution Efficiency of Deficient-type Sendai Virus Vector LLC-MK2 cells were seeded onto 100 mm culture dishes at $5 \times 10^6$ cells/dish, and after a 24 hr culture, the cells were washed once with MEM medium without serum. Then, the cells were infected with recombinant vaccinia virus (vTF7-3) (Fuerst, T. R. et al., Proc. Natl. Acad. Sci. USA 83, 8122–8126(1986)) expressing T7 RNA polymerase at room temperature for 1 hour (moi=2) (moi=2 to 3, preferably moi=2 is used). The virus used herein, was pretreated with 0.3 to 3 μg/ml psoralen and long-wave ultraviolet light (365 nm) for 2 to 20 min. Plasmids pSeV18+/ΔF-GFP, pGEM/NP, pGEM/P, and pGEM/L (Kato, A. et al., Genes cells 1, 569–579 (1996)) were suspended in Opti-MEM medium (GIBCO) at ratio of 12 μg, 4 μg, 2 μg, and 4 μg/dish, respectively. Then, SuperFect transfection reagent (1 μg DNA/5 μl, QIAGEN) was added and left to stand at room temperature for 15 min and 3 ml Opti-MEM medium containing 3% FBS was added. Thereafter, the cells were washed twice with MEM medium without serum, and then DNA-SuperFect mixture was added. After a 3 hr culture, cells were washed twice with MEM medium without serum, and cultured 48 hours in MEM medium containing 40 μg/ml cytosine β-D-arabinofuranoside (AraC, Sigma). Approximately 1/20 of field of view in 100 mm culture dish was observed by a fluorescence microscope and GFP-expressing cells were counted. To test the inactivation of vaccinia virus (vTF7-3), titer measurement by plaque formation (Yoshiyuki Nagai et al., virus experiment protocols, p291–296, 1995) was carried out.

Further, fixing the timing of recovery after transfection to day 3, psoralen and UV irradiation time were examined. Using vaccinia virus (vTF7-3) treated with each PLWUV treatment, reconstitution efficiency of Sendai virus was examined. Reconstitution was carried out by modifying the method of Kato et al., namely by the procedure described below. LLC-MK2 cells were seeded onto a 6-well microplate at $5 \times 10^5$ cells/well, and after an overnight culture (cells were considered to grow to $1 \times 10^6$ cells/well), PBS washed cells were infected with diluted vaccinia virus (vTF7-3) at $2 \times 10^6$ pfu/100 μl calibrated by titer before PLWUV treatment. After a 1 hour infection, 50 μl of Opti-MEM medium (GIBCO) was added with 1, 0.5, 1, and 4 μg of plasmid pGEM/NP, pGEM/P, pGEM/L, and additional type SeV cDNA (pSeV18+b (+))(Hasan, M. K. et al., J. General Virology 78: 2813–2820, 1997), respectively. 10 μl Super-Fect (QIAGEN) was further added and left to stand at room temperature for 15 min. Then, 1 ml of Opti-MEM (containing 40 μg/ml AraC) was added and overlaid onto the cells. Cells were recovered 3 days after transfection, then centrifuged and suspended in 100 μl/well PBS. The suspension was diluted 10, 100, and 1000-fold and 100 μl of resultant cell solution was inoculated into embryonated chicken eggs 10 days after fertilization, using 3 eggs for each dilution ($1 \times 10^5$, $1 \times 10^4$ and $1 \times 10^3$ cells, respectively). After 3 days, allantoic fluid was recovered from the eggs and virus reconstitution was examined by HA test. To calculate reconstitution efficiency, eggs showing HA activity that were inoculated with $1 \times 10^5$ cells, $1 \times 10^4$ cells and $1 \times 10^3$ cells, were counted as 1, 10, and 100 point(s), respectively.

<Results>

Results of Examples 12 and 13 are shown in FIGS. 40 to 43, and Table 2. The combination of envelope expressing plasmid and cell overlay increased the reconstitution efficiency of SeV/ΔF-GFP. Notable improvement was obtained in d3 to d4 (day 3 to day4) of P0 (before subculture) (FIG. 41). In Table 2, eggs were inoculated with cells 3 days after transfection. The highest reconstitution efficiency was obtained in day 3 when treated with 0.3 μg/ml psoralen for 20 min. Thus, these conditions were taken as optimal conditions (Table 2).

TABLE 2

Effect of PLWUV treatment of vaccinia virus on reconstitution of Sendai virus
(eggs were inoculated with cells 3 days after transfection)

| The number of inoculated cells | Score (a) | 0 μg/ml 0' | 0.3 μg/ml 20' | 1 μg/ml 5' | 1 μg/ml 10' | 1 μg/ml 20' | 3 μg/ml 2' | 3 μg/ml 5' | 3 μg/ml 10' |
|---|---|---|---|---|---|---|---|---|---|
| $10^5$ | 1 (a1) | 0 | 3 | 3 | 3 | 3 | 3 | 3 | 3 |
| $10^4$ | 10 (a2) | 0 | 3 | 2 | 3 | 3 | 1 | 3 | 1 |
| $10^3$ | 100 (a3) | 0 | 3 | 0 | 1 | 1 | 0 | 1 | 0 |
| Reconstitution Score | (a1 + a2 + a3) × b | 0 | 333 | 43 | 133 | 133 | 13 | 133 | 13 |

Reconstitution Score = (a1 + a2 + a3) × b

EXAMPLE 14

Preparation of LacZ-comprising, F-deficient GFP-non-comprising Sendai Virus Vector <Construction of F-deficient Type, LacZ Gene-comprising SeV Vector cDNA>

To construct cDNA comprising LacZ gene at Not I restriction site existing at the upstream region of NP gene of pSeV18$^+$/ΔF described in Example 1 (pSeV (+18:LacZ)/ΔF), PCR was performed to amplify the LacZ gene. PCR was carried out by adjusting LacZ gene to multiples of 6 (Hausmann, S et al., RNA 2, 1033–1045 (1996)) and using primer (5'-GCGCGGCCGCCGTACGGTGGCAACCAT-GTCGTTTACTTTGACCAA-3'/SEQ ID NO: 17) comprising Not I restriction site for 5' end, and primer (5'-GCGCG-GCCGCGATGAACTTTCACCCTAAGTTTTTCTTACTA CGGCGTACGCTATTACTTCTGACACCAGACCAACTG GTA-3'/SEQ ID NO: 18) comprising transcription termination signal of SeV (E), intervening sequence (I), transcription initiation signal (S), and Not I restriction site for 3' end, using pCMV-β (Clontech) as template. The reaction conditions were as follows. 50 ng pCMV-β, 200 μM dNTP (Pharmacia Biotech), 100 pM primers, 4 U Vent polymerase (New England Biolab) were mixed with the accompanying buffer, and 25 reaction temperature cycles of 94° C. 30 sec, 50° C. 1 min, 72° C. 2 min were used. Resultant products were electrophoresed with agarose gel electrophoreses. Then, 3.2 kb fragment was cut out and digested with NotI after purification. pSeV(+18:LacZ)/ΔF was obtained by ligating with NotI digested fragment of pSeV18+/ΔF.

<Conventional Method>

LLC-MK2 cells were seeded onto 100 mm culture dish at 5×10$^6$ cells/dish, and after a 24 hour culture, the cells were washed once with MEM medium without serum. Then, the cells were infected with recombinant vaccinia virus (vTF7-3) (Fuerst, T. R. et al., Proc. Natl. Acad. Sci. USA 83, 8122–8126 (1986)) expressing T7 RNA polymerase at room temperature for 1 hour (moi=2) (moi=2 to 3, preferably moi=2 is used) The virus used herein was pretreated with 3 μg/ml psoralen and long-wave ultraviolet light (365 nm) for 5 min. LacZ comprising, F-deficient type Sendai virus vector cDNA (pSeV(+18:LacZ) ΔF) pGEM/NP, pGEM/P, and pGEM/L (Kato, A. et al., Genes Cells 1, 569–579 (1996)) were suspended in Opti-MEM medium (GIBCO) at a ratio of 12 μg, 4 μg, 2 μg, and 4 μg/dish, respectively, 4 μg/dish envelope plasmid pGEM/FHN and SuperFect transfection reagent (1 μg DNA/5 μl, QIAGEN) were added and left to stand at room temperature for 15 min. Then, 3 ml Opti-MEM medium containing 3% FBS was added and the cells were washed twice with MEM medium without serum, and then the DNA-SuperFect mixture was added. After a 3 hr culture, cells were washed twice with MEM medium without serum, and cultured 24 hours in MEM medium containing 40 μg/ml cytosine β-D-arabinofuranoside (AraC, Sigma) and 7.5 μg/ml trypsin. Culture supernatants were removed and 5 ml of suspension of a 100 mm culture dish of F expressing LLC-MK2/F7 cells in MEM medium without serum (containing 40 μg/ml AraC and 7.5 μg/ml trypsin) was overlaid onto the cells. After further a 48 hr culture, the cells and supernatants were recovered and designated as P0-d3 samples. The P0-d3 pellets were suspended in Opti-MEM medium (2×10$^7$ cells/ml) and after 3 times of freeze-thawing, were mixed with lipofection reagent DOSPER (Boehringer Mannheim) (106 cells/25 μl DOSPER) and left to stand at room temperature for 15 min. Then, F expressing LLC-MK2/F7 cells were transfected with the mixture (10$^6$ cells/well, 24-well plate) and cultured with MEM medium without serum (containing 40 μg/ml AraC and 7.5 μg/ml trypsin) The culture supernatants were recovered on day 7, and designated as P1-d7 samples. Further, total volumes of supernatants were infected to F expressing LLC-MK2/F7 cells seeded onto 12-well plates at 37° C. for 1 hour. Then, after washing once with MEM medium, the cells were cultured in MEM medium without serum (containing 40 μg/ml AraC and 7.5 μg/ml trypsin). The culture supernatants were recovered on day 7, and were designated as P2-d7 samples. Further, total volumes of supernatants were infected to F expressing LLC-MK2/F7 cells seeded onto 6-well plates at 37° C. for 1 hour. Then, after washing once with MEM medium, the cells were cultured in MEM medium without serum (containing 7.5 μg/ml trypsin). The culture supernatants were recovered on day 7, and were designated as P3-d7 samples. Further, total volumes of supernatants were infected to F expressing LLC-MK2/F7 cells seeded onto 10 cm plates at 37° C. for 1 hour. Then, after washing once with MEM medium, the cells were cultured in MEM medium without serum (containing 40 μg/ml AraC and 7.5 μg/ml trypsin). The culture supernatants were recovered on day 7, and were designated as P4-d7 samples.

<Measurement of CIU by Counting LacZ-expressing Cells (LacZ-CIU)>

LLC-MK2 cells were seeded onto 6-well plate at 2.5×10$^6$ cells/well, and after a 24 hr culture, the cells were washed once with MEM medium without serum and infected with 1/10 fold serial dilution series of P3-d7 made using MEM medium at 37° C. for 1 hour. Then, the cells were washed once with MEM medium and 1.5 ml MEM medium containing 10% serum was added. After a three day culture at 37° C., cells were stained with β-Gal staining kit (Invitrogen). Result of experiment repeated three times is shown in FIG. 44. As the result of counting LacZ staining positive cell number, 1×10$^6$ CIU/ml. virus was obtained in P3-d7 samples in any case.

EXAMPLE 15

Regulation of Gene Expression Levels Using Polarity Effect in Sendai Virus

<Construction of SeV Genomic cDNA>

Figure 45A:
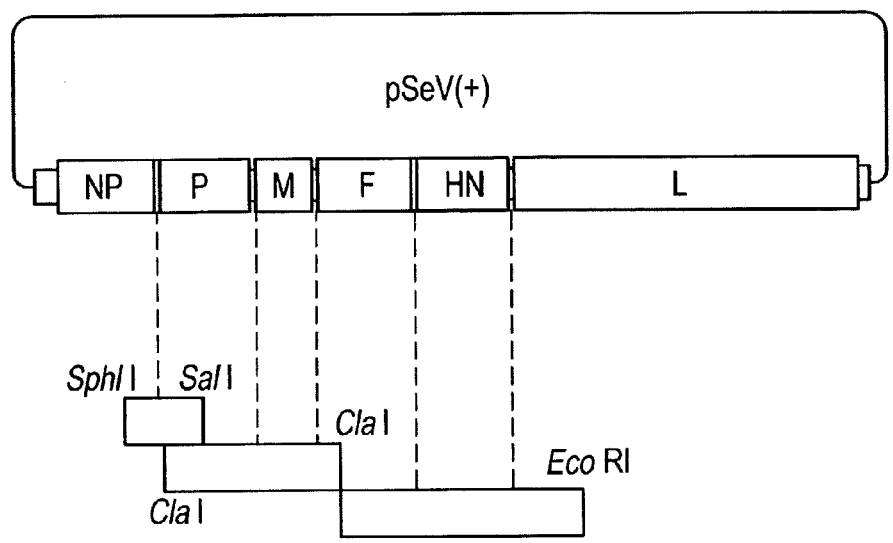

Additional NotI sites were introduced into Sendai virus (SeV) full length genomic cDNA, namely pSeV(+)(Kato, A. et al., Genes to Cells 1: 569–579, 1996), in between start signal and ATG translation initiation signal of respective genes. Specifically, fragments of pSeV(+) digested with SphI/SalI (2645 bp), ClaI (3246 bp), and ClaI/EcoRI (5146 bp) were separated with agarose gel electrophoreses and corresponding bands were cut out and then recovered and purified with QIAEXII Gel Extraction System (QIAGEN) as shown in FIG. 45(A). The SphI/SalI digested fragment, ClaI digested fragment, and ClaI/EcoRI digested fragment were ligated to LITMUS38 (NEW ENGLAND BIOLABS), pBluescriptII KS+ (STRATAGENE), and pBluescriptII KS+ (STRATAGENE), respectively, for subcloning. Quickchange Site-Directed Mutagenesis kit (STRATAGENE) was used for successive introduction of NotI sites. Primers synthesized and used for each introduction were,

```
sense strand:
5'-ccaccgaccacacccagcggccgcgacagccacggcttcgg-3',            (SEQ ID NO: 19)

antisense strand:
5'-ccgaagccgtggctgtcgcggccgctgggtgtggtcggtgg-3' for NP-P,   (SEQ ID NO: 20)

sense strand:
5'-gaaatttcacctaagcggccgcaatggcagatatctatag-3',             (SEQ ID NO: 21)

antisense strand:
5'-ctatagatatctgccattgcggccgcttaggtgaaatttc-3' for P-M,     (SEQ ID NO: 22)

sense strand:
5'-gggataaagtcccttgcggccgcttggttgcaaaactctcccc-3',          (SEQ ID NO: 23)

antisense strand:
5'-ggggagagttttgcaaccaagcggccgcaagggactttatccc-3' for M-F,  (SEQ ID NO: 24)

sense strand:
5'-ggtcgcgcggtactttagcggccgcctcaaacaagcacagatcatgg-3',      (SEQ ID NO:25)

antisense strand:
5'-ccatgatctgtgcttgtttgaggcggccgctaaagtaccgcgcgacc-3' for F-HN,  (SEQ ID NO: 26)

sense strand:
5'-cctgcccatccatgacctagcggccgcttcccattcaccctggg-3',         (SEQ ID NO: 27)

antisense strand:
5'-cccagggtgaatgggaagcggccgctaggtcatggatgggcagg-3' for HN-L.  (SEQ ID NO: 28)
```

Figure 45B:
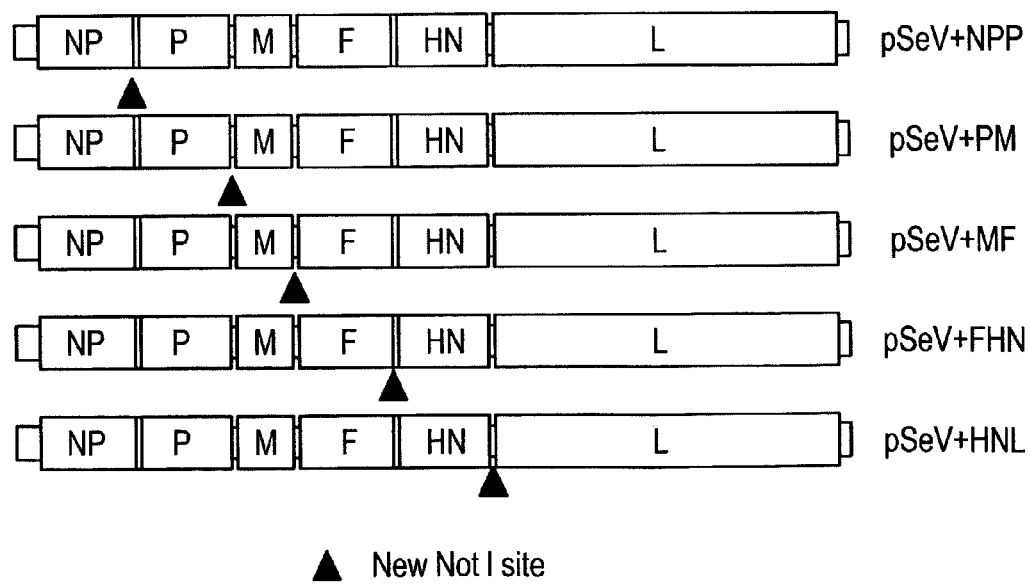

As templates, SalI/SphI fragment for NP-P, ClaI fragments for P-M and M-F, and ClaI/EcoRI fragments for F-HN and HN-L, which were subcloned as described above were used, and introduction was carried out according to the protocol accompanying Quickchange Site-Directed Mutagenesis kit. Resultants were digested again with the same enzyme used for subcloning, recovered, and purified. Then, they were assembled to Sendai virus genomic cDNA. As a result, 5 kinds of genomic cDNA of Sendai virus (pSeV(+)NPP, pSeV(+)PM, pSeV(+)MF, pSeV(+)FHN, and pSeV(+)HNL) in which NotI sites are introduced between each gene were constructed as shown in FIG. 45(B).

As a reporter gene to test gene expression level, human secreted type alkaline phosphatase (SEAP) was subcloned by PCR. As primers, 5' primer: 5'-gcggcgcgccatgctgctgct-gctgctgctgggcctg-3' (SEQ ID NO: 29) and 3' primer: 5'-gcggcgcgcccttatcatgtctgctcgaagcggccggccg-3' (SEQ ID NO: 30) added with AscI restriction sites were synthesized and PCR was performed. pSEAP-Basic (CLONTECH) was used as template and Pfu turbo DNA polymerase (STRATAGENE) was used as enzyme. After PCR, resultant products were digested with AscI, then recovered and purified by electrophoreses. As plasmid for subcloning, pBluescriptII KS+ incorporated in its NotI site with synthesized double strand DNA [sense strand: 5'-gcggccgcgtttaaacggcgcgccatt-taaatccgtagtaagaaaaacttagggtgaaagt tcatcgcggccgc-3' (SEQ ID NO: 31), antisense strand: 5'-gcggccgcgatgaactttcac-cctaagtttttcttactacggatttaaatggcgcgccgtt taaacgcggccgc-3' (SEQ ID NO: 32)] comprising multicloning site (PmeI-AscI-SwaI) and termination signal-intervening sequence-initiation signal was constructed (FIG. 46). To AscI site of the plasmid, recovered and purified RCR product was ligated and cloned. The resultant was digested with NotI and the SEAP gene fragment was recovered and purified by electrophoreses to ligate into 5 types of Sendai virus genomic cDNA and NotI site of pSeV18+ respectively. The resultant virus vectors were designated as pSeV(+)NPP/SEAP, pSeV(+)PM/SEAP, pSeV(+)MF/SEAP, pSeV(+)FHN/SEAP, pSeV(+)HNL/SEAP, and pSeV18(+)/SEAP, respectively.

<Virus Reconstitution>

LLC-MK2 cells were seeded onto 100 mm culture dishes at 2×10⁶ cells/dish, and after 24 hour culture the cells were infected with recombinant vaccinia virus (PLWUV-VacT7) (Fuerst, T. R. et al., Proc. Natl. Acad. Sci. USA 83–8122–8126, 1986, Kato, A. et al., Genes Cells 1: 569–579, 1996) expressing T7 polymerase for 1 hour (moi=2) at room temperature for 1 hour, in which the virus was pretreated with psoralen and UV. Each Sendai virus cDNA incorporated with SEAP, pGEM/NP, pGEM/P, and pGEM/L were suspended in Opti-MEM medium (GIBCO) at ratio of 12 μg, 4 μg, 2 μg, and 4 μg/dish, respectively, 110 μl of SuperFect transfection reagent (QIAGEN) was added, and left to stand at room temperature for 15 min and 3 ml Opti-MEM medium containing 3% FBS was added. Then, the cells were washed and DNA-SuperFect mixture was added. After a 3 to 5 hour culture, cells were washed twice with MEM medium without serum, and cultured 72 hours in MEM medium containing cytosine P-D-arabinofuranoside (AraC). These cells were recovered and the pellets were suspended with 1 ml PBS, freeze-thawed three times. The 100 µl of resultant was inoculated into chicken eggs, which was preincubated 10 days, and further incubated 3 days at 35° C., then, allantoic fluid was recovered. The recovered allantoic fluids were diluted to $10^{-5}$ to $10^{-7}$ and re-inoculated to chicken eggs to make it vaccinia virus-free, then recovered similarly and stocked in aliquots at −80° C. The virus vectors were designated as SeVNPP/SEAP, SeVPM/SEAP, SeVMF/SEAP, SeVFHN/SEAP, SeVHNL/SEAP, and SeV18/SEAP.

<Titer Measurement by Plaque Assay>

CV-1 cells were seeded onto 6-well plates at $5 \times 10^5$ cells/well and cultured for 24 hours. After washing with PBS, cells were incubated 1 hour with recombinant SeV diluted as $10^{-3}$, $10^{-4}$, $10^{-5}$, $10^{-6}$ and $10^{-7}$ by BSA/PBS (1% BSA in PBS), washed again with PBS, then overlaid with 3 ml/well of BSA/MEM/agarose (0.2% BSA+2×MEM, mixed with equivalent volume of 2% agarose) and cultured at 37° C., 0.5% $CO_2$ for 6 days. After the culture, 3 ml of ethanol/acetic acid (ethanol:acetic acid=1:5) was added and left to stand for 3 hours, then removed with agarose. After washing three times with PBS, cells were incubated with rabbit anti-Sendai virus antibody diluted 100-folds at room temperature for 1 hour. Then, after washing three times with PBS, cells were incubated with Alexa Flour™ labeled goat anti rabbit Ig(G+H) (Molecular Probe) diluted 200-folds at room temperature for 1 hour. After washing three times with PBS, fluorescence images were obtained by lumino-image analyzer LAS1000 (Fuji Film) and plaques were measured. Results are shown in FIG. 47. In addition, results of titers obtained are shown in Table 3.

TABLE 3

Results of titers of each recombinant Sendai virus measured from results of plaque assay

| Recombinant virus | Titer (pfu/ml) |
|---|---|
| SeV18/SEAP | $3.9 \times 10^9$ |
| SeVNPP/SEAP | $4.7 \times 10^8$ |
| SeVPM/SEAP | $3.8 \times 10^9$ |
| SeVMF/SEAP | $1.5 \times 10^{10}$ |
| SeVFHN/SEAP | $7.0 \times 10^9$ |
| SeVHNL/SEAP | $7.1 \times 10^9$ |

<Comparison of Reporter Gene Expression>

LLC-MK2 cells were seeded onto a 6-well plate at 1 to $5 \times 10^5$ cells/well and after a 24 hour culture, each virus vector was infected at moi=2. After 24 hours, 100 µl of culture supernatants was recovered and SEAP assay was carried out. Assay was accomplished with Reporter Assay Kit —SEAP— (Toyobo) and measured by lumino-image analyzer LAS1000 (Fuji Film). The measured values were indicated as relative values by designating value of SeV18+/SEAP as 100. As a result, SEAP activity was detected regardless of the position SEAP gene was inserted, indicated in FIG. 48. SEAP activity was found to decrease towards the downstream of the genome, namely the expression level decreased. In addition, when SEAP gene is inserted in between NP and P genes, an intermediate expression level was detected, in comparison to when SEAP gene is inserted in the upstream of NP gene and when SEAP gene is inserted between P and M genes.

EXAMPLE 16

Increase of Propagation Efficiency of Deficient SeV by Double Deficient ΔF-HN Overlay Method Since the SeV virus reconstitution method used now utilizes a recombinant vaccinia virus expressing T7 RNA polymerase (vTF7-3), a portion of the infected cells is killed by the cytotoxicity of the vaccinia virus. In addition, virus propagation is possible only in a portion of cells and it is preferable if virus propagation could be done efficiently and persistently in a more cells. However, in the case of paramyxovirus, cell fusion occurs when F and HN protein of the same kind virus exists on the cells surface at the same time, causing syncytium formation (Lamb and Kolakofsky, 1996, Fields virology, p1189). Therefore, FHN co-expressing cells were difficult to subculture. Therefore, the inventors thought that recovery efficiency of deficient virus may increase by overlaying helper cells expressing deleted protein (F and HN) to the reconstituted cells. By examining overlaying cells with different times of FHN expression, virus recovery efficiency of FHN co-deficient virus was notably increased.

LLC-MK2 cells ($1 \times 10^7$ cells/dish) grown to 100% confluency in 10 cm culture dishes was infected with PLWUV-treated vaccinia virus at moi=2 for 1 hour at room temperature. After that, mixing 12 µg/10 cm dish, 4 µg/10 cm dish, 2 µg/10 cm dish, 4 µg/10 cm dish, and 4 µg/10 cm dish of FHN-deficient cDNA comprising d2EGFP (pSeV18+/ΔFHN-d2GFP (Example 8)), pGEM/NP, pGEM/P, pGEM/L, and pGEM/FHN, respectively (3 ml/10 cm dish as final volume), and using gene introduction reagent SuperFect (QIAGEN), LLC-MK2 cells were introduced with genes using a method similar to that as described above for the reconstitution of F-deficient virus. After 3 hours, cells were washed three times with medium without serum, then, the detached cells were recovered by slow-speed centrifugation (1000 rpm/2 min) and suspended in serum free MEM medium containing 40 µg/ml AraC (Sigma) and 7.5 µg/ml trypsin (GIBCO) and added to cells and cultured overnight. FHN co-expressing cells separately prepared, which were 100% confluent 10 cm culture dishes, were induced with adenovirus AxCANCre at MOI=10, and cells at 4 hours, 6 hours, 8 hours, day 2, and day 3 were washed once with 5 ml PBS (−) and detached by cell dissociation solution (Sigma). Cells were collected by slow speed centrifugation (1000 rpm/2 min) and suspended in serum free MEM medium containing 40 µg/ml AraC (Sigma) and 7.5 µg/ml trypsin (GIBCO). This was then added to cells in which FHN co-deficient virus was reconstituted (P0) and cultured overnight. Two days after overlaying the cells, cells were observed using fluorescence microscopy to confirm the spread of virus by GFP expression within the cells. The results are shown in FIG. 49. When compared to the conventional case (left panel) without overlaying with cells, notably more GFP-expressing cells were observed when cells were overlaid with cells (right) These cells were recovered, suspended with $10^7$ cells/ml of Opti-MEM medium (GIBCO) and freeze-thawed for three times to prepare a cell lysate. Then, FHN co-expressing cells 2 days after induction were infected with the lysate at $10^6$ cells/100 µl/well, and cultured 2 days in serum free MEM medium containing 40 µg/ml AraC (Sigma) and 7.5 µg/ml trypsin (GIBCO) at 37° C. in a 5% $CO_2$ incubator, and the virus titer of culture supernatant of P1 cells were measured by CIU-GFP (Table 4). As a result, no virus amplification effect was detected 4 hours after FHN induction, and notable amplification effects were detected 6 hours or more after induction due to cell overlaying. Especially, viruses released into P1 cell culture supernatant were 10 times more after 6 hours when cell overlaying was done compared to when cell overlaying was not done.

TABLE 4

Amplification of deficient SeV by double deficient ΔF-HN cell overlay method

| GFP -CIU | FHNcell + ad/cre | | | | ×10³/ml |
|---|---|---|---|---|---|
| FHN cell- | 4 h | 6 h | 8 h | 2 d | 3 d |
| 8–10 | 6–9 | 80–100 | 70–100 | 60–100 | 20–50 |

EXAMPLE 17

Confirmation of Pseudotype Sendai Virus's Possession of F-deficient Genome

Western analysis of proteins of extracts of infected cells was carried out to confirm that the virus propagated by VSV-G gene expression described above is F-deficient type. As a result, proteins derived from Sendai virus were detected, whereas F protein was not detected, confirming that the virus is F-deficient type (FIG. 50).

EXAMPLE 18

Effect of Anti-VSV Antibody on Infectiousness of Pseudotype Sendai Virus Comprising F and HN Gene-deficient Genome To find out whether pseudotype Sendai virus comprising F and HN gene-deficient genome, which was obtained by using VSV-G expressing line, comprises VSV-G protein in its capsid, neutralizing activity of whether or not infectiousness is affected was examined using anti-VSV antibody. Virus solution and antibody were mixed and left to stand for 30 min at room temperature. Then, LLCG-L1 cells in which VSV-G expression has not been induced were infected with the mixture and gene-introducing capability on day 4 was analyzed by the existence of GFP-expressing cells. As a result, perfect inhibition of infectiousness was seen by anti-VSV antibody in the pseudotype Sendai virus comprising F and HN gene-deficient genome (VSV-G in the Figure), whereas no inhibition was detected in Sendai virus comprising proper capsid (F, HN in the Figure) (FIG. 51). Thus, the virus obtained in the present example was proven to be pseudotype Sendai virus comprising VSV-G protein as its capsid, and that its infectiousness can be specifically inhibited by the antibody.

EXAMPLE 19

Purification of Pseudotype Sendai Viruses Comprising F Gene-deficient and F and HN Gene-deficient Genomes by Density Gradient Ultracentrifugation Using culture supernatant of virus infected cells, sucrose density gradient centrifugation was carried out, to fractionate and purify pseudotype Sendai virus comprising deficient genomes of F gene and F and HN genes. Virus solution was added onto a sucrose solution with a 20 to 60% gradient, then ultracentrifuged for 15 to 16 hours at 29000 rpm using SW41 rotor (Beckman). After ultracentrifugation, a hole was made at the bottom of the tube, then 300 μl fractions were collected using a fraction collector. For each fraction, Western analysis were carried out to test that the virus is a pseudotype Sendai virus comprising a genome deficient in F gene or F and HN genes, and VSV-G protein as capsid. Western analysis was accomplished by the method as described above. As a result, in F-deficient pseudotype Sendai virus, proteins derived from the Sendai virus, HN protein, and VSV-G protein were detected in the same fraction, whereas F protein was not detected, confirming that it is a F-deficient pseudotype Sendai virus. On the other hand, in F and HN-deficient pseudotype Sendai virus, proteins derived from Sendai virus, and VSV-G protein were detected in the same fraction, whereas F and HN protein was not detected, confirming that it is F and HN deficient pseudotype Sendai virus (FIG. 52).

EXAMPLE 20

Overcoming of Haemagglutination by Pseudotype Sendai Virus Comprising F Gene-deficient and F and HN Gene-deficient Genomes LLC-MK2 cells were infected with either pseudotype Sendai virus comprising F gene-deficient or F and HN gene-deficient genome, or Sendai virus with normal capsid, and on day 3, 1% avian red blood cell suspension was added, and left to stand for 30 min at 4° C. Thereafter, cell surface of infected cells expressing GFP were observed. As a result, for virus with F gene-deficient genome and F-deficient pseudotype Sendai virus (SeV/ΔF, and pseudotype SeV/ΔF (VSV-G) by VSV-G), agglutination reaction was observed on the surface of infected cells, as well as for the Sendai virus with the original capsid. On the other hand, no agglutination reaction was observed on the surface of infected cells for pseudotype Sendai virus comprising F and HN gene-deficient genome (SeV/ΔF-HN(VSV-G)) (FIG. 53).

EXAMPLE 21

Infection Specificity of VSV-G Pseudotype Sendai Virus Comprising F Gene-deficient Genome to Cultured Cells Infection efficiency of VSV-G pseudotype Sendai virus comprising F gene-deficient genome to cultured cells was measured by the degree of GFP expression in surviving cells 3 days after infection using flow cytometry. LLC-MK2 cells showing almost the same infection efficiency in pseudotype Sendai virus comprising F gene-deficient genome and Sendai virus with original capsid were used as controls for comparison. As a result, no difference in infection efficiency was found in human ovary cancer HRA cells, whereas in Jurkat cells of T cell lineage about 2-fold increase in infection efficiency of VSV-G pseudotype Sendai virus comprising F gene-deficient genome was observed compared to controls (FIG. 54).

EXAMPLE 22

Construction of F-deficient Type Sendai Virus Vector Comprising NGF

<Reconstitution of NGF/SeV/ΔF>

Reconstitution of NGF/SeV/ΔF was accomplished according to the above described "Envelope plasmid+F expressing cells overlaying method". Measurement of titer was accomplished by a method using anti-SeV polyclonal antibody.

<Confirmation of Virus Genome of NGF/SeV/ΔF (RT-PCR)>

To confirm NGF/SeV/ΔF virus genome (FIG. 55, upper panel), culture supernatant recovered from LLC-MK2/F7 cells were centrifuged, and RNA was extracted using QIAamp Viral RNA mini kit (QIAGEN) according to the manufacturer's protocol. Using the RNA template, synthesis and PCR of RT-PCR was carried out using SUPER-SCRIPT™ ONE-STEP™ RT-PCR SYSTEM (GIBCO BRL). As control groups, additional type SeV cDNA (pSeV18+ b(+)) (Hasan, M. K. et al., J. General Virology 78: 2813–2820, 1997) was used. NGF-N and NGF-C were used as PCR primers. For NGF-N, forward: ACTTGCGGCCGC-CAAAGTTCAGTAATGTCCATGTTGTTCTACACTCTG (SEQ ID NO: 33), and for NGF-C, reverse: ATCCGCGGC-CGCGATGAACTTTCAC-CCTAAGTTTTTCTTACTACGGTCAGC-CTCTTCTTGTAGC CTTCCTGC (SEQ ID NO: 34) were used. As a result, when NGF-N and NGF-C were used as primers, an NGF specific band was detected for NGF/SeV/ΔF in the RT conditions. No band was detected for the control group (FIG. 55, bottom panel).

EXAMPLE 23

NGF Protein Quantification and Measurement of in Vitro Activity Expressed After Infection of F-deficient Type SeV Comprising NGF Gene Infection and NGF protein expression was accomplished using LLC-MK2/F or LLC-MK2 cells grown until almost confluent on culture plates of diameter of 10 cm or 6 cm. NGF/SeV/ΔF and. NGF/SeV/ΔF-GFP were infected to LLC-MK2/F cells, and NGF/SeV and GFP/SeV were infected to LLC-MK2 cells at m.o.i 0.01, and cultured 3 days with MEM medium without serum, containing 7.5 μg/ml trypsin (GIBCO). After the 3 day culture, in which almost 100% of cells are infected, medium was changed to MEM medium without trypsin and serum and further cultured for 3 days. Then, each culture supernatant were recovered and centrifuged at 48,000×g for 60 min. Then, quantification of NGF protein and measurement of in vitro activity for the supernatant were carried out. Although in the present examples, F-deficient type SeV (NGF/SeV/ΔF, NGF/SeV/ΔF-GFP)(see FIG. 55) are infected to LLC-MK2/F cells, if infected with a high m.o.i. (e.g. 1 or 3), namely, infected to cells that are nearly 100% confluent from the beginning, experiment giving similar results can be performed using F non-expressing cells.

For NGF protein quantification, ELISA kit NGF Emax Immuno Assay System (Promega) and the accompanying protocol were used. 32.4 μg/ml, 37.4 μg/ml, and 10.5 μg/ml of NGF protein were detected in NGF/SeV/ΔF, NGF/SeV/ΔF-GFP, and NGF/SeV infected cell culture supernatant, respectively. In the culture supernatant of NGF/SeV/ΔF and NGF/SeV/ΔF-GFP infected cells, high concentration of NGF protein exists, similar to culture supernatant of NGF/SeV infected cells, confirming that F-deficient type SeV expresses enough NGF.

The measurement of in vitro activity of NGF protein was accomplished by using a dissociated culture of primary chicken dorsal root ganglion (DRG; a sensory neuron of chicken) using survival activity as an index (Nerve Growth Factors (Wiley, N.Y.) pp. 95–109 (1989)). Dorsal root ganglion was removed from day 10 chicken embryo, and dispersed after 0.25% trypsin (GIBCO) treatment at 37° C. for 20 min. Using high-glucose D-MEM medium containing 100 units/ml penicillin (GIBCO), 100 units/ml streptomycin (GIBCO), 250 ng/ml amphotericin B (GIBCO) 20 μM 2-deoxyuridine (Nakarai), 20 μM 5-fluorodeoxyuridine (Nakarai) 2 mM L-glutamine (Sigma), and 5% serum, cells were seeded onto 96-well plate at about 5000 cells/well. Polylysin precoated 96-well plates (Iwaki) were further coated with laminin (Sigma) before use. At the start point, control NGF protein or previously prepared culture supernatant after SeV infection was added. After 3 days, cells were observed under a microscope as well as conducting quantification of surviving cells by adding Alamer blue (CosmoBio) and using the reduction activity by mitochondria as an index (measuring 590 nm fluorescence, with 530 nm excitation). Equivalent fluorescence signals were obtained in control (without NGF addition) and where 1/1000 diluted culture supernatant of cells infected with SeV/additional-type-GFP (GFP/SeV) was added, whereas the addition of 1/1000 diluted culture supernatant of cells infected with NGF/SeV/ΔF, NGF/SeV/ΔF-GFP, and NGF/SeV caused a notable increase in fluorescence intensity, and was judged as comprising a high number of surviving cells and survival activity (FIG. 56). The value of effect was comparable to the addition of amount of NGF protein calculated from ELISA. Observation under a microscope proved a similar effect. Namely, by adding culture supernatant of cells infected with NGF/SeV/ΔF, NGF/SeV/ΔF-GFP, and NGF/SeV, increase in surviving cells and notable neurite elongation was observed (FIG. 57). Thus, it was confirmed that NGF expressed after infection of NGF-comprising F-deficient type SeV is active form.

EXAMPLE 24

Detailed Analysis of F-expressing Cells

1. Moi and Induction Time Course of Adeno-Cre

By using different moi of Adeno-Cre, LLC-MK2/F cells were infected and after induction of F protein, the amount of protein expression and the change in cell shape were analyzed.

Expression level was slightly higher in moi=10 compared with moi=1 (FIG. 58). When expression amounts were analyzed at time points of 6 h, 12 h, 24 h, and 48 h after induction, high expression level of F protein at 48 h after induction was detected in all cases.

In addition, changes in cell shape were monitored in a time course as cells were infected with moi=1, 3, 10, 30, and 100. Although a notable difference was found up to moi=10, cytotoxicity was observed for moi=30 or over (FIG. 59).

2. Passage Number

After induction of F protein to LLC-MK2/F cells using Adeno-Cre, cells were passaged 7 times and expression level of F protein and the morphology of the cells were analyzed using microscopic observation. On the other hand, laser microscopy was used for analysis of intracellular localization of F protein after induction of F protein in cells passaged until the 20th generation.

For laser microscopic observation, LLC-MK2/F cells induced with F protein expression were put into the chamber glass and after overnight culture, media were removed and washed once with PBS, then fixed with 3.7% Formalin-PBS for 5 min. Then after washing cells once with PBS, cells were treated with 0.1% Triton X100-PBS for 5 min, and treated with anti-F protein monoclonal antibody (γ-236) (1/100 dilution) and FITC labeled goat anti-rabbit IgG antibody (1/200 dilution) in this order, and finally washed with PBS and observed with a laser microscope.

As a result, no difference was found in F protein expression levels in cells passaged up to 7 times (FIG. 60). No notable difference was observed in morphological change, infectiousness of SeV, and productivity. On the other hand, when cells passaged up to 20 times were analyzed for intracellular localization of F protein using the immuno-antibody method, no big difference was found up to 15 passages, but localization tendency of F protein was observed in cells passaged more than 15 times (FIG. 61).

Taken together, cells before 15 passages are considered desirable for the production of F-deficient SeV.

EXAMPLE 25

Correlation Between GFP-CIU and Anti-SeV-CIU

Correlation of the results of measuring Cell-Infected Unit (CIU) by two methods was analyzed. LLC-MK2 cells were seeded onto a 12-well plate at $2\times10^5$ cells/dish, and after a 24 hour culture, cells were washed once with MEM medium without serum, and infected with 100 μl/well SeV/ΔF-GFP. After 15 min, 1 ml/well serum-free MEM medium was added and further cultured for 24 hours. After the culture, cells were washed three times with PBS(−) and dried up (left to stand for approximately 10 to 15 min at room temperature) and 1 ml/well acetone was added to fix cells and was immediately removed. Cells were dried up again (left to stand for approximately 10 to 15 min at room temperature). Then, 300 μl/well of anti-SeV polyclonal antibody (DN-1) prepared from rabbits and diluted 1/100 with PBS(−) was added to cells and incubated at 37° C. for 45 min and washed three times with PBS(−). Then, to the cells, 300 μl/well of anti-rabbit IgG(H+D) fluorescence-labeled second antibody (AleX™ 568, Molecular Probes) diluted 1/200 with PBS(−) was added, and incubated at 37° C. for 45 min and washed three times with PBS(−). Then, cells with fluorescence were observed under fluorescence microscopy (Emission: 560 nm, Absorption: 645 nm, Filters: Leica).

As a control, cells were infected with 100 μl/well of SeV/ΔF-GFP and after 15 min, 1 ml/well of MEM without serum was added. After a further 24 hour culture, GFP-expressing cells were observed under fluorescence microscopy (Emission:-360 nm, Absorption: 470 nm, Filters: Leica) without further manipulations.

A Good correlation was obtained by evaluating the fluorescence intensity by quantification (FIG. 62).

EXAMPLE 26

Construction of Multicloning Site

A multicloning site was added to the SeV vector. The two methods used are listed below.
1. Several restriction sites in full-length genomic cDNA of Sendai virus (SeV) and genomic cDNA of pSeV18+ were disrupted, and another restriction site comprising the restriction site disrupted was introduced in between start signal and ATG translation initiation signal of each gene.
2. Into already constructed SeV vector cDNA, multicloning site sequence and transcription initiation signal— intervening sequence -termination signal were added and incorporated into NotI site.

In the case of method 1, as an introducing method, EagI-digested fragment (2644 bp), ClaI-digested fragment (3246 bp), ClaI/EcoRI-digested fragment (5146 bp), and EcoRI-digested fragment (5010 bp) of pSeV18+ were separated by agarose electrophoreses and the corresponding bands were cut out, then it was recovered and purified by QIAEXII Gel Extraction System (QIAGEN). EagI-digested fragment was ligated and subcloned into LITMUS38 (NEW ENGLAND BIOLABS) and ClaI-digested fragment, ClaI/EcoRI-digested fragment, and EcoRI-digested fragment were ligated and subcloned into pBluescriptII KS+ (STRATAGENE). Quickchange Site-Directed Mutagenesis kit (STRATAGENE) was used for successive disruption and introduction of restriction sites.

For disruption of restriction sites, Sal I: (sense strand) 5'-ggagaagtctcaacaccgtccacccaagataatcgatcag-3' (SEQ ID NO: 35) (antisense strand) 5'-ctgatcgattatcttgggtggacggtgt-tgagacttctcc-3' (SEQ ID NO: 36), Nhe I: (sense strand) 5'-gtatatgtgttcagttgagcttgctgtcggtctaaggc-3' (SEQ ID NO: 37), (antisense strand) 5'-gccttagaccgacagcaagctcaact-gaacacatatac-3' (SEQ ID NO: 38), Xho I: (sense strand) 5'-caatgaactctctagagaggctggagtcactaaagagttacctgg-3' (SEQ ID NO: 39) (antisense strand) 5'-ccaggtaactctttagtgactccagc-ctctctagagagttcattg-3' (SEQ ID NO: 40) and for introducing restriction sites, NP-P: (sense strand) 5'-gtgaaagttcatccac-cgatcggctcactcgaggccacacccaaccccaccg-3' (SEQ ID NO: 41), (antisense strand) 5'-cggtggggttgggtgtggcctcgagt-gagccgatcggtggatgaactttcac-3' (SEQ ID NO: 42), P-M: (sense strand) 5'-cttagggtgaaagaaatttcagctag-cacggcgcaatggcagatatc-3' (SEQ ID NO: 43), (antisense strand) 5'-gatatctgccattgcgccgtgctagctgaaatttctttcaccctaag-3' (SEQ ID NO: 44), M-F: (sense strand) 5'-cttagggataaagtc-ccttgtgcgcgcttggttgcaaaactctcccc-3' (SEQ ID NO: 45), (antisense strand) 5'-ggggagagttttgcaaccaagcgcgca-caagggactttatccctaag-3' (SEQ ID NO: 46), F-HN: (sense strand) 5'-ggtcgcgcggtactttagtcgacacct-caaacaagcacagatcatgg-3' (SEQ ID NO: 47), (antisense strand) 5'-ccatgatctgtgcttgtttgaggtgtcgactaaagtaccgcgcgacc-3' (SEQ ID NO: 48), HN-L: (sense strand) 5'-cccagggt-gaatgggaagggccggccaggtcatggatgggcaggagtcc-3' (SEQ ID NO: 49), (antisense strand) 5'-ggactcctgcccatccatgacctggc-cggcccttccattcaccctggg-3' (SEQ ID NO: 50), were synthesized and used for the reaction. After introduction, each fragment was recovered and purified similarly as described above, and cDNA were assembled.

In the case of method 2, (sense strand) 5'-ggccgcttaat-taacggtttaaacgcgcgccaacagtgttgataagaaaaacttagggtga aagt-tcatcac-3' (SEQ ID NO: 51), (antisense strand) 5'-ggccgt-gatgaactttcaccctaagttttcttatcaacactgttggcgcgcgtttaaacc gttaattaagc-3' (SEQ ID NO: 52), were synthesized, and after phosphorylation, annealed by 85° C. 2 min, 65° C. 15 min, 37° C. 15 min, and room temperature 15 min to incorporate into SeV cDNA. Alternatively, multicloning sites of pUC18 or pBluescriptII, or the like, are subcloned by PCR using primers comprising termination signal—intervening sequence—initiation signal and then incorporate the resultant into SeV cDNA. The virus reconstitution by resultant cDNA can be performed as described above.

EXAMPLE 27

Effects of Culture Temperature (32° C.) on Viral Reconstitution

To quantify the expression level of the gene comprised in virus, three types of SeV cDNAs as shown in FIG. 63 were used. To construct cDNA comprising a secretory alkaline phosphatase (SEAP) gene, a SEAP fragment (1638 bp) having the termination signal-intervening sequence-initiation signal downstream of the SEAP gene was excised using NotI, electrophoresed, purified, recovered, and incorporated to the NotI site of pSeV18+/ΔF-GFP to obtain pSeV18+SEAP/ΔF-GFP (FIG. 63).

Viral reconstitution was carried out in a similar manner as described above. In this case, since the virus is deficient in F gene, helper cells to supply F protein are used, and the helper cells are prepared using the Cre/loxP expression inducing system. The system utilizes the plasmid pCALNdLw (Arai, T. et al., J. Virol. 72: 1115–1121 (1998)) designed so as to induce the expression of gene product with Cre DNA recombinase, in which a transformant of the plasmid is infected with a Cre DNA recombinase-expressing recombinant adenovirus (AxCANCre) by the method of Saito, et al. (Saito, I. et al., Nucl. Acid. Res. 23, 3816–3821 (1995); Arai, T. et al., J. Virol. 72, 1115–1121 (1998)) to express inserted genes. In the case of SeV-F protein, the transformant cells containing the F gene are referred to as LLC-MK2/F7, and cells continuously expressing F protein after the induction with AxCANCre are referred to as LLC-MK2/F7/A.

Specifically, the viral reconstitution was carried out as follows. LLC-MK2 cells were plated on 100-mm diameter Petri dishes at 5×10 cells/dish, cultured for 24 h, and then infected with a recombinant vaccinia virus expressing T7 polymerase, which had been treated with the long-wavelength ultraviolet light (365 nm) for 20 min in the presence of psoralen (PLWUV-VacT7: Fuerst, T. R. et al., Proc. Natl. Acad. Sci. USA 83, 8122–8126 (1986)) at room temperature for 1 h (m.o.i.=2). A plasmid encoding SeV cDNA (FIG. 63), pGEM/NP, pGEM/P, pGEM/L, and pGEM/F-HN (Kato, A. et al., Genes Cells 1, 569–579 (1996)) were suspended in Opti-MEM (Gibco-BRL, Rockville, Md.) at weight ratios of 12 μg, 4 μg, 2 μg, 4 μg and 4 μg/dish, respectively. To the suspension, 1 μg DNA/5 μl equivalent SuperFect transfection reagent (Qiagen, Bothell, Wash.) were added and mixed. The mixture was allowed to stand at room temperature for 15 min and finally added to 3 ml of Opti-MEM containing 3% FBS. After the cells were washed with a serum-free MEM, the mixture was added to the cells and the cells were cultured for 5 h, the cells were washed twice with a serum-free MEM, and then cultured in MEM containing 40 μg/ml of cytosine β-D-arabinofuranoside (AraC: Sigma, St. Louis, Mo.) and 7.5 μg/ml of trypsin (Gibco-BRL, Rockville, Md.). After cultured for 24 h, cells continuously expressing F protein (LLC-MK2/F7/A) were layered at $8.5 \times 10^6$ cells/dish, and cultured in MEM containing 40 μg/ml of AraC and 7.5 μg/ml of trypsin for further 2 days at 37° C. (P0). These cells were recovered, and the pellet was suspended in 2 ml/dish of Opti-MEM. After three repeated cycles of freezing and thawing, the lysate thus obtained was transfected as a whole to LLC-MK2/F7/A cells, and the cells were cultured using a serum-free MEM containing 40 μg/ml of AraC and 7.5 μg/ml of trypsin at 32° C. (P1) Five to seven days later, an aliquot of the culture supernatant was sampled and infected to freshly prepared LLC-MK2/F7/A cells, and the cells were cultured using the serum-free MEM containing 40 μg/ml of AraC and 7.5 μg/ml of trypsin at 32° C. (P2). Three to five days later, the supernatant was infected again to freshly prepared LLC-MK2/F7/A cells, and the cells were cultured using a serum-free MEM containing only 7.5 μg/ml of trypsin at 32° C. for 3 to 5 days (P3). To the culture supernatant thus recovered, BSA was added to make a final concentration of 1%, and the resulting mixture was stored at −80° C. The stored virus solution was thawed and used in subsequent experiments.

Titers of virus solutions prepared by this method were $3 \times 10^8$ and $1.8 \times 10^8$ GFP-CIU/ml for SeV18+/ΔF-GFP and SeV18+SEAP/ΔF-GFP, respectively. In the measurement of these titers, with SeV18+/ΔF-GFP, the spread of plaque after its infection to F protein continuously expressing cells (LLC-MK2/F7/A) was examined at 32° C. and 37° C. As shown in FIG. 64, representing the micrograph 6 days after the infection, it was demonstrated that the spread of plaques significantly increased with cells cultured at 32° C. as compared with those cultured at 37° C. Thus, it has become evident that the reconstitution efficiency is enhanced by performing the SeV reconstitution at 32° C. after the stage P1, so that it is highly possible to enable the recovery of virus which has been hitherto difficult to obtain.

Two points are considered as the reason for the enhancement of reconstitution efficiency at 32° C. One point is that cytotoxicity due to AraC supplemented to inhibit the amplification of vaccinia virus is thought to be suppressed in culturing at 32° C. as compared with 37° C. Under the virus reconstituting conditions, when LLC-MK2/F7/A cells were cultured in a serum-free MEM containing 40 μg/ml of AraC and 7.5 μg/ml of trypsin, at 37° C., cell damages were caused already 3 to 4 days later with increased detached cells, while, at 32° C., the culture could be sufficiently continued for 7 to 10 days with the cells kept intact. In the case of reconstitution of SeV with an inferior transcription/replication efficiency or with a poor efficiency for infectious virion formation, the culture duration time is thought to be directly reflected in the achievement of reconstitution. A second point is that the expression of F protein is maintained in LLC-MK2/F7/A cells when the cells are cultured at 32° C. After LLC-MK2/F7/A cells which continuously express F protein were cultured at 37° C. to confluency on 6-well culture plates in MEM containing 10% FBS, the medium was replaced with a serum free MEM containing 7.5 μg/ml of trypsin, and the cells were further cultured at 32° C. or 37° C. The cells were recovered over time using a cell scraper, and semi-quantitatively analyzed for F protein inside the cells by Western-blotting using an anti-F protein antibody (mouse monoclonal). F protein expression was maintained for 2 days at 37° C., decreasing thereafter, while its expression was maintained at least for 8 days at 32° C. (FIG. 65). From these results, the validity of viral reconstitution at 32° C. (after P1 stage) has been also confirmed.

The above-described Western-blotting was carried out using the following method. Cells recovered from one well of a 6-well plate were stored at −80° C., then thawed in 100 μl of 1×diluted sample buffer for SDS-PAGE (Red Loading Buffer Pack; New England Biolabs, Beverly, Mass.), and heated at 98° C. for 10 min. After centrifugation, a 10-μl aliquot of the supernatant was loaded on SDS-PAGE gel (multigel 10/20; Daiichi Pure Chemicals Co., Ltd., Tokyo, Japan). After electrophoresis at 15 mA for 2.5 h, proteins were transferred to a PVDF membrane (Immobilon PVDF transfer membrane; Millipore, Bedford, Mass.) by semi-dry method at 100 mA for 1 h. The transfer membrane was immersed in a blocking solution (Block Ace; Snow Brand Milk Products Co., Ltd., Sapporo, Japan) at 4° C. for 1 h or more, then soaked in a primary antibody solution containing 10% Block Ace supplemented with 1/1000 volume of the anti-F protein antibody, and allowed to stand at 4° C. overnight. After washed three times with TBS containing 0.05% Tween 20 (TBST), and further three times with TBS, the membrane was immersed in a secondary antibody solution containing 10% Block Ace and supplemented with 1/5000 volume of the anti-mouse IgG+IgM antibody bound with HRP (Goat F(ab')2 Anti-Mouse IgG+IgM, HRP; BioSource Int., Camarillo, Calif.), and stirred at room temperature for 1 h. After the membrane was washed three times with TBST and then three times with TBS, the proteins on the membrane were detected by chemiluminescence method (ECL western blotting detection reagents; Amersham Pharmacia biotech, Uppsala, Sweden).

EXAMPLE 28

Quantification of Secondarily Released Virus-like Particles from SeV Deficient in F Gene (HA Assay, Western-Blotting)

Together with SeV18+/ΔF-GFP, using the autonomously replicating type SeV comprising all the viral proteins and comprising GFP fragment (780 bp) having the termination signal-intervening sequence-initiation signal downstream of the GFP gene at the NotI site (SeV18+GFP: FIG. 63), levels of secondarily released virus-like particles were compared.

To LLC-MK2 cells grown to confluency on 6-well plates, $3 \times 10^7$ CIU/ml each of virus solutions at 100 µl per well were added (m.o.i.=3) and the cells were allowed to be infected for 1 h. After the cells were washed with MEM, a serum-free MEM (1 ml) was added to each well, and the cells were cultured at 32° C., 37° C. and 38° C., respectively. Sampling was carried out every day, and immediately after the sampling, 1 ml of the fresh serum-free MEM was added to the remaining cells. Culturing and sampling were performed over time. Observation of GFP expression 3 days after the infection under a fluorescence microscope indicated almost the equal level of infection and similar expression of GFP with both types of viruses and under all the conditions at 32° C., 37° C. and 38° C. (FIG. 66).

Secondarily released virus-like particles were quantified by the hemagglutination activity (HA activity) assay performed according to the method of Kato et al. (Kato, A., et al., Genes Cell 1, 569–579 (1996)). That is, using plates with round-bottomed 96 wells, the virus solution was serially diluted with PBS to make a serial 2-fold dilutions in 50 µl for each well. To 50 µl of the virus solution were added 50 µl of a preserved chicken blood (Cosmobio, Tokyo, Japan) diluted to 1% with PBS, and the mixture was allowed to stand at 4° C. for 1 h. Then, agglutination of erythrocytes was examined. Among agglutinated samples, the highest dilution rate to achieve hemagglutination was judged as the HA activity. In addition, one hemagglutination unit (HAU) was calculated as $1 \times 10^6$ viruses, and the hemagglutination activity was also expressed by the number of virus-like particles (FIG. 67). Although, at lower temperatures, secondarily released virus-like particles were observed with SeV18+/ΔF-GFP, a remarkable decrease in the level of virus-like particle release was detected at 38° C. as compared with the autonomously replicating SeV (SeV18+ GFP).

To quantify the secondarily released virus-like particles from another point of view, the quantification thereof by Western-Blotting was performed. In a similar manner as described above, LLC-MK2 cells were infected at m.o.i.=3 with the virus, warmed at 37° C., and the culture supernatant and cells were recovered 2 days after the infection. The culture supernatant was centrifuged at 48,000 g for 45 min to recover the viral proteins. After SDS-PAGE, Western-Blotting was performed to detect proteins with an anti-M protein antibody. This anti-M protein antibody is a newly prepared polyclonal antibody, which has been prepared from the serum of rabbits immunized with a mixture of three synthetic peptides: corresponding to amino acids 1–13 (MADIYRFPKFSYE+Cys/SEQ ID NO: 53), 23–35 (LRT-GPDKKAIPH+Cys/SEQ ID NO: 54), and 336–348 (Cys+ NVVAKNIGRIRKL/SEQ ID NO: 55) of SeV-M protein. Western-Blotting was performed according to the method as described in Example 27, in which the primary antibody, anti-M protein antibody, was used at a ¼₀₀₀ (1:4000) dilution, and the secondary antibody, anti-rabbit IgG antibody bound with HRP (Anti-rabbit IgG (Goat) H+L conj.; ICN P., Aurola, Ohio) was used at a ⅕₀₀₀ (1:5000) dilution. With the autonomously replicating SeV (SeV18+GFP), a large amount of M protein was detected in the culture supernatant. With SeV18+/ΔF-GFP, however, a main portion (70%) of M protein was present in the cells, supporting that, with the F gene-deficient SeV, the release of virus-like particles is reduced at 37° C. as compared with the autonomously replicating SeV (FIG. 68).

EXAMPLE 29

Construction of Genomic cDNA of M Gene Deficient SeV Having EGFP Gene

In this construction, a full-length genomic cDNA of the M-deficient SeV deficient in M gene (pSeV18+/ΔM: WO00/09700) was used. The construction scheme was shown in FIG. 69. BstEII fragment (2098 bp) comprising the M-deficient site of pSeV18+/ΔM was subcloned to the BstEII site of pSE280 (Invitrogen, Groningen, Netherlands), in which EcoRV recognition site had been deleted by the previous digestion with SalI/XhoI followed by ligation (construction of pSE-BstEIIfrg). pEGFP having the GFP gene (TOYOBO, Osaka, Japan) was digested with Acc65I and EcoRI, and the 5'-end of the digest was blunted by filling in using the DNA blunting Kit (Takara, Kyoto, Japan) The blunted fragment was subcloned into pSE-BstEIIfrg that, after digested with EcoRV, had been treated with BAP (TOYOBO, Osaka, Japan). This BstEII fragment containing the EGFP gene was returned to the original pSeV18+/ΔM to construct the M gene-deficient SeV genomic cDNA (pSeV18+/ΔM-GFP) comprising the EGFP gene at the M-deficient site.

EXAMPLE 30

Construction of SeV Genomic cDNA Deficient in M and F Genes

The construction scheme described below is shown in FIG. 70. Using the pBlueNaeIfrg-ΔFGFP, which had been constructed by subcloning an NaeI fragment (4922 bp) of the F-deficient Sendai virus full-length genome cDNA comprising the EGFP gene at the F gene-deficient site (pSeV18+/ΔF-GFP) to the EcoRV site of pBluescript II (Stratagene, La Jolla, Calif.), the deletion of M gene was carried out. Deletion was designed so as to excise the M gene using the ApaLI site right behind the gene. That is, the ApaLI recognition site was inserted right behind the P gene so that the fragment to be excised becomes 6n (6 nucleotides long). Mutagenesis was performed using the Quick-Change™ Site-Directed Mutagenesis Kit (Stratagene, La Jolla, Calif.) according to the method described in the kit. Sequences of synthetic oligonucleotides used for the mutagenesis are 5'-agagtcactgaccaactagatcgtgcac-gaggcatcctaccatcctca-3'/SEQ ID NO: 56 and 5'-tgaggatgg-taggatgcctcgtgcacgatctagttggtcagtgactct-3'/SEQ ID NO: 57. After the mutagenesis, the resulting mutant cDNA was partially digested with ApaLI (at 37° C. for 5 min), recovered using the QIAquick PCR Purification Kit (QIAGEN, Bothell, Wash.), and then ligated as it was. The DNA was recovered again using the QIAquick PCR Purification Kit, digested with BsmI and StuI, and used to transform DH5α to prepare the M gene-deficient (and F gene-deficient) DNA (pBlueNaeIfrg-ΔMΔFGFP).

pBlueNaeIfrg-ΔMΔFGFP deficient in the M gene (and the F gene) was digested with SalI and ApaLI to recover a fragment (1480 bp) containing the M gene-deficient site. On the other hand, pSeV18+/ΔF-GFP was digested with ApaLI/NheI to recover a fragment (6287 bp) containing the HN gene, and these two fragments were subcloned into the SalI/NheI site of Litmus 38 (New England Biolabs, Beverly, Mass.) (construction of LitmusSalI/NheIfrg-ΔMΔFGFP). A fragment (7767 bp) recovered by digesting LitmusSalI/NheIfrg-ΔMΔFGFP with SalI/NheI and another fragment (8294 bp) obtained by digesting. pSeV18+/ΔF-GFP with SalI/NheI that did not comprise genes such as the M and HN genes were ligated to construct an M- and F-deficient Sendai virus full-length genome cDNA having the EGFP gene at the deficient site (pSeV18+/ΔMΔF-GFP). Structures of the M-deficient (and M- and F-deficient) viruses thus constructed were shown in FIG. 71.

EXAMPLE 31

Preparation of Helper Cells Expressing SeV-F and SeV-M Proteins

To prepare helper cells expressing M protein (and F protein) the same Cre/loxP expression induction system as that employed for the preparation of helper cells (LLC-MK2/F7 cells) for F protein was used.

<1> Construction of M Gene Expressing Plasmid

To prepare helper cells which induce the simultaneous expression of F and M proteins, the above-described LLC-MK2/F7 cells were used to transfer M gene to these cells by the above-mentioned system. However, since pCALNdLw/F which was used for the transfer of F gene had the neomycin resistance gene, it was essential to transfer a different drug resistance gene for the use of the cells. Therefore, first, according to the scheme described in FIG. 72, the neomycin resistance gene of the M gene-comprising plasmid (pCALNdLw/M: M gene was inserted at the SwaI site of pCALNdLw) was replaced with the hygromycin resistance gene. That is, after pCALNdLw/M was digested with HincII and EcoT22I, a fragment containing M gene (4737 bp) was isolated by electrophoresis on agarose, and the corresponding band was excised and recovered using the QIAEXII Gel Extraction System. At the same time, the pCALNdLw/M was digested with XhoI to recover a fragment (5941 bp) containing no neomycin resistance gene, and then further digested with HincII to recover a fragment (1779 bp). Hygromycin resistance gene was prepared by performing PCR with pcDNA3.1hygro(+) (Invitrogen, Groningen, Netherlands) as the template using a pair of primers: hygro-5' (5'-tctgagtcgctcggtacgatgaaaaagc-ctgaactcaccgcgacgtctgtcgag-3'/SEQ ID NO: 58) and hygro-3' (5'-aatgcatgatcagtaaattacaatgaa-catcgaacccagagtcccgcctattcctttgc cctcggacgagtgctggggcgtc-3'/SEQ ID NO: 59), and recovering the PCR product using the QIAquick PCR Purification Kit, then digesting the product with XhoI and EcoT22I. pCALNdLw-hygroM was constructed by ligating these three fragments.

<2> Cloning of Helper Cells Which Induce the Expression of SeV-M (and SeV-F) Protein(s)

Transfection was performed using the Superfect Transfection Reagent by the method described in the protocol of the Reagent as follows LLC-MK2/F7 cells were plated on 60 mm diameter Petri dishes at 5×10⁵ cells/dish, and cultured in D-MEM containing 10% FBS for 24 h. pCALNdLw-hygroM (5 µg) was diluted in D-MEM containing no FBS and antibiotics (150 µl in total) and stirred. To the mixture, the Superfect Transfection Reagent (30 µl) was added. The mixture was stirred again, and allowed to stand at room temperature for 10 min. Then, to the resulting mixture was added D-MEM containing 10% FBS (1 ml). The transfection mixture thus prepared was stirred, and added to LLC-MK2/F7 cells which had been once washed with PBS. After a 3 h culture in an incubator at 37° C. in 5% CO₂ atmosphere, the transfection mixture was removed, and the cells were washed three times with PBS. To the cells, D-MEM containing 10% FBS (5 ml) was added, and then, the cells were cultured for 24 h. After cultured, the cells were detached using trypsin, plated on a 96-well plate at about 5 cells/well dilution, and cultured in D-MEM containing 10% FBS supplemented with 150 µg/ml hygromycin (Gibco-BRL, Rockville, Md.) for about 2 weeks. A clone which had propagated from a single cell was cultured to expand to a 6-well plate culture. One hundred and thirty clones in total thus prepared were analyzed in the following.

<3>Analysis of Helper Cell Clones Which Induce the Expression of SeV-M (and SeV-F) Protein(s)

One hundred and thirty clones thus obtained were semi-quantitatively analyzed for expression levels of M protein by Western-blotting. Each clone was plated on 6-well plates, and, at its nearly confluent state, infected at m.o.i.=5 with a recombinant adenovirus expressing Cre-DNA recombinase (AxCANCre) diluted in MEM containing 5% FBS according to the method of Saito et al. (Saito, I. et al., Nucl. Acid. Res. 23, 3816–3821 (1995); Arai, T. et al., J. Virol. 72, 1115–1121 (1998)). After the culture at 32° C. for 2 days, the culture supernatant was removed. The cells were washed once with PBS, and detached using a scraper for recovery. After performing SDS-PAGE by applying 1/10 amount of the cells thus recovered per lane, Western-Blotting was carried out using the anti-M protein antibody according to the method described in Examples 27 and 28. Among 130 clones, those which showed relatively high expression levels of M protein were also analyzed using the anti-F protein antibody (f236: Segawa, H. et al., J. Biochem. 123, 1064–1072 (1998)) by Western-blotting. Both results are described in FIG. 73.

EXAMPLE 32

Reconstitution of SeV Virus Deficient in M Gene

Reconstitution of SeV deficient in the M gene (SeV18+/ΔM-GFP) was carried out in conjunction with assessment of clones described in Example 31. That is, it was examined whether the expansion of GFP protein was observed (whether the supply of M protein from cells was achieved) by the addition of P0 lysate of SeV18+/ΔM-GFP to each clone. Preparation of P0 lysate was carried out according to the method described in Example 27 as follows. LLC-MK2 cells were plated on 100-mm diameter Petri dishes at 5×10⁶ cells/dish, cultured for 24 h, and then infected at m.o.i.=2 with PLWUV-VacT7 at room temperature for 1 h. Plasmids: pSeV18+/ΔM-GFP, pGEM/NP, pGEM/P, pGEM/L, pGEM/

F-HN and pGEM/M were suspended in Opti-MEM at weight ratios of 12 µg, 4 µg, 2 µg, 4 µg, 4 µg and 4 µg/dish, respectively. To the suspension, 1 µg DNA/5 µl equivalent of SuperFect transfection reagent were added and mixed. The mixture was allowed to stand at room temperature for 15 min and finally added to 3 ml of Opti-MEM containing 3% FBS. After the cells were washed with a serum-free MEM, the mixture was added to the cells and the cells were cultured. After a 5 h culture, the cells were washed twice with a serum-free MEM, and cultured in MEM containing 40 µg/ml AraC and 7.5 µg/ml trypsin. After cultured for 24 h, LLC-MK2/F7/A cells were layered at $8.5 \times 10^6$ cells/dish, and further cultured in MEM containing 40 µg/ml AraC and 7.5 µg/ml trypsin at 37° C. for 2 days. These cells were recovered, the pellet was suspended in 2 ml/dish Opti-MEM, and P0 lysate was prepared by repeating 3 cycles of freezing and thawing. On the other hand, 10 different clones were plated on 24-well plates, infected, at near confluency, with AxCANCre at m.o.i.=5, and cultured at 32° C. for 2 days after the infection. These cells were transfected with P0 lysate of SeV18+/ΔM-GFP at 200 µl/well each, and cultured using a serum-free MEM containing 40 µg/ml AraC and 7.5 µg/ml trypsin at 32° C. Spread of GFP protein due to SeV18+/ΔM-GFP was observed with #18 and #62 clones (FIG. 74). Especially, the spread was more rapid with #62, which was used in subsequent experiments. Hereafter, as to the cells, those prior to the induction with AxCANCre are referred to as LLC-MK2/F7/M62, and those after the induction which continuously express F and M proteins are referred to as LLC-MK2/F7/M62/A. Preparation of SeV18+/ΔM-GFP was continued using LLC-MK2/F7/M62/A cells, and, 6 days after the infection with P2, $9.5 \times 10^6$, and, 5 days after the infection with P4, $3.7 \times 10^7$ GFP-CIU viruses were prepared.

It is thought that, also in this experiment, the recovery of SeV18+/ΔM-GFP virus has become possible only because the technical improvement, namely "culturing at 32° C. after the P1 stage" as shown in Example 27 was available. Supply of M protein trans from cells expressing the protein (LLC-MK2/F7/M62/A) may be a cause for the recovery of SeV18+/ΔM-GFP, but the spread was extremely slow so as to be observed finally 7 days after the P1 infection (FIG. 74). That is, these results have supported that, also in the reconstitution experiment of the virus, "culturing at 32° C. after the P1 stage" is very effective in reconstituting SeV with an inferior transcription-replication efficiency or with a poor infectious virion forming efficiency.

EXAMPLE 33

Productivity of SeV Deficient in M Gene

Productivity aspect of this M gene-deficient virus was also investigated. LLC-MK2/F7/M62/A cells were plated on 6-well plates and cultured at 37° C. The cells which reached nearly confluence were moved to the environment at 32° C. and, one day after, infected at m.o.i.=0.5 with SeV18+/ΔM-GFP. The culture supernatant was recovered over time to be replaced with a fresh medium. Supernatants thus recovered were assayed for CIU and HAU. Four to six days after the infection, the largest amount of viruses was recovered (FIG. 75). Although HAU was maintained even 6 days or more after the infection, cytotoxicity was strongly exhibited at this point, indicating that this hemagglutination was caused by HA protein not originating in virus particles but by the activity of HA protein free or bound to cell debris. That is, it seems advisable to recover the culture supernatant by the fifth day after the infection for collecting the virus.

EXAMPLE 34

Structural Confirmation of M Gene-deficient SeV

The viral gene of SeV18+/ΔM-GFP was confirmed by RT-PCR, and the viral protein by Western-blotting. In RT-PCR, the virus at the P2 stage 6 days after the infection was used. In the RNA recovery from virus solution, QIAamp Viral RNA Mini Kit (QIAGEN, Bothell, Wash.) was used, and, in the cDNA preparation, Thermoscript RT-PCR System. (Gibco-BRL, Rockville, Md.) was utilized. Both systems were performed by the methods described in the protocols attached to the kits. As the primer for cDNA preparation, the random hexamer supplied with the kit was used. To confirm that the product was formed starting from RNA, RT-PCR was performed in the presence or absence of the reverse transcriptase. PCR was performed with the cDNA prepared above as the template using two pairs of primers: one combination of F3593 (5'-ccaatctaccatcagcatcags-3'/SEQ ID NO: 60) on the P gene and R4993 (5'-ttcccttcatcgactatgacc-3'/SEQ ID NO: 61) on the F gene, and another combination of F3208 (5'-agagaacaagactaaggctacc-3'/SEQ ID NO: 62) similarly on the P gene and R4993. As expected from the gene structure of SeV18+/ΔM-GFP, amplifications of 1073 bp and 1458 bp DNAs were observed from the former and latter combinations, respectively (FIG. 76). In the case of the reverse transcriptase being omitted (RT−), no amplification of the gene occurred, and in the case of M gene being inserted in stead of GFP gene (pSeV18+GFP), 1400 bp and 1785 bp DNAs were amplified, respectively, clearly different in size from the results described above, supporting that this virus is of an M gene deficient structure.

Confirmation in terms of protein was also performed by Western-blotting. LLC-MK2 cells were infected at m.o.i.=3 with SeV18+/ΔM-GFP, SeV18+/ΔF-GFP and SeV18+GFP, respectively, and the culture supernatants and cells were recovered 3 days after the infection. The culture supernatant was centrifuged at 48,000 g for 45 min to recover viral proteins. After SDS-PAGE, Western-blotting was performed to detect proteins using the anti-M protein antibody, anti-F protein antibody, and DN-1 antibody (rabbit polyclonal) which mainly detects NP protein according to the method described in Examples 27 and 28. Since, in cells infected with SeV18+/ΔM-GFP, M protein was not detected while F or NP protein was observed, it was also confirmed in terms of protein that this virus had the structure of SeV18+/ΔM-GFP (FIG. 77). In this case, F protein was not observed in cells infected with SeV18+/ΔF-GFP, while all the virus proteins examined were detected in cells infected with SeV18+GFP. In addition, as to the virus proteins in the culture supernatant, very little amount of NP protein was observed in the case of infection with SeV18+/ΔM-GFP, indicating that there was no or very little secondarily released virus-like particle.

EXAMPLE 35

Quantitative Analysis Concerning the Presence or Absence of Secondarily Released Virus-like Particles of M Gene-deficient SeV As described in Example 34, LLK-MK2 cells were infected at m.o.i.=3 with SeV18+/ΔM-GFP, and the culture supernatant was recovered 3 days after the infection, filtered through an 0.45 μm pore diameter filter, and centrifuged at 48,000 g for 45 min to recover virus proteins, which were subjected to Western-blotting to semi-quantitatively detect virus proteins in the culture supernatant. As the control, samples, which had been similarly prepared from cells infected with SeV18+/ΔF-GFP, were used. Serial dilutions of respective samples were prepared, and subjected to Western-blotting to detect proteins using the DN-1 antibody (primarily recognizing NP protein). The viral protein level in the culture supernatant of cells infected with SeV18+/ΔM-GFP was estimated to be about 1/100 that of cells infected with SeV18+/ΔF-GFP (FIG. 78). Furthermore, HA activities of the samples were 64 HAU for SeV18+/ΔF-GFP versus <2 HAU for SeV18+/ΔM-GFP.

Time courses were also examined for the same experiments. That is, LLC-MK2 cells were infected at m.o.i.=3 with SeV18+/ΔM-GFP, and the culture supernatant was recovered over time (every day) to measure HA activity (FIG. 79). Four days or more after the infection, HA activity was detected, though little. However, the measurement of LDH activity, an indicator of cytotoxicity, for the sample revealed a clear cytotoxicity caused 4 days or more after the infection in the SeV18+/ΔM-GFP-infected cells (FIG. 80), indicating a high possibility that the elevation of HA activity was not due to virus-like particles, but due to the activity by HA protein bound to or free from cell debris. Furthermore, the culture supernatant obtained 5 days after the infection was examined using cationic liposomes, Dosper Liposomal Transfection Reagent (Roche, Basel, Switzerland). That is, the culture supernatant (100 μl) was mixed with Dosper (12.5 μl), allowed to stand at room temperature for 10 min, and transfected to LLC-MK2 cells cultured to confluency on 6-well plates. Inspection under a fluorescence microscope 2 days after the transfection revealed that many GFP-positive cells were observed in the supernatant of cells infected with SeV18+/ΔF-GFP which contained secondarily released virus-like particles, while very few or almost no GFP-positive cell was observed in the supernatant of cells infected with SeV18+/ΔM-GFP (FIG. 81). From the above results, it was able to conclude that the secondary release of virus-like particles could be almost completely suppressed by the deficiency of M protein.

EXAMPLE 36

Reconstitution of SeV Deficient in Both F and M Genes

Reconstitution of SeV deficient in both F and M genes (SeV18+/ΔMΔF-GFP) was performed by the same method for the reconstitution of SeV18+/ΔM-GFP as described in Example 32. That is, LLC-MK2 cells were plated on 100-mm diameter Petri dishes at 5×10⁶ cells/dish, cultured for 24 h, and then infected at m.o.i.=2 with PLWUV-VacT7 at room temperature for 1 h. Plasmids: pSeV18+/ΔMΔF-GFP, pGEM/NP, pGEM/P, pGEM/L, pGEM/F-HN and pGEM/M were suspended in Opti-MEM at weight ratios of 12 μg, 4 μg, 2 μg, 4 μg, 4 μg and 4 μg/dish, respectively. To the suspension, 1 μg DNA/5 μl equivalent of SuperFect transfection reagent were added and mixed. The mixture was allowed to stand at room temperature for 15 min and finally added to 3 ml of Opti-MEM containing 3% FBS. After the cells were washed with a serum-free MEM, the mixture was added to the cells and the cells were cultured. After a 5 h culture, the cells were washed twice with a serum-free MEM, and cultured in MEM containing 40 μg/ml AraC and 7.5 μg/ml trypsin. After cultured for 24 h, LLC-MK2/F7/M62/A cells were layered at 8.5×10⁶ cells/dish, and further cultured in MEM containing 40 μg/ml AraC and 7.5 μg/ml trypsin at 37° C. for 2 days. These cells were recovered, the pellet was suspended in 2 ml/dish of Opti-MEM, and P0 lysate was prepared by repeating 3 cycles of freezing and thawing. On the other hand, LLC-MK2/F7/M62/A cells were plated on 24-well plates, moved, at near confluency, to the environment at 32° C., and cultured for 1 day. These cells thus prepared were transfected with P0 lysate of SeV18+/ΔMΔF-GFP at 200 μl/well each, and cultured using a serum-free MEM containing 40 μg/ml AraC and 7.5 μg/ml trypsin at 32° C. With P0, well spread GFP positive cells were observed. With P1, a spread of GFP positive cells was also observed, though very weak (FIG. 82). In the case where LLC-MK2/F7/M62/A cells were infected with SeV18+/ΔF-GFP or SeV18+/ΔM-GFP, a smooth spread of GFP positive cells was observed with both viruses (FIG. 83). Cells expressing both F and M (LLC-MK2/F7/M62/A cells) were infected with SeV18+/ΔF-GFP or SeV18+/ΔM-GFP at m.o.i.=0.5. Three and six days later, sampling was carried out, and the sample was mixed with 1/6.5 volume of 7.5% BSA (final concentration=1%) and stored. Productivity of vectors was investigated by measuring the titers. As a result, SeV18+/ΔF-GFP was recovered as virus solution of 10⁸ or more GFP-CIU/ml and SeV18+/ΔM-GFP was recovered as virus solution of 10⁷ or more GFP-CIU/ml (Table 5). That is, these results indicated that M and F proteins can be supplied successfully from the cells.

TABLE 5

|  | 3 days after infection | 6 days after infection | |
|---|---|---|---|
| SeV18+/ΔF-GFP | $1.0 \times 10^8$ | $1.7 \times 10^8$ | |
| SeV18+/ΔM-GFP | $1.0 \times 10^7$ | $3.6 \times 10^7$ | GFP-CIU |

EXAMPLE 37

Helper Cells Improved to Express SeV-F and M Proteins

In the case of using M and F-expressing LLC-MK2/F7/M62/A cells as helper cells, virus particles of both M- and F-deficient (M and F-deficient) SeV (SeV18+/ΔMΔF-GFP) could not be recovered. However, it was possible to reconstitute and produce both F-deficeint SeV (SeV18+/ΔF-GFP) and M-deficient 5 eV (SeV18+/ΔM-GFP), suggesting that the Cre/loxP expression inducing system in the helper cells is basically capable of trans supply of both M and F proteins. To effectively use the Cre/loxP expression inducing system and reconstitute both M- and F-deficient SeV, it was necessary to further increase amounts of M and F proteins expressed using this system.

<1> Constitution of M and F Expression Plasmid

To enable helper cells to simultaneously induce the expression of M and F proteins, the above-described LLC-MK2/F7/M62 cells that had been already prepared was improved by introducing M and F genes into these cells so as to function under the Cre/loxP expression inducing system. Since pCALNdLw/F used for the F gene transduction carried the neo^r geneand pCALNdLw/hygroM used for the M gene transduction carried the hygromycin resistance gene, a different drug resistance gene should be used for the additional genes to be introduced into the above cells.

According to the scheme described in FIG. 84, the neo[r] gene of the F gene-carrying plasmid (pCALNdLw/F:pCALNdLw containing F gene at SwaI site) was replaced with the Zeocin resistance gene. Namely, after pCALNdLw/F was digested with SpeI and EcoT22I, a fragment (5477 bp) containing the F gene was separated by agarose electrophoresis, and the corresponding band excised from the gel was recovered using a QIAEXII Gel Extraction System. Separately, another pCALNdLw/F was cleaved with XhoI to recover a fragment (6663 bp) containing no neo[r] gene, which was further digested with SpeI to recover a 1761 bp fragment. The Zeocin resistance gene was prepared by performing PCR using pcDNA3.1Zeo(+) (Invitrogen, Groninen, Netherlands) as a template and a pair of primers: zeo-5' (5'-T CTCGAGTCGCTCGGTACGatggccaagttgaccagtgccgttccgg tgctcac-3'/SEQ ID NO: 65) and zeo-3' (5'-AATGCATGAT CAGTAAATTACAATGAACATCGAACCCCAGAGTCC CGCtcagtcctgctcctcggccacgaagtgcacgcagttg-3'/SEQ ID NO: 66). The PCR product was recovered using a QIAquick PCR Purification Kit followed by digestion with XhoI and EcoT22I. pCALNdLw-zeoF was constituted by ligating these three fragments. Then, pCALNdLw-zeoM was constructed by recombining the drug resistance gene-containing fragment of pCALNdLw/hygroM with the XhoI fragment containing the Zeocin resistance gene.

<2> Cloning of Helper Cells

Transfection was carried out using a LipofectAMINE PLUS reagent (Invitrogen, Groningen, Netherlands) as described below according to the method described in the attached protocol. LLC-MK2/F7/M62 cells were placed in 60-mm Petri dishes at 5×10 cells/dish, and cultured in D-MEM containing 10% FBS for 24 h. pCALNdLw-zeoF and pCALNdLw-zeoM (1 µg each, 2 µg in total) were diluted in D-MEM containing no FBS and antibiotics (total volume: 242 µl), and, after stirring, LipofectAMINE PLUS reagent (8 µl) was added thereto. The resulting mixture was stirred and allowed to stand at room temperature for 15 min. Then, LipofectAMINE reagent (12 µl) previously diluted in D-MEM containing no FBS and antibiotics (250 µl in total) was added, and the mixture was allowed to stand at room temperature for 15 min. Furthermore, D-MEM (2 ml) containing no FBS and antibiotics was added, and, after stirring, the transfection mixture thus prepared was added to LLC-MK2/F7/M62 cells which had been washed once in PBS. After a 3-h culturing at 37° C. in a 5% $CO_2$ incubater, D-MEM containing 20% FBS (2.5 ml) was added to the culture without removing the transfection mixture, and the cells were further incubated for 24 h. After the culture, cells were detached using trypsin, plated on 96-well plates at about 5 cells/well or 25 cells/well dilution, and cultured in D-MEM containing 10% FBS supplemented with 500 µg/ml Zeocin (Gibco-BRL, Rockville, Md.) for about 2 weeks. A clone which had propagated from a single cell was cultured to expand to a 6-well culture plate. Ninety-eight clones in total thus prepared were analyzed in the following.

Ninety-eight clones thus obtained were semi-quantitatively analyzed for expression levels of M and F proteins by Western blotting. Each clone was plated on 12-well plates, and, at its nearly confluent state, infected at m.o.i.=5 with a recombinant adenovirus expressing Cre DNA recombinase (AxCANCre) diluted in MEM containing 5% FBS according to the method of Saito et al. (Saito, I. et al., Nucl. Acid. Res. 23, 3816–3821 (1995); Arai, T. et al., J. Virol. 72, 1115–1121 (1998)). After culturing at 32° C. for 2 days, the culture supernatant was removed. The cells were washed once with PBS, detached using a scraper, and recovered. After performing SDS-PAGE by applying ⅕ amount of the cells thus recovered per lane, Western-Blotting was carried out using the anti-M antibody and anti-F antibody (f236: Segawa, H. et al., J. Biochem. 123, 1064–1072 (1998)). Among the 98 clones analyzed, results of 9 clones are shown in FIG. 85.

EXAMPLE 38

Reconstitution of SeV Deficient in Both M and F Genes

Reconstitution of SeV deficient in both M and F genes (SeV18+/ΔMΔF-GFP) was carried out and the assessment of clones described in Example 37 was confirmed. That is, it was assessed whether the reconstitution of SeV18+/ΔMΔF-GFP could be achieved using P0 lysate (lysate of transfected cells). P0 lysate was prepared as follows. LLC-MK2 cells were plated on 100-mm diameter Petri dishes at $5×10^6$ cells/dish, cultured for 24 h, and then infected at m.o.i.=2 with PLWUV-VacT7 at room temperature for 1 h. Plasmids pSeV18+/ΔMΔF-GFP, pGEM/NP, pGEM/P, pGEM/L, pGEM/F-HN and pGEM/M were suspended in Opti-MEM at weight ratios of 12 µg, 4 µg, 2 µg, 4 µg, 4 µg and 4 µg/dish, respectively. SuperFect transfection reagent (1 µg DNA/5 µl equivalent) was added to the suspension and mixed. The mixture was allowed to stand at room temperature for 15 min and added to 3 ml of Opti-MEM containing 3% FBS. After the cells were washed with a serum-free MEM, the mixture was added to the cells and cultured. After a 5-h culturing, the cells were washed twice with a serum-free MEM and cultured in MEM containing 40 µg/ml AraC and 7.5 µg/ml trypsin. After culturing for 24 h, LLC-MK2/F7/A cells were layered at $8.5×10^6$ cells/dish, and these cells were further cultured in MEM containing 40 µg/ml AraC and 7.5 µg/ml trypsin at 37° C. for 2 days. These cells were recovered, the pellet was suspended in 2 ml/dish Opti-MEM, and P0 lysate was prepared by repeating 3 cycles of freezing and thawing. Separately, newly cloned cells were plated on 24-well plates, infected, at near confluency, with AxCAN-Cre at m.o.i.=5, and cultured at 32° C. for 2 days after the infection. These cells were transfected with P0 lysate of SeV18+/ΔMΔF-GFP at 200 µl/well each, and cultured using a serum-free MEM containing 40 µg/ml AraC and 7.5 µg/ml trypsin at 32° C. Spread of GFP protein was observed in 20 clones examined, indicating the successful recovery of M and F-deficient SeV. Results of virus reconstitution in several clones among those examined are shown in FIG. 86. Especially, in the clone #33 (LLC-MK2/F7/M62/#33), infectious virions having the titer of $10^8$ GFP-CIU/mL or more were recovered at its p3 stage (passaged three times), indicating that this clone is highly promising as a virus producing cell. These results reveal that the introduction of both M and F genes into LLC-MK2/F7/M62 cells successfully prepared cells from which M and F-deficient SeV can be recovered at a high frequency. It is considered that the original LLC-MK2/F7/M62 cells expressed M and F proteins at a sufficient level, and that the recovery of M and F-deficient SeV has become possible by introducing both M and F genes into the cells, thereby slightly raising the M and F protein expression levels.

EXAMPLE 39

Virus Productivity from M and F-deficient SeV

The virus productivity of this M and F-deficient SeV was also investigated. LLC-MK2/F7/M62/#33 cells were placed in 6-well plates and cultured at 37° C. The cells at near confluency were infected at a MOI of 5 with AxCANCre (LLC-MK2/F7/M62/#33/A), and cultured at 32° C. for 2 days after the infection. Then, the cells were infected at a MOI of 0.5 with SeV18+/ΔMΔF-GFP, and the culture supernatant was recovered at intervals and replaced with a fresh medium. Supernatants thus recovered were examined for their CIU and HAU. On and after the second day of infection, viruses having the titer of $10^8$ CIU/ml or more were continuosuly recovered (FIG. 87). Furthermore, the time-course changes in CIU and HAU were parallel to each other, and most of virus particles produced had infectivity, indicating the efficient virus production.

EXAMPLE 40

Confirmation of the Structure of M gene- and F Gene-deficient SeV

The viral gene of SeV18+/ΔMΔF-GFP was confirmed by RT-PCR, and the viral protein by Western-blotting. In RT-PCR, the virus at the P2 stage5 days after the infection (P2d5) was used. RNA was recovered from virus solution using QIAamp Viral RNA Mini Kit (QIAGEN, Bothell, Wash.), and cDNA preparation and RT-PCR, was performed using SuperScript One-Step RT-PCR System (Gibco-BRL, Rockville, Md.), according to the methods described in the attached protocols. PCR was performed using, as the primer for cDNA preparation and RT-PCR, two pairs of primers: one combination of F3208 (5'-agagaacaagactaaggctacc-3'/SEQ ID NO: 62) on the P gene and GFP-RV (5'-cagatgaact-tcagggtcagcttg-3'/SEQ ID NO: 67) on the GFP gene, and another combination of said F3208 and R6823 (5'-tgggt-gaatgagagaatcagc-3'/SEQ ID NO: 68) on the HN gene. As expected from the gene structure of SeV18+/ΔMΔF-GFP, amplifications of 644 bp and 1495 bp DNAs were observed from the former and latter combinations (FIG. 88). Furthermore, from SeV18+/ΔM-GFP and SeV18+/ΔF-GFP, genes in size expected from their respective structures were amplified, and their sizes were clearly different from those obtained from SeV18+/ΔMΔF-GFP, supporting that SeV18+/ΔMΔF-GFP lacks both of M and F genes.

This was also confirmed by the protein level by Western-blotting. LLC-MK2 cells were infected at m.o.i.=3 with SeV18+/ΔMΔF-GFP, SeV18+/ΔM-GFP, SeV18+/ΔF-GFP and SeV18+GFP, and the cells were recovered 2 days after the infection. After SDS-PAGE, Western-blotting was performed according to the method described in Examples 27 and 28 to detect proteins using the anti-M antibody, anti-F antibody, and DN-1 antibody (rabbit polyclonal) that mainly detects NP protein. In cells infected with SeV18+/ΔMΔF-GFP, both M and F proteins were not detected while NP protein was observed. Thus, the protein level examination also confirmed the structure of SeV18+/ΔMΔF-GFP (FIG. 89). In this experiment, F protein was not observed in cells infected with SeV18+/ΔF-GFP and M protein was not observed in cells infected with SeV18+/ΔM-GFP, while all the viral proteins examined were detected in cells infected with SeV18+GFP.

EXAMPLE 41

Quantitative Analysis of the Presence or Absence of Secondarily Released Particles of SeV Deficient in M- and F- Genes Time courses were also examined for the same experiments. Specifically, LLC-MK2 cells were infected at m.o.i.=3 with SeV18+/ΔMΔF-GFP, and the culture supernatant was recovered over time (every day) to measure HA activity (FIG. 90). Four days or more after the infection, very little HA activity was detected. This elevation of HA activity was thought to be probably not due to virus-like particles, but due to HA protein bound to or free from cell debris, similar to the case of SeV18+/ΔM-GFP. Furthermore, the culture supernatant obtained 5 days after the infection was examined using cationic liposomes, Dosper Liposomal Transfection Reagent (Roche, Basel, Switzerland). Specifically, the culture supernatant (100 μl) was mixed with Dosper (12.5 μl), allowed to stand at room temperature for 10 min. The resulting mixture was used to transfect LLC-MK2 cells cultured to confluency on 6-well plates. Inspection under a fluorescence microscope 2 days after the transfection revealed that many GFP-positive cells were observed for the supernatant of cells infected with SeV18+/ΔF-GFP which contained secondarily released particles, while very few or almost no GFP-positive cell was observed for the supernatant of cells infected with SeV18+/ΔMΔF-GFP (FIG. 91). This result indicates that the cells transfected with SeV18+/ΔMΔF-GFP contains almost no secondarily released virus particles.

EXAMPLE 42

Viral Infectivity of M and F-deficient SeV and M-deficient SeV (in Vitro)

Efficiency of introduction of gene transfer vector into non-dividing cells and intracellular expression efficiency are important and essential for the assessment of the capability of the vector.

Primary cultures of rat cerebral cortex nerve cells were prepared by the following method. Pregnant SD rat was anesthesized by ether and decapitated on the $17^{th}$ day after conception. After disinfecting the abdomen with isodine and 80% ethanol, the uterus was transferred into a 10-cm Petri dish, and the fetus (embryo) was taken out. Next, the scalp and cranial bone of fetus were cutwith a pair of INOX5 tweezers, the brain was picked up and collected in a 35-mm diameter Petri dish. Portions of the cerebellum and brain stem were removed with a pair of oculist scissors, the cerebrum was divided into hemispheres, the remaining brain stem was removed, olfactory bulb was taken out with a pair of tweezers, and then the meninx was removed also using a pair of tweezers. Finally, after the removal of diencephalon and hippocampus using a pair of oculist scissors, the cerebral corex was collected in a Petri dish, cut into small pieces with a surgical knife, and collected into a 15-mm centrifuge tube. The cortex was treated with 0.3 mg/ml papain at 37° C. for 10 min, treated in a serum-containing medium (5 ml), and washed. The cells were then dispersed. The cells were strained through a 70-μm strainer, collected by centrifugation, dispersed by gentle pipetting, and then counted. The cells were placed in poly-L-lysine (PLL)-coated 24-well culture plates at $2 \times 10^5$ or $4 \times 10^5$ cells/well, and, 2 days after seeding, infected at MOI of 3 with M and F-deficient SeV (SeV18+/ΔMΔF-GFP) and M-deficient SeV (SeV18+/ΔM-GFP). Thirty-six hours after the infection, the cells were immuno-stained with the nerve cell-specific marker MAP2, and infected cells were identified by merging with GFP-expressing cells (SeV-infected cells)

Immunostaining with MAP2 was carried out as follows. After infected cells were washed with PBS, the cells were fixed with 4% paraformaldehyde at room temperature for 10 min, washed in PBS, and then blocked using PBS containing 2% normal goat serum at room temperature for 60 min. Next, the cells were reacted with a 1/200-fold diluted anti-MAP2 antibody (Sigma, St. Louis, Mo.) at 37° C. for 30 min, washed with PBS, and then reacted with a 1/200-fold diluted secondary antibody (goat anti mouse IgG Alexa568: Molecular Probes Inc., Eugene, Oreg.) at 37° C. for 30 min. After the cells were washed with PBS, fluorescence intensity of the cells was observed under a fluorescence microscope (DM IRB-SLR: Leica, Wetzlar, Germany).

In both M and F-deficient SeV (SeV18+/ΔMΔF-GFP) and M-deficient SeV (SeV18+/ΔM-GFP), almost all MAP2-positive cells were GFP-positive (FIG. 92). That is, nearly all the prepared nerve cells were efficiently infected with SeV, confirming that both M and F-deficient SeV and M-deficient SeV are highly effectively introduced into non-dividing cells and expressed the transgenes

EXAMPLE 43

Viral Infectivity of M and F-deficient SeV and M-deficient SeV (in Vivo)

M and F-deficient SeV (SeV18+/ΔMΔF-GFP) and M-deficient SeV (SeV18+/ΔM-GFP), whose in vivo infectivity was evaluated as described above, (5 μl) (1×10$^9$ p.f.u./ml) were intraventricularly administered into the left ventricle of a gerbil using the stereo method. Two days after the administration, the brain was surgically excised to prepare frozen slices. These slices were observed under a fluorescence microscope to examine the presence or absence of infection based on the fluorescence intensity of GFP. By the administration of both M and F-deficient SeV (SeV18+/ΔMΔF-GFP) and M-deficient SeV (SeV8+/ΔM-GFP), many GFP-positive cells were observed among cells in both left and right ventricles, such as ependymal cells (FIG. 93). This result confirmed that both M and F-deficient and M-deficient SeVs enables efficient gene transfer and expression of the transgene in vivo.

EXAMPLE 44

Cytotoxicity of M and F-deficient SeV and M-deficient SeV

Viral cytotoxcity was assessed using CV-1 and HeLa cells in which SeV infection-dependent cytotoxicity could be observed. As a control, cytotoxicity of SeV having replicability (wild type: SeV18+GFP) and F-deficient SeV (SeV18+/ΔF-GFP) was also measured. Experimental procedures are described in detail below. CV-1 cells or HeLa cells were placed in 96-well plates at 2.5×10$^4$ cells/well (100 μl/well) and cultured. MEM containing 10% FBS was used for culturing both cells. After culturing for 24 h, the cells were infected by adding at 5 μl/well a solution of SeV18+GFP, SeV18+/ΔF-GFP, SeV18+/ΔM-GFP or SeV18+/ΔMΔF-GFP diluted with MEM containing 1% BSA, and, 6 h later, the culture medium containing the virus solution was removed, and replaced with MEM medium containing no FBS. Three days after the infection, the culture superntant was sampled, and the cytotoxicity was quantified using a Cytotoxicity Detection Kit (Roche, Basel, Switzerland) according to the method described in the instruction attached to the kit. Comparing to SeV having the replicability, deficiency in M or F gene attenuated cytotoxicity (as in SeV18+/ΔF-GFP and SeV18+/ΔM-GFP), and deficiency in both genes (as in SeV18+/ΔMΔF-GFP) additively attenuated cytotoxicity (FIG. 94).

As described above, "M and F-deficient SeV vector" that has been successfully reconstituted for the first time in the present invention, has the infectivity against a variety of cells including non-dividing cells, contains almost no secondarily released virus particles, and, furthermore, has attenuated cytotoxicity. Thus, the vector of this invention can be a gene transfer vector with a wide range of applicability.

INDUSTRIAL APPLICABILITY

The present invention provides envelope gene-deficient paramyxovirus vectors. The present invention establishes a practical, novel, envelope gene-deficient vector system based on a negative-strand RNA virus for the first time. The achievement in recovering infectious deficient virus particles from cDNA of F gene-deficient, M gene-deficient, and FHN gene-deficient genome and so on using helper cells, paved the way for the research and development of novel vectors for gene therapy, taking advantage of the excellent characteristics of the Sendai virus. The deficient type Sendai virus vector in the present invention is capable of introducing a gene into various cell types with an extremely high efficiency and expressing the exogenous gene at a phenomenally high level. Furthermore, the vector is expressed in infected cells persistently, and is a highly safe vector that completely lacks the capability to cause virus propagation, since it does not release secondary infectious virus particles. The vector provided by the present invention is expected to be variously applied as a vector for in vivo and ex vivo gene therapy.

---

The invention claimed is:

1. A Sendai virus particle comprising a complex comprising (a) a negative-strand single-stranded RNA expressing NP, P, and L proteins and modified not to express at least one of F and HN proteins, wherein the RNA is derived from a Sendai virus, and (b) NP, P, and L proteins, wherein the Sendai virus particle, after introduction into a cell, is capable of replicating said RNA, but incapable of releasing infective viral particles and propagating to adjacent cells.

2. The Sendai virus particle according to claim 1, wherein the negative-strand single-stranded RNA expresses M protein.

3. The Sendai virus particle according to claim 1, comprising F and HN proteins.

4. The Sendai virus particle according to claim 1, comprising VSV-G protein.

5. The Sendai virus particle according to claim 1, wherein the negative-strand single-stranded RNA further encodes an exogenous gene.

6. A DNA encoding (i) negative-strand single-stranded RNA expressing NP, P, and L proteins and modified not to express at least one of F and HN proteins, wherein the RNA is derived from a Sendai virus, or (ii) the complementary strand of the RNA, wherein a complex comprising the RNA and NP, P, and L proteins, after introduction into a cell, is capable of replicating said RNA, but incapable of releasing infective viral particles and propagating to adjacent cells.

7. A method for producing virus particles which, after introduction into a cell, are capable of replicating a negative-strand single-stranded RNA comprised in the virus particles, but incapable of releasing infective viral particles and propagating to adjacent cells, comprising the following steps of:

(a) expressing a DNA encoding (i) a negative-strand single-stranded RNA expressing NP, P, and L proteins and modified not to express at least one of F and HN proteins, wherein the RNA is derived from a Sendai virus, or (ii) the complementary strand of the RNA, by introducing into cells expressing at least one envelope protein, (b) culturing said cells, and (c) recovering virus particles from the culture supernatant.

8. A method for producing virus particles which, after introduction into a cell, are capable of replicating a negative-strand single-stranded RNA comprised in the virus particles, but incapable of releasing infective viral particles and propagating to adjacent cells, comprising the steps of:

(a) introducing a complex comprising a negative-strand single-stranded RNA expressing NP, P, and L proteins and modified not to express at least one of F and HN proteins, wherein the RNA is derived from a Sendai virus, and NP, P, and L proteins, into cells expressing at least one envelope protein, (b) culturing said cells, and (c) recovering virus particles from the culture supernatant.

9. The method according to claim 7 or 8, further comprising co-culturing the cells with cells expressing at least the envelope protein.

10. The method of claim 7 or 8, wherein the cell culture is carried out at 35° C. or less.

11. The method according to claim 7 or 8, wherein the cells express F and/or HN proteins so that the recovered virus particles comprise F and HN proteins.

12. The method according to claim 7 or 8, wherein the cells express VSV-G protein.

13. The method according to claim 9, wherein the co-culture is an overlaying culture.

14. A cell comprising a Sendai virus comprising a complex comprising:

(a) a negative-strand single-stranded RNA expressing NP, P, and L proteins and modified not to express at least one of F and HN proteins, wherein the RNA is derived from a Sendai virus, and (b) NP, P, and L proteins, wherein the Sendai virus in the cell is capable of replicating said RNA, but incapable of releasing infective viral particles and propagating to adjacent cells.

15. A ribonucleoprotein complex comprising:

(a) a negative-strand single-stranded RNA expressing NP, P, and L proteins and modified not to express at least one of F and HN proteins, wherein the RNA is derived from a Sendai virus, and (b) NP, P, and L proteins, wherein the complex, after introduction into a cell, is capable of replicating said RNA, but incapable of releasing infective viral particles and propagating to adjacent cells.

16. A cell comprising a ribonucleoprotem complex comprising:
(a) a negative-strand single-stranded RNA expressing NP, P, and L proteins and modified not to express at least one of F and HN proteins, wherein the RNA is derived from a Sendai virus, and
(b) NP, P, and L proteins, wherein the complex in the cell is capable of replicating said RNA, but incapable of releasing infective viral particles and propagating to adjacent cells.

* * * * *

UNITED STATES PATENT AND TRADEMARK OFFICE
CERTIFICATE OF CORRECTION

PATENT NO.         : 7,226,786 B2
APPLICATION NO.    : 10/316535
DATED              : June 5, 2007
INVENTOR(S)        : Kaio Kitazato et al.

It is certified that error appears in the above-identified patent and that said Letters Patent is hereby corrected as shown below:

Title Pg, Item (56) Page 2, Other Publications, Left Column, Lines 2 and 37, replace "Speilhofer" with --Spielhofer--:

Title Page, Item (56) Page 3, Other Publications, replace "LipofectA MINE" with --LipofectAMINE--;

Column 2, Line 29, replace "triptase" with --tryptase--;

Column 6, Line 6, replace "and-X56131" with --and X56131--;

Column 6, Line 59, replace "Hemaggulutinating" with --Hemagglutinating--;

Column 12, Line 34, replace "neuramimidase" with --neuraminidase--;

Column 14, Line 16, replace "sites on the both ends" with --sites on both ends--;

Column 16, Line 67, replace "it can used in" with --it can be used in--;

Column 17, Line 37, replace "proeins" with --proteins--;

Column 17, Line 59, replace "peferably" with --preferably--;

Column 19, Line 34, replace "When using as vaccines" with --When used as vaccines--;

Column 19, Line 37, replace "as cancer a treatment" with --as a cancer treatment--;

Column 21, Line 46, replace "represents cells that was transfected" with --represents cells that were transfected--;

Column 28, Line 2, replace "absense" with --absence--;

Column 33, Line 46, replace "The-result showed-that" with --The result showed that--;

Column 42, Line 32, replace "Inmost" with --In most--;

Column 47, Line 14, replace "mixed and lest standing" with --mixed and left standing--;

Column 49, Line 34, replace "added to cells were and incubated" with --added to cells and were incubated--;

UNITED STATES PATENT AND TRADEMARK OFFICE
CERTIFICATE OF CORRECTION

PATENT NO. : 7,226,786 B2
APPLICATION NO. : 10/316535
DATED : June 5, 2007
INVENTOR(S) : Kaio Kitazato et al.

It is certified that error appears in the above-identified patent and that said Letters Patent is hereby corrected as shown below:

Column 52, Line 18, replace "After further a" with --After a further--;

Column 55, Line 6, replace "P-D-arabinofranoside" with --β-D-arabinofranoside--;

Column 56, Line 16, replace "in a more cells" with --in more cells--;

Column 67, Line 59, replace "5'-tctgagtcgctcggtacgatgaaaaagcctgaa ctcaccgcgacgtctgtcgag-3' /SEQ ID NO:58" with --5'-tctcgagtcg ctcggtacgatgaaaaagcctgaactcaccgcgacgtctgtcgag-3' /SEQ ID NO: 58--;

Column 72, Line 48, replace "F-deficeint" with --F-deficient--;

Column 72, Line 49, replace "5 eV" with --SeV--;

Column 72, Line 64, replace "geneand" with --gene and--;

Column 75, Line 21, replace "stage5" with --stage 5--;

Column 76, Line 40, replace "cutwith" with --cut with--; and

Column 103, Claim 16, Line 1, replace "ribonucleoprotem" with --ribonucleoprotein--.

Signed and Sealed this

Twenty-eighth Day of July, 2009

JOHN DOLL
*Acting Director of the United States Patent and Trademark Office*